US011014963B2

(12) United States Patent
Hornsperger et al.

(10) Patent No.: US 11,014,963 B2
(45) Date of Patent: May 25, 2021

(54) TRIFLUOROMETHYLPROPANAMIDE DERIVATIVES AS HTRA1 INHIBITORS

(71) Applicant: Hoffmann-La Roche Inc., Little Falls, NJ (US)

(72) Inventors: Benoit Hornsperger, Basel (CH); Roberto Iacone, Basel (CH); Hans P. Maerki, Basel (CH); Peter Mohr, Basel (CH); Michael Reutlinger, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/121,300

(22) Filed: Sep. 4, 2018

(65) Prior Publication Data

US 2018/0371016 A1 Dec. 27, 2018

Related U.S. Application Data

(63) Continuation of application No. PCT/EP2017/054677, filed on Mar. 1, 2017.

(30) Foreign Application Priority Data

Mar. 4, 2016 (EP) .................................... 16158637

(51) Int. Cl.

| | |
|---|---|
| ***C07K 5/083*** | (2006.01) |
| ***C07K 5/08*** | (2006.01) |
| ***C07K 5/087*** | (2006.01) |
| ***C07K 5/097*** | (2006.01) |
| ***C07K 5/093*** | (2006.01) |
| ***A61P 43/00*** | (2006.01) |
| ***A61P 27/02*** | (2006.01) |
| ***A61P 27/00*** | (2006.01) |
| ***A61P 9/00*** | (2006.01) |
| ***A61P 9/10*** | (2006.01) |
| ***C07K 5/062*** | (2006.01) |
| ***C07K 5/09*** | (2006.01) |
| ***C07K 5/072*** | (2006.01) |
| ***C07K 5/068*** | (2006.01) |
| ***C07K 5/078*** | (2006.01) |
| ***C07K 5/065*** | (2006.01) |
| ***C07K 5/06*** | (2006.01) |

(52) U.S. Cl.

CPC ........ *C07K 5/0806* (2013.01); *C07K 5/06026* (2013.01); *C07K 5/06078* (2013.01); *C07K 5/06086* (2013.01); *C07K 5/06121* (2013.01); *C07K 5/06139* (2013.01); *C07K 5/06191* (2013.01); *C07K 5/081* (2013.01); *C07K 5/0804* (2013.01); *C07K 5/0812* (2013.01); *C07K 5/0815* (2013.01); *C07K 5/0819* (2013.01); *C07K 5/0821* (2013.01); *C07K 5/0827* (2013.01)

(58) Field of Classification Search

CPC ......... A61P 43/00; A61P 27/02; A61P 27/00; A61P 9/00; A61P 9/10; C07K 5/083; C07K 5/08; C07K 5/087; C07K 5/097; C07K 5/093

See application file for complete search history.

(56) References Cited

U.S. PATENT DOCUMENTS

| | | | |
|---|---|---|---|
| 9,980,929 | B2 | 5/2018 | Hornsperger et al. |
| 10,428,108 | B2 | 10/2019 | Hornsperger et al. |
| 2005/0027101 | A1 | 3/2005 | Gutheil et al. |

FOREIGN PATENT DOCUMENTS

| | | | |
|---|---|---|---|
| EP | 2 371 839 | A1 | 10/2011 |
| WO | 96/02499 | A1 | 2/1996 |
| WO | 99/07734 | A2 | 2/1999 |
| WO | 00/61542 | A1 | 10/2000 |
| WO | 2005/035525 | A2 | 4/2005 |
| WO | 2008/101160 | A2 | 8/2008 |
| WO | 2012/093101 | A1 | 7/2012 |
| WO | 2014/002053 | A1 | 1/2014 |
| WO | 2016/100555 | A1 | 6/2016 |
| WO | 2016/135070 | A1 | 9/2016 |
| WO | 2016/180751 | A1 | 11/2016 |

OTHER PUBLICATIONS

Derstine et al., 1996, caplus an 1996:494556.*

AMD, 2020, https://www.reviewofophthalmology.com/article/whats-ahead-for-the-treatment-of-dry-amd.*

AMGPrevention, 2020, https://www.allaboutvision.com/conditions/and-prevention.htm.*

He et al., 2020, https://care.diabetesjournals.org/content/41/10/2202.*

McIver, 1993, caplus an 1993:626432.*

Isr and Written Opinion for PCT/EP2017/054677 (dated Jul. 4, 2017).

Jacobo, Sarah Melissa P. et al., "Focus on Molecules: HtrA1 and neovascular AMD" Experimental Eye Research (XP028884160), 94(1):4-5 ( 2012).

(Continued)

*Primary Examiner* — Sun Jae Yoo

(74) *Attorney, Agent, or Firm* — Bradley E. Davis

(57) ABSTRACT

The invention provides novel compounds having the general formula (I)

(I)

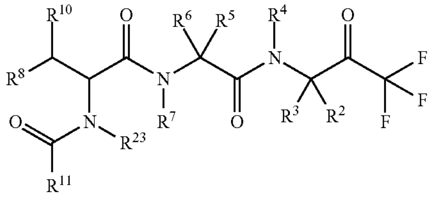

wherein $R^2$, $R^3$, $R^4$, $R^5$, $R^6$, $R^7$, $R^3$, $R^8$, $R^{10}$, $R^{11}$ and $R^{23}$ are as described herein, compositions including the compounds and methods of using the compounds.

48 Claims, No Drawings

(56) References Cited

OTHER PUBLICATIONS

Sasubilli, Ramakrishna et al., "General Inverse Solid-Phase Synthesis Method for C-Terminally Modified Peptide Mimetics" Journal of Combinatorial Chemistry (XP002522469), 6(6):911-915 (Nov. 1, 2004).

Truebestein et al., "Substrate-induced remodeling of the active site regulates human HTRA1 activity" Nat Structural Molec Biol (XP055124206), 18(3):386-388 (Feb. 6, 2011).

Akahoshi et al., "Synthesis, Structure—Activity Relationships, and Pharmacokinetic Profiles of Nonpeptidic Difluoromethylene Ketones as Novel Inhibitors of Human Chymase" J. Med. Chem. 44(8):1297-1304 ( 2001).

International Preliminary Report on Patentability (IPRP) for PCT/EP2017/070985 dated Feb. 26, 2019.

International Search Report for PCT/EP2017/070985 dated Sep. 25, 2017.

Liver disease, Mayo Clinic, <https://www.rnayoclinic.org/diseases-conditions/liver-problerns/symptorns-causes/syc-20374502>, Accessed Mar. 1, 2020.

Bernstein, Peter R. et al., "Examination of Peptidic alpha-beta Diamino-alpha-alpha-difluoroketones as Inhibitors of human Leukocyte Elastase" Bioorganic and Medicinal Chemistry Letters (XP002768444), 4(18):2175-2178 (Oct. 1, 1994)

Cregge et al., "Inhibition of Human Neutrophil Elastase. 4. Design, Synthesis, X-ray Crystallographic Analysis and Structure-Activity Relationships for a Series of P2-Modified, Orally Active Peptidyl Pentafluoroethyl Ketones" Journal of Medicinal Chemistry 41:2451-2480 ( 1998).

Doherty A. M. et al., "Design and Synthesis of Potent, Selective, and Orally Active Fluorine-Containing Renin Inhibitors" Journal of Medicinal Chemistry (XP002768443), 35:2-14 (Jan. 1, 1992).

Giovani, Simone et al., "Plasmodium falciparum subtilisin-like protease 1: discovery of potent difluorostatone-based inhibitors" RSC Advances (XP002768447), 5:22431-22448 (Feb. 19, 2015).

International Preliminary Report on Patentability (IPRP) for PCT/EP2017/067519 dated Jan. 22, 2019.

"International Preliminary Report on Patentability—PCT/EP2017/071019":pp. 1-8 (Mar. 7, 2019).

International Search Report for PCT/EP2017/067519 dated Aug. 14, 2017.

'International Search Report—PCT/EP2017/071019':pp. 1-8 (Sep. 27, 2017).

IPRP and Written Opinion for PCT/EP2017/054682 (dated May 4, 2017).

Skiles et al., "Inhibition of human leukocyte elastase by N-substituted peptides containing a,a-Difluorostatone residues at P1" J. Med. Chem. 35:4795-4808 ( 1992).

Perni et al., "Inhibitors of hepatitis C virus NS3.4A protease 2. Warhead SAR and optimization" Bioorganic & Medicinal Chemistry Letters 14(6):1441-1446 ( 2004).

* cited by examiner

TRIFLUOROMETHYLPROPANAMIDE DERIVATIVES AS HTRA1 INHIBITORS

RELATED APPLICATIONS

This application is a continuation of International Application No. PCT/EP2017/054677 filed Mar. 1, 2017, claiming priority application number EP 16158637.5 filed Mar. 4, 2016, each of which are incorporated herein by reference in its entirety.

The present invention relates to organic compounds useful for therapy or prophylaxis in a mammal, and in particular to serine protease HtrA1 inhibitors for the treatment or prophylaxis of HtrA1-mediated ocular diseases, such as wet or dry age-related macular degeneration, geographic atrophy, diabetic retinopathy, retinopathy of prematurity and polypoidal choroidal vasculopathy.

The present invention provides novel compounds of formula (I)

(I)

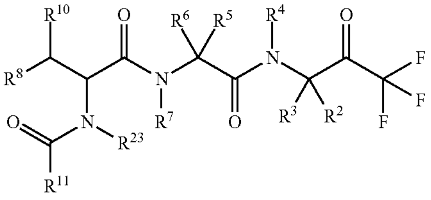

wherein $R^2$, $R^3$, $R^4$, $R^6$, $R^7$, $R^{10}$ and $R^{23}$ are independently selected from i) H, ii) $C_{1-6}$-alkyl, and iii) $C_{3-8}$-cycloalkyl;

$R^5$ is selected from i) aryl substituted with $R^{12}$, $R^{13}$ and $R^{14}$ ii) aryl-$C_{1-6}$-alkyl substituted with $R^{12}$, $R^{13}$ and $R^{14}$ iii) heteroaryl substituted with $R^{12}$, $R^{13}$ and $R^{14}$, and iv) heteroaryl-$C_{1-6}$-alkyl substituted with $R^{12}$, $R^{13}$ and $R^{14}$;

$R^8$ is selected from i) H, ii) hydroxy, iii) amino-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$, iv) aminocarbonyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$, v) aminocarbonyl-$C_{1-6}$-alkyl substituted on the nitrogen atom by one or two substituents selected from H, $C_{1-6}$-alkylcarbonyl, $C_{1-6}$-alkoxycarbonyl, $C_1$alkyl, arylcarbonyl and heteroarylcarbonyl, wherein arylcarbonyl and heteroarylcarbonyl are substituted with $R^{15}$, $R^{16}$ and $R^{17}$, vi) carboxy, vii) carboxy-$C_{1-6}$-alkyl, viii) $C_{1-6}$-alkoxy, ix) $C_{1-6}$-haloalkoxy, x) $C_{1-6}$-alkoxycarbonyl, xi) $C_{1-6}$-alkoxycarbonyl-$C_{1-6}$-alkyl, xii) $C_{3-8}$-cycloalkyl, xiii) aryl substituted with $R^{15}$, $R^{16}$ and $R^{17}$, xiv) aryl-$C_{1-6}$-alkyl substituted with $R^{15}$, $R^{16}$ and $R^{17}$, xv) aryl-$C_{1-6}$-alkoxy substituted with $R^{15}$, $R^{16}$ and $R^{17}$, xvi) heteroaryl substituted with $R^{15}$, $R^{16}$ and $R^{17}$, xvii) heteroaryl-$C_{1-6}$-alkyl substituted with $R^{15}$, $R^{16}$ and $R^{17}$, and xviii) heteroaryl-$C_{1-6}$-alkoxy substituted with $R^{15}$, $R^{16}$ and $R^{17}$ xix) heterocycloalkyl substituted with $R^{15}$, $R^{16}$ and $R^{17}$, xx) heterocycloalkyl-$C_{1-6}$-alkyl substituted with $R^{15}$, $R^{16}$ and $R^{17}$, xxi) heterocycloalkyl-$C_{1-6}$-alkoxy substituted with $R^{15}$, $R^{16}$ and $R^{17}$, xxii) cyano-$C_{1-6}$-alkyl, and xxiii) halo-$C_{1-6}$-alkoxy;

$R^{11}$ is selected from i) amino-$C_{1-6}$-alkyl substituted on the nitrogen atom by $R^{21}$ and $R^{22}$, ii) $C_{3-8}$-cycloalkyl substituted with $R^{18}$, $R^{19}$ and $R^{20}$, iii) $C_{3-8}$-cycloalkyl-$C_{1-6}$-alkyl substituted with $R^{18}$, $R^{19}$ and $R^{20}$, iv) $C_{3-8}$-cycloalkyl(halo)-$C_{1-6}$-alkyl substituted with $R^{18}$, $R^{19}$ and $R^{20}$, v) aryl substituted with $R^{18}$, $R^{19}$ and $R^{20}$, vi) aryl-$C_{1-6}$-alkyl substituted with $R^{18}$, $R^{19}$ and $R^{20}$, vii) aryl-$C_{3-8}$-cycloalkyl substituted with $R^{18}$, $R^{19}$ and $R^{20}$, viii) aryl-heterocycloalkyl substituted with $R^{18}$, $R^{19}$ and $R^{20}$ ix) aryl(halo)-$C_{1-6}$-alkyl substituted with $R^{18}$, $R^{19}$ and $R^{20}$, x) aryl(halo)-$C_{3-8}$-cycloalkyl substituted with $R^{18}$, $R^{19}$ and $R^{20}$, xi) aryl(halo)-heterocycloalkyl substituted with $R^{18}$, $R^{19}$ and $R^{20}$, xii) aryloxy-$C_{1-6}$-alkyl substituted with $R^{18}$, $R^{19}$ and $R^{20}$ xiii) aryloxy-$C_{3-8}$-cycloalkyl substituted with $R^{18}$, $R^{19}$ and $R^{20}$, xiv) aryloxy-heterocycloalkyl substituted with $R^{18}$, $R^{19}$ and $R^{20}$, xv) aryloxy(halo)-$C_{3-8}$-cycloalkyl substituted with $R^{18}$, $R^{19}$ and $R^{20}$, xvi) aryloxy(halo)-heterocycloalkyl substituted with $R^{18}$, $R^{19}$ and $R^{20}$ xvii) aryloxy(halo)-$C_{1-6}$-alkyl, xviii) heterocycloalkyl substituted with $R^{18}$, $R^{19}$ and $R^{20}$, xix) heterocycloalkyl-$C_{1-6}$-alkyl substituted with $R^{18}$, $R^{19}$ and $R^{20}$, xx) heterocycloalkyl-$C_{3-8}$-cycloalkyl substituted with $R^{18}$, $R^{19}$ and $R^{20}$, xxi) heterocycloalkyl(halo)-$C_{3-8}$-cycloalkyl substituted with $R^{18}$, $R^{19}$ and $R^{20}$, xxii) heterocycloalkyl(halo)-$C_{1-6}$-alkyl substituted with $R^{18}$, $R^{19}$ and $R^{20}$, xxiii) heteroaryl substituted with $R^{18}$, $R^{19}$ and $R^{20}$, xxiv) heteroaryl-$C_{1-6}$-alkyl substituted with $R^{18}$, $R^{19}$ and $R^{20}$, xxv) heteroaryl-$C_{3-8}$-cycloalkyl substituted with $R^{18}$, $R^{19}$ and $R^{20}$, xxvi) heteroaryl(halo)-$C_{3-8}$-cycloalkyl substituted with $R^{18}$, $R^{19}$ and $R^{20}$, xxvii) heteroaryl(halo)-$C_{1-6}$-alkyl substituted with $R^{18}$, $R^{19}$ and $R^{20}$, xxviii) heteroaryloxy-$C_{1-6}$-alkyl substituted with $R^{18}$, $R^{19}$ and $R^{20}$, xxix) heteroaryloxy-$C_{3-8}$-cycloalkyl substituted with $R^{18}$, $R^{19}$ and $R^{20}$, xxx) heteroaryloxy(halo)-$C_{3-8}$-cycloalkyl substituted with $R^{18}$, $R^{19}$ and $R^{20}$, and xxxi) heteroaryloxy(halo)-$C_{1-6}$-alkyl substituted with $R^{18}$, $R^{19}$ and $R^{20}$ xxxii) aryl(cycloalkyl)-$C_{1-6}$-alkyl substituted with $R^{18}$, $R^{19}$ and $R^{20}$, xxxiii) aryl(haloalkyl)-$C_{1-6}$-alkyl substituted with $R^{18}$, $R^{19}$ and $R^{20}$, xxxiv) aryl(heterocycloalkyl)-$C_{1-6}$-alkyl substituted with $R^{18}$, $R^{19}$ and $R^{20}$, and xxxv) aryl(hydroxy,haloalkyl)-$C_{1-6}$-alkyl substituted with $R^{18}$, $R^{19}$ and $R^{20}$;

$R^{12}$, $R^{13}$, $R^{14}$, $R^{15}$, $R^{16}$, $R^{17}$, $R^{18}$, $R^{19}$ and $R^{20}$ are independently selected from i) H, ii) cyano, iii) halogen, iv) oxo, v) $C_{1-6}$-alkyl, vi) amino substituted on the nitrogen atom by two substituents independently selected from H, $C_{1-6}$-alkyl, $C_{1-6}$-alkoxycarbonyl, arylcarbonyl and heteroarylcarbonyl, vii) amino-$C_{1-6}$-alkyl substituted on the nitrogen atom by two substituents independently selected from H, $C_{1-6}$-alkyl, $C_{1-6}$-alkoxycarbonyl, arylcarbonyl and heteroarylcarbonyl, viii) halo-$C_{1-6}$-alkyl, ix) $C_{3-8}$-cycloalkyl, x) $C_{1-6}$-alkoxycarbonyl-$C_{1-6}$-alkyl, xi) carboxy-$C_{1-6}$-alkyl, xii) $C_{1-6}$-alkoxycarbonyl-$C_{1-6}$alkylaminocarbonyl-$C_{1-6}$alkyl, xiii) carboxy-$C_{1-6}$-alkylaminocarbonyl-$C_{1-6}$alkyl, xiv) $C_{1-6}$-alkoxy, xv) halo-$C_{1-6}$-alkoxy, xvi) $C_{1-6}$-alkoxycarbonyl-$C_{1-6}$-alkoxy, xvii) hydroxycarbonyl-$C_{1-6}$-alkoxy, xviii) carboxy-$C_{1-6}$-alkoxy, xix) $C_{1-6}$-alkoxycarbonyl-$C_{1-6}$-alkylaminocarbonyl-$C_{1-6}$-alkoxy, xx) carboxy-$C_{1-6}$-alkylaminocarbonyl-$C_{1-6}$-alkoxy, heterocycloalkyl, and xxi) cyano;

$R^{21}$ and $R^{22}$ are independently selected from i) H, ii) $C_{1-6}$-alkoxycarbonyl, iii) carboxy-$C_{1-6}$-alkyl, iv) arylcarbonyl, and v) heteroarylcarbonyl;

or pharmaceutically acceptable salts;

with the proviso that CAS 1349796-81-1 is excluded.

Inhibition of the serine protease HtrA1, which belongs to an evolutionarily conserved family of HtrA proteins, has the potential to protect and treat tissue damage caused by the degeneration of retinal or photoreceptor cells in the human eye. The pathophysiological relevance of HtrA1 in the progression of the age-related macular degeneration has been firmly established by human genetic studies where a SNP in the HtrA1 promoter region results in increased HtrA1 transcript and protein levels. Age-related macular degeneration is the leading cause of severe irreversible central vision loss and blindness in individuals over 65 years of age in developed countries. There are two forms of AMD: dry AMD and wet AMD. Wet AMD (also known as exudative AMD), is associated with pathologic posterior choroidal neovascularization subsequent to the disruption of the delimiting Bruch's membrane. Tissue edema due to the leakage from the abnormal blood vessels damages the macula and impairs vision, eventually leading to blindness. In dry AMD, drusen have been reported in the macula of the eye, the cells in the macula die for the progressive accumulation of the drusen, resulting in progressive vision loss. Dry AMD is clinically described to occur in three stages: 1) early, 2) intermediate, and 3) advanced dry AMD. Dry AMD can also progress into wet AMD during any stage of the disease. Treatment strategies for wet AMD exists and the current standard of care is Lucentis (Genentech/Roche) and Eylea (Regeneron), an anti-VEGF antibody and an anti-VEGF trap injected intravitreally respectively. There are no current treatments for preventing loss of vision for the dry form and for preventing progression of dry AMD to local atrophy of the retinal tissue. As discussed above, HtrA1 risk alleles have been associated, with high statistical significance, with the AMD onsets and the protein has been reported to be present in drusen. These studies and further evidences provide relevance that HtrA1 is a fundamental factor involved in the pathophysiology and progression in AMD. This concept is further confirmed in different AMD disease models, where increased HtrA1 protein levels in the retina tissue have been shown to be responsible for the degradation of extracellular matrix (ECM) proteins like fibronectin, fibulins and aggrecan. The physiological balance between production and disintegration of the ECM components allows for both creation and maintenance of proper retina tissue architecture. Such balance has been reported to be lost in the progression of the age-related macular degeneration. In particular, the fibulins (mainly-3, -5, -6) have been reported to be important components of the Bruch's membrane in maintaining the integrity of elastic lamina and organization of the retina tissue overall. Several variants in fibulin 5 and fibulin 3 were reported to be associated with AMD. Missense mutations of the fibulin 5 gene have been associated with reduced secretion of fibulin 5. Different studies have reported that Htra1 protease activity is directed to the cleavage of the fibulins as substrates. A direct inhibition of HtrA1 protease activity is expected to provide a protection reducing degradation of extracellular matrix proteins, in particular fibulins and fibrionectin, therefore preserving the retina tissue structure. The relevance of HtrA1's role in maintenance of the physiological homeostasis of the ECM components is firmly provided by the identification of human loss-of-function mutations causing familial ischemic cerebral small-vessel disease. The molecular mechanism underlies in the deficient TGFbeta inhibition by HtrA1 resulting in increased signaling levels, which in conjunction with deficient HtrA1-mediated degradation of various extracellular matrix components determine thickening of the intima responsible for the ischemic small-vessels. Given its fundamental role in regulating intracellular signaling pathways (e.g. TGFbeta) and the regulation of ECM proteins turnover, HtrA1 has been involved in several pathologies, as ocular diseases, rheumatoid arthritis, osteoarthritis, Alzheimer's disease, and some types of cancer.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of HtrA1, particularly in the treatment or prophylaxis of wet or dry age-related macular degeneration, geographic atrophy, diabetic retinopathy, retinopathy of prematurity and polypoidal choroidal vasculopathy.

The term “amino” denotes a —$NH_2$ group.

The term “amino-$C_{1-6}$-alkyl” denotes an $C_{1-6}$-alkyl group wherein one of the hydrogen atoms of the $C_{1-6}$-alkyl group has been replaced by an amino group. Examples of amino-$C_{1-6}$-alkyl groups are aminomethyl, aminoethyl or aminopropyl. Particular examples of amino-$C_{1-6}$-alkyl is aminomethyl.

The term “aminocarbonyl” denotes a group of the formula —C(O)—R', wherein R' is an amino group.

The term “aminocarbonyl-$C_{1-6}$-alkyl” denotes an $C_{1-6}$-alkyl group wherein one of the hydrogen atoms of the $C_{1-6}$-alkyl group has been replaced by an aminocarbonyl group. Examples of aminocarbonyl-$C_{1-6}$-alkyl groups are aminocarbonylmethyl, aminocarbonylethyl or aminocarbonylpropyl The term “$C_{1-6}$-alkoxy” denotes a group of the formula —O—R', wherein R' is an $C_{1-6}$-alkyl group. Examples of $C_{1-6}$-alkoxy groups include methoxy, ethoxy, n-propoxy, isopropoxy, n-butoxy, isobutoxy and tert-butoxy. Particular examples are methoxy and tert-butoxy. in the case of $R^8$, particular example is tert-butoxy. in the case of $R^{12}$, particular example is methoxy.

The term “$C_{1-6}$-alkoxycarbonyl” denotes a group of the formula —C(O)—R', wherein R' is a $C_{1-6}$-alkoxy group. Particular example of $C_{1-6}$-alkoxycarbonyl is a group wherein R' is tert-butoxy.

The term “$C_{1-6}$-alkoxycarbonyl-$C_{1-6}$-alkoxy” denotes an $C_{1-6}$-alkoxy group wherein one of the hydrogen atoms of the $C_{1-6}$-alkoxy group has been replaced by a $C_{1-6}$-alkoxycarbonyl group. Particular example of $C_{1-6}$-alkoxycarbonyl-$C_{1-6}$-alkoxy is a methoxy wherein one of the hydrogen atoms has been replaced by tert-butoxycarbonyl.

The term “$C_{1-6}$-alkoxycarbonyl-$C_{1-6}$-alkyl” denotes an $C_{1-6}$-alkyl group wherein one of the hydrogen atoms of the $C_{1-6}$-alkyl group has been replaced by a $C_{1-6}$-alkoxycarbonyl group. Particular example of $C_{1-6}$-alkoxycarbonyl-$C_{1-6}$-alkyl is a methyl wherein one of the hydrogen atoms has been replaced by tert-butoxycarbonyl.

The term “$C_{1-6}$alkoxycarbonyl-$C_{1-6}$alkylaminocarbonyl-$C_{1-6}$alkoxy” denotes an $C_{1-6}$-alkoxy group wherein one of the hydrogen atoms of the $C_{1-6}$-alkoxy group has been replaced by a $C_1$-6alkoxycarbonyl-$C_{1-6}$alkylaminocarbonyl group. Particular example is methoxy wherein one of the hydrogen atoms has been replaced by ter-butoxycarbonylmethylamino.

The term “$C_{1-6}$alkoxycarbonyl-$C_{1-6}$alkylaminocarbonyl-$C_{1-6}$alkyl” denotes an $C_{1-6}$-alkyl group wherein one of the hydrogen atoms of the $C_{1-6}$-alkyl group has been replaced by a $C_{1-6}$alkoxycarbonyl-$C_{1-6}$alkylaminocarbonyl group. Particular example is methyl wherein one of the hydrogen atoms has been replaced by ter-butoxycarbonylmethylaminocarbonyl.

The term “$C_{1-6}$alkoxycarbonyl-$C_{1-6}$alkylaminocarbonyl” denotes a group of the formula —C(O)—R', wherein R' is a $C_{1-6}$alkoxycarbonyl-$C_{1-6}$alkylamino group. Particular example is a group wherein R' is ter-butoxycarbonylmethylamino.

The term “$C_{1-6}$-alkoxycarbonyl-$C_{1-6}$-alkylamino” denotes a group of the formula —NH—R', wherein R' is an $C_{1-6}$-alkoxycarbonyl-$C_{1-6}$-alkyl group. Particular example is a group wherein R' is ter-butoxycarbonylmethyl.

The term “$C_{1-6}$-alkoxycarbonyl-$C_{1-6}$-alkyl” denotes an $C_{1-6}$-alkyl group wherein one of the hydrogen atoms of the $C_{1-6}$-alkyl group has been replaced by an $C_{1-6}$-alkoxycarbonyl group. Particular example is a methyl wherein one of the hydrogen atoms of has been replaced by a ter-butoxycarbonyl.

The term “$C_{1-6}$-alkyl” denotes a monovalent linear or branched saturated hydrocarbon group of 1 to 6 carbon atoms. Examples of $C_{1-6}$-alkyl include methyl, ethyl, propyl, isopropyl, n-butyl, iso-butyl, sec-butyl, tert-butyl and pentyl. Particular $C_{1-6}$-alkyl groups are methyl and isopropyl. In the case of $R^2$, particular example is isopropyl.

The term “aryl” denotes a monovalent aromatic carbocyclic mono- or bicyclic ring system comprising 6 to 10 carbon ring atoms. Examples of aryl group include phenyl and naphthyl. Particular aryl group is phenyl.

The term “aryl(cycloalkyl)-$C_{1-6}$-alkyl” denotes a cycloalkyl-$C_{1-6}$-alkyl group wherein one of the hydrogen atoms of the $C_{1-6}$-alkyl group has been replaced by an aryl group. Particular examples are groups wherein the aryl group is phenyl. Further particular examples are phenyl-cyclopropylmethyl and phenyl-cyclobutylmethyl.

The term “aryl(halo)-$C_{1-6}$-alkyl” denotes a halo-$C_{1-6}$-alkyl group wherein one of the hydrogen atoms of the halo-$C_{1-6}$-alkyl group has been replaced by an aryl group. Particular examples are groups wherein the aryl group is phenyl. Further particular example is phenyl-difluoromethyl.

The term “aryl(heterocycloalkyl)-$C_{1-6}$-alkyl” denotes a heterocycloalkyl-$C_{1-6}$-alkyl group wherein one of the hydrogen atoms of the $C_{1-6}$-alkyl group has been replaced by an aryl group. Particular examples are groups wherein the aryl group is phenyl. More particular examples are groups wherein the aryl group is phenyl and the heterocycloalkyl group is dioxolanyl. Further particular example is phenyl-dioxolanylmethyl.

The term “aryl(hydroxy, halo)-$C_{1-6}$-alkyl” denotes a $C_{1-6}$-alkyl group wherein one of the hydrogen atoms of the $C_{1-6}$-alkyl group has been replaced by an hydroxy group and wherein at least one of the hydrogen atoms of the $C_{1-6}$-alkyl group has been replaced by the same or different halogen atoms. Particular example is 1,1,1-trifluoro-2-hydroxy-ethyl.

The term “aryl-$C_{1-6}$-alkyl” denotes an —$C_{1-6}$-alkyl group wherein one of the hydrogen atoms of the $C_{1-6}$-alkyl group has been replaced by an aryl group. Particular aryl-$C_{1-6}$-alkyl group is phenyl-$C_{1-6}$-alkyl. Further particular examples of aryl-$C_{1-6}$-alkyl are phenylmethyl and phenylpropyl. Furthermore particular examples of aryl-$C_{1-6}$-alkyl is phenylmethyl.

The term “aryl-$C_{1-6}$-alkoxy” denotes an —$C_{1-6}$-alkoxy group wherein one of the hydrogen atoms of the —$C_{1-6}$-alkoxy group has been replaced by an aryl group. Particular examples are groups wherein the aryl group is phenyl. Particular aryl-$C_{1-6}$-alkoxy group is phenylmethoxy.

The term “aryloxy” denotes a group of the formula —O—R', wherein R' is an aryl group. Particular examples of aryloxy group are groups wherein R' is phenyl.

The term “aryloxy-$C_{1-6}$-alkyl” denotes an $C_{1-6}$-alkyl group wherein one of the hydrogen atoms of the $C_{1-6}$-alkyl group has been replaced by an aryloxy group. Particular examples are groups wherein the aryloxy group is phenoxy. Further particular example of aryloxy-$C_{1-6}$-alkyl is phenoxyalkyl. Further particular example is phenoxymethyl.

The term “aryloxy(halo)-$C_{1-6}$-alkyl” denotes a halo-$C_{1-6}$-alkyl group wherein one of the hydrogen atoms of the halo-$C_{1-6}$-alkyl group has been replaced by an aryloxy group. Particular examples are groups wherein the aryloxy group is phenoxy.

The term "arylcarbonyl" denotes a group of the formula —C(O)—R', wherein R' is an aryl group. Particular example is a group wherein R' is phenyl.

The term "aryl(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by an aryl group. Particular examples are groups wherein the aryl group is phenyl. Further particular example is phenyl-difluorocyclopropyl.

The term "aryl-$C_{3-8}$-cycloalkyl" denotes a halo-$C_{3-8}$-cycloalkyl group wherein one of the hydrogen atoms of the $C_{3-8}$-cycloalkyl group has been replaced by an aryl group. Particular examples are groups wherein the aryl group is phenyl. Further particular example is phenylcyclopropyl.

The term "aryloxy-$C_{3-8}$-cycloalkyl" denotes a $C_{3-8}$-cycloalkyl group wherein one of the hydrogen atoms of the $C_{3-8}$-cycloalkyl group has been replaced by an aryloxy group. Particular examples are groups wherein the aryloxy group is phenoxy. Further particular example is phenyl-difluorocyclopropyl.

The term "aryloxy(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by an aryloxy group. Particular examples are groups wherein the aryloxy group is phenoxy. Further particular example is phenoxy-difluorocyclopropyl.

The term "aryloxy-$C_{3-8}$-cycloalkyl" denotes a $C_{3-8}$-cycloalkyl group wherein one of the hydrogen atoms of the $C_{3-8}$-cycloalkyl group has been replaced by an aryloxy group. Particular examples are groups wherein the aryloxy group is phenoxy. Further particular example is phenoxy-cyclopropyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "carboxy" denotes a —COOH group.

The term "carboxy-$C_{1-6}$-alkoxy" denotes an $C_{1-6}$-alkoxy group wherein one of the hydrogen atoms of the $C_{1-6}$-alkoxy group has been replaced by a carboxy group. Particular example is carboxymethoxy.

The term "carboxy-$C_{1-6}$-alkyl" denotes an $C_{1-6}$-alkyl group wherein one of the hydrogen atoms of the $C_{1-6}$-alkyl group has been replaced by a carboxy group. Particular example is carboxymethyl.

The term "carboxy-$C_{1-6}$-alkylaminocarbonyl-$C_{1-6}$alkoxy" denotes an $C_{1-6}$-alkoxy group wherein one of the hydrogen atoms of the $C_{1-6}$-alkoxy group has been replaced by a carboxy-$C_{1-6}$-alkylaminocarbonyl group. Particular example is carboxymethylaminocarbonylmethoxy.

The term "carboxy-$C_{1-6}$alkylaminocarbonyl-$C_{1-6}$alkyl" denotes an $C_{1-6}$-alkyl group wherein one of the hydrogen atoms of the $C_{1-6}$-alkyl group has been replaced by a carboxy-$C_{1-6}$alkylaminocarbonyl group. Particular example is carboxymethylaminocarbonylmethyl.

The term "carboxy-$C_{1-6}$alkylaminocarbonyl group" denotes a group of the formula —C(O)—R', wherein R' is a carboxy-$C_{1-6}$alkylamino group. Particular example is carboxymethylamino.

The term "carboxy-$C_{1-6}$alkylamino" denotes a group of the formula —NH—R', wherein R' is a carboxy-$C_{1-6}$alkyl group. Particular example is a group wherein R' is carboxymethyl.

The term "cyano" denotes a —C≡N group.

The term "cyano-$C_{1-6}$-alkyl" denotes an $C_{1-6}$-alkyl group wherein one of the hydrogen atoms of the $C_{1-6}$-alkyl group has been replaced by a cyano group. Examples of cyano-$C_{1-6}$-alkyl include cyanomethyl, cyanoethyl, cyanopropyl and cyanobutyl. Particular example is cyanomethyl.

The term "$C_{3-8}$-cycloalkyl" denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Particular monocyclic cycloalkyl groups are cyclopropyl, cyclobutanyl, cyclopentyl and cyclohexyl. More particular monocyclic cycloalkyl group is cyclohexyl.

The term "$C_{3-8}$-cycloalkyl(halo)-$C_{1-6}$-alkyl" denotes a halo-$C_{1-6}$-alkyl group wherein one of the hydrogen atoms of the halo-$C_{1-6}$-alkyl group has been replaced by an $C_{3-8}$-cycloalkyl group.

The term "$C_{3-8}$-cycloalkyl-$C_{1-6}$-alkyl" denotes an —$C_{1-6}$-alkyl group wherein one of the hydrogen atoms of the $C_{1-6}$-alkyl group has been replaced by an $C_{3-8}$-cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Particular examples of cycloalkylalkyl are cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Further particular examples cycloalkylalkyl is cyclohexylethyl.

The term "halo-$C_{1-6}$-alkoxy" denotes an $C_{1-6}$-alkoxy group wherein at least one of the hydrogen atoms of the $C_{1-6}$-alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups is trifluoromethoxy.

The term "halo-$C_{1-6}$-alkyl" denotes an $C_{1-6}$-alkyl group wherein at least one of the hydrogen atoms of the $C_{1-6}$-alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoromethyl.

The term "halo-$C_{3-8}$-cycloalkyl" denotes an $C_{3-8}$-cycloalkyl group wherein at least one of the hydrogen atoms of the $C_{3-8}$-cycloalkyl group has been replaced by the same or different halogen atoms.

The term "halogen" and "halo" are used interchangeably herein and denote fluoro, chloro, bromo or iodo. Particular halogen is chloro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, and benzothiophenyl. Particular heteroaryl groups are pyrazinyl, pyridinyl, pyrimidinyl, pyrrolidinyl and thiophenyl. In the case of substituent $R^{11}$, particular heteroaryl groups are pyrazinyl, pyridinyl, pyrimidinyl and thiophenyl. In the case of substituent $R^8$, particular heteroaryl group is pyridinyl.

The term "heteroaryl(halo)-$C_{1-6}$-alkyl" denotes a halo-$C_{1-6}$-alkyl group wherein one of the hydrogen atoms of the halo-$C_{1-6}$-alkyl group has been replaced by a heteroaryl group.

The term "heteroaryl-$C_{1-6}$-alkyl" denotes an $C_{1-6}$-alkyl group wherein one of the hydrogen atoms of the $C_{1-6}$-alkyl group has been replaced by a heteroaryl group.

The term "heteroaryl-$C_{1-6}$-alkoxy" denotes an $C_{1-6}$-alkoxy group wherein one of the hydrogen atoms of the $C_{1-6}$-alkoxy group has been replaced by a heteroaryl group.

The term "heteroaryloxy" denotes a group of the formula —O—R', wherein R' is a heteroaryl group.

The term "heteroaryloxy-$C_{1-6}$-alkyl" denotes an $C_{1-6}$-alkyl group wherein one of the hydrogen atoms of the $C_{1-6}$-alkyl group has been replaced by anheteroaryloxy group.

The term "heteroaryloxy(halo)-$C_{1-6}$-alkyl" denotes a halo-$C_{1-6}$-alkyl group wherein one of the hydrogen atoms of the halo-$C_{1-6}$-alkyl group has been replaced by a heteroaryloxy group.

The term "heteroarylcarbonyl" denotes a group of the formula —C(O)—R', wherein R' is a heteroaryl group.

The term "heteroaryl(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heteroaryl group.

The term "heteroaryl-$C_{3-8}$-cycloalkyl" denotes a halo-$C_{3-8}$-cycloalkyl group wherein one of the hydrogen atoms of the $C_{3-8}$-cycloalkyl group has been replaced by a heteroaryl group.

The term "heteroaryloxy-$C_{3-8}$-cycloalkyl" denotes a $C_{3-8}$-cycloalkyl group wherein one of the hydrogen atoms of the $C_{3-8}$-cycloalkyl group has been replaced by a heteroaryloxy group.

The term "heteroaryloxy(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heteroaryloxy group.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. In the case of $R^{11}$, particular heterocycloalkyl are piperidinyl and pyrrolidinyl.

The term "heterocycloalkyl-$C_{1-6}$-alkyl" denotes an $C_{1-6}$-alkyl group wherein one of the hydrogen atoms of the $C_{1-6}$-alkyl group has been replaced by a heterocycloalkyl group.

The term "heterocycloalkyl-$C_{1-6}$-alkoxy" denotes an $C_{1-6}$-alkoxy group wherein one of the hydrogen atoms of the $C_{1-6}$-alkoxy group has been replaced by a heterocycloalkyl group.

The term "heterocycloalkyl(halo)-$C_{1-6}$-alkyl" denotes a halo-$C_{1-6}$-alkyl group wherein one of the hydrogen atoms of the halo-$C_{1-6}$-alkyl group has been replaced by a heterocycloalkyl group.

The term "heterocycloalkyl(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heterocycloalkyl group.

The term "hydroxy" denotes a —OH group.

The term "hydroxycarbonyl" denotes a —C(O)OH group. It is also named "carboxy".

The term "hydroxycarbonyl-$C_{1-6}$-alkoxy" denotes an $C_{1-6}$-alkoxy group wherein one of the hydrogen atoms of the $C_{1-6}$-alkoxy group has been replaced by a hydroxycarbonyl group. Particular example is hydroxycarbonylmethyl.

The term "oxo" denotes a =O group.

The term "phenoxy" denotes a group of the formula —O—R', wherein R' is a phenyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol L.

The abbreviation ug means microgram and is equivalent to the symbol μg.

CAS 1349796-81-1 discloses the compound of formula X (X)

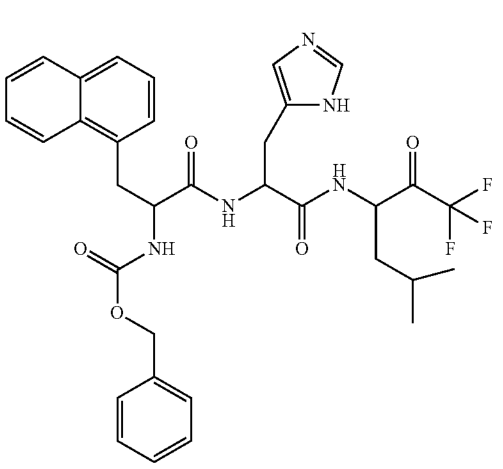

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

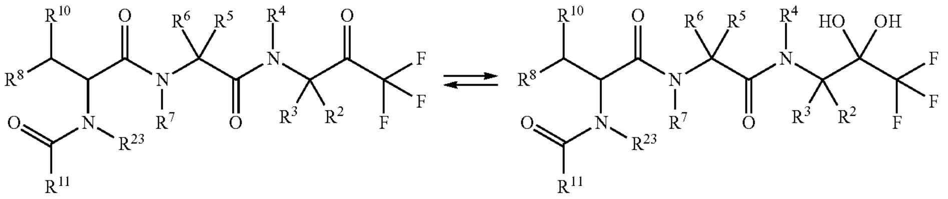

Depending on the individual compound and the conditions it has been exposed, the $CF_3$-ketone moiety in compounds I exist in part, mainly or totally in form of its hydrate. Thus, any description of a $CF_3$-ketone moiety always describes both ketone and hydrate form.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Another embodiment of the present invention are compounds according to formula (I) as described herein, wherein $R^2$, $R^3$, $R^4$, $R^6$, $R^7$, $R^{10}$ and $R^{23}$ are independently selected from
- i) H,
- ii) $C_{1-6}$-alkyl, and
- iii) $C_{3-8}$-cycloalkyl;

$R^5$ is selected from
- i) aryl substituted with $R^{12}$, $R^{13}$ and $R^{14}$,
- ii) aryl-$C_{1-6}$-alkyl substituted with $R^{12}$, $R^{13}$ and $R^{14}$,
- iii) heteroaryl substituted with $R^{12}$, $R^{13}$ and $R^{14}$, and
- iv) heteroaryl-$C_{1-6}$-alkyl substituted with $R^{12}$, $R^{13}$ and $R^{14}$;

$R^8$ is selected from
- i) H,
- ii) hydroxy,
- iii) amino-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
- iv) aminocarbonyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
- v) aminocarbonyl-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
- vi) carboxy,
- vii) carboxy-$C_{1-6}$-alkyl,
- viii) $C_{1-6}$-alkoxy,
- ix) $C_{1-6}$-haloalkoxy,
- x) $C_{1-6}$-alkoxycarbonyl,
- xi) $C_{1-6}$-alkoxycarbonyl-$C_{1-6}$-alkyl, xii) $C_{3-8}$-cycloalkyl,
xiii) aryl substituted with $R^{15}$, $R^{16}$ and $R^{17}$,
xiv) aryl-$C_{1-6}$-alkyl substituted with $R^{15}$, $R^{16}$ and $R^{17}$,
xv) aryl-$C_{1-6}$-alkoxy substituted with $R^{15}$, $R^{16}$ and $R^{17}$,
xvi) heteroaryl substituted with $R^{15}$, $R^{16}$ and $R^{17}$,
xvii) heteroaryl-$C_{1-6}$-alkyl substituted with $R^{15}$, $R^{16}$ and $R^{17}$, and
xviii) heteroaryl-$C_{1-6}$-alkoxy substituted with $R^{15}$, $R^{16}$ and $R^{17}$
xix) heterocycloalkyl substituted with $R^{15}$, $R^{16}$ and $R^{17}$,
xx) heterocycloalkyl-$C_{1-6}$-alkyl substituted with $R^{15}$, $R^{16}$ and $R^{17}$, and
xxi) heterocycloalkyl-$C_{1-6}$-alkoxy substituted with $R^{15}$, $R^{16}$ and $R^{17}$;

$R^{11}$ is selected from
i) amino-$C_{1-6}$-alkyl substituted on the nitrogen atom by $R^{21}$ and $R^{22}$,
ii) $C_{3-8}$-cycloalkyl substituted with $R^{18}$, $R^{19}$ and $R^{20}$,
iii) $C_{3-8}$-cycloalkyl-$C_{1-6}$-alkyl substituted with $R^{18}$, $R^{19}$ and $R^{20}$,
iv) $C_{3-8}$-cycloalkyl(halo)-$C_{1-6}$-alkyl substituted with $R^{18}$, $R^{19}$ and $R^{20}$,
v) aryl substituted with $R^{18}$, $R^{19}$ and $R^{20}$,
vi) aryl-$C_{1-6}$-alkyl substituted with $R^{18}$, $R^{19}$ and $R^{20}$,
vii) aryl-$C_{3-8}$-cycloalkyl substituted with $R^{18}$, $R^{19}$ and $R^{20}$,
viii) aryl-heterocycloalkyl substituted with $R^{18}$, $R^{19}$ and $R^{20}$
ix) aryl(halo)-$C_{1-6}$-alkyl substituted with $R^{18}$, $R^{19}$ and $R^{20}$,
x) aryl(halo)-$C_{3-8}$-cycloalkyl substituted with $R^{18}$, $R^{19}$ and $R^{20}$,
xi) aryl(halo)-heterocycloalkyl substituted with $R^{18}$, $R^{19}$ and $R^{20}$,
xii) aryloxy-$C_{1-6}$-alkyl substituted with $R^{18}$, $R^{19}$ and $R^{20}$,
xiii) aryloxy-$C_{3-8}$-cycloalkyl substituted with $R^{18}$, $R^{19}$ and $R^{20}$,
xiv) aryloxy-heterocycloalkyl substituted with $R^{18}$, $R^{19}$ and $R^{20}$,
xv) aryloxy(halo)-$C_{3-8}$-cycloalkyl substituted with $R^{18}$, $R^{19}$ and $R^{20}$,
xvi) aryloxy(halo)-heterocycloalkyl substituted with $R^{18}$, $R^{19}$ and $R^{20}$
xvii) aryloxy(halo)-$C_{1-6}$-alkyl,
xviii) heterocycloalkyl substituted with $R^{18}$, $R^{19}$ and $R^{20}$
xix) heterocycloalkyl-$C_{1-6}$-alkyl substituted with $R^{18}$, $R^{19}$ and $R^{20}$,
xx) heterocycloalkyl-$C_{3-8}$-cycloalkyl substituted with $R^{18}$, $R^{19}$ and $R^{20}$,
xxi) heterocycloalkyl(halo)-$C_{3-8}$-cycloalkyl substituted with $R^{18}$, $R^{19}$ and $R^{20}$,
xxii) heterocycloalkyl(halo)-$C_{1-6}$-alkyl substituted with $R^{18}$, $R^{19}$ and $R^{20}$,
xxiii) heteroaryl substituted with $R^{18}$, $R^{19}$ and $R^{20}$,
xxiv) heteroaryl-$C_{1-6}$-alkyl substituted with $R^{18}$, $R^{19}$ and $R^{20}$,
xxv) heteroaryl-$C_{3-8}$-cycloalkyl substituted with $R^{18}$, $R^{19}$ and $R^{20}$,
xxvi) heteroaryl(halo)-$C_{3-8}$-cycloalkyl substituted with $R^{18}$, $R^{19}$ and $R^{20}$,
xxvii) heteroaryl(halo)-$C_{1-6}$-alkyl substituted with $R^{18}$, $R^{19}$ and $R^{20}$,
xxviii) heteroaryloxy-$C_{1-6}$-alkyl substituted with $R^{18}$, $R^{19}$ and $R^{20}$,
xxix) heteroaryloxy-$C_{3-8}$-cycloalkyl substituted with $R^{18}$, $R^{19}$ and $R^{20}$,
xxx) heteroaryloxy(halo)-$C_{38}$-cycloalkyl substituted with $R^{18}$, $R^{19}$ and $R^{20}$, and
xxxi) heteroaryloxy(halo)-$C_{1-6}$-alkyl substituted with $R^{18}$, $R^{19}$ and $R^{20}$;

$R^{12}$, $R^{13}$, $R^{14}$, $R^{15}$, $R^{16}$, $R^{17}$, $R^{18}$, $R^{19}$ and $R^{20}$ are independently selected from
i) H,
ii) cyano,
iii) halogen,
iv) oxo,
v) $C_{1-6}$-alkyl,
vi) amino substituted on the nitrogen atom by two substituents independently selected from H, $C_{1-6}$-alkyl, $C_{1-6}$-alkoxycarbonyl, arylcarbonyl and heteroarylcarbonyl,
vii) amino-$C_{1-6}$-alkyl substituted on the nitrogen atom by two substituents independently selected from H, $C_{1-6}$-alkyl, $C_{1-6}$-alkoxycarbonyl, arylcarbonyl and heteroarylcarbonyl,
viii) $C_{1-6}$-alkyl,
ix) halo-$C_{1-6}$-alkyl,
x) $C_{3-8}$-cycloalkyl,
xi) $C_{1-6}$-alkoxycarbonyl-$C_{1-6}$-alkyl,
xii) carboxy-$C_{1-6}$-alkyl,
xiii) $C_{1-6}$-alkoxycarbonyl-$C_{1-6}$alkylaminocarbonyl-$C_{1-6}$alkyl,
xiv) carboxy-$C_{1-6}$-alkylaminocarbonyl-$C_{1-6}$alkyl,
xv) $C_{1-6}$-alkoxy,
xvi) halo-$C_{1-6}$-alkoxy,
xvii) $C_{1-6}$-alkoxycarbonyl-$C_{1-6}$-alkoxy,
xviii) carboxy-$C_{1-6}$-alkoxy,
xix) $C_{1-6}$-alkoxycarbonyl-$C_{1-6}$-alkylaminocarbonyl-$C_{1-6}$-alkoxy,
xx) carboxy-$C_{1-6}$-alkylaminocarbonyl-$C_{1-6}$-alkoxy, and
xxi) heterocycloalkyl;

$R^{21}$ and $R^{22}$ are independently selected from
i) H,
ii) $C_{1-6}$-alkoxycarbonyl,
iii) carboxy-$C_{1-6}$-alkyl,
iv) arylcarbonyl, and
v) heteroarylcarbonyl;

or pharmaceutically acceptable salts;

with the proviso that CAS 1349796-81-1 is excluded.

Another embodiment of the present invention are compounds according to formula (I) as described herein, wherein
$R^2$ is $C_{1-6}$-alkyl;
$R^3$, $R^4$, $R^6$, $R^7$, $R^{10}$ and $R^{23}$ are H;
$R^5$ is selected from
i) phenyl substituted with $R^{12}$, $R^{13}$ and $R^{14}$, and
ii) phenyl-$C_{1-6}$-alkyl substituted with $R^{12}$, $R^{13}$ and $R^{14}$,
$R^8$ is selected from
i) H,
ii) hydroxy,
iii) carboxy-$C_{1-6}$-alkyl,
iv) $C_{1-6}$-alkoxy,
v) $C_{1-6}$-alkoxycarbonyl-$C_{1-6}$-alkyl,
vi) $C_{3-8}$-cycloalkyl,
vii) phenyl substituted with $R^{15}$, $R^{16}$ and $R^{17}$,
viii) phenyl-$C_{1-6}$-alkoxy substituted with $R^{15}$, $R^{16}$ and $R^{17}$,
ix) pyridinyl substituted with $R^{15}$, $R^{16}$ and $R^{17}$;
x) amino-$C_{1-6}$-alkyl substituted on the nitrogen atom by one or two substituents selected from H, $C_{1-6}$-alkoxycarbonyl, pyridinylcarbonyl, pyridazinylcarbonyl and pyrazinylcarbonyl, wherein pyridinylcarbonyl, pyridazinylcarbonyl and pyrazinylcarbonyl are substituted with $R^{15}$, $R^{16}$ and $R^{17}$, xi) aminocarbonyl substituted on the nitrogen atom by H,
xii) cyano-$C_{1-6}$-alkyl, and
xiii) halo-$C_{1-6}$-alkoxy;
$R^{11}$ is selected from
i) amino-$C_{1-6}$-alkyl substituted on the nitrogen atom by $R^{21}$ and $R^{22}$,
ii) phenyl substituted with $R^{18}$, $R^{19}$ and $R^{20}$,
iii) naphtyl substituted with $R^{18}$, $R^{19}$ and $R^{20}$,
iv) phenyl-$C_{1-6}$-alkyl substituted with $R^{18}$, $R^{19}$ and $R^{20}$,
v) phenyl-$C_{3-8}$-cycloalkyl substituted with $R^{18}$, $R^{19}$ and $R^{20}$,
vi) phenyl(halo)-$C_{1-6}$-alkyl substituted with $R^{18}$, $R^{19}$ and $R^{20}$,
vii) phenoxy-$C_{1-6}$-alkyl substituted with $R^{18}$, $R^{19}$ and $R^{20}$,
viii) heteroaryl substituted with $R^{18}$, $R^{19}$ and $R^{20}$, wherein heteroaryl is selected from pyrazinyl, pyridinyl, pyrimidinyl and thiophenyl,
ix) pyridinyl-$C_{1-6}$-alkyl substituted with $R^{15}$, $R^{16}$ and $R^{17}$, and
x) heterocycloalkyl substituted with $R^{15}$, $R^{16}$ and $R^{17}$, wherein heterocycloalkyl is selected from pyrrolidinyl and piperidinyl;
xi) $C_{3-8}$-cycloalkyl substituted with $R^{18}$, $R^{19}$ and $R^{20}$,
xii) phenyl(cycloalkyl)-$C_{1-6}$-alkyl substituted with $R^{18}$, $R^{19}$ and $R^{20}$,
xiii) phenyl(haloalkyl)-$C_{1-6}$-alkyl substituted with $R^{18}$, $R^{19}$ and $R^{20}$,
xiv) phenyl(heterocycloalkyl)-$C_{1-6}$-alkyl substituted with $R^{18}$, $R^{19}$ and $R^{20}$, and
xv) phenyl(hydroxy,haloalkyl)-$C_{1-6}$-alkyl substituted with $R^{18}$, $R^{19}$ and $R^{20}$;
$R^{12}$ is selected from
i) H, and
ii) $C_{1-6}$-alkoxy;
iii) $C_{1-6}$-alkoxycarbonyl-$C_{1-6}$-alkoxy, and
iv) hydroxycarbonyl-$C_{1-6}$-alkoxy;
$R^{13}$, $R^{14}$, $R^{17}$ and $R^{20}$ are H;
$R^{15}$ is selected from
i) H,
ii) cyano,
iii) halogen,
iv) $C_{1-6}$-alkoxycarbonyl-$C_{1-6}$-alkoxy, and
v) carboxy-$C_{1-6}$-alkoxy;
vi) amino substituted on the nitrogen atom by one H and one substituent selected from H, $C_{1-6}$-alkoxycarbonyl and pyridinylcarbonyl;
$R^{16}$ is selected from
i) H, and
ii) halogen;
$R^{18}$ is selected from
i) H,
ii) halogen,
iii) oxo,
iv) $C_{1-6}$-alkyl,
v) amino-$C_{1-6}$-alkyl substituted on the nitrogen atom by one H and one substituents selected from H and $C_{1-6}$-alkoxycarbonyl,
vi) $C_1$-s-alkoxycarbonyl-$C_{1-6}$-alkoxy,
vii) carboxy-$C_{1-6}$-alkoxy,
viii) $C_{1-6}$alkoxycarbonyl-$C_{1-6}$alkylaminocarbonyl-$C_{1-6}$alkoxy, and
ix) carboxy-$C_{1-6}$alkylaminocarbonyl-$C_{1-6}$alkoxy
x) halo-$C_{1-6}$-alkyl,
xi) halo-$C_{1-6}$-alkoxy,
xii) $C_{1-6}$-alkoxy, and
xiii) cyano;
$R^{19}$ is selected from
i) H,
ii) halogen,
iii) $C_{1-6}$-alkoxycarbonyl-$C_{1-6}$-alkyl, and
iv) carboxy-$C_{1-6}$-alkoxy;
$R^{21}$ is selected from
i) H,
i) $C_{1-6}$-alkoxycarbonyl, and
ii) pyridinylcarbonyl;
$R^{22}$ is H;
or pharmaceutically acceptable salts.

Another particular embodiment of the present invention are compounds according to formula (I) as described herein, wherein $R^2$ is $C_{1-6}$-alkyl;
$R^3$, $R^4$, $R^6$, $R^7$, $R^{10}$ and $R^{23}$ are H;
$R^5$ is selected from
i) phenyl substituted with $R^{12}$, $R^{13}$ and $R^{14}$, and
ii) phenyl-$C_{1-6}$-alkyl substituted with $R^{12}$, $R^{13}$ and $R^{14}$,
$R^8$ is selected from
i) H,
ii) hydroxy,
iii) carboxy-$C_{1-6}$-alkyl,
iv) $C_{1-6}$-alkoxy,
v) $C_{1-6}$-alkoxycarbonyl-$C_{1-6}$-alkyl,
vi) $C_{3-8}$-cycloalkyl,
vii) phenyl substituted with $R^{15}$, $R^{16}$ and $R^{17}$,
viii) phenyl-$C_{1-6}$-alkoxy substituted with $R^{15}$, $R^{16}$ and $R^{17}$,
ix) pyridinyl substituted with $R^{15}$, $R^{16}$ and $R^{17}$;
$R^{11}$ is selected from
i) amino-$C_{1-6}$-alkyl substituted on the nitrogen atom by $R^{21}$ and $R^{22}$
ii) phenyl substituted with $R^{18}$, $R^{19}$ and $R^{20}$,
iii) naphtyl substituted with $R^{18}$, $R^{19}$ and $R^{20}$,
iv) phenyl-$C_{1-6}$-alkyl substituted with $R^{18}$, $R^{19}$ and $R^{20}$,
v) phenyl-$C_{3-8}$-cycloalkyl substituted with $R^{18}$, $R^{19}$ and $R^{20}$,
vi) phenyl(halo)-$C_{1-6}$-alkyl substituted with $R^{18}$, $R^{19}$ and $R^{20}$,
vii) phenoxy-$C_{1-6}$-alkyl substituted with $R^{18}$, $R^{19}$ and $R^{20}$,
viii) heteroaryl substituted with $R^{18}$, $R^{19}$ and $R^{20}$, wherein heteroaryl is selected from pyrazinyl, pyridinyl, pyrimidinyl and thiophenyl,
ix) pyridinyl-$C_{1-6}$-alkyl substituted with $R^{15}$, $R^{16}$ and $R^{17}$, and
x) heterocycloalkyl substituted with $R^{15}$, $R^{16}$ and $R^{17}$, wherein heterocycloalkyl is selected from pyrrolidinyl and piperidinyl;
$R^{12}$ is selected from
i) H, and
ii) $C_{1-6}$-alkoxy;
$R^{13}$, $R^{14}$, $R^{17}$ and $R^{20}$ are H;
$R^{15}$ is selected from
i) H,
ii) cyano,
iii) halogen,
iv) $C_{1-6}$-alkoxycarbonyl-$C_{1-6}$-alkoxy, and
v) carboxy-$C_{1-6}$-alkoxy;
$R^{16}$ is selected from
i) H, and
ii) halogen;
$R^{18}$ is selected from
i) H,
ii) halogen,
iii) oxo,
iv) $C_{1-6}$-alkyl, v) amino-$C_{1-6}$-alkyl substituted on the nitrogen atom by one H and one substituents selected from H and $C_{1-6}$-alkoxycarbonyl,
vi) $C_{1-6}$-alkoxycarbonyl-$C_{1-6}$-alkoxy,
vii) carboxy-$C_{1-6}$-alkoxy,
viii) $C_{1-6}$alkoxycarbonyl-$C_{1-6}$alkylaminocarbonyl-$C_{1-6}$alkoxy, and
ix) carboxy-$C_{1-6}$alkylaminocarbonyl-$C_{1-6}$alkoxy;
$R^{19}$ is selected from
i) H,
ii) halogen,
iii) $C_{1-6}$-alkoxycarbonyl-$C_{1-6}$-alkyl, and
iv) carboxy-$C_{1-6}$-alkoxy;
$R^{21}$ is selected from
i) H,
ii) $C_{1-6}$-alkoxycarbonyl, and
iii) pyridinylcarbonyl;
$R^{22}$ is H;
or pharmaceutically acceptable salts.

Another particular embodiment of the present invention are compounds according to formula (I) as described herein, wherein $R^2$ is $C_{1-6}$-alkyl.

Also a furthermore particular embodiment of the present invention are compounds according to formula (I) as described herein, wherein $R^2$ is isopropyl.

A particular embodiment of the present invention are compounds according to formula (I) as described herein, wherein $R^3$, $R^4$, $R^6$, $R^7$, $R^{10}$ and $R^{23}$ are H.

In a further particular embodiment of the present invention are compounds according to formula (I) as described herein, wherein $R^5$ is selected from
i) phenyl substituted with $R^{12}$, $R^{13}$ and $R^{14}$, and
ii) phenyl-$C_{1-6}$-alkyl substituted with $R^{12}$, $R^{13}$ and $R^{14}$.

A more particular embodiment of the present invention are compounds according to formula (I) as described herein, wherein $R^5$ is phenyl substituted with one $C_{1-6}$-alkoxy.

A particular embodiment of the present invention are compounds according to formula (I) as described herein, wherein $R^8$ is selected from
i) H,
ii) hydroxy,
iii) carboxy-$C_{1-6}$-alkyl,
iv) $C_{1-6}$-alkoxy,
v) $C_{1-6}$-alkoxycarbonyl-$C_{1-6}$-alkyl,
vi) $C_{3-8}$-cycloalkyl,
vii) phenyl substituted with $R^{15}$, $R^{16}$ and $R^{17}$,
viii) phenyl-$C_{1-6}$-alkoxy substituted with $R^{15}$, $R^{16}$ and $R^{17}$,
ix) pyridinyl substituted with $R^{15}$, $R^{16}$ and $R^{17}$
x) amino-$C_{1-6}$-alkyl substituted on the nitrogen atom by one or two substituents selected from H, $C_{1-6}$-alkoxycarbonyl, pyridinylcarbonyl, pyridazinylcarbonyl and pyrazinylcarbonyl, wherein pyridinylcarbonyl, pyridazinylcarbonyl and pyrazinylcarbonyl are substituted with $R^{15}$, $R^{16}$ and $R^{17}$,
xi) aminocarbonyl substituted on the nitrogen atom by H,
xii) cyano-$C_{1-6}$-alkyl, and
xiii) halo-$C_{1-6}$-alkoxy.

Also a particular embodiment of the present invention are compounds according to formula (I) as described herein, wherein $R^8$ is selected from
i) H,
ii) hydroxy,
iii) carboxy-$C_{1-6}$-alkyl,
iv) $C_{1-6}$-alkoxy,
v) $C_{1-6}$-alkoxycarbonyl-$C_{1-6}$-alkyl,
vi) $C_{3-8}$-cycloalkyl,
vii) phenyl substituted with $R^{15}$, $R^{16}$ and $R^{17}$,
viii) phenyl-$C_{1-6}$-alkoxy substituted with $R^{15}$, $R^{16}$ and $R^{17}$,
ix) pyridinyl substituted with $R^{15}$, $R^{16}$ and $R^{17}$.

A more particular embodiment of the present invention are compounds according to formula (I) as described herein, wherein $R^8$ is selected from
i) H,
ii) hydroxy,
iii) phenyl substituted with $R^{15}$, $R^{16}$ and $R^{17}$,
iv) phenyl-$C_{1-6}$-alkoxy substituted with $R^{15}$, $R^{16}$ and $R^{17}$, and
v) $C_{1-6}$-alkoxy.

Also more particular embodiment of the present invention are compounds according to formula (I) as described herein, wherein $R^8$ is selected from
i) H,
ii) hydroxy,
iii) phenyl substituted with $R^{15}$, $R^{16}$ and $R^{17}$,
iv) phenyl-$C_{1-6}$-alkoxy substituted with $R^{15}$, $R^{16}$ and $R^{17}$.

A furthermore particular embodiment of the present invention are compounds according to formula (I) as described herein, wherein $R^8$ is phenyl substituted with $R^{15}$, $R^{16}$ and $R^{17}$.

A particular embodiment of the present invention are compounds according to formula (I) as described herein, wherein $R^6$ is H.

Another embodiment of the present invention are compounds according to formula (I) as described herein, wherein $R^{11}$ is selected from
i) amino-$C_{1-6}$-alkyl substituted on the nitrogen atom by $R^{21}$ and $R^{22}$,
ii) phenyl substituted with $R^{18}$, $R^{19}$ and $R^{20}$,
iii) naphtyl substituted with $R^{18}$, $R^{19}$ and $R^{20}$
iv) phenyl-$C_{1-6}$-alkyl substituted with $R^{18}$, $R^{19}$ and $R^{20}$,
v) phenyl-$C_{3-8}$-cycloalkyl substituted with $R^{18}$, $R^{19}$ and $R^{20}$,
vi) phenyl(halo)-$C_{1-6}$-alkyl substituted with $R^{18}$, $R^{19}$ and $R^{20}$,
vii) phenoxy-$C_{1-6}$-alkyl substituted with $R^{18}$, $R^{19}$ and $R^{20}$,
viii) heteroaryl substituted with $R^{18}$, $R^{19}$ and $R^{20}$, wherein heteroaryl is selected from pyrazinyl, pyridinyl, pyrimidinyl and thiophenyl,
ix) pyridinyl-$C_{1-6}$-alkyl substituted with $R^{15}$, $R^{16}$ and $R^{17}$, and
x) heterocycloalkyl substituted with $R^{15}$, $R^{16}$ and $R^{17}$, wherein heterocycloalkyl is selected from pyrrolidinyl and piperidinyl,
xi) $C_{3-8}$-cycloalkyl substituted with $R^{18}$, $R^{19}$ and $R^{20}$,
xii) phenyl(cycloalkyl)-$C_{1-6}$-alkyl substituted with $R^{18}$, $R^{19}$ and $R^{20}$,
xiii) phenyl(heterocycloalkyl)-$C_{1-6}$-alkyl substituted with $R^{18}$, $R^{19}$ and $R^{20}$, and
xiv) phenyl(hydroxy, halo)-$C_{1-6}$-alkyl substituted with $R^{18}$, $R^{19}$ and $R^{20}$.

Also another embodiment of the present invention are compounds according to formula (I) as described herein, wherein $R^{11}$ is selected from
i) amino-$C_{1-6}$-alkyl substituted on the nitrogen atom by $R^{21}$ and $R^{22}$,
ii) phenyl substituted with $R^{18}$, $R^{19}$ and $R^{20}$,
iii) naphtyl substituted with $R^{18}$, $R^{19}$ and $R^{20}$,
iv) phenyl-$C_{1-6}$-alkyl substituted with $R^{18}$, $R^{19}$ and $R^{20}$,
v) phenyl-$C_{3-8}$-cycloalkyl substituted with $R^{18}$, $R^{19}$ and $R^{20}$,
vi) phenyl(halo)-$C_{1-6}$-alkyl substituted with $R^{18}$, $R^{19}$ and $R^{20}$, vii) phenoxy-$C_{1-6}$-alkyl substituted with $R^{18}$, $R^{19}$ and $R^{20}$, viii) heteroaryl substituted with $R^{18}$, $R^{19}$ and $R^{20}$, wherein heteroaryl is selected from pyrazinyl, pyridinyl, pyrimidinyl, pyrrolidinyl and thiophenyl, ix) pyridinyl-$C_{1-6}$-alkyl substituted with $R^{15}$, $R^{16}$ and $R^{17}$, and x) piperazinyl substituted with $R^{15}$, $R^{16}$ and $R^{17}$.

Also a particular embodiment of the present invention are compounds according to formula (I) as described herein, wherein $R^{11}$ is selected from i) $C_{3-8}$-alkyl substituted with $R^{18}$, $R^{19}$ and $R^{20}$, ii) phenyl substituted with $R^{18}$, $R^{19}$ and $R^{20}$, iii) phenyl-$C_{1-6}$-alkyl substituted with $R^{18}$, $R^{19}$ and $R^{20}$, iv) phenyl(halo)-$C_{1-6}$-alkyl substituted with $R^{18}$, $R^{19}$ and $R^{20}$, and v) thiophenyl substituted with $R^{18}$, $R^{19}$ and $R^{20}$.

Also another particular embodiment of the present invention are compounds according to formula (I) as described herein, wherein $R^{11}$ is selected from i) phenyl substituted with $R^{18}$, $R^{19}$ and $R^{20}$, ii) phenyl-$C_{1-6}$-alkyl substituted with $R^{18}$, $R^{19}$ and $R^{20}$, iii) phenyl(halo)-$C_{1-6}$-alkyl substituted with $R^{18}$, $R^{19}$ and $R^{20}$, and iv) thiophenyl substituted with $R^{18}$, $R^{19}$ and $R^{20}$.

Also a more particular embodiment of the present invention are compounds according to formula (I) as described herein, wherein $R^{11}$ is selected from i) phenyl substituted with $R^{18}$, $R^{19}$ and $R^{20}$, and ii) phenyl(halo)-$C_{1-6}$-alkyl substituted with $R^{18}$, $R^{19}$ and $R^{20}$.

Another embodiment of the present invention are compounds according to formula (I) as described herein, wherein $R^{12}$ is selected from i) H, and ii) $C_{1-6}$-alkoxy, iii) $C_{1-6}$-alkoxycarbonyl-$C_{1-6}$-alkoxy, and iv) hydroxycarbonyl-$C_{1-6}$-alkoxy.

Also another embodiment of the present invention are compounds according to formula (I) as described herein, wherein $R^{12}$ is selected from i) H, ii) hydroxycarbonyl-$C_{1-6}$-alkoxy, and iii) $C_{1-6}$-alkoxy.

Also another embodiment of the present invention are compounds according to formula (I) as described herein, wherein $R^{12}$ is selected from i) H, ii) $C_{1-6}$-alkoxy.

Another particular embodiment of the present invention are compounds according to formula (I) as described herein, wherein $R^{12}$ is $C_{1-6}$-alkoxy.

Another embodiment of the present invention are compounds according to formula (I) as described herein, wherein $R^{13}$, $R^{14}$, $R^{17}$ and $R^{20}$ are H.

Also an embodiment of the present invention are compounds according to formula (I) as described herein, wherein $R^{15}$ is selected from i) H, ii) cyano, iii) halogen, iv) $C_{1-6}$-alkoxycarbonyl-$C_{1-6}$-alkoxy, and v) carboxy-$C_{1-6}$-alkoxy, vi) amino substituted on the nitrogen atom by one H and one substituent selected from H, $C_{1-6}$-alkoxycarbonyl and pyridinylcarbonyl.

Also an embodiment of the present invention are compounds according to formula (I) as described herein, wherein $R^{15}$ is selected from i) H, ii) cyano, iii) halogen, iv) $C_{1-6}$-alkoxycarbonyl-$C_{1-6}$-alkoxy, and v) carboxy-$C_{1-6}$-alkoxy.

Also an embodiment of the present invention are compounds according to formula (I) as described herein, wherein $R^{15}$ is selected from i) H, ii) cyano, iii) halogen, iv) carboxy-$C_{1-6}$-alkoxy, v) amino substituted on the nitrogen atom by one H and one substituent selected from H, $C_{1-6}$-alkoxycarbonyl and pyridinylcarbonyl.

Another particular embodiment of the present invention are compounds according to formula (I) as described herein, wherein $R^{15}$ is selected from i) H, ii) cyano, iii) halogen, and iv) carboxy-$C_{1-6}$-alkoxy.

Another embodiment of the present invention are compounds according to formula (I) as described herein, wherein $R^{16}$ is H.

Another embodiment of the present invention are compounds according to formula (I) as described herein, wherein $R^{18}$ is selected from i) H, ii) halogen, iii) oxo, iv) $C_{1-6}$-alkyl, v) amino-$C_{1-6}$-alkyl substituted on the nitrogen atom by one H and one substituents selected from H and $C_{1-6}$-alkoxycarbonyl, vi) $C_{1-6}$-alkoxycarbonyl-$C_{1-6}$-alkoxy, vii) carboxy-$C_{1-6}$-alkoxy, viii) $C_{1-6}$alkoxycarbonyl-$C_{1-6}$alkylaminocarbonyl-$C_{1-6}$-alkoxy, and ix) carboxy-$C_{1-6}$alkylaminocarbonyl-$C_{1-6}$-alkoxy, x) halo-$C_{1-6}$-alkyl, xi) halo-$C_{1-6}$-alkoxy, xii) $C_{1-6}$-alkoxy, and xiii) cyano.

Another embodiment of the present invention are compounds according to formula (I) as described herein, wherein $R^{18}$ is selected from i) H, ii) halogen, iii) oxo, iv) $C_{1-6}$-alkyl, v) amino-$C_{1-6}$-alkyl substituted on the nitrogen atom by one H and one substituents selected from H and $C_{1-6}$-alkoxycarbonyl, vi) $C_{1-6}$-alkoxycarbonyl-$C_{1-6}$-alkoxy, vii) carboxy-$C_{1-6}$-alkoxy, viii) $C_{1-6}$alkoxycarbonyl-$C_{1-6}$alkylaminocarbonyl-$C_{1-6}$-alkoxy, and ix) carboxy-$C_{1-6}$alkylaminocarbonyl-$C_{1-6}$-alkoxy.

Another particular embodiment of the present invention are compounds according to formula (I) as described herein, wherein $R^{18}$ is selected from i) H, ii) halogen, iii) amino-$C_{1-6}$-alkyl substituted on the nitrogen atom by two H, and iv) carboxy-$C_{1-6}$-alkoxy, v) $C_{1-6}$-alkyl, vi) halo-$C_{1-6}$-alkyl.

Another particular embodiment of the present invention are compounds according to formula (I) as described herein, wherein $R^{18}$ is selected from i) H, ii) halogen, iii) amino-$C_{1-6}$-alkyl substituted on the nitrogen atom by two H, and iv) carboxy-$C_{1-6}$-alkoxy.

Another more particular embodiment of the present invention are compounds according to formula (I) as described herein, wherein $R^{18}$ is halogen.

Another embodiment of the present invention are compounds according to formula (I) as described herein, wherein $R^{19}$ is selected from i) H, ii) halogen, iii) $C_{1-6}$-alkoxycarbonyl-$C_{1-6}$-alkyl, and iv) carboxy-$C_{1-6}$-alkoxy.

Another particular embodiment of the present invention are compounds according to formula (I) as described herein, wherein $R^{19}$ is selected from i) H, and ii) halogen.

Another more particular embodiment of the present invention are compounds according to formula (I) as described herein, wherein $R^{19}$ is halogen.

Another embodiment of the present invention are compounds according to formula (I) as described herein, wherein $R^{21}$ is selected from i) H, ii) $C_{1-6}$-alkoxycarbonyl, and iii) pyridinylcarbonyl.

Another embodiment of the present invention are compounds according to formula (I) as described herein, wherein $R^{22}$ is H.

A more particular embodiment of the present invention are compounds according to formula (I) as described herein, wherein $R^2$ is $C_{1-6}$-alkyl;

$R^3$, $R^4$, $R^6$, $R^7$, $R^{10}$ and $R^{23}$ are H;

$R^5$ is phenyl substituted with one $C_{1-6}$-alkoxy;

$R^8$ is phenyl substituted with $R^{15}$, $R^{16}$ and $R^{17}$.

$R^{11}$ is selected from i) phenyl substituted with $R^{18}$, $R^{19}$ and $R^{20}$, ii) phenyl(halo)-$C_{1-6}$-alkyl substituted with $R^{18}$, $R^{19}$ and $R^{20}$;

$R^{15}$ is selected from i) H, ii) cyano, iii) halogen, and iv) carboxy-$C_{1-6}$-alkoxy;

$R^{16}$ is H;

$R^{17}$ and $R^{20}$ are H;

$R^{18}$ and $R^{19}$ are is halogen;

or pharmaceutically acceptable salts.

Particular examples of compounds of formula (I) as described herein are selected from N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

(2S)-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]-2-(3-pyridin-3-ylpropanoylamino)propanamide;

N-[(2S)-3-(3-fluorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

3-chloro-N-[(2S)-3-(3-fluorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

5-chloro-N-[(2S)-3-(3-fluorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

(2S)-2-[[2-(3-chlorophenyl)-2,2-difluoroacetyl]amino]-3-(3-fluorophenyl)-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-chlorophenyl)-2,2-difluoroacetyl]amino]-3-(3-fluorophenyl)-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3-chlorophenyl)-2,2-difluoroacetyl]amino]-3-(3-cyanophenyl)-N-[(1S)-1-(4-methoxyphenyl)-2-oxo-2-[[(3S)-1,1,1-trifluoro-4-methyl-2-oxopentan-3-yl]amino]ethyl]propanamide;

5-chloro-N-[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-pyridin-3-ylpropan-2-yl]benzamide;

3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-pyridin-3-ylpropan-2-yl]benzamide;

(2S)-2-[[2-(2-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-pyridin-3-ylpropanamide;

N-[(2S)-3-(2-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

(2S)-2-[[2-(3-chlorophenyl)-2,2-difluoroacetyl]amino]-3-(2-cyanophenyl)-N-[(1S)-1-(4-methoxyphenyl)-2-oxo-2-[[(3S)-1,1,1-trifluoro-4-methyl-2-oxopentan-3-yl]amino]ethyl]propanamide;

tert-butyl 2-[4-[(2S)-2-[(3-chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate;

tert-butyl 2-[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-(pyridine-2-carbonylamino)propyl]phenoxy]acetate;

tert-butyl 2-[4-[(2S)-2-[[2-(2-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate;

tert-butyl 2-[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate;

tert-butyl 2-[3-[(2S)-2-[(3-chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate;

tert-butyl 2-[3-[(2S)-2-[[2-(2-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

(2S)-2-[(2,2-difluoro-2-phenylacetyl)amino]-N-[(1S)-1-(4-methoxyphenyl)-2-oxo-2-[[(3S)-1,1,1-trifluoro-4-methyl-2-oxopentan-3-yl]amino]ethyl]propanamide;

2,5-dichloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

1-(3-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopropane-1-carboxamide;

(2S)-2-[[2-(2-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3-chlorophenyl)acetyl]amino]-N-[(1S)-1-(4-methoxyphenyl)-2-oxo-2-[[(3 S)-1,1,1-trifluoro-4-methyl-2-oxopentan-3-yl]amino]ethyl]propanamide;

2-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

(2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-chlorophenyl)acetyl]amino]-N-[(1S)-1-(4-methoxyphenyl)-2-oxo-2-[[(3 S)-1,1,1-trifluoro-4-methyl-2-oxopentan-3-yl]amino]ethyl]propanamide;

(2S)-2-[(2-fluoro-2-phenylacetyl)amino]-N-[(1S)-1-(4-methoxyphenyl)-2-oxo-2-[[(3 S)-1,1,1-trifluoro-4-methyl-2-oxopentan-3-yl]amino]ethyl]propanamide;

5-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

5-bromo-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

(2S)-2-[[2-(4-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3,4-dichlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

2-(3-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-methylpropanamide;

(2S)-2-[[2-(3-chlorophenyl)-2,2-difluoroacetyl]amino]-3-methoxy-N-[(1S)-1-(4-methoxyphenyl)-2-oxo-2-[[(3S)-1,1,1-trifluoro-4-methyl-2-oxopentan-3-yl]amino]ethyl]propanamide;

3-chloro-N-[(2S)-3-methoxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

(2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-[(2-methylpropan-2-yl)oxy]propanamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-3-[(2-methylpropan-2-yl)oxy]-1-oxopropan-2-yl]pyridine-2-carboxamide;

3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-3-[(2-methylpropan-2-yl)oxy]-1-oxopropan-2-yl]benzamide;

5-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-3-[(2-methylpropan-2-yl)oxy]-1-oxopropan-2-yl]thiophene-2-carboxamide;

(2S)-2-[[2-(2-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-[(2-methylpropan-2-yl)oxy]propanamide;

3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-phenylmethoxypropan-2-yl]benzamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-phenylmethoxypropan-2-yl]pyridine-2-carboxamide;

tert-butyl (4S)-4-[(3-chlorobenzoyl)amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoate;

tert-butyl (4S)-4-[[2-(3-chlorophenyl)-2,2-difluoroacetyl]amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoate;

N-[(2S)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrazine-2-carboxamide;

N-[(2S)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]-1-methylpyrrolidine-3-carboxamide;

N-[(2S)-3-(3,4-dichlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrazine-2-carboxamide;

N-[(2S)-3-(3,4-dichlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyridine-2-carboxamide;

N-[(2S)-3-(3,4-dichlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrimidine-5-carboxamide;

N-[(2S)-3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]pyrazine-2-carboxamide;

N-[(2S)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrazine-2-carboxamide;

N-[(2S)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrimidine-5-carboxamide;

N-[(2S)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]-1-methylpiperidine-4-carboxamide;

N-[(2R)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrimidine-5-carboxamide;

N-[(2R)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrazine-2-carboxamide;

N-[(2S)-3-(3,4-dichlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyridine-2-carboxamide;

N-[(2S)-3-(3,4-dichlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrazine-2-carboxamide;

N-[(2S)-3-cyclohexyl-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]naphthalene-2-carboxamide;

tert-butyl N-[2-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]carbamate;

tert-butyl N-[[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenyl]methyl]carbamate;

tert-butyl N-[[2-chloro-4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenyl]methyl]carbamate;

tert-butyl N-[[4-[2-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]phenyl]methyl]carbamate;

tert-butyl 2-[6-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]pyridin-2-yl]oxyacetate;

tert-butyl 2-[4-[[(2S)-3-(3-chlorophenyl)-1-[[(1S)-1-(4-methoxyphenyl)-2-oxo-2-[[(3 S)-1,1,1-trifluoro-4-methyl-2-oxopentan-3-yl]amino]ethyl]amino]-1-oxopropan-2-yl]carbamoyl]phenoxy]acetate;

tert-butyl 2-[6-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]pyridin-3-yl]oxyacetate;

tert-butyl 2-[4-[[(2S)-3-(3-chlorophenyl)-1-[[(1S)-1-(4-methoxyphenyl)-2-oxo-2-[[(3 S)-1,1,1-trifluoro-4-methyl-2-oxopentan-3-yl]amino]ethyl]amino]-1-oxopropan-2-yl]carbamoyl]-2-oxopyridin-1-yl]acetate;

tert-butyl 2-[3-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetate;

tert-butyl 2-[5-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]-2-oxopyridin-1-yl]acetate;

tert-butyl 2-[4-[2-[[(2S)-3-(3-chlorophenyl)-1-[[(1S)-1-(4-methoxyphenyl)-2-oxo-2-[[(3 S)-1,1,1-trifluoro-4-methyl-2-oxopentan-3-yl]amino]ethyl]amino]-1-oxopropan-2-yl]amino]-2-oxoethoxy]phenoxy]acetate;

tert-butyl 2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetate;

tert-butyl 2-[4-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetate;

N-[3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

N-[(2S)-3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]-3-methylpyridine-2-carboxamide;

N-[(2S)-3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]-4-methylpyridine-3-carboxamide;

N-[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

N-[(2R)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyridine-2-carboxamide;

N-[(2R)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrazine-2-carboxamide;

N-[(2R)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrimidine-5-carboxamide;

tert-butyl N-[[4-[[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenyl]methyl]carbamate;

tert-butyl N-[[4-[2-[[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]phenyl]methyl]carbamate;

tert-butyl 2-[[2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetate;

tert-butyl 2-[[2-[3-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetate;

tert-butyl 2-[[2-[4-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetate;

tert-butyl 2-[[2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetate;

2-[4-[(2S)-2-[(3-chlorobenzoyl)amino]-3-[[(1S)-1-(4-methoxyphenyl)-2-oxo-2-[[(3 S)-1,1,1-trifluoro-4-methyl-2-oxopentan-3-yl]amino]ethyl]amino]-3-oxopropyl]phenoxy]acetic acid;

2-[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-(pyridine-2-carbonylamino)propyl]phenoxy]acetic acid;

2-[4-[(2S)-2-[[2-(2-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid;

2-[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid;

2-[3-[(2S)-2-[(3-chlorobenzoyl)amino]-3-[[(1S)-1-(4-methoxyphenyl)-2-oxo-2-[[(3 S)-1,1,1-trifluoro-4-methyl-2-oxopentan-3-yl]amino]ethyl]amino]-3-oxopropyl]phenoxy]acetic acid;

2-[3-[(2S)-2-[[2-(2-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid;

(4S)-4-[(3-chlorobenzoyl)amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoic acid;

(4S)-4-[[2-(3-chlorophenyl)-2,2-difluoroacetyl]amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoic acid;

(2S)-2-[(2-aminoacetyl)amino]-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]propanamide, trifluoroacetic acid salt;

4-(aminomethyl)-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide, trifluoroacetic acid salt;

4-(aminomethyl)-3-chloro-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide, trifluoroacetic acid salt;

(2S)-2-[[2-[4-(aminomethyl)phenyl]acetyl]amino]-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]propanamide, trifluoroacetic acid salt;

2-[6-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]pyridin-2-yl]oxyacetic acid;

2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

2-[6-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]pyridin-3-yl]oxyacetic acid;

2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]-2-oxopyridin-1-yl]acetic acid;

2-[3-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

2-[5-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]-2-oxopyridin-1-yl]acetic acid;

2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

2-[4-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

4-(aminomethyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide, trifluoroacetic acid salt;

(2S)-2-[[2-[4-(aminomethyl)phenyl]acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide, trifluoroacetic acid salt;

2-[[2-[4-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid;

2-[[2-[3-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid;

2-[[2-[4-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid;

2-[[2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid;

(2S)-2-[[2-(3-chlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

N-[(2S)-3-hydroxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

3-chloro-N-[(2S)-3-hydroxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

5-chloro-N-[(2S)-3-hydroxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

(2S)-2-[[2-(2-chlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

N-[2-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]pyridine-2-carboxamide;

and pharmaceutically acceptable salts thereof.

Also particular examples of compounds of formula (I) as described herein are selected from N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

3-chloro-N-[(2S)-3-(3-fluorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

(2S)-2-[[2-(3-chlorophenyl)-2,2-difluoroacetyl]amino]-3-(3-fluorophenyl)-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-chlorophenyl)-2,2-difluoroacetyl]amino]-3-(3-fluorophenyl)-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3-chlorophenyl)-2,2-difluoroacetyl]amino]-3-(3-cyanophenyl)-N-[(1S)-1-(4-methoxyphenyl)-2-oxo-2-[[(3S)-1,1,1-trifluoro-4-methyl-2-oxopentan-3-yl]amino]ethyl]propanamide;

5-chloro-N-[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

(2S)-2-[[2-(2-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-pyridin-3-ylpropanamide;

(2S)-2-[[2-(3-chlorophenyl)-2,2-difluoroacetyl]amino]-3-(2-cyanophenyl)-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3,4-dichlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

2-[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid;

2-[3-[(2S)-2-[(3-chlorobenzoyl)amino]-3-[[(1S)-1-(4-methoxyphenyl)-2-oxo-2-[[(3 S)-1,1,1-trifluoro-4-methyl-2-oxopentan-3-yl]amino]ethyl]amino]-3-oxopropyl]phenoxy]acetic acid;

4-(aminomethyl)-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide, trifluoroacetic acid salt;

4-(aminomethyl)-3-chloro-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide, trifluoroacetic acid salt;

(2S)-2-[[2-[4-(aminomethyl)phenyl]acetyl]amino]-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]propanamide, trifluoroacetic acid salt;

2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

2-[3-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

(2S)-2-[[2-(3-chlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-chlorophenyl)-2,2-difluoroacetyl]amino]-3-hydroxy-N-[(1S)-1-(4-methoxyphenyl)-2-oxo-2-[[(3 S)-1,1,1-trifluoro-4-methyl-2-oxopentan-3-yl]amino]ethyl]propanamide;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

AcOH=acetic acid, Boc=t-butyloxycarbonyl, BuLi=butyllithium, CDI=1,1-carbonyldiimidazole, Cbz=carboxybenzyl, DCM=dichloromethane, DBU=2,3,4,6,7,8,9,10-octahydro-pyrimido[1,2-a]azepine, DCE=1,2-dichloroethane, DIAD=diisopropyl-azodicarboxylate, DIBALH=di-i-butylaluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, $Et_2O$=diethylether, $Et_3N$=triethylamine, eq=equivalents, Fmoc=fluorenylmethoxycarbonyl, HATU=O-(7-azabenzotriazol-1-yl)-1,1,3,3-tetramethyluronium hexafluorophosphate, HPLC=high performance liquid chromatography, HOBt=1-hydroxybenzo-triazole, Huenig's base=iPr2NEt=N-ethyl diisopropylamine, IPC=in process control, LAH=lithium aluminium hydride, LDA=lithium diisopropylamide, $LiBH_4$=lithium borohydride, MeOH=methanol, $NaBH_3CN$, sodium cyanoborohydride, $NaBH_4$=sodium borohydride, NaI=sodium iodide, PG=protecting group, Red-Al=sodium bis(2-methoxyethoxy) aluminium hydride, RT=room temperature, TBDMSCl=t-butyldimethylsilyl chloride, TBTU=O-benzotriazol-1-yl-N,N,N',N'-tetramethyl-uronium tetrafluoroborate, TFA=trifluoroacetic acid, THF=tetrahydrofuran, quant=quantitative.

Amide coupling of N-protected-α-amino acid compounds 1 (scheme 1), such as Boc-L-phenyl alanine, with trifluoromethyl compounds 2 can be accomplished by using one of the well-known coupling reagents such as TBTU, HATU, EDCI/HOBt, etc. and a base like Huenig's base or triethyl amine in a solvent like N,N-dimethylformamide preferably between 0° C. and room temperature to give compounds 3 (step a). Subsequent deprotection under appropriate conditions, depending on the nature of the protecting group PG (step b), gives compounds 4 (e.g. acidic conditions such as treatment with 4M HCl in dioxane in a solvent like MeOH or treatment with TFA in DCM around room temperature can be used for removal of a Boc protecting group, catalytic hydrogenation conditions using suitable catalysts such as Pd/C, $Pd(OH)_2$ in a solvent like MeOH, EtOH or AcOEt around room temperature can be used for removal of a Cbz protecting group, treatment with a mild base such as piperidine in a solvent like DCM around room temperature can be used for removal of a Fmoc protecting group, etc.). Reaction of compounds 4 with a N-protected-α-amino acid compounds 5, such as (2S)-2-(tert-butoxycarbonylamino)-3-(3-chlorophenyl)propanoic acid, can be performed by using one of various coupling reagents such as TBTU, HATU, EDCI/HOBt, etc., and a base like Huenig's base or triethyl amine in a solvent like N,N-dimethylformamide preferably between 0° C. and room temperature to give compounds 6 (step c). Subsequent deprotection under appropriate conditions, depending on the nature of the protecting group PG (step d), gives compounds 7 (e.g. acidic conditions such as treatment with 4M HCl in dioxane in a solvent like MeOH or treatment with TFA in DCM around room temperature can be used for removal of a Boc protecting group, catalytic hydrogenation conditions using suitable catalysts such as Pd/C, $Pd(OH)_2$ in a solvent like MeOH, EtOH or AcOEt around room temperature can be used for removal of a Cbz protecting group, treatment with a mild base such as piperidine in a solvent like DCM around room temperature can be used for removal of a Fmoc protecting group, etc.). Reaction of compounds 7 with the appropriate carboxylic acid compounds 8 (for the synthesis of specific examples of compounds 8, see schemes 5, 6, 7 and 8), activated by one of the various coupling reagents such as TBTU, HATU, EDCI/HOBt, etc., and a base like Huenig's base or triethyl amine in a solvent like N,N-dimethylformamide preferably between 0° C. and room temperature gives compounds 9 (step e).

Compounds 9 containing a protected amino function as e.g. a tert-butoxycarbonylamino group can be converted into the corresponding primary or secondary amine compounds 9 using conditions as described for the removal of tert-butoxycarbonylamino groups in step b. Compounds 9 carrying a free amino function can be reacted with suitable carboxylic acid derivatives under standard coupling conditions by using a coupling reagent such as HATU and a base like Huenig's base in a solvent like N,N-dimethylformamide preferably between 0° C. and room temperature giving further modified compounds 9.

Oxidation of compounds 9 can e.g. be performed using Swern's conditions (oxalyl chloride, dimethyl sulfoxide, triethyl amine in dichloromethane between −78° C. and RT) or with the help of an appropriate specific oxidizing agent as Dess-Martin Periodinane in a solvent like DCM between 0° C. and room temperature and gives the final products I (step f).

Compounds I containing a tert-butylester, a 4-(methylphenyl)-diphenylmethyl, a tert-butylether, a tert-butyl-dimethyl-silyloxy or a tert-butoxycarbonylamino moiety in $R^5$, $R^8$, $R^{10}$ or $R^{11}$ can be converted into the corresponding carboxylic acids, amides, alcohols or amines under appropriate conditions depending on the nature of the functional groups, resulting in modified final compounds I (step g), (e.g. acidic conditions such as treatment with 4M HCl in dioxane in a solvent like dioxane or THF can be used for removal of tert-butyl-dimethyl-silyloxy groups and treatment with TFA in DCM around room temperature can be used for removal of tert-butylether, 4-(methylphenyl)-diphenylmethyl, tert-butylester and tert-butoxycarbonylamino groups).

Compounds I carrying a free amino function can be reacted with suitable carboxylic acid derivatives under standard coupling conditions by using a coupling reagent such as HATU and a base like Huenig's base in a solvent like N,N-dimethylformamide or preferably with suitable acid chlorides in presence of a base such as Huenig's base or triethyl amine in a solvent like DCM or DMF preferably between 0° C. and room temperature or with suitable N-hydroxysuccinimide activated carboxylic acid derivatives in presence of a base such as aqueous $Na_2CO_3$, $NaHCO_3$ or triethyl amine in a solvent like DCM, THF or DME/THF preferably between −20° C. and room temperature, thus giving further modified final compounds I The acid chlorides can be obtained by treatment of the corresponding acids with thionyl chloride, $PCl_3$, $PCl_5$ or preferably oxalyl chloride, catalyzed by DMF, in a solvent like DCM between 0° C. and room temperature. The N-hydroxysuccinimide activated carboxylic acid compounds can be obtained by treatment of the corresponding acids with 1-hydroxypyrrolidine-2,5-dione in presence of a coupling reagent such as DCC or EDC and a base such as Huenig's base, triethyl amine or pyridine in a solvent like DCM preferably between 0° C. and room temperature.

Scheme 1

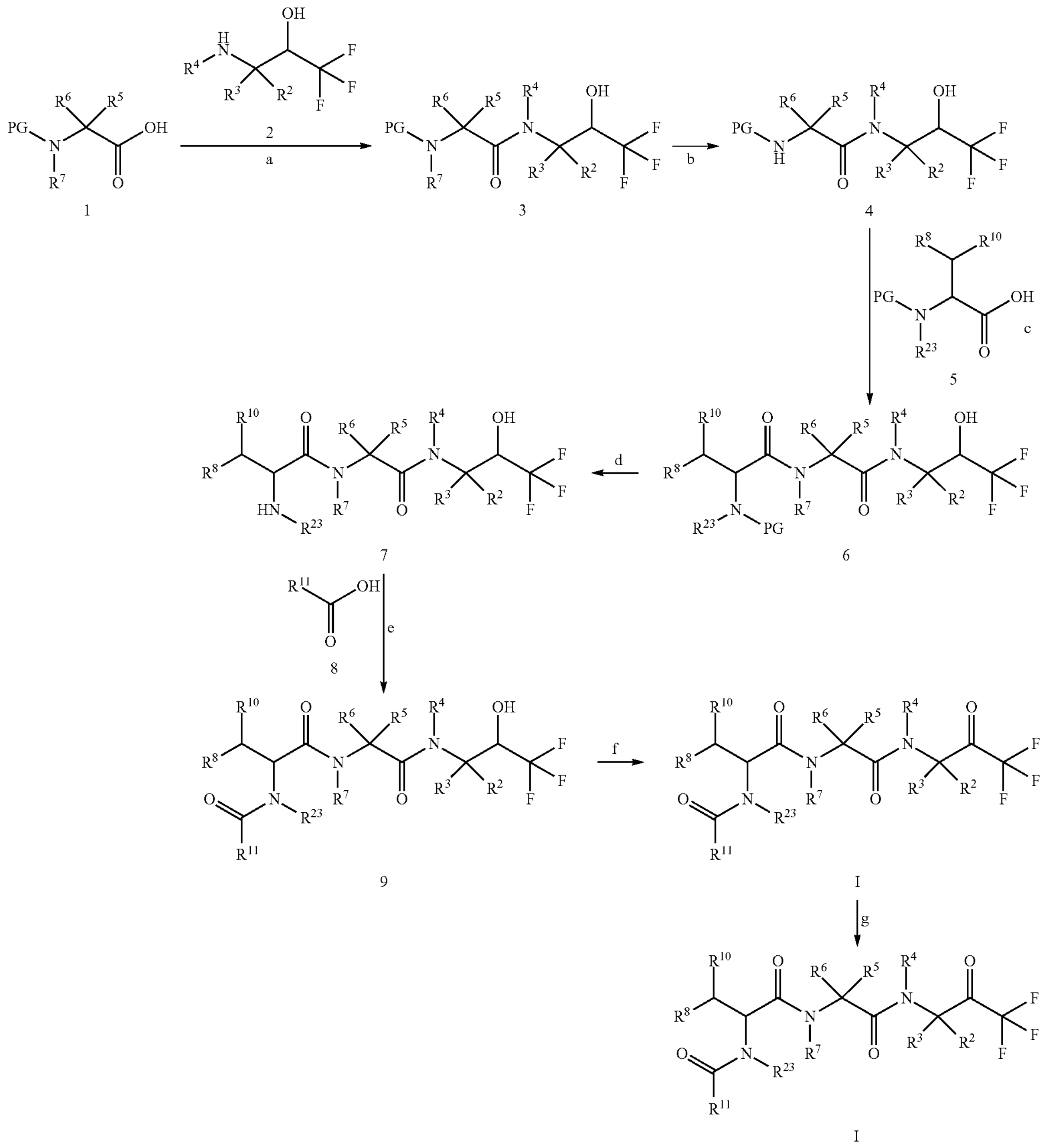

PG is e.g. Boc, Cbz, Fmoc

Compounds 2 can be prepared by a variety of conditions, which may be exemplified by the general synthetic procedure below (scheme 4). Known N-protected-oxazolidin-5-one derivatives 52, preferably with fully defined stereochemistry, can be prepared by formylation of the corresponding enantiopure N-protected-α-amino acid derivatives 51, such as Cbz-L-Valine, with paraformaldehyde in presence of Lewis acid catalysts, such as $ZnCl_2$, $AlCl_3$, $BF_3$ or preferably in presence of Brönsted acid catalysts, such as pTsOH, CSA, AcOH, $H_2SO_4$, in a solvent like toluene, and in a temperature range preferably between 75° C. and about 90° C. (step a). Subsequent nucleophilic addition of a trifluoromethylating reagent, such as trifluoromethyltrimethylsilane (Ruppert's reagent), in the presence of a catalytic amount of a fluoride source such as TBAF or CsF, in a solvent like THF, and in a temperature range preferably between 0° C. and about 10° C., followed by deprotection of the TMS group by treatment in MeOH, gives compounds 53 with preferred stereochemistry as shown if $R^2$═H (step b). Stereoselective reduction of compounds 53 using suitable reducing agents such as $NaBH_4$, $LiBH_4$, $LiBHEt_3$, DIBALH, $NaBH_4$—$CeCl_3$ preferably $NaBH_4$—

$ZnCl_2$, in a solvent like MeOH, EtOH, IPA, tBuOH, THF, DMF, preferably in tert-butyl methyl ether around room temperature, followed by alkaline hydrolysis with a base, such as aqueous or non aqueous sodium, potassium or cesium carbonate, sodium or potassium hydroxide, in a solvent like MeOH, EtOH and water around room temperature, gives compounds 54 (step c). Finally, deprotection under appropriate conditions, depending on the nature of the protecting group PG (step d), gives compounds 55 (e.g. acidic conditions such as treatment with 4M HCl in dioxane in a solvent like MeOH or treatment with TFA in DCM around room temperature can be used for removal of a Boc protecting group, catalytic hydrogenation conditions using suitable catalysts such as Pd/C, $Pd(OH)_2$ in a solvent like MeOH, EtOH or AcOEt around room temperature can be used for removal of a Cbz protecting group, treatment with a mild base such as piperidine in a solvent like DCM around room temperature can be used for removal of a Fmoc protecting group). Alternatively, the hydroxy function of N-protected-α-amino trifluoromethyl alcohol derivatives 54 can be protected with a suitable protecting group, such as MOM, MEM, PMB or preferably THP using the appropriate conditions known by the person skilled in the art to give compounds 56 (step e). Subsequent N-alkylation by treatment of compounds 56 with an appropriate base, such as NaH, KH, NaHMDS, LiHMDS, LDA, in a solvent like THF, dioxane, DMF, in a temperature range between −78° C. and 0° C., followed by addition of alkyl or cycloalkyl halides, such as MeI, EtI, iPrI, CyPrI, etc., gives compounds 57 (step f). Finally, removal of both protecting groups PG and PG' under appropriate conditions, depending on the nature of the protecting group (step g), gives compounds 2 (e.g. acidic conditions such as treatment with 4M HCl in dioxane in a solvent like MeOH around room temperature can be used for removal of Boc, MOM, MEM or THP protecting groups, catalytic hydrogenation conditions using suitable catalysts such as Pd/C, $Pd(OH)_2$ in a solvent like MeOH, EtOH or AcOEt around room temperature can be used for removal of Cbz or PMB protecting groups).

Scheme 4

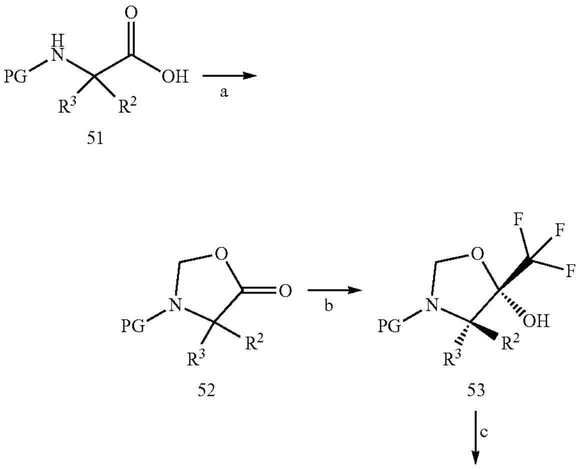

51 52 53

-continued

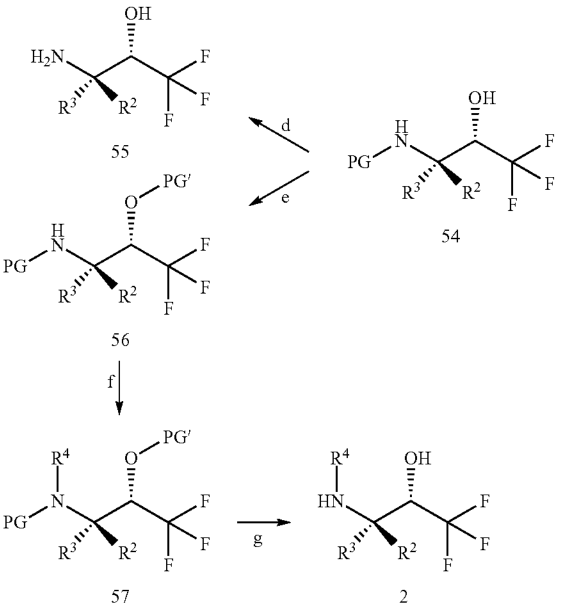

55 54 56 57 2

PG is e.g. Boc, Cbz, Fmoc
PG' is e.g. MOM, MEM, Cbz, THP

Carboxylic acid derivatives 8 from the family of optionally substituted (2-tert-butoxy-2-oxo-ethoxy)pyridine-2-carboxylic acid derivatives 103 or 113 or from the family of optionally substituted 1-(2-tert-butoxy-2-oxo-ethyl)-oxo-pyridine-3 or 4-carboxylic acid compounds 123 or 133, can be prepared e.g. as exemplified by the synthetic procedures shown below (scheme 5 and scheme 6).

Optionally substituted hydroxypyridine-2-carboxylic acid derivatives 100 and 110 (scheme 5) react selectively at the carboxylic group with benzyl bromide or benzyl chloride in presence of a base such as triethyl amine, $K_2CO_3$ or $Cs_2CO_3$, in a solvent like acetone, EtOAc or preferably DMF, and in temperature range between 40° C. and 80° C., to give the benzyl ester derivatives 101 and 111 (step a). Subsequent O-alkylation of the hydroxy group with tert-butyl 2-bromoacetate or tert-butyl 2-chloroacetate in presence of a base such as $K_2CO_3$ or $Cs_2CO_3$, in a solvent like EtOAc, DMF or preferably acetone, and in temperature range between 60° C. and 80° C., preferably around reflux for acetone, gives the corresponding benzyl (2-tert-butoxy-2-oxo-ethoxy)pyridine-2-carboxylate derivatives 102 and 112 as major products (step b). Catalytic hydrogenation using heterogeneous conditions such as Pd/C, in a solvent like MeOH, EtOH, or AcOEt around room temperature and under atmospheric pressure, gives the (2-tert-butoxy-2-oxo-ethoxy)pyridine-2-carboxylic acid derivatives 103 and 113 (step c).

Scheme 5

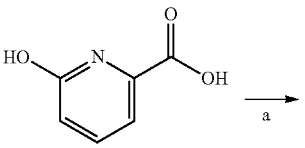

100

-continued

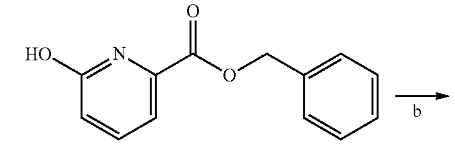

101

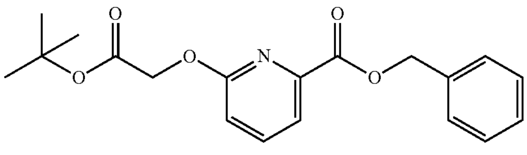

102

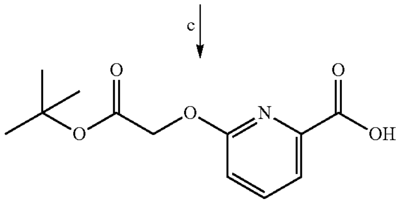

103

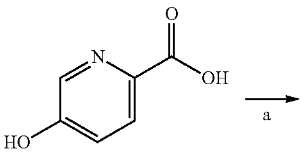

110

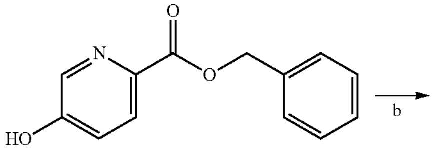

111

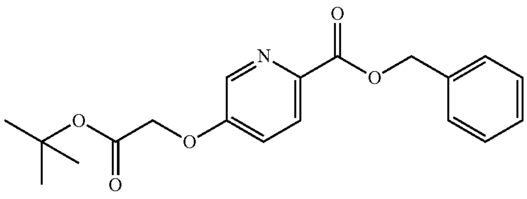

112

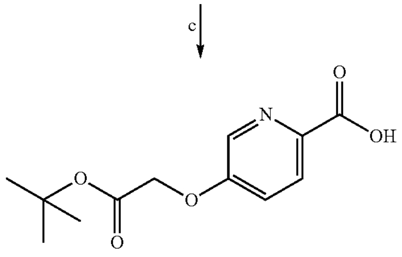

113

Optionally substituted pyridone derivatives 120 and 130 (scheme 6) react selectively at the carboxylic group with benzyl bromide or benzyl chloride in presence of a base such as triethyl amine, $K_2CO_3$ or $Cs_2CO_3$, in a solvent like acetone, EtOAc or preferably DMF, and in temperature range between 40° C. and 80° C., to give the benzyl ester derivatives 121 and 131 (step a). Subsequent N-alkylation of the pyridone nitrogen with tert-butyl 2-bromoacetate or tert-butyl 2-chloroacetate in presence of a base such as $K_2CO_3$ or $Cs_2CO_3$, in a solvent like EtOAc, DMF or preferably acetone, and in temperature range between 60° C. and 80° C., preferably around reflux for acetone, gives the corresponding benzyl 1-(2-tert-butoxy-2-oxo-ethyl)-oxo-pyridine-3 or 4-carboxylate derivatives 122 and 132 as major products (step b). Catalytic hydrogenation using heterogeneous conditions such as Pd/C, in a solvent like MeOH, EtOH, or AcOEt around room temperature and under atmospheric pressure, gives the 1-(2-tert-butoxy-2-oxo-ethyl)-oxo-pyridine-3 or 4-carboxylic acid derivatives 123 and 133 (step c).

Scheme 6

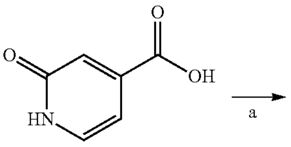

120

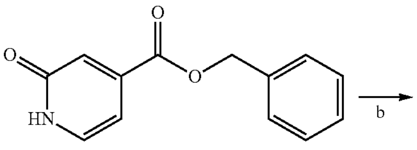

121

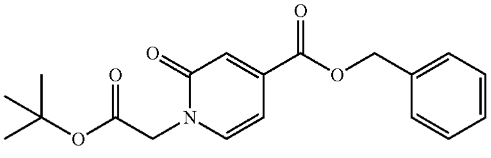

122

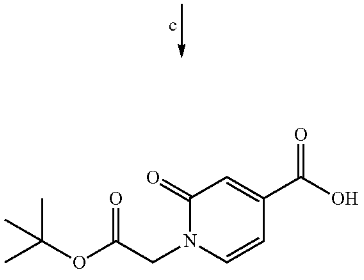

123

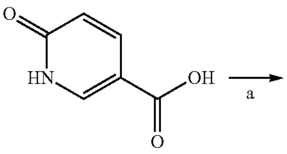

130

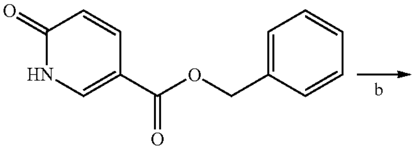

131

-continued

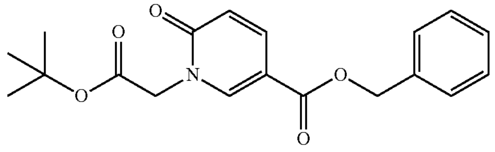

132

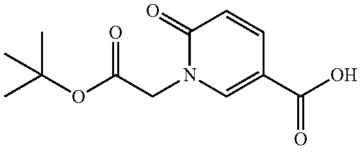

133

Carboxylic acid derivatives 8 from the family of optionally substituted 3,3,3-trifluoro-2-phenyl-propanoic acid compounds 143 or from the family of optionally substituted 2-phenyl-1,3-dioxolane-2-carboxylic acid compounds 152 can be prepared e.g. as exemplified by the synthetic procedures shown below (scheme 7 and scheme 8).

Optionally substituted ethyl 3,3,3-trifluoro-2-hydroxy-2-phenyl-propanoate derivatives 140 (scheme 7) can react with mesyl chloride in presence of a base such as triethyl amine or Huenig's base in a solvent like acetonitrile or dichloromethane and in temperature range between −5° C. to room temperature, to give the ester derivatives 141 (step a). Subsequent catalytic hydrogenation of the mesylate group using heterogeneous conditions such as Pd/C, in a solvent like MeOH or EtOH around room temperature and under 3 bar hydrogen pressure, gives the ethyl 3,3,3-trifluoro-2-phenyl-propanoate derivatives 142 (step b). Hydrolysis under acidic conditions using concentrated HCl in a solvent like dioxane in a temperature range between 80° C. to 110° C., preferably around reflux, delivers the 3,3,3-trifluoro-2-phenyl-propanoic acid building block 143 (step c).

Scheme 7

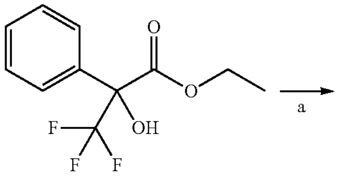

140

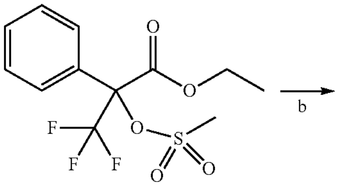

141

-continued

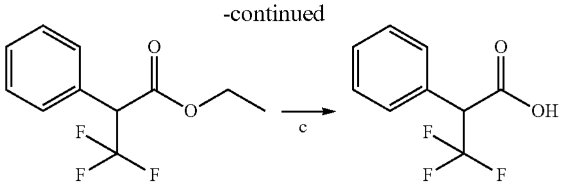

142 143

Optionally substituted ethyl 2-(3-chlorophenyl)-2-oxoacetate derivatives 150 (scheme 8) can react with 2-chloroethanol in presence of a base such as potassium tert-butoxide in a solvent like DMF or THF and in a temperature range between −60° C. to room temperature, to give the ester derivatives 141 (step a). Subsequent hydrolysis under standard conditions, e.g., LiOH in a mixture of water, MeOH or EtOH, preferably THF, in a temperature range of 0° C. to room temperature, delivers the 2-phenyl-1,3-dioxolane-2-carboxylic acid building blocks 152 (step b).

Scheme 8

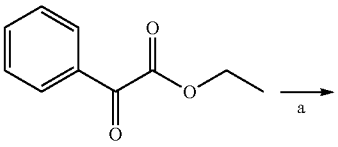

150

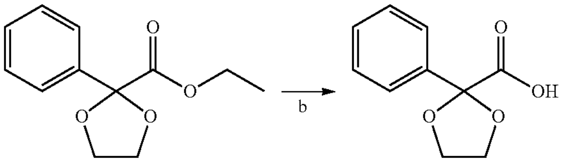

151 152

Also an embodiment of the present invention is a process to prepare a compound of formula (I) as defined above comprising the reaction of a compound of formula (II) in oxidative conditions;

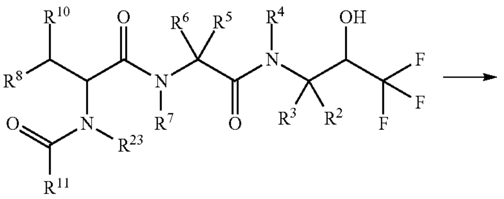

(II)

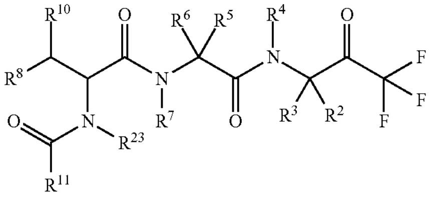

(I)

wherein $R^2$, $R^3$, $R^4$, $R^5$, $R^6$, R, $R^3$, $R^8$, $R^{10}$, $R^{11}$ and $R^{23}$ are as defined above.

In particular, in the presence of 1,1,1-Triacetoxy-1,1-dihydro-1,2-benziodoxol-3(1H)-one (Dess-Martin periodane), in a solvent like DCM between 0° C. and room temperature.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of ocular diseases, in particular HtrA1-mediated ocular diseases, more particularly wet or dry age-related macular degeneration, geographic atrophy, diabetic retinopathy, retinopathy of prematurity or polypoidal choroidal vasculopathy.

In a particular embodiment, the compounds of formula (I) or their pharmaceutically acceptable salts and esters can be used for the treatment or prophylaxis of wet or dry age-related macular degeneration, geographic atrophy, diabetic retinopathy, retinopathy of prematurity or polypoidal choroidal vasculopathy.

The present invention also relates to the use of a compound according to formula (I) as described herein for the preparation of a medicament for the treatment or prophylaxis of wet or dry age-related macular degeneration, geographic atrophy, diabetic retinopathy, retinopathy of prematurity and polypoidal choroidal vasculopathy.

Also an object of the invention is a method for the treatment or prophylaxis of wet or dry age-related macular degeneration, geographic atrophy, diabetic retinopathy, retinopathy of prematurity and polypoidal choroidal vasculopathy, which method comprises administering an effective amount of a compound according to formula (I) as described herein.

Also an embodiment of the present invention are compounds of formula (I) as described herein, when manufactured according to any one of the described processes.

Assay Procedures

Protein Purification for Use in Enzymatic Assays

Human HtrA1 protein comprising the catalytic and the PDZ domain from amino acid Asp161 up to Pro480 of was expressed in BL21(DE3) cells as an N-terminal fusion protein with a 6×His-SUMO tag. The transformed cells were grown in LB medium at 37° C. until the optical density at 600 nm was between 0.6 and 0.8. Then, the temperature was decreased to 18° C. and the recombinant protein production induced by adding IPTG to a final concentration of 250 mM. Fermentation was performed over night at 18° C.

The protein was purified to homogeneity following a four-step procedure. 40 g of cells were suspended in 50 mM HEPES pH 7.8, 250 mM NaCl, 10 mM MgCl2, 0.35% CHAPS, 10% glycerol containing 20 tabs per liter of EDTA-free cOmplete Protease Inhibitor (Roche) as well as 30 mg/l DNAse and Rnase. The cells were broken by a single passage through a homogenizer at 750 bar and then centrifuged at 20'000×g for 30 minutes. The clear supernatant was applied on a triple 5 ml HisTrap column (GE Healthcare) equilibrated in 50 mM HEPES pH 7.8, 500 mM NaCl, 0.35% CHAPS, 10% glycerol. After washing with stepwise increasing concentrations of imidazole (20 mM, 40 mM, 50 mM) HtrA1 fusion protein was eluted within a linear gradient from 10 to 100% of the same buffer containing 500 mM imidazole. HtrA1 containing fractions were pooled, concentrated and then applied to a Superdex S200 prep grade (XK26/100—GE Healthcare) column equilibrated in 50 mM ethanolamine pH 9.6, 500 mM NaCl, 0.35% CHAPS, 10% glycerol, 0.02% sodium azide. In order to cleave the SUMO fusion protein and to release active HtrA1, the pooled fractions from the size exclusion chromatography were blended with SUMO protease (Life Technologies) and incubated ca. 20 hours at RT. HtrA1 was isolated out of the reaction solution by chromatography on a Superdex S200 prep grade (XK26/100—GE Healthcare) column equilibrated 50 mM ethanolamine pH 9.6, 500 mM NaCl, 0.35% CHAPS, 10% glycerol, 0.02% sodium azide. Fractions containing active HtrA1 were pooled and concentrated. Following the above strategy 150 mg of the HtrA1 (catalytical domain/PDZ construct) could be purified. As shown by RP-HPLC and SDS-PAGE, >98% pure protein was obtained.

HtrA1 Enzyme Inhibition Assay

Enzyme activity is measured by observing the increase in fluorescence intensity caused by cleavage of a peptide substrate containing a fluorophore, whose emission is quenched in the intact peptide.

Assay buffer: 500 mM Tris pH 8.0, 200 mM NaCl, 0.025% CHAPS, 0.005% BSG

Enzyme: human HtrA1 Cat-PDZ, final concentration 1 nM

Substrate: Mca-Ile-Arg-Arg-Val-Ser-Tyr-Ser-Phe-Lys (Dnp)-Lys, final concentration 500 nM (from Innovagen Cat: SP-5076-1, Lot: 89584.02)

Mca=(7-Methoxycoumarin-4-yl)acetyl

Dnp=2,4-Dinitrophenyl

Final volume: 51 μl

Excitation 320 nm, emission 390 nm

After a pre-incubation of the HtrA1 protease for 30 min with compounds, substrate is added to the wells and initial RFU is measured. Upon incubation for 2 hours at RT, the enzymatic activity cleaved the substrate releasing fluorescent Mca-peptide conjugate and the final RFU value is measured. The presence of inhibitors leads to a decreased final RFU.

For the analysis ΔRFU is calculated as $RFU_{end}$-$RFU_{start}$ and then percent inhibition is calculated with the following formula:

$$PCT\_\text{Inhibition}=100-100*(\Delta RFU_{compound}-\Delta RFU_{blank})/(\Delta RFU_{negctrl}-\Delta RFU_{blank})$$

where neg.ctrl is protease with substrate and DMSO blank is as neg. ctrl without protease compound is as neg. ctrl with test compounds at desired concentration The $IC_{50}$ is determined using a 4-point Hill-fit equation where x=concentration of test compound A=extrapolated value of the curve at effector concentration equals 0

B=extrapolated value of the curve at effector concentration equals infinite

C=concentration at the inflection point of the sigmoidal curve ($IC_{50}$)

D=Hill coefficient of slope at the inflection point of the fitted curve $$Y(x) = A + \frac{B - A_D}{1 + \left(\frac{C}{x}\right)}$$

As a counter screen the compounds are added to the protease-substrate reaction mix only after 2 h incubation, when all the substrate is turned over, to identify auto-fluorescent or absorbing compounds giving false positive hits.

| Example | IC50 (μM) |
|---|---|
| 1 | 0.0012 |
| 2 | 0.059 |
| 3 | 0.0026 |
| 4 | 0.0018 |
| 5 | 0.0019 |
| 6 | 0.00062 |
| 7 | 0.00083 |
| 8 | 0.00062 |
| 9 | 0.0014 |
| 10 | 0.032 |
| 11 | 0.0098 |
| 12 | 0.0031 |
| 13 | 0.0049 |
| 14 | 0.0011 |
| 15 | 0.005 |
| 16 | 0.0061 |
| 17 | 0.00049 |
| 18 | 0.0012 |
| 19 | 0.0011 |
| 20 | 0.0011 |
| 21 | 0.21 |
| 22 | 0.018 |
| 23 | 0.021 |
| 24 | 0.029 |
| 25 | 0.086 |
| 26 | 0.008 |
| 27 | 0.032 |
| 28 | 0.11 |
| 29 | 0.00182 |
| 30 | 0.11 |
| 31 | 0.044 |
| 32 | 0.013 |
| 33 | 0.026 |
| 34 | 0.0016 |
| 35 | 0.00097 |
| 36 | 0.0076 |
| 37 | 0.012 |
| 38 | 0.016 |
| 39 | 0.0014 |
| 40 | 0.069 |
| 41 | 0.0023 |
| 42 | 0.0018 |
| 43 | 0.0019 |
| 44 | 0.0017 |
| 45 | 0.061 |
| 46 | 0.0021 |
| 47 | 0.00076 |
| 48 | 0.0077 |
| 49 | 0.13 |
| 50 | 0.0066 |
| 51 | 0.0026 |
| 52 | 0.021 |
| 53 | 0.046 |
| 54 | 0.027 |
| 55 | 0.032 |
| 56 | 0.22 |
| 57 | 0.4 |
| 58 | 0.42 |
| 59 | 0.0025 |
| 60 | 0.014 |
| 61 | 0.012 |
| 62 | 0.032 |
| 63 | 0.0014 |
| 64 | 0.001 |
| 65 | 0.0023 |
| 66 | 0.0024 |
| 67 | 0.0025 |
| 68 | 0.0032 |
| 69 | 0.0071 |
| 70 | 0.0073 |
| 71 | 0.014 |
| 72 | 0.0015 |

-continued

| Example | IC50 (μM) |
|---|---|
| 73 | 0.00071 |
| 74 | 0.0036 |
| 75 | 0.014 |
| 76 | 0.0066 |
| 77 | 0.038 |
| 78 | 0.0059 |
| 79 | 0.082 |
| 80 | 0.082 |
| 81 | 0.22 |
| 86 | 0.0087 |
| 87 | 0.0023 |
| 88 | 0.057 |
| 89 | 0.16 |
| 90 | 0.31 |
| 91 | 0.066 |
| 92 | 0.089 |
| 93 | 0.15 |
| 94 | 0.45 |
| 95 | 0.15 |
| 97 | 0.0079 |
| 98 | 0.0015 |
| 99 | 0.0024 |
| 100 | 0.81 |
| 101 | 0.029 |
| 102 | 0.14 |
| 103 | 0.29 |
| 104 | 0.15 |
| 105 | 0.35 |
| 106 | 0.11 |
| 107 | 0.17 |
| 108 | 0.098 |
| 109 | 0.57 |
| 110 | 0.19 |
| 111 | 0.31 |
| 112 | 0.12 |
| 113 | 0.086 |
| 114 | 0.029 |
| 115 | 0.0043 |
| 116 | 0.63 |
| 117 | 0.065 |
| 118 | 0.028 |
| 119 | 0.0081 |
| 120 | 0.038 |
| 121 | 0.000695 |
| 122 | 0.0012 |
| 123 | 0.0017 |
| 124 | 0.0174 |
| 125 | 0.0029 |
| 126 | 0.0039 |
| 127 | 0.0014 |
| 128 | 0.0225 |
| 129 | 0.0009 |
| 130 | 0.0015 |
| 131 | 0.0059 |
| 132 | 0.0014 |
| 133 | 0.0051 |
| 134 | 0.0079 |
| 135 | 0.0104 |
| 136 | 0.0105 |
| 137 | 0.0071 |
| 138 | 0.0348 |
| 139 | 0.024 |
| 140 | 0.0215 |
| 141 | 0.0018 |
| 142 | 0.0285 |
| 143 | 0.0046 |
| 144 | 0.0059 |
| 145 | 0.0107 |
| 146 | 0.0311 |
| 147 | 0.0712 |
| 148 | 0.364 |
| 149 | 0.01 |
| 150 | 0.0414 |
| 151 | 0.0172 |
| 152 | 0.0902 |
| 153 | 0.0191 |
| 154 | 0.0548 |

-continued

| Example | IC50 (μM) |
|---|---|
| 155 | 0.0546 |
| 156 | 0.0225 |
| 157 | 0.0196 |
| 158 | 0.0046 |
| 159 | 0.004 |
| 160 | 0.0033 |
| 161 | 0.0318 |
| 162 | 0.0043 |
| 163 | 0.000602 |
| 165 | 0.0008 |
| 166 | 0.0005 |
| 170 | 0.0006 |
| 171 | 0.0009 |
| 173 | 0.0019 |
| 174 | 0.0068 |
| 175 | 0.0012 |
| 176 | 0.0085 |
| 177 | 0.0032 |
| 178 | 0.0023 |
| 179 | 0.008 |
| 181 | 0.002 |
| 182 | 0.0433 |
| 183 | 0.0133 |
| 184 | 0.0039 |
| 185 | 0.0095 |
| 186 | 0.001703 |
| 187 | 0.0028 |
| 188 | 0.0013 |
| 189 | 0.0073 |
| 190 | 0.0047 |
| 191 | 0.0058 |
| 192 | 0.0164 |
| 193 | 0.0114 |
| 194 | 0.0114 |
| 195 | 0.004 |
| 196 | 0.0007 |
| 197 | 0.0037 |
| 198 | 0.0034 |
| 199 | 0.0025 |
| 200 | 0.0203 |
| 201 | 0.0061 |
| 202 | 0.0014 |
| 203 | 0.0135 |
| 204 | 0.025 |
| 205 | 0.0378 |
| 206 | 0.0085 |
| 207 | 0.0192 |
| 208 | 0.004 |
| 209 | 0.0359 |
| 210 | 0.0056 |
| 211 | 0.0019 |
| 212 | 0.0011 |
| 213 | 0.0031 |
| 214 | 0.0061 |
| 215 | 0.0054 |
| 216 | 0.0004 |

Compounds of formula (I) and their pharmaceutically acceptable salts or esters thereof as described herein have $IC_{50}$ values between 0.00001 μM and 1000 μM, particular compounds have $IC_{50}$ values between 0.0005 μM and 500 μM, further particular compounds have $IC_{50}$ values between 0.0005 μM and 50 μM, more particular compounds have $IC_{50}$ values between 0.0005 μM and 5 μM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations; lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg, can be administered either by single dose per day or per week, or by multiple doses (2 to 4) per day, or by multiple doses per week. In case of parenteral application, such as intramuscularly, intravenously, or intraocularly, the formulation can contain 0.001% to 15% by weight of medicament and the required dose, which can be between 0.01 and 25 mg, can be administered either by single dose per day, per week or per month, or by multiple doses (2 to 4) per day, or by multiple doses per week or per month. It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations: aq.=aqueous; CAS-RN=Chemical Abstracts Service Registry Number; HPLC=high performance liquid chromatography; MS=mass spectrum; sat.=saturated Intermediate A-1

(S)-2-Amino-3-(3-chlorophenyl)-N—((S)-1-(4-methoxyphenyl)-2-oxo-2-(((2S,3S)-1,1,1-trifluoro-2-hydroxy-4-methylpentan-3-yl)amino)ethyl)propanamide

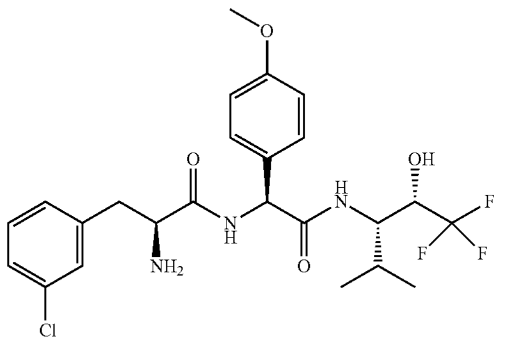 [SMILES: COc1ccc([C@H](NC(=O)[C@@H](N)Cc2cccc(Cl)c2)C(=O)N[C@@H](C(C)C)[C@H](O)C(F)(F)F)cc1]

[A] tert-Butyl ((S)-1-(4-methoxyphenyl)-2-oxo-2-(((2S,3S)-1,1,1-trifluoro-2-hydroxy-4-methylpentan-3-yl)amino)ethyl)carbamate

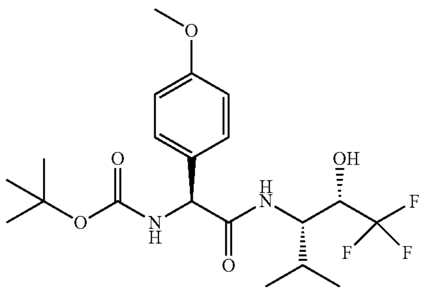 [SMILES: COc1ccc([C@H](NC(=O)OC(C)(C)C)C(=O)N[C@@H](C(C)C)[C@H](O)C(F)(F)F)cc1]

In a round-bottomed flask, (S)-2-((tert-butoxycarbonyl)amino)-2-(4-methoxyphenyl)acetic acid (1 g, 3.55 mmol) (2S,3S)-3-amino-1,1,1-trifluoro-4-methylpentan-2-ol×HCl (0.738 g, 3.55 mmol) and HATU (1.49 g, 3.91 mmol) were dissolved in DMF (20 mL) and the mixture cooled to 0° C. Hunig's base (1.86 mL, 10.7 mmol) was added to the reaction mixture which was stirred at this temperature for 15 min, then allowed to warm up to room temperature and stirring was continued for 5 hours. The mixture was diluted with EtOAc, poured into 1N HCl (15 mL) and the aqueous layer was extracted with EtOAc (2×40 mL). Combined organics were washed with a sat. $NaHCO_3$ solution (15 mL), then brine before being dried over $Na_2SO_4$, filtered and concentrated in vacuo. The residue was purified by silica gel flash chromatography eluting with a 0 to 70% EtOAc-heptane gradient to give the title compound (1.37 g, 86%) as a an off-white solid. MS: 435.3 (M+H$^+$).

[B] (S)-2-Amino-2-(4-methoxyphenyl)-N-((2S,3S)-1,1,1-trifluoro-2-hydroxy-4-methylpentan-3-yl)acetamide

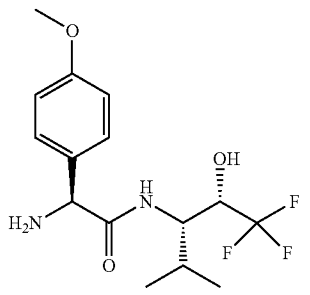 [SMILES: COc1ccc([C@H](N)C(=O)N[C@@H](C(C)C)[C@H](O)C(F)(F)F)cc1]

4M HCl in dioxane (3.94 mL, 15.8 mmol) was added at 0° C. to a solution of tert-butyl ((S)-1-(4-methoxyphenyl)-2-oxo-2-(((2S,3S)-1,1,1-trifluoro-2-hydroxy-4-methylpentan-3-yl)amino)ethyl)carbamate (1.37 g, 3.15 mmol) in MeOH (18 mL). The reaction mixture was stirred at this temperature for 10 min and then allowed to warm to room temperature and stirring was continued for 6 hours. The mixture was evaporated to dryness and the residue was triturated with diisopropylether. The solid precipitate was filtered off and further dried under the high vacuum to give the title compound (1.19 g, 97%, HCl salt) as colorless solid. MS: 335.2 (M+H$^+$).

[C] tert-Butyl ((S)-3-(3-chlorophenyl)-1-(((S)-1-(4-methoxyphenyl)-2-oxo-2-(((2S,3S)-1,1,1-trifluoro-2-hydroxy-4-methylpentan-3-yl)amino)ethyl)amino)-1-oxopropan-2-yl)carbamate

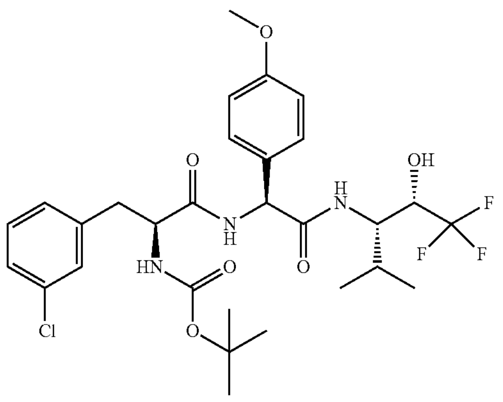 [SMILES: COc1ccc([C@H](NC(=O)[C@H](Cc2cccc(Cl)c2)NC(=O)OC(C)(C)C)C(=O)N[C@@H](C(C)C)[C@H](O)C(F)(F)F)cc1]

In a round-bottomed flask, (S)-2-amino-2-(4-methoxyphenyl)-N-((2S,3S)-1,1,1-trifluoro-2-hydroxy-4-methylpentan-3-yl)acetamide hydrochloride (0.418 g, 1.13 mmol), (2S)-2-(tert-butoxycarbonylamino)-3-(3-chlorophenyl)propanoic acid (0.338 g, 1.13 mmol) and HATU (0.471 g, 1.24 mmol) were dissolved in DMF (4 mL) and the mixture cooled to 0° C. Hünig's base (0.591 mL, 3.38 mmol) was added to the reaction mixture which was stirred at this temperature for 10 min, then allowed to warm up to room temperature and stirring was continued for 2.5 hours. The mixture was diluted with EtOAc, poured into a 1N aqueous HCl solution (5 mL) and the aqueous layer was extracted with EtOAc (2×20 mL). Combined organics were washed with a sat. $NaHCO_3$ solution (5 mL), then brine before being dried over $Na_2SO_4$, filtered and concentrated in vacuo. The residue was purified by silica gel flash chromatography eluting with a 0 to 70% EtOAc-heptane gradient to give the title compound (0.598 g, 84%) as an off-white solid. MS: 616.4 ($M+H^+$).

[D] (S)-2-Amino-3-(3-chlorophenyl)-N—((S)-1-(4-methoxyphenyl)-2-oxo-2-(((2S,3S)-1,1,1-trifluoro-2-hydroxy-4-methylpentan-3-yl)amino)ethyl)propanamide

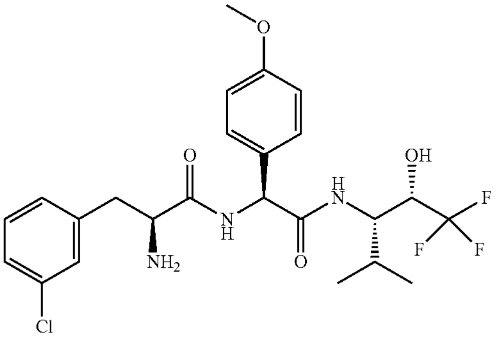 [SMILES: COc1ccc([C@H](NC(=O)[C@@H](N)Cc2cccc(Cl)c2)C(=O)N[C@@H](C(C)C)[C@H](O)C(F)(F)F)cc1]

4M HCl in dioxane (1.46 mL, 5.82 mmol) was added at 0° C. to a solution of tert-butyl ((S)-3-(3-chlorophenyl)-1-(((S)-1-(4-methoxyphenyl)-2-oxo-2-(((2S,3S)-1,1,1-trifluoro-2-hydroxy-4-methylpentan-3-yl)amino)ethyl)amino)-1-oxopropan-2-yl)carbamate (0.598 g, 0.971 mmol) in MeOH (6 mL). The reaction mixture was stirred at this temperature for 10 min and then allowed to warm up to room temperature and stirring was continued for 5 hours. The mixture was evaporated to dryness and the residue was triturated with diisopropylether. The solid precipitate was filtered off and further dried under the high vacuum to give the title compound (0.476 g, 86%, HCl salt) as an off-white solid. MS: 516.3 ($M+H^+$).

Intermediate A-2

(S)-2-Amino-3-(3-fluorophenyl)-N—((S)-1-(4-methoxyphenyl)-2-oxo-2-(((2S,3S)-1,1,1-trifluoro-2-hydroxy-4-methylpentan-3-yl)amino)ethyl)propanamide

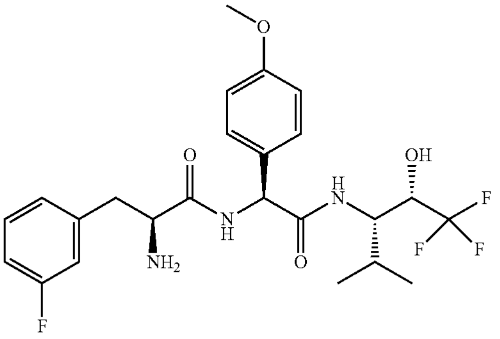

was prepared in analogy to intermediate A-1, but using in step C] (2S)-2-(tert-butoxycarbonylamino)-3-(3-fluorophenyl)propanoic acid, to give the title compound as light green solid as hydrochloride; MS: 500.4 ($M+H^+$).

Intermediate A-3

(S)-2-Amino-3-(3-cyanophenyl)-N—((S)-1-(4-methoxyphenyl)-2-oxo-2-(((2S,3S)-1,1,1-trifluoro-2-hydroxy-4-methylpentan-3-yl)amino)ethyl)propanamide

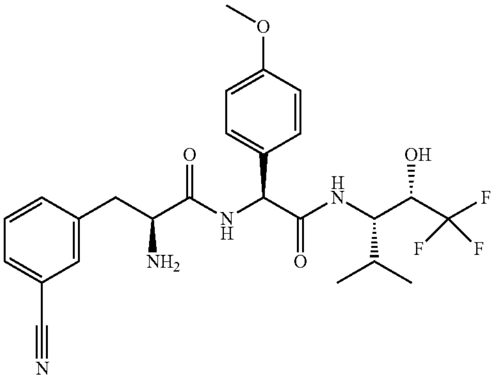 [SMILES: COc1ccc([C@H](NC(=O)[C@@H](N)Cc2cccc(C#N)c2)C(=O)N[C@@H](C(C)C)[C@H](O)C(F)(F)F)cc1]

was prepared in analogy to intermediate A-1, but using in step [C] (2S)-2-(tert-butoxycarbonylamino)-3-(3-cyanophenyl)propanoic acid, to give the title compound as light brown solid as hydrochloride; MS: 507.3 ($M+H^+$).

Intermediate A-4

(2S)-2-Amino-N-[(1S)-1-(4-methoxyphenyl)-2-oxo-2-[[(2S,3S)-1,1,1-trifluoro-2-hydroxy-4-methylpentan-3-yl]amino]ethyl]-3-pyridin-3-ylpropanamide

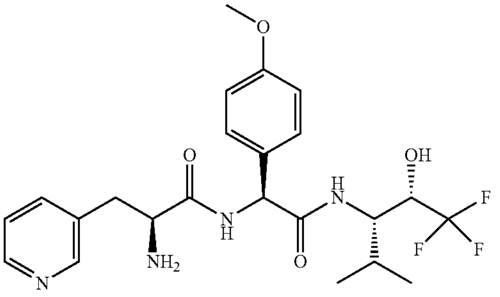 [SMILES: COc1ccc([C@H](NC(=O)[C@@H](N)Cc2cccnc2)C(=O)N[C@@H](C(C)C)[C@H](O)C(F)(F)F)cc1]

was prepared in analogy to intermediate A-1, but using in step [C] (2S)-2-(tert-butoxycarbonylamino)-3-(3-pyridyl) propanoic acid, to give the title compound as off-white solid as hydrochloride; MS: 483.4 ($M+H^+$).

Intermediate A-5

(2S)-2-Amino-3-(2-cyanophenyl)-N-[(1S)-1-(4-methoxyphenyl)-2-oxo-2-[[(2S,3S)-1,1,1-trifluoro-2-hydroxy-4-methylpenta-3-yl]amino]ethyl]propanamide

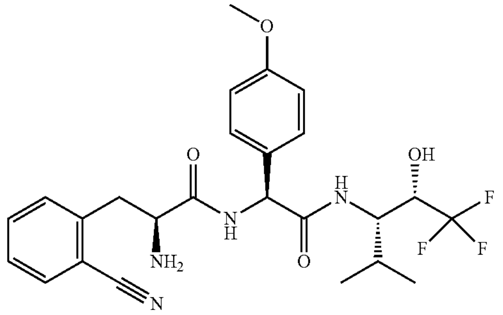 [SMILES: COc1ccc([C@H](NC(=O)[C@@H](N)Cc2ccccc2C#N)C(=O)N[C@@H](C(C)C)[C@H](O)C(F)(F)F)cc1]

was prepared in analogy to intermediate A-1, but using in step [C] (2S)-2-(tert-butoxycarbonylamino)-3-(2-cyanophenyl)propanoic acid, to give the title compound as off-white solid as hydrochloride; MS: 483.4 (M+H$^+$).

Intermediate A-6 tert-Butyl 2-[4-[(2S)-2-amino-3-[[(1S)-1-(4-methoxyphenyl)-2-oxo-2-[[(2S,3S)-1,1,1-trifluoro-2-hydroxy-4-methylpentan-3-yl]amino]ethyl]amino]-3-oxopropyl]phenoxy]acetate

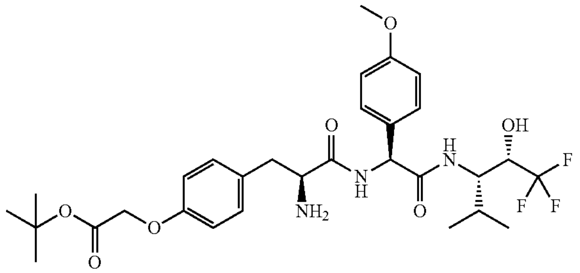 [SMILES: COc1ccc([C@H](NC(=O)[C@@H](N)Cc2ccc(OCC(=O)OC(C)(C)C)cc2)C(=O)N[C@@H](C(C)C)[C@H](O)C(F)(F)F)cc1]

was prepared in analogy to intermediate A-1, but using in step [C] (2S)-2-[(2-methylpropan-2-yl)oxycarbonylamino]-3-[4-[2-[(2-methylpropan-2-yl)oxy]-2-oxoethoxy]phenyl] propanoic acid (Intermediate K-1) and replacing in step D methanol by dioxane as solvent, to give the title compound as colorless solid as hydrochloride; MS: 612.3 (M+H$^+$).

Intermediate A-7 tert-Butyl 2-[3-[(2S)-2-amino-3-[[(1S)-1-(4-methoxyphenyl)-2-oxo-2-[[(2S,3S)-1,1,1-trifluoro-2-hydroxy-4-methylpentan-3-yl]amino]ethyl]amino]-3-oxopropyl]phenoxy]acetate

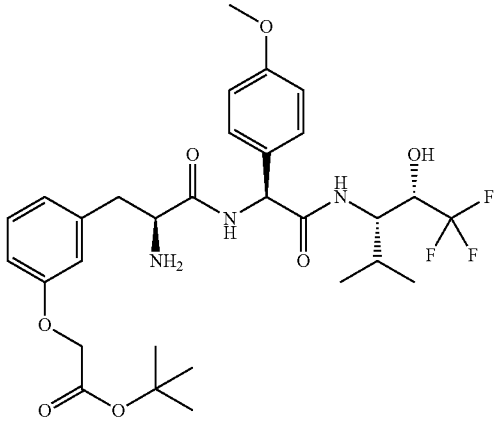 [SMILES: COc1ccc([C@H](NC(=O)[C@@H](N)Cc2cccc(OCC(=O)OC(C)(C)C)c2)C(=O)N[C@@H](C(C)C)[C@H](O)C(F)(F)F)cc1]

was prepared in analogy to intermediate A-1, but using in step [C] (2S)-2-[(2-methylpropan-2-yl)oxycarbonylamino]-3-[3-[2-[(2-methylpropan-2-yl)oxy]-2-oxoethoxy]phenyl] propanoic acid (Intermediate K-2) and replacing in step D methanol by dioxane as solvent, to give the title compound as colorless solid as hydrochloride; MS: 612.3 (M+H$^+$).

Intermediate A-8

(2S)-2-Amino-N-[(1S)-1-(4-methoxyphenyl)-2-oxo-2-[[(2S,3S)-1,1,1-trifluoro-2-hydroxy-4-methylpentan-3-yl]amino]ethyl]propanamide

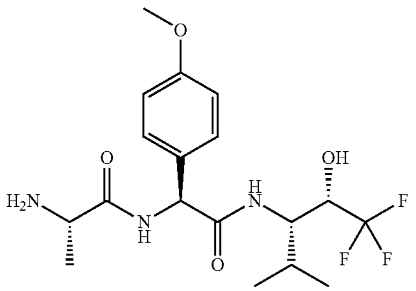 [SMILES: COc1ccc([C@H](NC(=O)[C@H](C)N)C(=O)N[C@@H](C(C)C)[C@H](O)C(F)(F)F)cc1]

was prepared in analogy to intermediate A-1, but using in step [C] (2S)-2-(tert-butoxycarbonylamino)propanoic acid, to give the title compound as colorless solid as hydrochloride; MS: 406.5 (M+H$^+$).

Intermediate A-9

(2S)-2-Amino-3-methoxy-N-[(1S)-1-(4-methoxyphenyl)-2-oxo-2-[[(2S,3S)-1,1,1-trifluoro-2-hydroxy-4-methylpentan-3-yl]amino]ethyl]propanamide

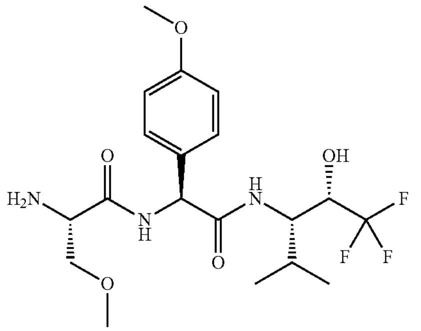 [SMILES: COC[C@H](N)C(=O)N[C@H](C(=O)N[C@@H](C(C)C)[C@H](O)C(F)(F)F)c1ccc(OC)cc1]

was prepared in analogy to intermediate A-1, but using in step [C] (2S)-2-(tert-butoxycarbonylamino)-3-methoxy-propanoic acid, to give the title compound as a light yellow solid as hydrochloride; MS: 436.3 (M+H$^+$).

Intermediate A-10

(S)-2-Amino-3-(tert-butoxy)-N—((S)-1-(4-methoxyphenyl)-2-oxo-2-(((2S,3S)-1,1,1-trifluoro-2-hydroxy-4-methylpentan-3-yl)amino)ethyl)propanamide

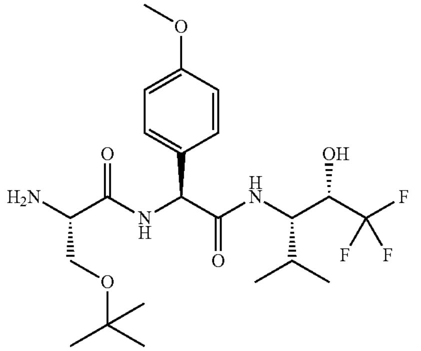 [SMILES: COc1ccc([C@H](NC(=O)[C@@H](N)COC(C)(C)C)C(=O)N[C@@H](C(C)C)[C@H](O)C(F)(F)F)cc1]

was prepared in analogy to intermediate A-1, but using in step [C] (2S)-3-tert-butoxy-2-(tert-butoxycarbonylamino) propanoic acid and replacing in step D methanol by dioxane as solvent, to give the title compound as colorless solid as hydrochloride; MS: 478.3 (M+H$^+$).

Intermediate A-11

(2S)-2-Amino-N-[(1S)-1-(4-methoxyphenyl)-2-oxo-2-[[(2S,3S)-1,1,1-trifluoro-2-hydroxy-4-methylpentan-3-yl]amino]ethyl]-3-phenylmethoxypropanamide

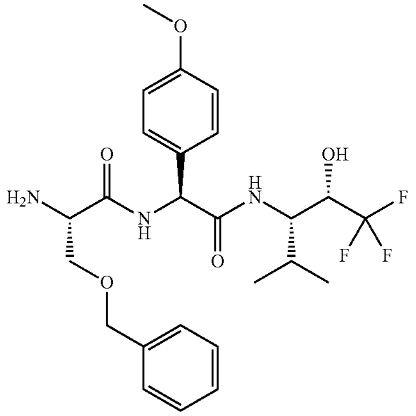 [SMILES: COc1ccc([C@H](NC(=O)[C@@H](N)COCc2ccccc2)C(=O)N[C@@H](C(C)C)[C@H](O)C(F)(F)F)cc1]

was prepared in analogy to intermediate A-1, but using in step [C] (2S)-3-benzyloxy-2-(tert-butoxycarbonylamino) propanoic acid, to give the title compound as off-white solid as hydrochloride; MS: 512.3 (M+H$^+$).

Intermediate A-12 tert-Butyl (4S)-4-amino-5-[[(1S)-1-(4-methoxyphenyl)-2-oxo-2-[[(2S,3S)-1,1,1-trifluoro-2-hydroxy-4-methylpentan-3-yl]amino]ethyl]amino]-5-oxopentanoate

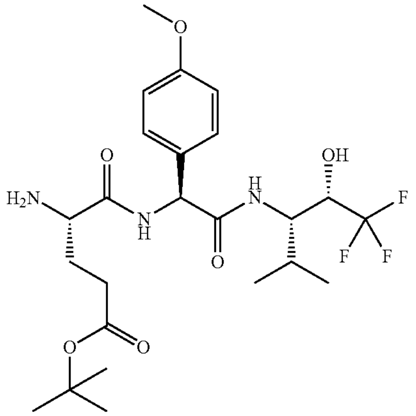 [SMILES: COc1ccc([C@H](NC(=O)[C@@H](N)CCC(=O)OC(C)(C)C)C(=O)N[C@@H](C(C)C)[C@H](O)C(F)(F)F)cc1]

was prepared in analogy to intermediate A-1, but using in step [C] (2S)-5-tert-butoxy-2-(tert-butoxycarbonylamino)-5-oxo-pentanoic acid and replacing in step D methanol by dioxane as solvent, to give the title compound as colorless solid; MS: 520.3 (M+H$^+$).

Intermediate A-13

2-[4-[[(2S)-3-(3-(Chlorophenyl)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxopropan-2-yl]carbamoyl]phenoxy]acetic Acid

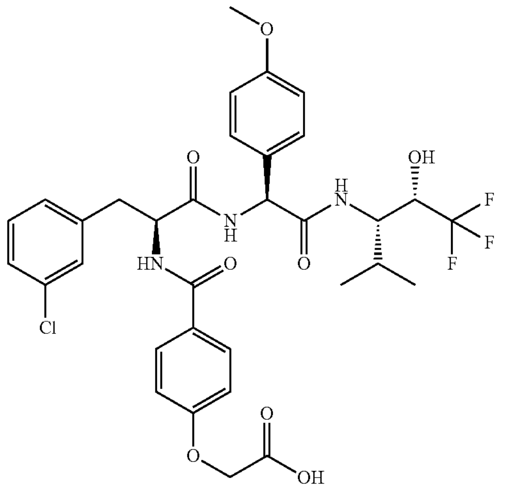 [SMILES: COc1ccc([C@H](NC(=O)[C@H](Cc2cccc(Cl)c2)NC(=O)c2ccc(OCC(=O)O)cc2)C(=O)N[C@@H](C(C)C)[C@H](O)C(F)(F)F)cc1]

[A] tert-Butyl 2-[4-[[(2S)-3-(3-chlorophenyl)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxopropan-2-yl]carbamoyl]phenoxy]acetate

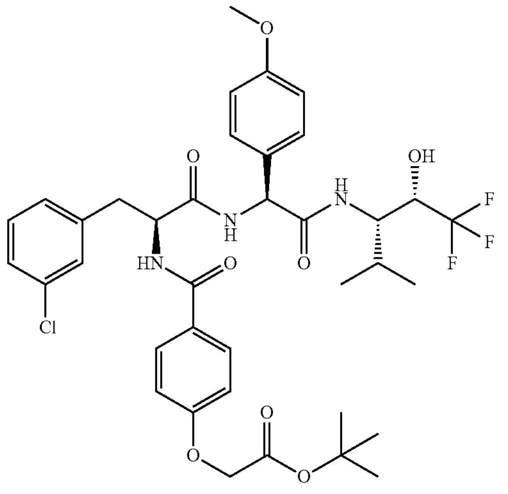 [SMILES: COc1ccc([C@H](NC(=O)[C@H](Cc2cccc(Cl)c2)NC(=O)c2ccc(OCC(=O)OC(C)(C)C)cc2)C(=O)N[C@@H](C(C)C)[C@H](O)C(F)(F)F)cc1]

(S)-2-Amino-3-(3-chlorophenyl)-N—((S)-1-(4-methoxyphenyl)-2-oxo-2-(((2S,3S)-1,1,1-trifluoro-2-hydroxy-4-methylpentan-3-yl)amino)ethyl)propanamide hydrochloride (Intermediate A-1, 0.06 g, 0.109 mmol), 4-(2-tert-butoxy-2-oxo-ethoxy)benzoic acid (0.027 g, 0.109 mmol) and HATU (0.045 g, 0.119 mmol) were dissolved in DMF (1 mL) in a round-bottomed flask, and the mixture cooled to 0° C. Hünig's base (0.057 mL, 0.326 mmol) was added to the reaction mixture which was stirred at this temperature for 10 min, then allowed to warm up to room temperature and stirring was continued for 2 hours. The mixture was diluted with EtOAc, poured into a 1N aqueous HCl solution (5 mL) and the aqueous layer was extracted with EtOAc (2×10 mL). Combined organics were washed with a sat. $NaHCO_3$ solution (5 mL), then brine before being dried over $Na_2SO_4$, filtered and concentrated in vacuo. The residue was purified by silica gel flash chromatography eluting with a 0 to 100% EtOAc-heptane gradient to give the title compound (0.079 g, 95%) as colorless solid. MS: 750.6 (M+H$^+$).

[B] 2-[4-[[(2S)-3-(3-Chlorophenyl)-1-[[(4-methoxyphenyl)-2-oxo-2-[[(2S,3S)-1,1,1-trifluoro-2-hydroxy-4-methylpentan-3-yl]amino]ethyl]amino]-1-oxopropan-2-yl]carbamoyl]phenoxy]acetic Acid

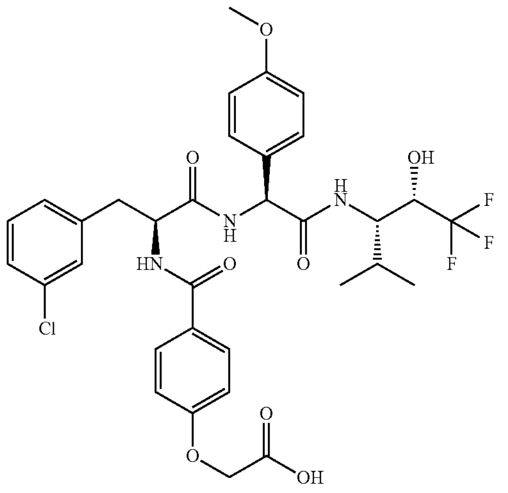 [SMILES: COc1ccc([C@H](NC(=O)[C@H](Cc2cccc(Cl)c2)NC(=O)c2ccc(OCC(=O)O)cc2)C(=O)N[C@@H](C(C)C)[C@H](O)C(F)(F)F)cc1]

To a solution of tert-butyl 2-[4-[[(2S)-3-(3-chlorophenyl)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxopropan-2-yl]carbamoyl]phenoxy]acetate (0.079 g, 0.105 mmol) in DCM (0.5 mL) was added TFA (0.405 mL, 5.26 mmol) and the reaction mixture was stirred at room temperature for 2 hours. The mixture was concentrated in vacuo, the residue was triturated in diisopropylether, filtered and further dried under high vacuum to give the title compound (0.057 g, 62%) as an off-white solid. MS: 694.3 (M+H$^+$).

Intermediate A-14

2-[3-[[(2S)-3-(3-Chlorophenyl)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxopropan-2-yl]carbamoyl]phenoxy]acetic Acid

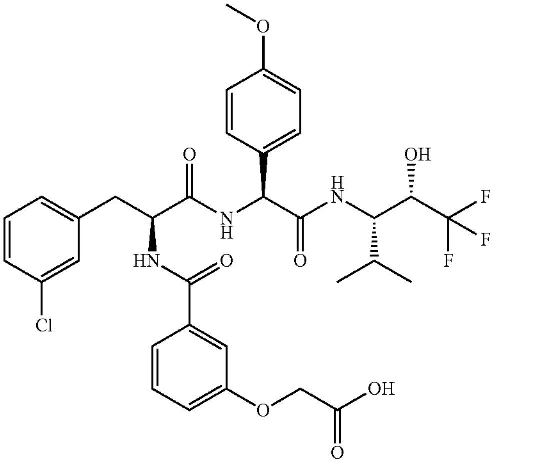 [SMILES: COc1ccc([C@H](NC(=O)[C@H](Cc2cccc(Cl)c2)NC(=O)c2cccc(OCC(=O)O)c2)C(=O)N[C@@H](C(C)C)[C@H](O)C(F)(F)F)cc1]

was prepared in analogy to intermediate A-13, but using in step [A] 3-(2-tert-butoxy-2-oxo-ethoxy)benzoic acid, to give the title compound as colorless solid; MS: 694.5 (M+H$^+$).

Intermediate A-15

2-[4-[[(2S)-3-(3-Cyanophenyl)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxopropan-2-yl]carbamoyl]phenoxy]acetic Acid

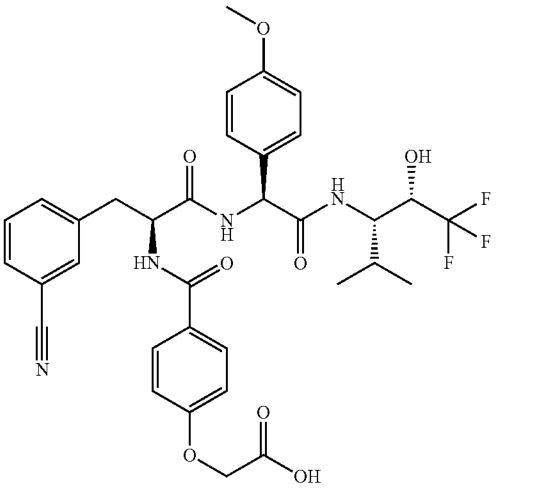 [SMILES: COc1ccc([C@H](NC(=O)[C@H](Cc2cccc(C#N)c2)NC(=O)c2ccc(OCC(=O)O)cc2)C(=O)N[C@@H](C(C)C)[C@H](O)C(F)(F)F)cc1]

was prepared in analogy to intermediate A-13, but using in step [A] (S)-2-amino-3-(3-cyanophenyl)-N—((S)-1-(4-methoxyphenyl)-2-oxo-2-(((2S,3S)-1,1,1-trifluoro-2-hydroxy-4-methylpentan-3-yl)amino)ethyl)propanamide hydrochloride (Intermediate A-3), to give the title compound as colorless solid; MS: 685.3 (M+H$^+$).

Intermediate A-16

2-[3-[[(2S)-3-(3-Cyanophenyl)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxopropan-2-yl]carbamoyl]phenoxy]acetic Acid

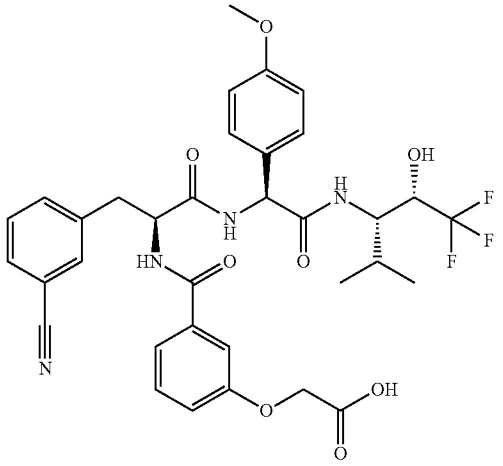 [SMILES: COc1ccc([C@H](NC(=O)[C@H](Cc2cccc(C#N)c2)NC(=O)c2cccc(OCC(=O)O)c2)C(=O)N[C@@H](C(C)C)[C@H](O)C(F)(F)F)cc1]

was prepared in analogy to intermediate A-13, but using in step [A] (S)-2-amino-3-(3-cyanophenyl)-N—((S)-1-(4-methoxyphenyl)-2-oxo-2-(((2S,3S)-1,1,1-trifluoro-2-hydroxy-4-methylpentan-3-yl)amino)ethyl)propanamide hydrochloride (Intermediate A-3) and 3-(2-tert-butoxy-2-oxo-ethoxy)benzoic acid, to give the title compound as colorless solid; MS: 685.3 (M+H$^+$).

Intermediate A-17 tert-Butyl N-[(5S)-5-amino-6-[[(1S)-1-(4-methoxyphenyl)-2-oxo-2-[[(2S,3S)-1,1,1-trifluoro-2-hydroxy-4-methylpentan-3-yl]amino]ethyl]amino]-6-oxohexyl]carbamate

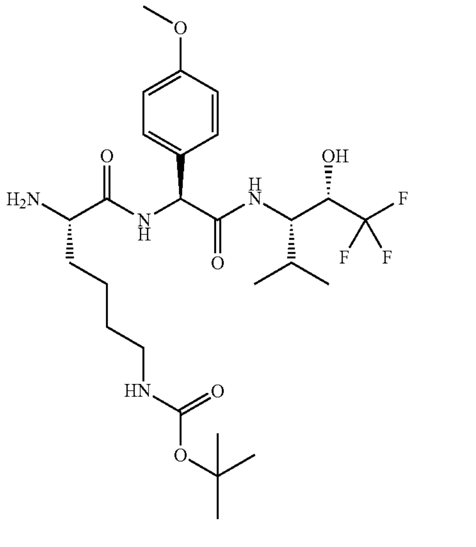 [SMILES: COc1ccc([C@H](NC(=O)[C@@H](N)CCCCNC(=O)OC(C)(C)C)C(=O)N[C@@H](C(C)C)[C@H](O)C(F)(F)F)cc1]

[A] tert-butyl N-[(5S)-5-(9H-fluoren-9-ylmethoxycarbonylamino)-6-[[(1S)-1-(4-methoxyphenyl)-2-oxo-2-[[(2S,3S)-1,1,1-trifluoro-2-hydroxy-4-methylpentan-3-yl]amino]ethyl]amino]-6-oxohexyl] carbamate

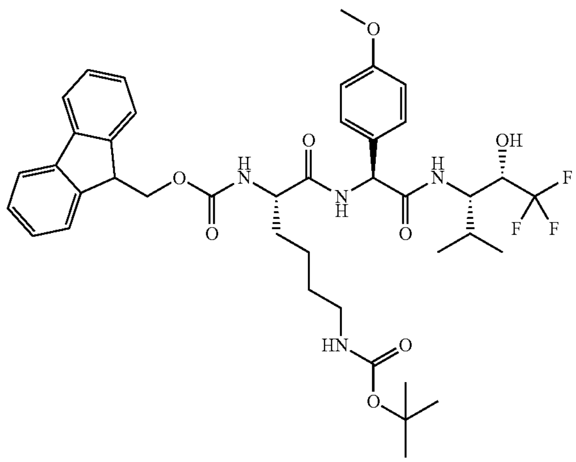 [SMILES: COc1ccc([C@H](NC(=O)[C@H](CCCCNC(=O)OC(C)(C)C)NC(=O)OCC2c3ccccc3-c3ccccc32)C(=O)N[C@@H](C(C)C)[C@H](O)C(F)(F)F)cc1]

To a solution of (S)-2-amino-2-(4-methoxyphenyl)-N-((2S,3S)-1,1,1-trifluoro-2-hydroxy-4-methylpentan-3-yl)acetamide hydrochloride (Intermediate A-1 [B], 0.200 g, 0.539 mmol), (2S)-6-(tert-butoxycarbonylamino)-2-(9H-fluoren-9-ylmethoxycarbonylamino)hexanoic acid (0.253 g, 0.539 mmol) and HATU (0.246 g, 0.647 mmol) in DMF (2 mL) cooled to 0° C. was added Huenig's base (0.283 mL, 1.62 mmol). The reaction mixture was stirred for 15 minutes, then allowed to warm up and stirred at room temperature for 2.5 hours. The mixture was diluted with EtOAc, poured into water and the aqueous phase was extracted with EtOAc. Combined organics were washed with brine, dried over $Na_2SO_4$, filtered and evaporated. The residue was purified by silica gel flash chromatography eluting with a 10 to 80% EtOAc-heptane gradient to give the title compound (0.350 g, 78%) as a white solid. MS: 785.4 ($M+H^+$).

[B] tert-Butyl N-[(5S)-5-amino-6-[[(1S)-1-(4-methoxyphenyl)-2-oxo-2-[[(2S,3S)-1,1,1-trifluoro-2-hydroxy-4-methylpentan-3-yl]amino]ethyl]amino]-6-oxohexyl]carbamate

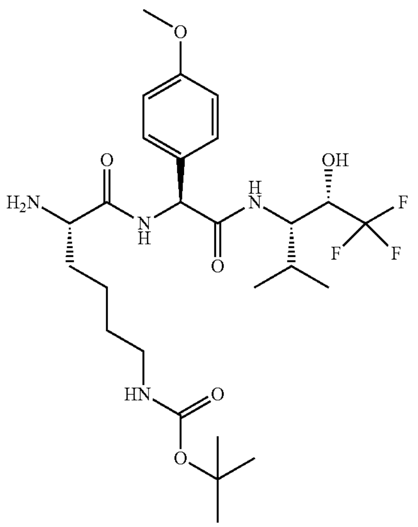 [SMILES: COc1ccc([C@H](NC(=O)[C@@H](N)CCCCNC(=O)OC(C)(C)C)C(=O)N[C@@H](C(C)C)[C@H](O)C(F)(F)F)cc1]

To a solution of tert-butyl N-[(5S)-5-(9H-fluoren-9-ylmethoxycarbonylamino)-6-[[(1S)-1-(4-methoxyphenyl)-2-oxo-2-[[(2S,3S)-1,1,1-trifluoro-2-hydroxy-4-methylpentan-3-yl]amino]ethyl]amino]-6-oxohexyl]carbamate (0.350 g, 0.446 mmol) in DMF (3 mL) was added diethylamine (0.230 mL, 2.6 mmol) and the reaction mixture stirred at room temperature for 2 hours. The solvent was evaporated to dryness and the residue was purified by silica gel flash chromatography eluting with a 0 to 15% MeOH-DCM gradient to give the title compound (0.192 g, 69%) as a light yellow solid. MS: 563.3 ($M+H^+$).

Intermediate A-18 tert-Butyl N-[(4S)-4-amino-5-[[(1S)-1-(4-methoxyphenyl)-2-oxo-2-[[(2S,3S)-1,1,1-trifluoro-2-hydroxy-4-methylpentan-3-yl]amino]ethyl]amino]-5-oxopentyl]carbamate

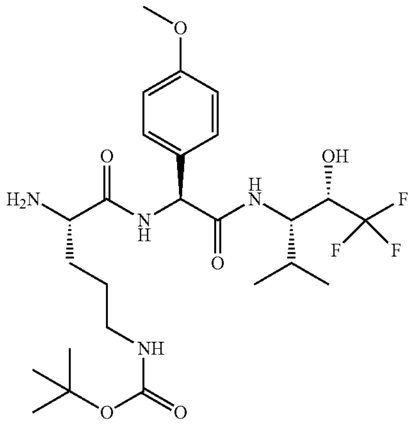 [SMILES: COc1ccc([C@H](NC(=O)[C@@H](N)CCCNC(=O)OC(C)(C)C)C(=O)N[C@@H](C(C)C)[C@H](O)C(F)(F)F)cc1]

was prepared in analogy to intermediate A-17, but using in step [A] (2S)-5-(tert-butoxycarbonylamino)-2-(9H-fluoren-9-ylmethoxycarbonylamino)pentanoic acid, to give the title compound as a light yellow waxy solid. MS: 549.3 (M+H$^+$).

Intermediate A-19 tert-Butyl N-[[4-[(2S)-2-amino-3-[[(1S)-1-(4-methoxyphenyl)-2-oxo-2-[[(2S,3S)-1,1,1-trifluoro-2-hydroxy-4-methylpentan-3-yl]amino]ethyl]amino]-3-oxopropyl]phenyl]methyl]carbamate

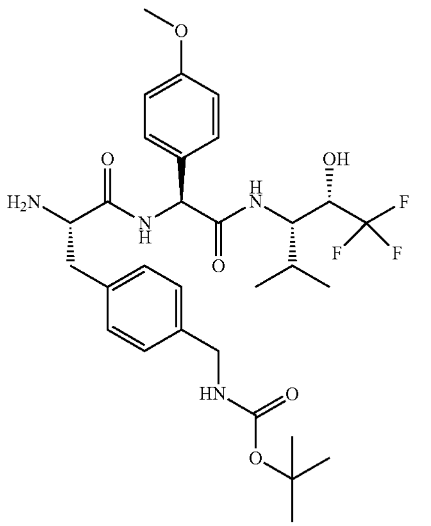 [SMILES: COc1ccc([C@H](NC(=O)[C@@H](N)Cc2ccc(CNC(=O)OC(C)(C)C)cc2)C(=O)N[C@@H](C(C)C)[C@H](O)C(F)(F)F)cc1]

was prepared in analogy to intermediate A-17, but using in step [A] (2S)-3-[4-[(tert-butoxycarbonylamino)methyl]phenyl]-2-(9H-fluoren-9-ylmethoxycarbonylamino)propanoic acid, to give the title compound as a white solid. MS: 611.3 (M+H$^+$).

Intermediate A-20

(2S)-2-Amino-3-[tert-butyl(dimethyl)silyl]oxy-N-[(1S)-1-(4-methoxyphenyl)-2-oxo-2-[[(2S,3S)-1,1,1-trifluoro-2-hydroxy-4-methylpentan-3-yl]amino]ethyl]propanamide

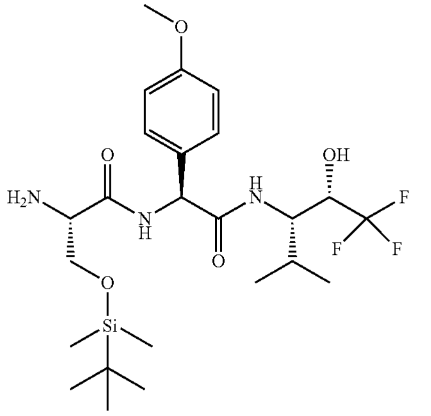 [SMILES: COc1ccc([C@H](NC(=O)[C@@H](N)CO[Si](C)(C)C(C)(C)C)C(=O)N[C@@H](C(C)C)[C@H](O)C(F)(F)F)cc1]

[A] 9H-Fluoren-9-ylmethyl N-[(2S)-3-[tert-butyl(dimethyl)silyl]oxy-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxopropan-2-yl]carbamate

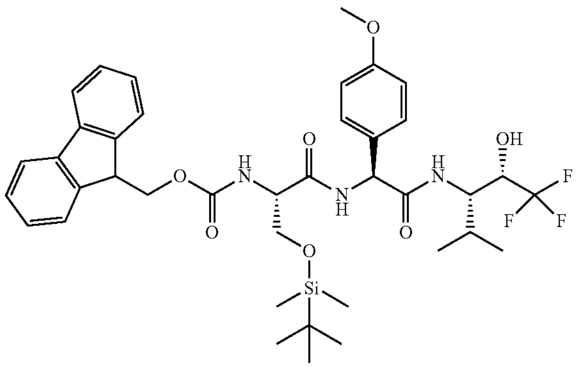 [SMILES: COc1ccc([C@H](NC(=O)[C@H](CO[Si](C)(C)C(C)(C)C)NC(=O)OCC2c3ccccc3-c3ccccc32)C(=O)N[C@@H](C(C)C)[C@H](O)C(F)(F)F)cc1]

To a solution of (S)-2-amino-2-(4-methoxyphenyl)-N-((2S,3S)-1,1,1-trifluoro-2-hydroxy-4-methylpentan-3-yl)acetamide hydrochloride (Intermediate A-1 [B], 0.240 g, 0.647 mmol) in DMF (10 mL) cooled to 0° C. with an ice bath was added Huenig's base (0.565 mL, 3.24 mmol). Then, (2S)-3-[tert-butyl (dimethyl)silyl]oxy-2-(9H-fluoren-9-ylmethoxycarbonylamino)propanoic acid (0.286 g, 0.647 μmol) followed by HATU (0.295 g, 0.777 mmol) were added and the reaction mixture was stirred at this temperature for 1 hour. The mixture was diluted with EtOAc, poured into a sat. $NaHCO_3$ aqueous solution and the aqueous layer extracted with EtOAc. Combined organics were washed with $NH_4Cl$ and brine, then dried over $Na_2SO_4$, filtered and evaporated. The residue was purified by silica gel flash chromatography, eluting with a 0 to 60% EtOAc/heptane gradient to give the title compound (0.321 g, 65%) as a colorless solid. MS: 758.4 (M+H$^+$).

[B] (2S)-2-Amino-3-[tert-butyl(dimethyl)silyl]oxy-N-[(1S)-1-(4-methoxyphenyl)-2-oxo-2-[[(2S,3S)-1,1,1-trifluoro-2-hydroxy-4-methylpentan-3-yl]amino]ethyl]propanamide

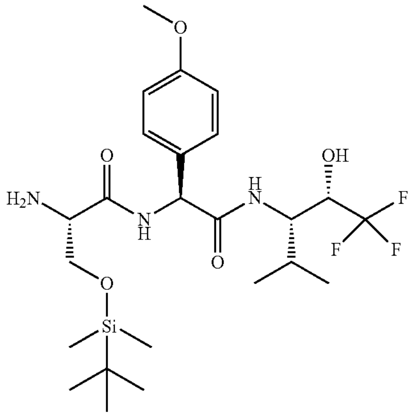 [SMILES: COc1ccc([C@H](NC(=O)[C@@H](N)CO[Si](C)(C)C(C)(C)C)C(=O)N[C@@H](C(C)C)[C@H](O)C(F)(F)F)cc1]

To a solution of 9H-fluoren-9-ylmethyl N-[(2S)-3-[tert-butyl(dimethyl)silyl]oxy-1-[[(1S)-1-(4-methoxyphenyl)-2- oxo-2-[[(2S,3S)-1,1,1-trifluoro-2-hydroxy-4-methylpentan-3-yl]amino]ethyl]amino]-1-oxopropan-2-yl]carbamate (0.315 g, 0.416 mmol) in DCM (3 mL) was added diethylamine (0.434 mL, 4.16 mmol) and the reaction mixture was stirred at room temperature overnight. The solvent was evaporated and the residue purified by silica gel flash chromatography, eluting with a 0 to 100% EtOAc-heptane gradient to give the title compound (0.161 g, 72%) as a colorless solid. MS: 536.3 ($M+H^+$).

Intermediate A-21

(2S)-2-Amino-N-[(1S)-1-(4-methoxyphenyl)-2-oxo-2-[[(2S,3S)-1,1,1-trifluoro-2-hydroxy-4-methylpentan-3-yl]amino]ethyl]-3-(trifluoromethoxy)propanamide

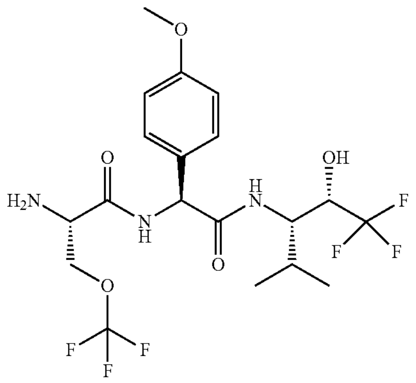 [SMILES: COc1ccc([C@H](NC(=O)[C@@H](N)COC(F)(F)F)C(=O)N[C@@H](C(C)C)[C@H](O)C(F)(F)F)cc1]

[A] Benzyl (2S)-[(2-(2-methylpropan-2-yl)oxycarbonylamino]-3-(trifluoromethoxy)propanoate

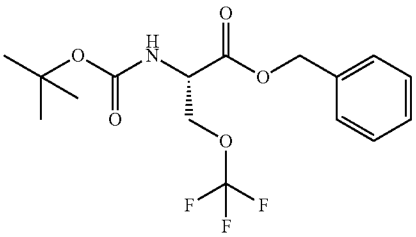 [SMILES: CC(C)(C)OC(=O)N[C@@H](COC(F)(F)F)C(=O)OCc1ccccc1]

In a sealed tube, potassium fluoride (0.123 g, 2.12 mmol, dried on the high vacuum overnight), silver trifluoromethanesulfonate (0.385 g, 1.5 mmol), selectfluor (0.266 g, 0.750 mmol) and benzyl (2S)-2-(tert-butoxycarbonylamino)-3-hydroxy-propanoate (0.148 g, 0.5 mmol) were added successively under Argon. Then, dry EtOAc (2.5 mL), 2-fluoropyridine (0.129 mL, 1.5 mmol) and (trifluoromethyl) trimethylsilane (0.240 mL, 1.5 mmol) were added successively under argon and the reaction mixture was stirred at room temperature overnight. The mixture was filtered through a plug of Decalite and washed with EtOAc. The filtrate was evaporated and the residue purified by silica gel flash chromatography, eluting with 0-100% EtOAc/heptane gradient to give the title compound (0.064 g, 72%) as a colorless oil. MS: 308.0 ($M-tBu+H^+$).

[B] (2S)-2-[(2-Methylpropan-2-yl)oxycarbonylamino]-3-(trifluoromethoxy)propanoic Acid

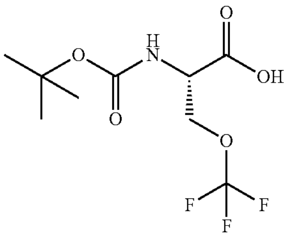 [SMILES: CC(C)(C)OC(=O)N[C@@H](COC(F)(F)F)C(=O)O]

A solution of benzyl (2S)-2-[(2-methylpropan-2-yl)oxycarbonylamino]-3-(trifluoromethoxy)propanoate (0.121 g, 0.333 mmol) in methanol (7 mL) was purged several times with Ar, then Pd on C (0.018 g, 0.017 mmol) was added and the reaction mixture was stirred at room temperature under a hydrogen atmosphere for 2 hours. The catalyst was removed by filtration and the filtrate concentrated in vacuo to give the title compound (0.085 g, 93%) as a colorless solid. MS: 272.2 ($M-H^-$).

[C] tert-Butyl N-[(2S)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxo-3-(trifluoromethoxy)propan-2-yl]carbamate

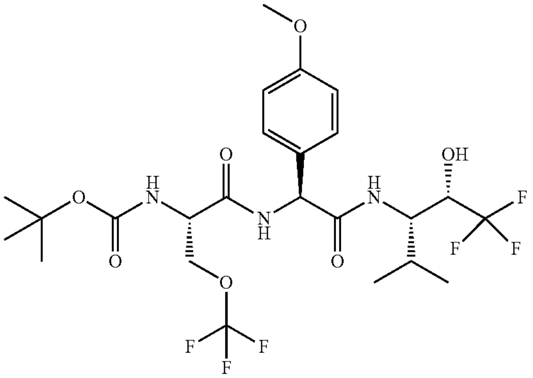 [SMILES: COc1ccc([C@H](NC(=O)[C@H](COC(F)(F)F)NC(=O)OC(C)(C)C)C(=O)N[C@@H](C(C)C)[C@H](O)C(F)(F)F)cc1]

To a solution of (S)-2-amino-2-(4-methoxyphenyl)-N-((2S,3S)-1,1,1-trifluoro-2-hydroxy-4-methylpentan-3-yl)acetamide hydrochloride (Intermediate A-1 [B], 0.115 g, 0.311 mmol), (2S)-2-[(2-methylpropan-2-yl)oxycarbonylamino]-3-(trifluoromethoxy)propanoic acid (0.085 g, 0.311 mmol) and HATU (0.130 g, 0.342 mmol) in DMF (1 mL) cooled to 0° C. was added Huenig's base (0.163 mL, 0.933 mmol). The reaction mixture was stirred for 15 minutes, then allowed to warm up to room temperature and stirred at room temperature for 1 hour. The mixture was diluted with EtOAc, poured into water and the aqueous layer was extracted with EtOAc. Combined organics were washed with brine, dried over $Na_2SO_4$, filtered and evaporated. The residue was purified by silica gel flash chromatography eluting with a 0 to 100% EtOAc-heptane gradient to give the title compound (0.041 g, 22%) as a colorless solid. MS: 590.3 ($M+H^+$).

[D] (2S)-2-Amino-N-[(1S)-1-(4-methoxyphenyl)-2-oxo-2-[[(2S,3S)-1,1,1-trifluoro-2-hydroxy-4-methylpentan-3-yl]amino]ethyl]-3-(trifluoromethoxy)propanamide

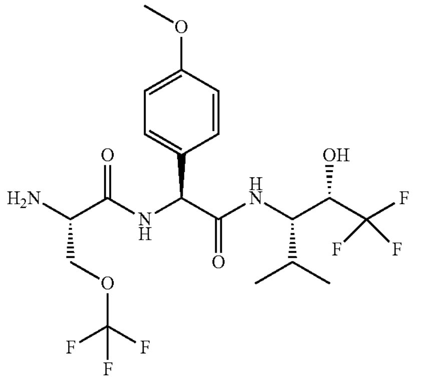 [SMILES: COc1ccc([C@H](NC(=O)[C@@H](N)COC(F)(F)F)C(=O)N[C@@H](C(C)C)[C@H](O)C(F)(F)F)cc1]

To a solution of tert-butyl N-[(2S)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxo-3-(trifluoromethoxy)propan-2-yl]carbamate (0.41 g, 0.069 mmol) in methanol (1 mL) was added 4M HCl in dioxane (0.174 mL, 0.695 mmol) and the reaction mixture was stirred at room temperature overnight. The mixture was evaporated to dryness and the residue was triturated with diisopropylether. The solid precipitate was filtered off and further dried under the high vacuum to give the title compound (0.034 g, 94%, HCl salt) as an orange solid. MS: 490.2 (M+H$^+$).

Intermediate A-22

(2S)-2-amino-N-[(1S)-1-(4-methoxyphenyl)-2-oxo-2-[[(2S,3S)-1,1,1-trifluoro-2-hydroxy-4-methylpentan-3-yl]amino]ethyl]-N'-[(4-methylphenyl)-diphenylmethyl]butanediamide

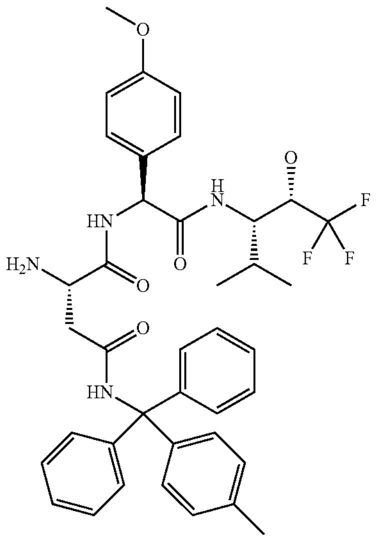 [SMILES: COc1ccc([C@H](NC(=O)[C@@H](N)CC(=O)NC(c2ccccc2)(c2ccccc2)c2ccc(C)cc2)C(=O)N[C@@H](C(C)C)[C@H](O)C(F)(F)F)cc1]

was prepared in analogy to intermediate A-17, but using in step [A] (2S)-4-[[diphenyl(p-tolyl)methyl]amino]-2-(9H-fluoren-9-ylmethoxycarbonylamino)-4-oxo-butanoic acid, to give the title compound as a yellow waxy solid. MS: 705.3 (M+H$^+$).

Intermediate A-23

(2S)-2-Amino-N-[(1S)-1-(4-methoxyphenyl)-2-oxo-2-[[(2S,3S)-1,1,1-trifluoro-2-hydroxy-4-methylpentan-3-yl]amino]ethyl]-N'-[(4-methylphenyl)-diphenylmethyl]butanediamide

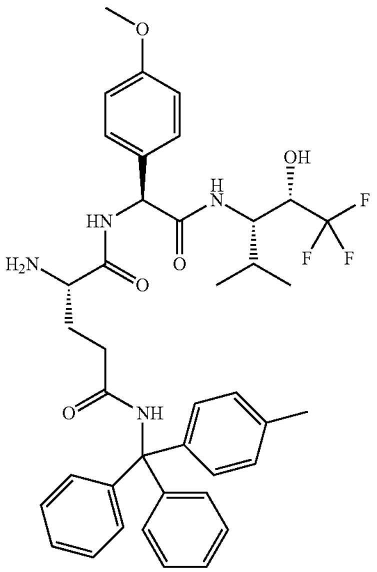 [SMILES: COc1ccc([C@H](NC(=O)[C@@H](N)CCC(=O)NC(c2ccccc2)(c2ccccc2)c2ccc(C)cc2)C(=O)N[C@@H](C(C)C)[C@H](O)C(F)(F)F)cc1]

was prepared in analogy to intermediate A-17, but using in step [A] (2S)-5-[[diphenyl(p-tolyl)methyl]amino]-2-(9H-fluoren-9-ylmethoxycarbonylamino)-5-oxo-pentanoic acid, to give the title compound as a yellow foam. MS: 719.4 (M+H$^+$).

Intermediate A-24

(2S)-2-Amino-3-cyano-N-[(1S)-1-(4-methoxyphenyl)-2-oxo-2-[[(2S,3S)-1,1,1-trifluoro-2-hydroxy-4-methylpentan-3-yl]amino]ethyl]propanamide

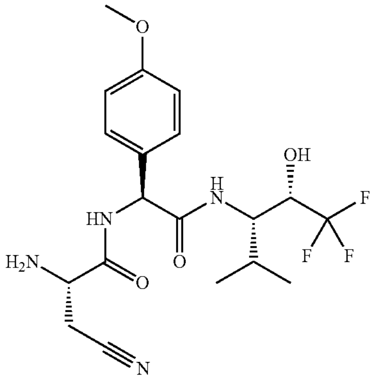 [SMILES: COc1ccc([C@H](NC(=O)[C@@H](N)CC#N)C(=O)N[C@@H](C(C)C)[C@H](O)C(F)(F)F)cc1]

was prepared in analogy to intermediate A-1, but using in step [C] (2S)-2-(tert-butoxycarbonylamino)-3-cyano-propanoic acid and replacing in step [D] methanol by dioxane as solvent, to give the title compound as a colorless solid as hydrochloride. MS: 431.2 (M+H$^+$).

Intermediate B-1

(2S)-2-Amino-3-(3-chlorophenyl)-N-[(1S and 1R)-2-oxo-1-phenyl-2-[[(2S,3S)-1,1,1-trifluoro-2-hydroxy-4-methylpentan-3-yl]amino]ethyl]propanamide

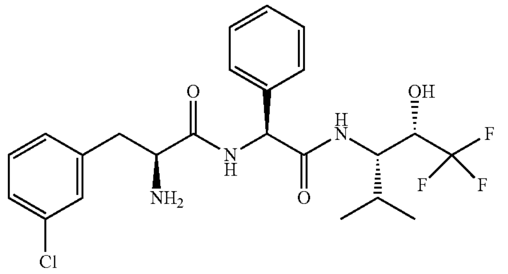 [SMILES: CC(C)[C@H](NC(=O)[C@@H](NC(=O)[C@@H](N)Cc1cccc(Cl)c1)c1ccccc1)[C@H](O)C(F)(F)F]

was prepared in analogy to intermediate A-1, but using in step [A] (2S)-2-(tert-butoxycarbonylamino)-2-phenyl-acetic, to give the title compound as colorless solid as hydrochloride; MS: 486.2 (M+H$^+$).

Intermediate B-2

(2S)-2-Amino-3-(3,4-dichlorophenyl)-N-[(1S and 1R)-)-2-oxo-1-phenyl-2-[[(2S,3S)-1,1,1-trifluoro-2-hydroxy-4-methylpentan-3-yl]amino]ethyl]propanamide

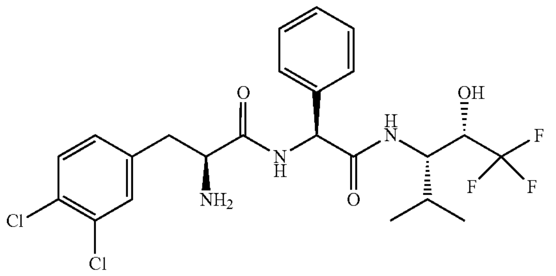 [SMILES: CC(C)[C@H](NC(=O)[C@@H](NC(=O)[C@@H](N)Cc1ccc(Cl)c(Cl)c1)c1ccccc1)[C@H](O)C(F)(F)F]

was prepared in analogy to intermediate A-1, but using in step [A] (2S)-2-(tert-butoxycarbonylamino)-2-phenyl-acetic and in step [C] (2S)-2-(tert-butoxycarbonylamino)-3-(3,4-chlorophenyl)propanoic acid, to give the title compound as off-white solid as hydrochloride; MS: 520.2 (M+H$^+$).

Intermediate B-3

(2R)-2-Amino-3-(3-chlorophenyl)-N-[(1S and 1R)-)-2-oxo-1-phenyl-2-[[(2S,3S)-1,1,1-trifluoro-2-hydroxy-4-methylpentan-3-yl]amino]ethyl]propanamide

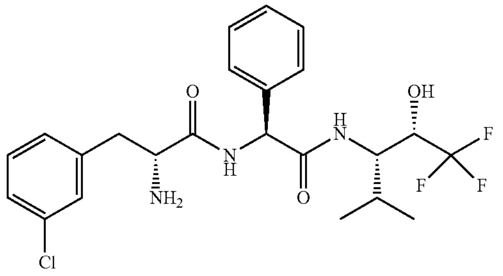 [SMILES: CC(C)[C@H](NC(=O)[C@@H](NC(=O)[C@H](N)Cc1cccc(Cl)c1)c1ccccc1)[C@H](O)C(F)(F)F]

was prepared in analogy to intermediate A-1, but using in step [A] (2S)-2-(tert-butoxycarbonylamino)-2-phenyl-acetic and in step [C] (2R)-2-(tert-butoxycarbonylamino)-3-(3-chlorophenyl)propanoic acid, to give the title compound as light brown foam as hydrochloride; MS: 486.2 (M+H$^+$).

Intermediate C-1

(2S)-2-Amino-3-(3-chlorophenyl)-N-[(1S and 1R)-1-(3-methoxyphenyl)-2-oxo-2-[[(1S,2S)-3,3,3-trifluoro-2-hydroxy-1-isopropyl-propyl]amino]ethyl]propanamide

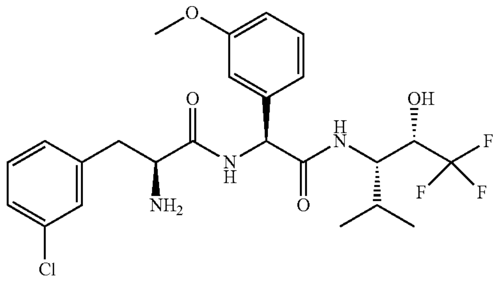 [SMILES: COc1cccc([C@H](NC(=O)[C@@H](N)Cc2cccc(Cl)c2)C(=O)N[C@@H](C(C)C)[C@H](O)C(F)(F)F)c1]

was prepared in analogy to intermediate A-1, but using in step [A] (2S)-2-(tert-butoxycarbonylamino)-2-(3-methoxyphenyl)acetic acid, to give the title compound as light brown gum as hydrochloride; MS: 516.2 (M+H$^+$).

Intermediate D-1

(2S)-2-[[(2S)-2-Amino-3-(3-chlorophenyl)propanoyl]amino]-3-phenyl-N-[(2S,3S)-1,1,1-trifluoro-2-hydroxy-4-methylpentan-3-yl]propanamide

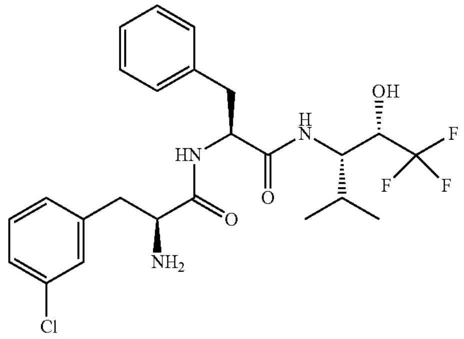 [SMILES: CC(C)[C@H](NC(=O)[C@H](Cc1ccccc1)NC(=O)[C@@H](N)Cc1cccc(Cl)c1)[C@H](O)C(F)(F)F]

was prepared in analogy to intermediate A-1, but using in step [A] (2S)-2-(tert-butoxycarbonylamino)-3-phenyl-propanoic acid, to give the title compound as colorless solid as hydrochloride; MS: 500.2 (M+H$^+$).

Intermediate D-2

(2S)-2-[[(2R)-2-Amino-3-(3-chlorophenyl)propanoyl]amino]-3-phenyl-N-[(2S,3S)-1,1,1-trifluoro-2-hydroxy-4-methylpentan-3-yl]propanamide

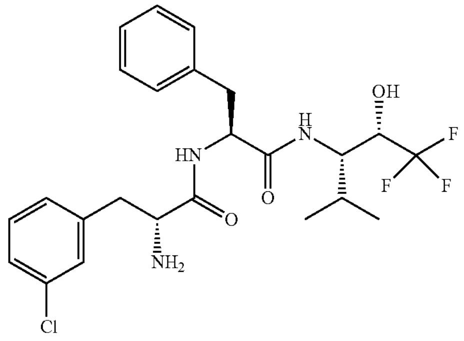 [SMILES: CC(C)[C@H](NC(=O)[C@H](Cc1ccccc1)NC(=O)[C@H](N)Cc1cccc(Cl)c1)[C@H](O)C(F)(F)F]

was prepared in analogy to intermediate A-1, but using in step [A] (2S)-2-(tert-butoxycarbonylamino)-3-phenyl-propanoic acid and in step [C] (2R)-2-(tert-butoxycarbonylamino)-3-(3-chlorophenyl)propanoic acid, to give the title compound as off-white solid as hydrochloride; MS: 500.2 (M+H$^+$).

Intermediate D-3

(S)-2-Amino-3-(3,4-dichlorophenyl)-N—((S)-1-oxo-3-phenyl-1-(((2S,3S)-1,1,1-trifluoro-2-hydroxy-4-methylpentan-3-yl)amino)propan-2-yl)propanamide

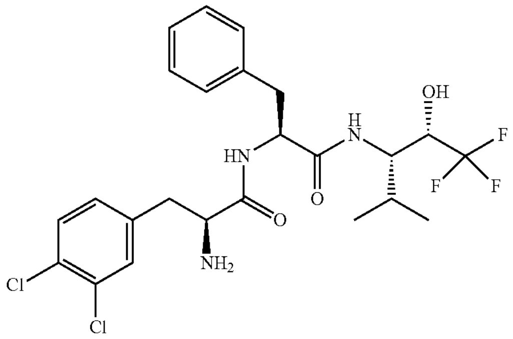 [SMILES: CC(C)[C@H](NC(=O)[C@H](Cc1ccccc1)NC(=O)[C@@H](N)Cc1ccc(Cl)c(Cl)c1)[C@H](O)C(F)(F)F]

was prepared in analogy to intermediate A-1, but using in step [A] (2S)-2-(tert-butoxycarbonylamino)-3-phenyl-propanoic acid and in step [C] (2S)-2-(tert-butoxycarbonylamino)-3-(3,4-chlorophenyl)propanoic acid, to give the title compound as off-white solid as hydrochloride; MS: 534.4 (M+H$^+$).

Intermediate D-4

(S)-2-Amino-3-cyclohexyl-N—((S)-1-oxo-3-phenyl-1-(((2S,3S)-1,1,1-trifluoro-2-hydroxy-4-methylpentan-3-yl)amino)propan-2-yl)propanamide

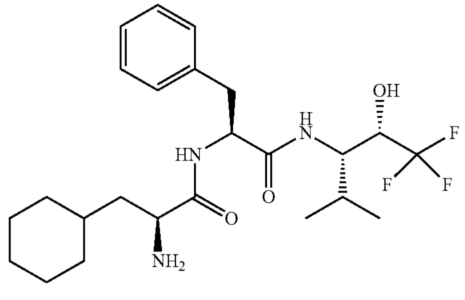 [SMILES: CC(C)[C@H](NC(=O)[C@H](Cc1ccccc1)NC(=O)[C@@H](N)CC1CCCCC1)[C@H](O)C(F)(F)F]

was prepared in analogy to intermediate A-1, but using in step [A] (2S)-2-(tert-butoxycarbonylamino)-3-phenyl-propanoic acid and in step [C] (2S)-2-(tert-butoxycarbonylamino)-3-cyclohexyl-propanoic acid, to give the title compound as off-white solid as hydrochloride; MS: 472.3 (M+H$^+$).

Intermediate E-1 tert-Butyl 2-[4-[(1S)-1-[[(2S)-2-amino-3-(3-fluorophenyl)propanoyl]amino]-2-oxo-2-[[(2S,3S)-1,1,1-trifluoro-2-hydroxy-4-methylpentan-3-yl]amino]ethyl]phenoxy]acetate

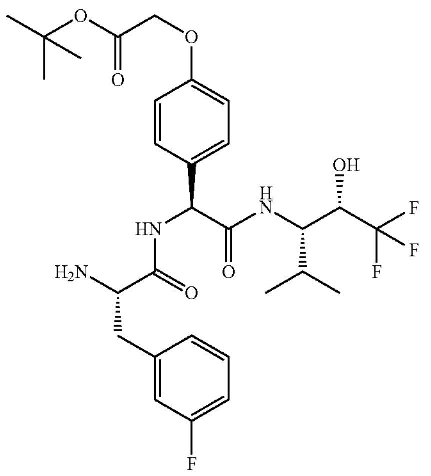 [SMILES: CC(C)[C@H](NC(=O)[C@@H](NC(=O)[C@@H](N)Cc1cccc(F)c1)c1ccc(OCC(=O)OC(C)(C)C)cc1)[C@H](O)C(F)(F)F]

was prepared in analogy to intermediate A-2, but using in step [A] (2S)-2-(tert-butoxycarbonylamino)-2-[4-(2-tert-butoxy-2-oxo-ethoxy)phenyl]acetic acid and replacing in the deprotection steps [B] and [D] methanol by dioxane as solvent, to give the title compound as light brown solid as hydrochloride; MS: 600.4 ($M+H^+$).

Intermediate J-1

3,3,3-Trifluoro-2-[3-(trifluoromethyl)phenyl]propanoic Acid

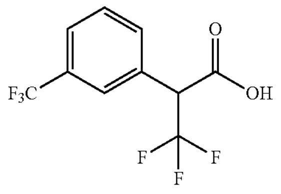 [SMILES: O=C(O)C(c1cccc(C(F)(F)F)c1)C(F)(F)F]

[A] Ethyl 3,3,3-trifluoro-2-methylsulfonyloxy-2-[3-(trifluoromethyl)phenyl]propanoate

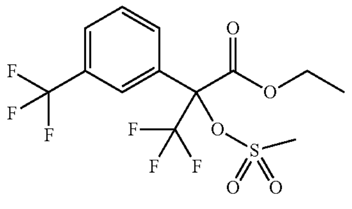 [SMILES: CCOC(=O)C(OS(C)(=O)=O)(c1cccc(C(F)(F)F)c1)C(F)(F)F]

To a solution of ethyl 3,3,3-trifluoro-2-hydroxy-2-[3-(trifluoromethyl)phenyl]propanoate (0.5 g, 1.58 mmol) in acetonitrile (5 mL) cooled to −5° C. was added TEA (0.882 mL, 6.33 mmol). Then, methanesulfonyl chloride (0.493 μL, 6.33 mmol) was added dropwise and the solution was stirred at this temperature for 20 minutes. The mixture was poured into ice/water and extracted with DCM. Combined organics were washed with brine, dried over $Na_2SO_4$ and evaporated to dryness. The residue was purified by silica gel flash chromatography, eluting with a 0 to 40% EtOAc-heptane gradient to give the title compound (0.470 g, 75%) as a colorless liquid. MS: 299.1 ($M-OS(O)_2CH_3^+$).

[B] Ethyl 3,3,3-trifluoro-2-[3-(trifluoromethyl)phenyl]propanoate

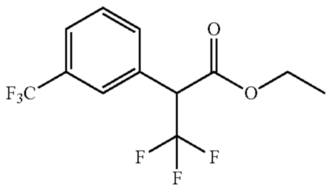 [SMILES: CCOC(=O)C(c1cccc(C(F)(F)F)c1)C(F)(F)F]

In a sealed vessel, a solution of ethyl 3,3,3-trifluoro-2-methylsulfonyloxy-2-[3-(trifluoromethyl)phenyl]propanoate (0.470 g, 1.19 mmol) in methanol (5 mL) was purged several times with Ar, then Pd on C (0.254 mg, 0.238 mmol) was added and the reaction mixture was stirred at room temperature under 3 bar hydrogen for 10 hours. The catalyst was removed by filtration and the filtrate concentrated in vacuo to give the title compound (0.358 g, 100%) as a colorless liquid. MS: 394.3 ($M-H^-$).

[C] 3,3,3-Trifluoro-2-[3-(trifluoromethyl)phenyl]propanoic Acid

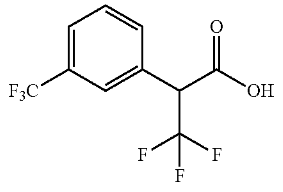 [SMILES: O=C(O)C(c1cccc(C(F)(F)F)c1)C(F)(F)F]

To a solution of ethyl 3,3,3-trifluoro-2-[3-(trifluoromethyl)phenyl]propanoate (0.205 g, 0.683 mmol) in dioxane (1.5 mL) was added conc. HCl (0.75 mL, 9.13 mmol) and the reaction mixture was heated at reflux for 40 hours. The mixture was allowed to cool to room temperature, then DCM was added and the phases separated. The aqueous phase was extracted with DCM. Combined organics were extracted with a sat. $Na_2CO_3$ aqueous solution. Combined aqueous layers were acidified to pH 1 with a 2M HCl aqueous solution and extracted with DCM. The organic phases were washed with brine, dried over $Na_2SO_4$, filtered, and evaporated to dryness to to give the title compound (0.070 g, 37%) as a light yellow solid. MS: 543.3 ($2M-H^-$).

Intermediate J-2

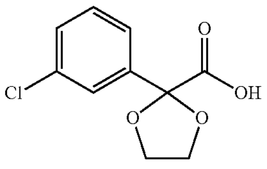 [SMILES: O=C(O)C1(c2cccc(Cl)c2)OCCO1]

[A] Ethyl 2-(3-chlorophenyl)-1,3-dioxolane-2-carboxylate

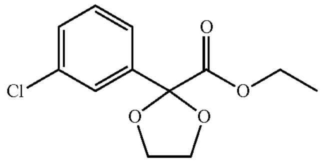 [SMILES: CCOC(=O)C1(c2cccc(Cl)c2)OCCO1]

To a solution of 2-chloroethanol (0.503 μL, 7.5 mmol) in a 2/1 mixture of DMF/THF (6 mL) was added ethyl 2-(3-chlorophenyl)-2-oxoacetate (1.06 g, 5 mmol) and the solution was cooled to −60° C. Potassium tert-butoxide (0.842 g, 7.5 mmol) in DMF (15 mL) was added dropwise over 30 minutes at this temperature. The reaction mixture was stirred for 1.5 hours, then allowed to warm to room temperature and stirred overnight. The mixture was diluted with EtOAc, poured into a 1M $NH_4Cl$ aqueous solution and the aqueous layer was extracted with EtOAc. Combined organics were washed with water, brine, dried over $Na_2SO_4$, filtered and evaporated to dryness to give the title compound (1.2 g, 94%) as a colourless oil. The crude product was used in the next step with no further purification.

[B] 2-(3-Chlorophenyl)-1,3-dioxolane-2-carboxylic Acid

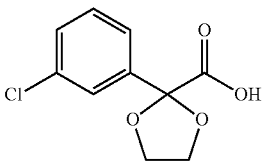 [SMILES: O=C(O)C1(c2cccc(Cl)c2)OCCO1]

To a solution of ethyl 2-(3-chlorophenyl)-1,3-dioxolane-2-carboxylate (0.196 g, 0.764 mmol) in THF (6 mL) cooled to 0° C. was added a 1M aqueous solution of LiOH (1.53 mL, 1.53 mmol) and the reaction was stirred for 2 hours. The mixture was diluted with EtOAc, poured in a 1M $KHSO_4$ aqueous solution and the aqueous layer was extracted with EtOAc. Combined organics were washed with brine, dried over $Na_2SO_4$, filtered and evaporated to dryness to give the title compound (0.175 g, 100%) as a colourless oil. The crude product was used in the next step with no further purification. MS: 227.1 ($M-H^-$).

Intermediate K-1

(2S)-2-[(2-Methylpropan-2-yl)oxycarbonylamino]-3-[4-[2-[(2-methylpropan-2-yl)oxy]-2-oxoethoxy]phenyl]propanoic Acid

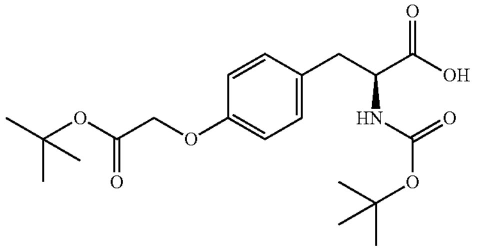 [SMILES: CC(C)(C)OC(=O)COc1ccc(C[C@H](NC(=O)OC(C)(C)C)C(=O)O)cc1]

[A] Benzyl (2S)-2-[(2-methylpropan-2-yl)oxycarbonylamino]-3-[4-[2-[(2-methylpropan-2-yl)oxy]-2-oxoethoxy]phenyl]propanoate

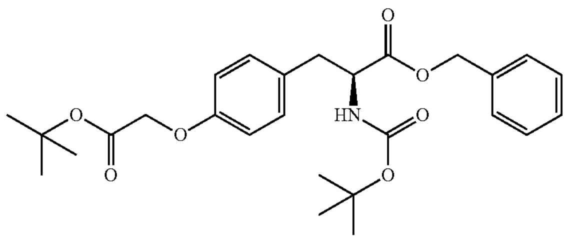 [SMILES: CC(C)(C)OC(=O)COc1ccc(C[C@H](NC(=O)OC(C)(C)C)C(=O)OCc2ccccc2)cc1]

To a solution of benzyl (2S)-2-(tert-butoxycarbonylamino)-3-(4-hydroxyphenyl)propanoate (0.5 g, 1.35 mmol) in DMF (20 ml) were successively added potassium carbonate (0.372 g, 2.69 mmol) and tert-butyl 2-bromoacetate (0.199 ml, 1.35 mmol). The reaction mixture was stirred overnight at room temperature. The mixture was diluted with EtOAc, poured into $H_2O$ (25 ml) and the aqueous layer was extracted with EtOAc (2×20 ml). Combined organics were dried over $Na_2SO_4$, filtered and evaporated. The crude material was purified by flash chromatography eluting with a 0 to 60% EtOAc in heptane gradient to yield the title compound (0.588 g, 88%) as a colorless solid; MS: 484.3 ($M-H^-$).

[B] (2S)-2-[(2-Methylpropan-2-yl)oxycarbonylamino]-3-[4-[2-[(2-methylpropan-2-yl)oxy]-2-oxoethoxy]phenyl]propanoic Acid

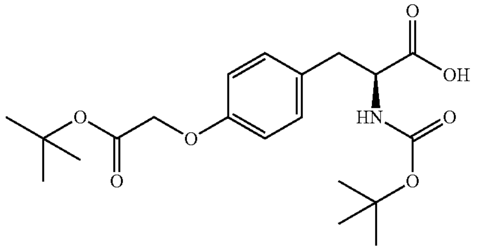 [SMILES: CC(C)(C)OC(=O)COc1ccc(C[C@H](NC(=O)OC(C)(C)C)C(=O)O)cc1]

A solution of benzyl (2S)-2-[(2-methylpropan-2-yl)oxycarbonylamino]-3-[4-[2-[(2-methylpropan-2-yl)oxy]-2-oxoethoxy]phenyl]propanoate (0.588 g, 1.21 mmol) in methanol (20 ml) was purged several times with Ar, then Pd on C (0.064 g, 0.061 mmol) was added and the reaction mixture was stirred at room temperature under a hydrogen atmosphere for 1 hour. The catalyst was removed by filtration and the filtrate concentrated in vacuo to give the title compound (0.468 g, 98%) as a colorless solid; MS: 394.3 ($M-H^-$).

Intermediate K-2

(2S)-2-[(2-Methylpropan-2-yl)oxycarbonylamino]-3-[3-[2-[(2-methylpropan-2-yl)oxy]-2-oxoethoxy]phenyl]propanoic Acid

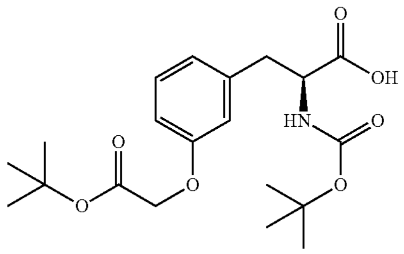 [SMILES: CC(C)(C)OC(=O)COc1cccc(C[C@H](NC(=O)OC(C)(C)C)C(=O)O)c1]

[A] Benzyl (2S)-3-(3-hydroxyphenyl)-2-[(2-methylpropan-2-yl)oxycarbonylamino]propanoate

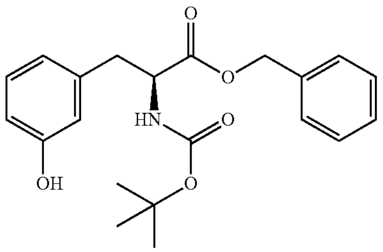 [SMILES: CC(C)(C)OC(=O)N[C@@H](Cc1cccc(O)c1)C(=O)OCc1ccccc1]

A solution of (2S)-2-(tert-butoxycarbonylamino)-3-(3-hydroxyphenyl)propanoic acid (0.5 g, 1.78 mmol) and cesium carbonate (0.290 g, 0.889 mmol) in DMF (20 mL) was stirred at room temperature for 1.5 hours. Then, benzyl bromide (0.304 g, 1.78 mmol) was added and the reaction mixture was stirred at room temperature overnight. The mixture was diluted with EtOAc, poured into water and acetic acid was added to adjust the pH to 4. The aqueous phase was extracted with EtOAc (2×10 mL) and the combined organics were washed with brine, dried over $Na_2SO_4$, filtered and evaporated. The residue was purified by flash chromatography eluting with a 0 to 40% EtOAc in heptane gradient to yield the title compound (0.539 g, 82%) as a colorless and viscous oil; MS: 370.3 ($M-H^-$).

[B] Benzyl (2S)-2-[(2-methylpropan-2-yl)oxycarbonylamino]-3-[3-[2-[(2-methylpropan-2-yl)oxy]-2-oxoethoxy]phenyl]propanoate

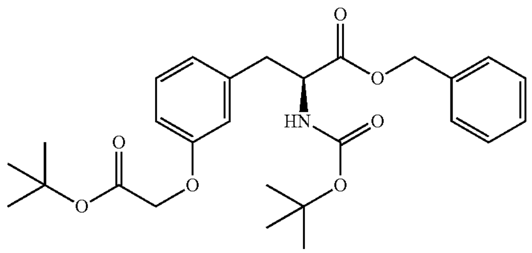 [SMILES: CC(C)(C)OC(=O)COc1cccc(C[C@H](NC(=O)OC(C)(C)C)C(=O)OCc2ccccc2)c1]

was prepared in analogy to intermediate K-1[A], but using benzyl (2S)-3-(3-hydroxyphenyl)-2-[(2-methylpropan-2-yl)oxycarbonylamino]propanoate (Intermediate K-2 [A]), to give the title compound as colorless solid.

[C] (2S)-2-[(2-Methylpropan-2-yl)oxycarbonylamino]-3-[3-[2-[(2-methylpropan-2-yl)oxy]-2-oxoethoxy]phenyl]propanoic Acid

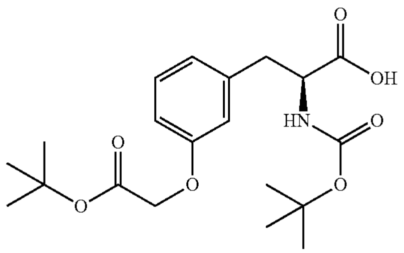 [SMILES: CC(C)(C)OC(=O)COc1cccc(C[C@H](NC(=O)OC(C)(C)C)C(=O)O)c1]

was prepared in analogy to intermediate K-1 [B], but using benzyl (2S)-2-[(2-methylpropan-2-yl)oxycarbonylamino]-3-[3-[2-[(2-methylpropan-2-yl)oxy]-2-oxoethoxy]phenyl]propanoate (Intermediate K-2 [B]), to give the title compound as colorless foam; MS: 394.3 ($M-H^-$).

Intermediate K-3

2-[4-[2-[(2-Methylpropan-2-yl)oxy]-2-oxoethoxy]phenoxy]acetic Acid

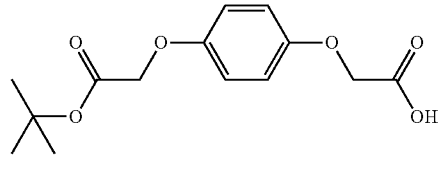 [SMILES: CC(C)(C)OC(=O)COc1ccc(OCC(=O)O)cc1]

was prepared in analogy to intermediate K-1, but using in step [A] tert-butyl 2-(4-hydroxyphenoxy)acetate instead of benzyl (2S)-2-(tert-butoxycarbonylamino)-3-(4-hydroxyphenyl)propanoate and benzyl 2-bromoacetate instead of tert-butyl 2-bromoacetate, to give the title compound as colorless solid; MS: 281.3 ($M-H^-$).

Intermediate L-1

6-(2-(tert-Butoxy)-2-oxoethoxy)picolinic Acid

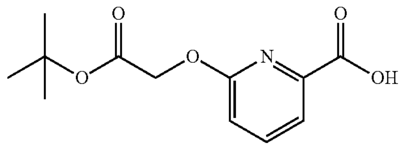 [SMILES: CC(C)(C)OC(=O)COc1cccc(C(=O)O)n1]

[A] Benzyl 6-hydroxypicolinate

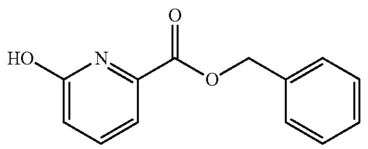 [SMILES: O=C(OCc1ccccc1)c1cccc(O)n1]

To a solution of 6-hydroxypyridine-2-carboxylic acid (1 g, 7.19 mmol) in DMF (15 mL) was added TEA (1.5 ml, 10.8 mmol) and the mixture was heated to 40° C. for 1 hour. Then, benzyl bromide (0.897 mL, 7.55 mmol) was added and the reaction mixture was heated to 77° C. for 3 hours. The mixture was cooled down to room temperature, diluted with EtOAc and poured into a sat. $NaHCO_3$ solution (50 mL) and the aqueous layer was extracted with EtOAc (2×50 mL). Combined organics were washed with brine, dried over $Na_2SO_4$, filtered, evaporated and further dried in high vacuum to yield the crude title compound (1.33 g, 81%) as light brown solid; MS: 230.1 ($M+H^+$).

[B] Benzyl 6-(2-(tert-butoxy)-2-oxoethoxy)picolinate

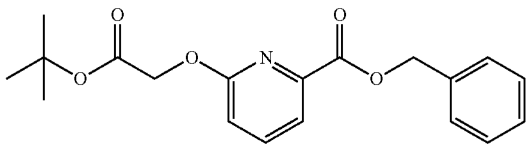 [SMILES: CC(C)(C)OC(=O)COc1cccc(C(=O)OCc2ccccc2)n1]

To a solution of benzyl 6-(2-(tert-butoxy)-2-oxoethoxy) picolinate (0.302 g, 1.32 mmol) in acetone (30 ml) were successively added potassium carbonate (0.868 g, 6.28 mmol) and tert-butyl 2-bromoacetate (0.186 mL, 1.26 mmol). The reaction mixture was heated to 65° C. for 3 h. The mixture was cooled to room temperature, the solid precipitate was filtered off and the filtrate concentrated in vacuo. The residue was purified by flash chromatography eluting with a 0 to 20% EtOAc in heptane gradient to yield the title compound (0.3 g, 70%) as a colorless solid; MS: 344.2 ($M+H^+$).

[C] 6-(2-(tert-Butoxy)-2-oxoethoxy)picolinic Acid

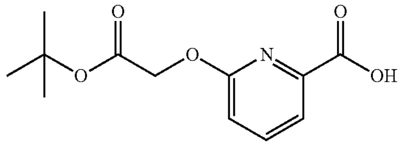 [SMILES: CC(C)(C)OC(=O)COc1cccc(C(=O)O)n1]

was prepared in analogy to intermediate K-1 [B], but using benzyl 6-(2-(tert-butoxy)-2-oxoethoxy)picolinate (Intermediate L-1 [B]), to give the title compound as colorless solid; MS: 252.3 ($M-H^-$).

Intermediate L-2

5-(2-(tert-Butoxy)-2-oxoethoxy)picolinic Acid

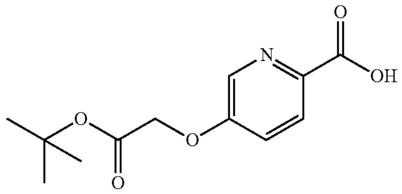 [SMILES: CC(C)(C)OC(=O)COc1ccc(C(=O)O)nc1]

was prepared in analogy to intermediate L-1, but using in step [A] 5-hydroxypyridine-2-carboxylic acid, to give the title compound as yellow solid; MS: 254.2 ($M+H^+$).

Intermediate L-3

1-(2-(tert-Butoxy)-2-oxoethyl)-2-oxo-1,2-dihydropyridine-4-carboxylic Acid

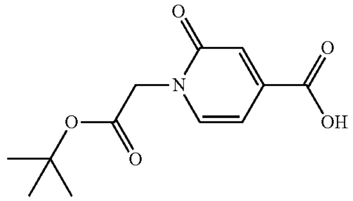 [SMILES: CC(C)(C)OC(=O)Cn1ccc(C(=O)O)cc1=O]

was prepared in analogy to intermediate L-1, but using in step [A] 2-hydroxypyridine-4-carboxylic acid, to give the title compound as colorless solid; MS: 252.2 ($M-H^-$).

Intermediate L-4

1-[2-[(2-Methylpropan-2-yl)oxy]-2-oxoethyl]-6-oxopyridine-3-carboxylic Acid

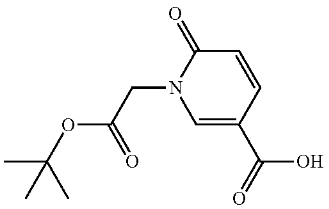 [SMILES: CC(C)(C)OC(=O)Cn1cc(C(=O)O)ccc1=O]

was prepared in analogy to intermediate L-1, but using in step [A] 6-hydroxypyridine-3-carboxylic acid, to give the title compound as colorless solid; MS: 252.3 (M−H$^-$).

Example 1

N-[(2S)-3-(3-Chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide

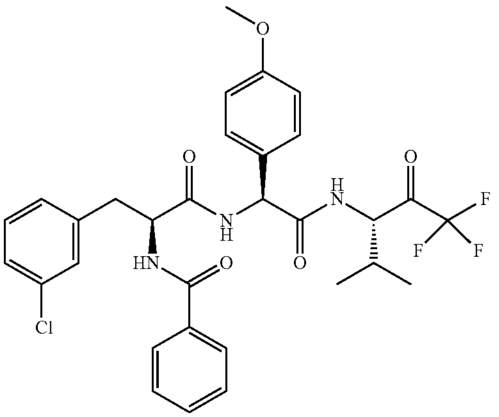 [SMILES: COc1ccc([C@H](NC(=O)[C@H](Cc2cccc(Cl)c2)NC(=O)c2ccccc2)C(=O)N[C@H](C(=O)C(F)(F)F)C(C)C)cc1]

[A] N-[(2S)-3-(3-Chlorophenyl)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxopropan-2-yl]benzamide

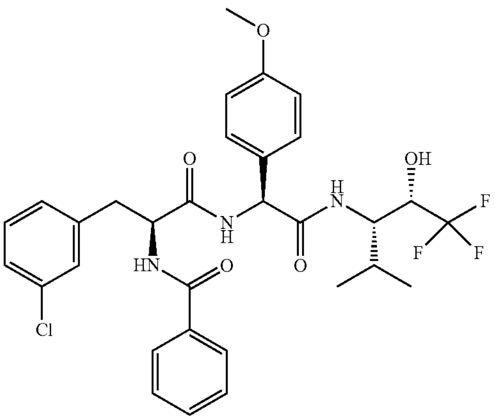 [SMILES: COc1ccc([C@H](NC(=O)[C@H](Cc2cccc(Cl)c2)NC(=O)c2ccccc2)C(=O)N[C@@H](C(C)C)[C@H](O)C(F)(F)F)cc1]

In a round-bottomed flask, (S)-2-amino-3-(3-chlorophenyl)-N—((S)-1-(4-methoxyphenyl)-2-oxo-2-(((2S,3S)-1,1,1-trifluoro-2-hydroxy-4-methylpentan-3-yl)amino)ethyl) propanamide hydrochloride (Intermediate A-1, 0.021 g, 0.038 mmol), benzoic acid (0.005 g, 0.038 mmol) and HATU (0.016 g, 0.041 mmol) were dissolved in DMF (1 mL) and the mixture cooled to 0° C. Hunig's base (0.020 mL, 0.114 mmol) was added to the reaction mixture which was stirred at this temperature for 10 min, then allowed to warm up to room temperature and stirring was continued for 2 hours. The mixture was diluted with EtOAc, poured into 1M HCl (5 mL) and the aqueous layer was extracted with EtOAc (2×10 mL). Combined organics were washed with a sat. $NaHCO_3$ solution (5 mL), then brine before being dried over $Na_2SO_4$, filtered and concentrated in vacuo. The residue was purified by silica gel flash chromatography eluting with a 0 to 100% EtOAc-heptane gradient to give the title compound (0.012 g, 51%) as a colorless solid. MS: 620.3 (M+H$^+$).

[B] N-[(2S)-3-(3-Chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide

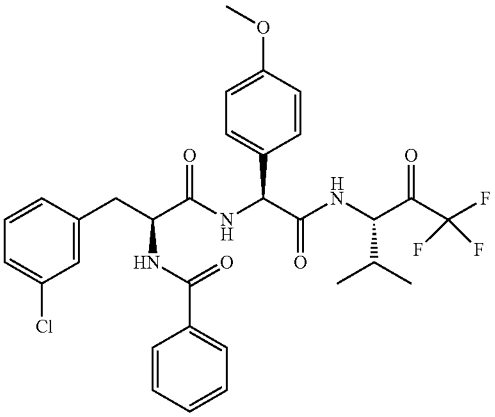 [SMILES: COc1ccc([C@H](NC(=O)[C@H](Cc2cccc(Cl)c2)NC(=O)c2ccccc2)C(=O)N[C@H](C(=O)C(F)(F)F)C(C)C)cc1]

To a suspension of N-[(2S)-3-(3-chlorophenyl)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxo-propan-2-yl]benzamide (0.012 g, 0.019 mmol) in DCM (1 mL) was added 15% Dess-Martin periodinane in DCM solution (0.121 mL, 0.058 mmol) and the reaction mixture was stirred at room temperature overnight. A spatula of solid $Na_2S_2O_3$ was added and stirring was continued for 5 min. The resulting white suspension was diluted with DCM/water, poured into a sat. $NaHCO_3$ solution (5 mL) and then extracted with DCM (10 mL). The organic layer was washed with brine, dried over $Na_2SO_4$, filtered and evaporated. The residue was purified by silica gel flash chromatography, eluting with a 0-70% EtOAc-heptane gradient to give the title compound (0.007 g, 58%) as a colorless solid. MS: 618.3 (M+H$^+$).

The following examples listed in Table 1 were prepared in analogy to the procedures described for the preparation of example 1 by using the indicated intermediate and carboxylic acid in step [A]

TABLE 1

| Ex | Name<br>Structure<br>Aspect | Reactant to be used in step [A] | MS (M + H$^+$) |
|---|---|---|---|
| 2 | (2S)-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]-2-(3-pyridin-3-ylpropanoylamino)propanamide<br>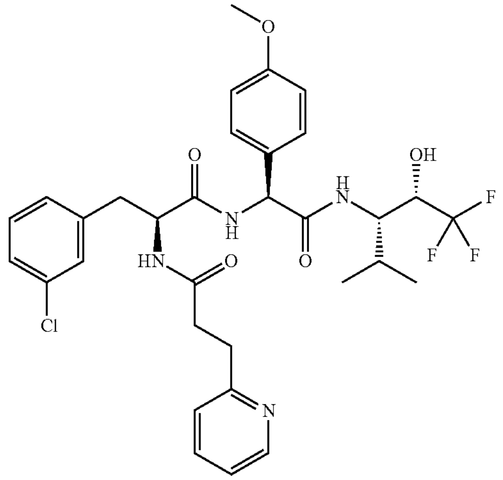<br>Colorless amorphous | Intermediate A-1<br>and<br>3-(3-pyridyl)propanoic acid | 647.3 |
| 3 | N-[(2S)-3-(3-fluorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide<br>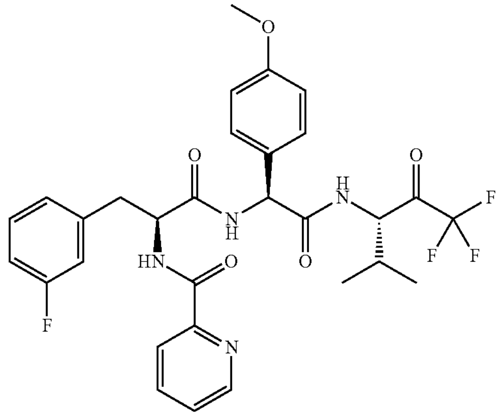<br>Colorless waxy solid | Intermediate A-2<br>and<br>pyridine-2-carboxylic acid | 603.3 |

TABLE 1-continued

| Ex | Name<br>Structure<br>Aspect | Reactant to be used in step [A] | MS (M + H⁺) |
|---|---|---|---|
| 4 | 3-chloro-N-[(2S)-3-(3-fluorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide<br>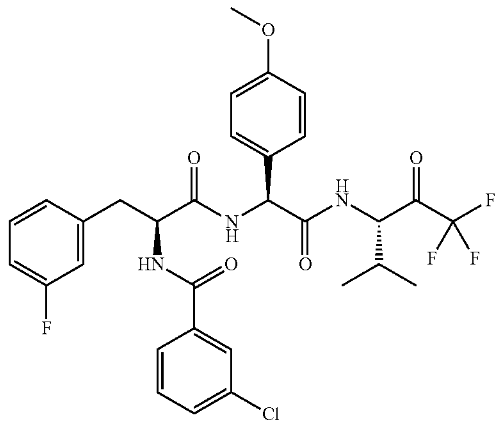<br>Colorless solid | Intermediate A-2 and 3-chlorobenzoic acid | 636.3 |
| 5 | 5-chloro-N-[(2S)-3-(3-fluorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide<br>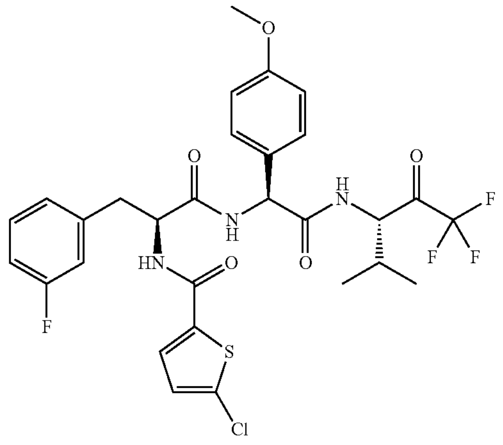<br>Colorless solid | Intermediate A-2 and 5-chlorothiophene-2-carboxylic acid | 642.2 |
| 6 | (2S)-2-[[2-(3-chlorophenyl)-2,2-difluoroacetyl]amino]-3-(3-fluorophenyl)-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-2 and 2-(3-chlorophenyl)-2,2-difluoro-acetic acid | 686.3 |

TABLE 1-continued

| Ex | Name<br>Structure<br>Aspect | Reactant to be used in step<br>[A] | MS<br>(M + H+) |
|---|---|---|---|
| | 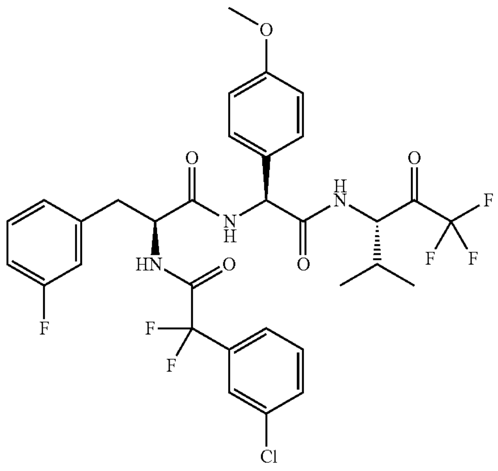<br>Colorless solid | | |
| 7 | (2S)-2-[[2-(2-chlorophenyl)-2,2-difluoroacetyl]amino]-3-(3-fluorophenyl)-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-2<br>and<br>2-(2-chlorophenyl)-2,2-difluoro-acetic acid | 686.3 |
| | 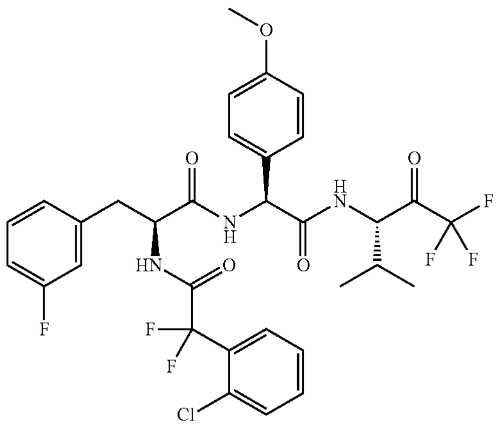<br>Colorless solid | | |
| 8 | (2S)-2-[[2-(3-chloropehnyl)-2,2-difluoroacetyl]amino]-3-(3-cyanophenyl)-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-3<br>and<br>2-(3-chlorophenyl)-2,2-difluoro-acetic acid | 693.3 |

TABLE 1-continued

| Ex | Name<br>Structure<br>Aspect | Reactant to be used in step<br>[A] | MS<br>(M + H$^+$) |
|---|---|---|---|
| | 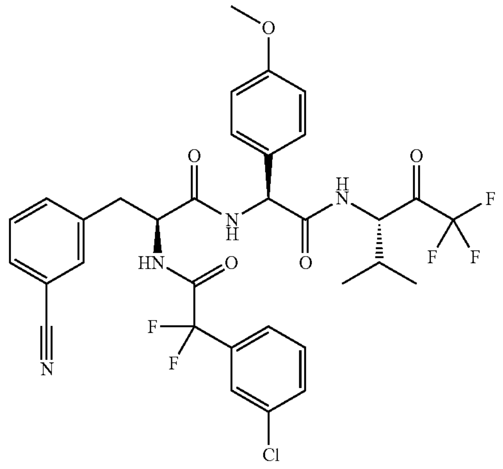<br>Colorless waxy solid | | |
| 9 | 5-chloro-N-[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide<br>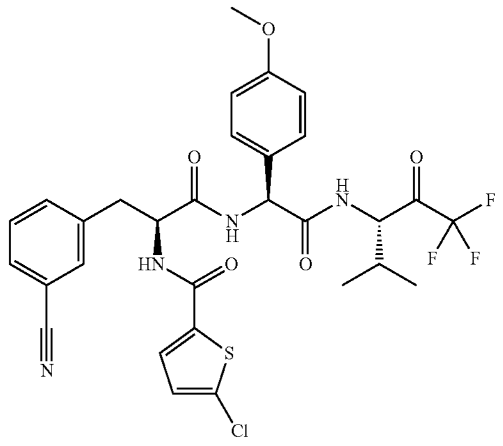<br>Colorless waxy solid | Intermediate A-3<br>and<br>5-chlorothiophene-2-carboxylic acid | 649.4 |
| 10 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-pyridin-3-ylpropan-2-yl]benzamide | Intermediate A-4<br>and<br>benzoic acid | 585.5 |

TABLE 1-continued

| Ex | Name<br>Structure<br>Aspect | Reactant to be used in step [A] | MS (M + H+) |
|---|---|---|---|
| | 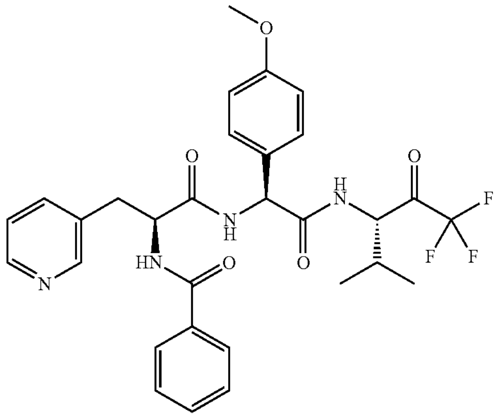<br>Colorless solid | | |
| 11 | 3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-pyridin-3-ylpropan-2-yl]benzamide<br>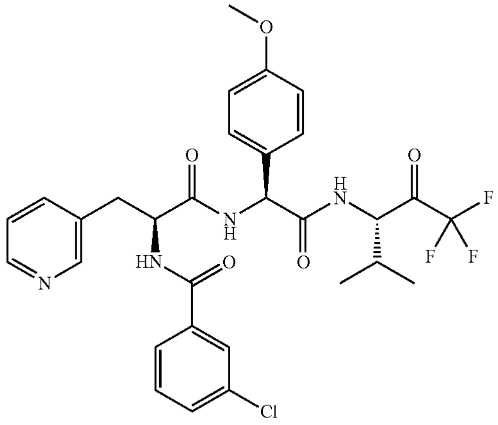<br>Off-white solid | Intermediate A-4<br>and<br>3-chlorobenzoic acid | 619.5 |
| 12 | (2S)-2-[[2-(2-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-pyridin-3-ylpropanamide | Intermediate A-4<br>and<br>2-(2-chlorophenyl)-2,2-difluoro-acetic acid | 669.5 |

TABLE 1-continued

| Ex | Name<br>Structure<br>Aspect | Reactant to be used in step<br>[A] | MS<br>(M + H+) |
|---|---|---|---|
| | 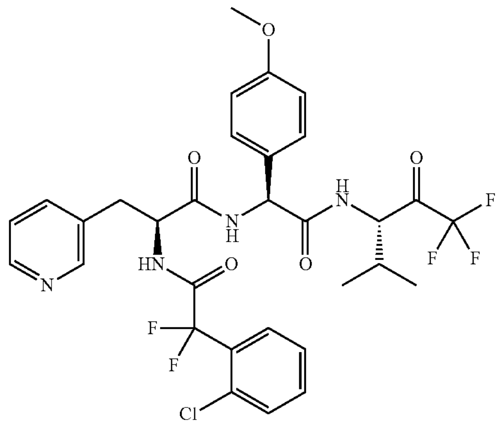<br>Colorless amorphous | | |
| 13 | N-[(2S)-3-(2-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide<br>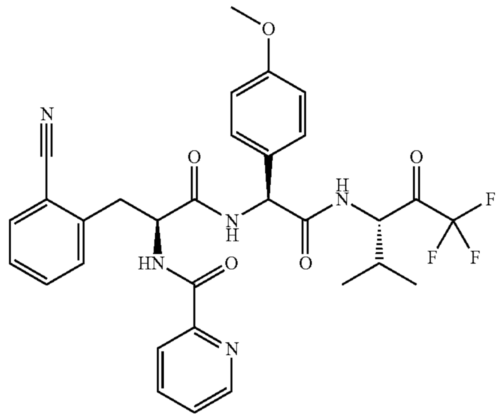<br>Colorless amorphous | Intermediate A-5<br>and<br>pyridine-2-carboxylic acid | 610.5 |
| 14 | (2S)-2-[[2-(3-chlorophenyl)-2,2-difluoroacetyl]amino]-3-(2-cyanophenyl)-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-5<br>and<br>2-(3-chlorophenyl)-2,2-difluoro-acetic acid | 693.3 |

TABLE 1-continued

| Ex | Name<br>Structure<br>Aspect | Reactant to be used in step [A] | MS (M + H$^+$) |
|---|---|---|---|
| | 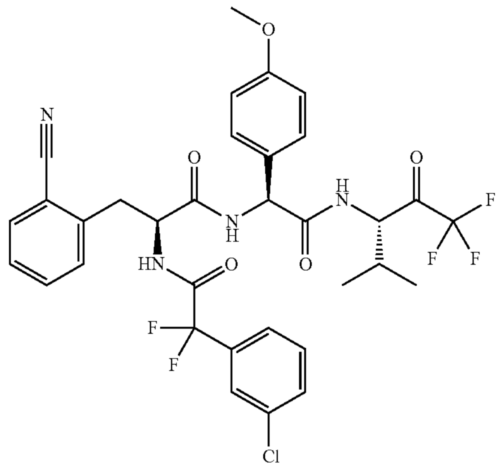<br>Colorless solid | | |
| 15 | tert-butyl 2-[4-[(2S)-2-[(3-chlorobenzyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate<br>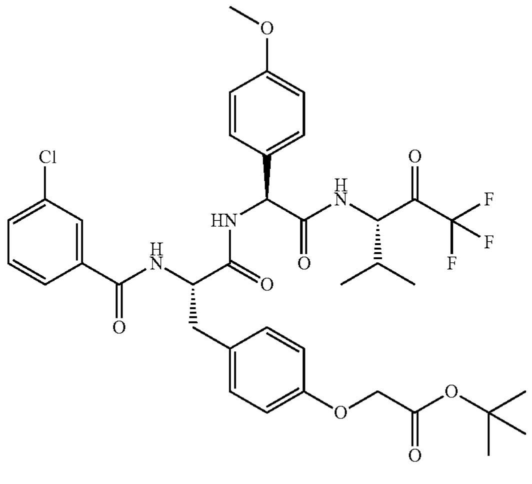<br>Colorless solid | Intermediate A-6 and 3-chlorobenzoic acid | 748.4 |
| 16 | tert-butyl 2-[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-(pyridine-2-carbonylamino)propyl]phenoxy]acetate | Intermediate A-6 and pyridine-2-carboxylic acid | 715.4 |

TABLE 1-continued

| Ex | Name<br>Structure<br>Aspect | Reactant to be used in step<br>[A] | MS<br>(M + H$^+$) |
|---|---|---|---|
| | 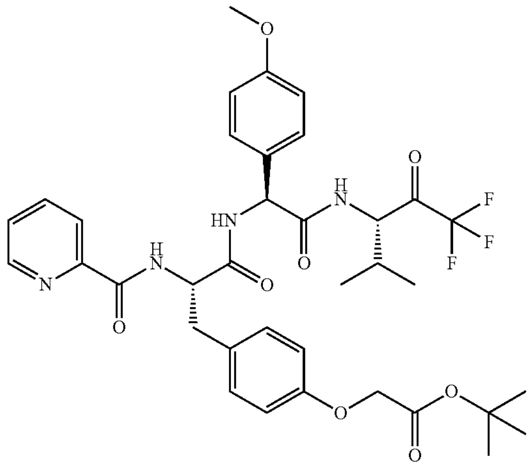<br>Colorless solid | | |
| 17 | tert-butyl 2-[4-[(2S)-2-[[2-(2-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate<br>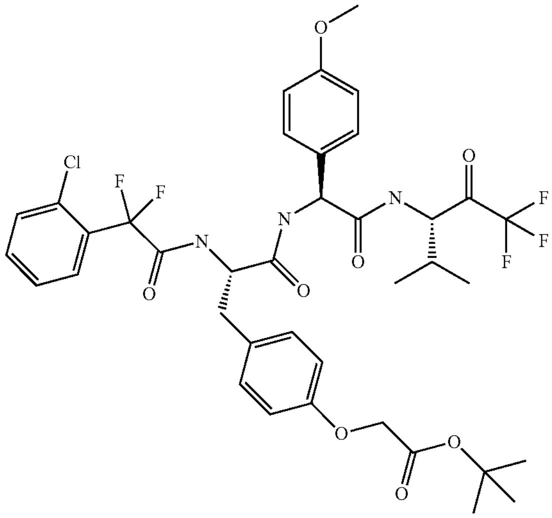<br>Colorless waxy solid | Intermediate A-6<br>and<br>2-(2-chlorophenyl)-2,2-difluoro-acetic acid | 798.3 |
| 18 | tert-butyl 2-[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate | Intermediate A-6<br>and<br>2-(3-chlorophenyl)-2,2-difluoro-acetic acid | 798.3 |

TABLE 1-continued

| Ex | Name<br>Structure<br>Aspect | Reactant to be used in step<br>[A] | MS<br>(M + H$^+$) |
|---|---|---|---|
| | 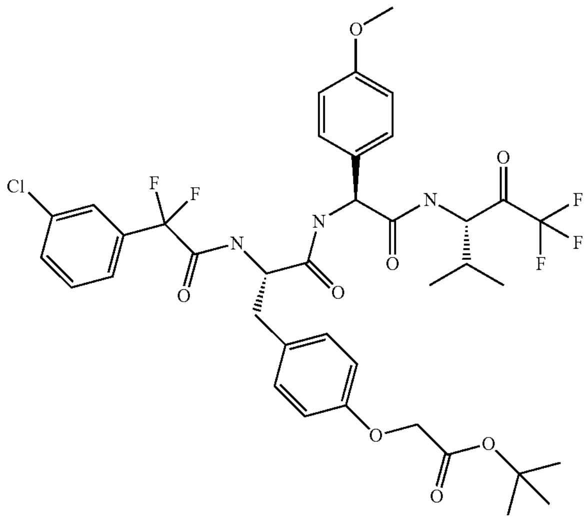<br>Colorless waxy solid | | |
| 19 | tert-butyl 2-[3-[(2S)-2-[(3-chlorobenzoyl)amino]-3-[[(1S)-1-(4-methoxyphenyl)-2-oxo-2-2[[(3S)-1,1,1-trifluoro-4-methyl-2-oxopentan-3-yl]amino]ethyl]amino]-3-oxopropyl]phenoxy]acetate | Intermediate A-7<br>and<br>3-chlorobenzoic acid | 748.3 |
| | 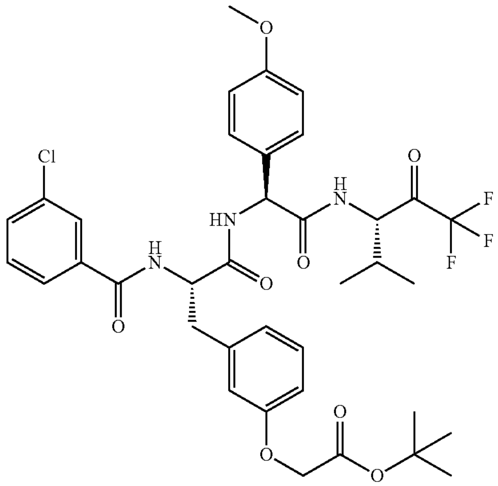<br>Colorless solid | | |
| 20 | tert-butyl 2-[3-[(2S)-2-[[2-(2-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate | Intermediate A-7<br>and<br>2-(2-chlorophenyl)-2,2-difluoro-acetic acid | 798.4 |

TABLE 1-continued

| Ex | Name<br>Structure<br>Aspect | Reactant to be used in step [A] | MS (M + H+) |
|---|---|---|---|
| | 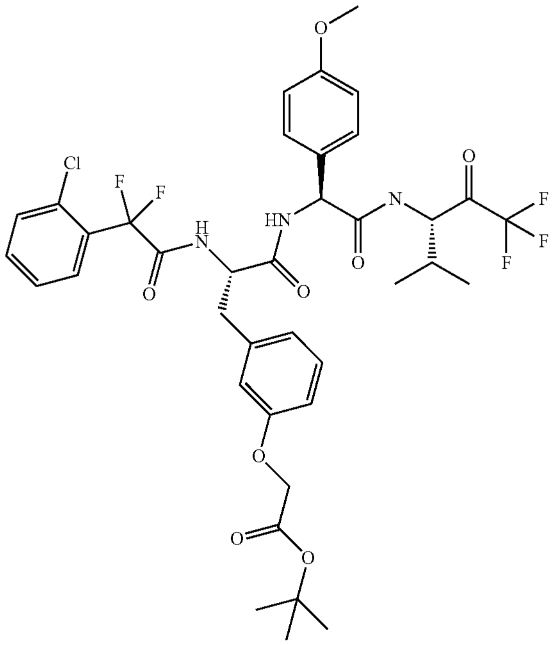<br>Colorless waxy solid | | |
| 21 | N-[(2S)-1-[[1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide<br>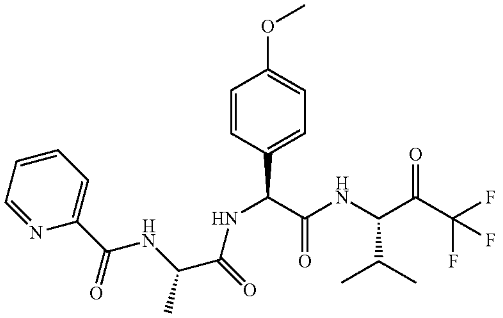<br>Colorless solid | Intermediate A-8 and pyridine-2-carboxylic acid | 509.5 |
| 22 | (2S)-2-[(2,2-difluoro-2-phenylacetyl)amino]-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-8 and 2,2-difluoro-2-phenyl-acetic acid | 558.4 |

TABLE 1-continued

| Ex | Name<br>Structure<br>Aspect | Reactant to be used in step<br>[A] | MS<br>(M + H$^+$) |
|---|---|---|---|
| | 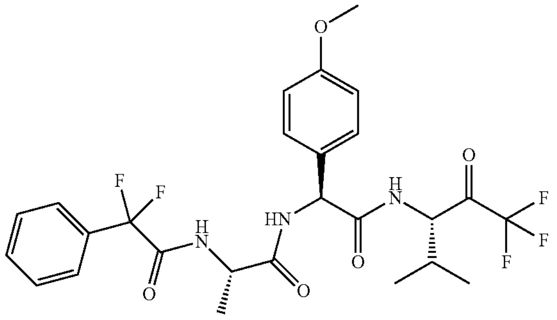<br>Colorless solid | | |
| 23 | 2,5-dichloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide<br>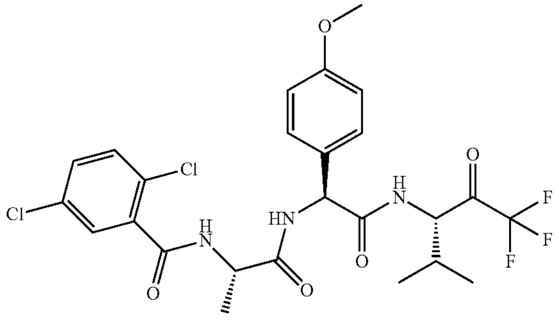<br>Colorless solid | Intermediate A-8<br>and<br>2,5-dichlorobenzoic acid | 576.3 |
| 24 | 3-chloro-N-[(2S)-1-[[(1S)-1-(4-methoxyphenyl)-2-oxo-2-[[(3S)-1,1,1-trifluoro-4-methyl-2-oxoopentan-3-yl]amino]ethyl]amino]-1-oxopropan-2-yl]benzamide<br>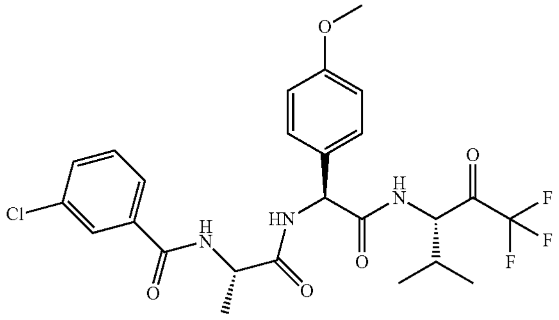<br>Colorless solid | Intermediate A-8<br>and<br>3-chlorobenzoic acid | 542.4 |
| 25 | 1-(3-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopropane-1-carboxamide | Intermediate A-8<br>and<br>1-(3-chlorophenyl)cyclopropane-carboxylic acid | 582.4 |

TABLE 1-continued

| Ex | Name<br>Structure<br>Aspect | Reactant to be used in step<br>[A] | MS<br>(M + H+) |
|---|---|---|---|
| | 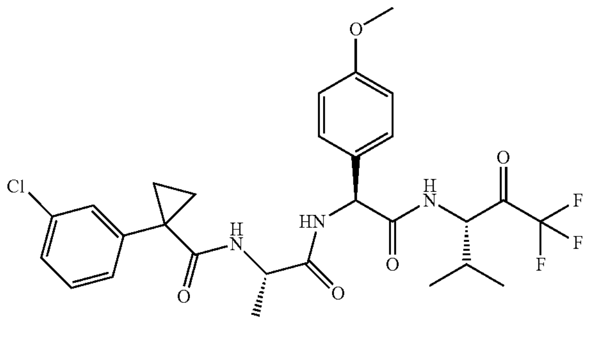<br>Colorless solid | | |
| 26 | (2S)-2-[[2-(2-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-8<br>and<br>2-(2-chlorophenyl)-2,2-difluoro-acetic acid | 592.3 |
| | 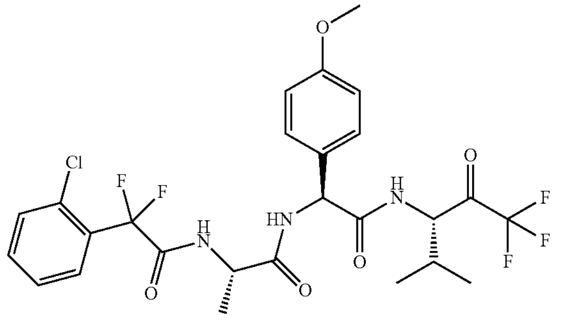<br>Colorless solid | | |
| 27 | (2S)-2-[[2-(3-chlorophenyl)acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-8<br>and<br>2-(3-chlorophenyl)acetic acid | 556.2 |
| | 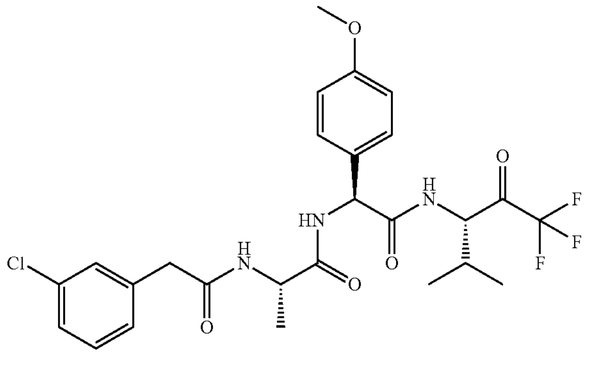<br>Colorless solid | | |
| 28 | 2-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide | Intermediate A-8<br>and<br>2-chlorobenzoic acid | 542.2 |

TABLE 1-continued

| Ex | Name<br>Structure<br>Aspect | Reactant to be used in step<br>[A] | MS<br>(M + H⁺) |
|---|---|---|---|
| | 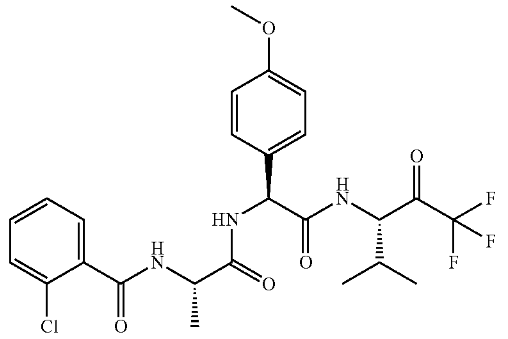<br>Colorless solid | | |
| 29 | (2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide<br>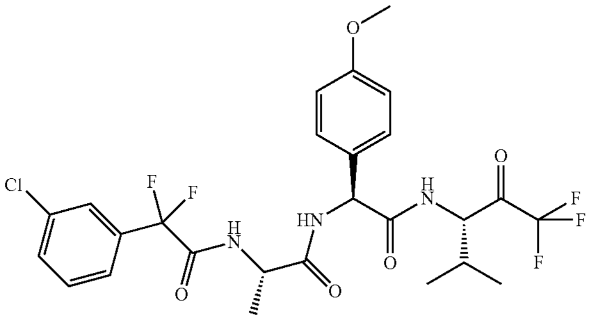<br>Colorless waxy solid | Intermediate A-8<br>and<br>2-(3-chlorophenyl)-2,2-difluoro-acetic acid | 592.2 |
| 30 | (2S)-2-[[2-(2-chlorophenyl)acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide<br>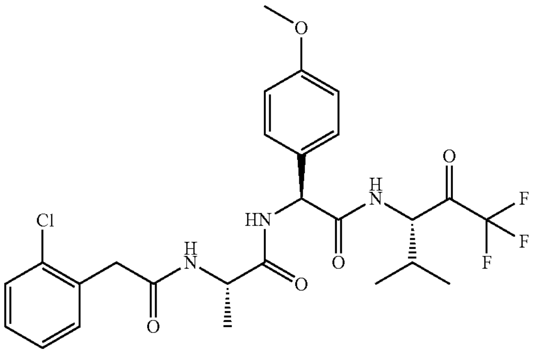<br>Colorless solid | Intermediate A-8<br>and<br>2-(2-chlorophenyl)acetic acid | 556.2 |
| 31 | (2S)-2-[(2-fluoro-2-phenylacetyl)amino]-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-8<br>and<br>2-fluoro-2-phenyl-acetic acid | 558.3 |

TABLE 1-continued

| Ex | Name<br>Structure<br>Aspect | Reactant to be used in step [A] | MS (M + H$^+$) |
|---|---|---|---|
| | 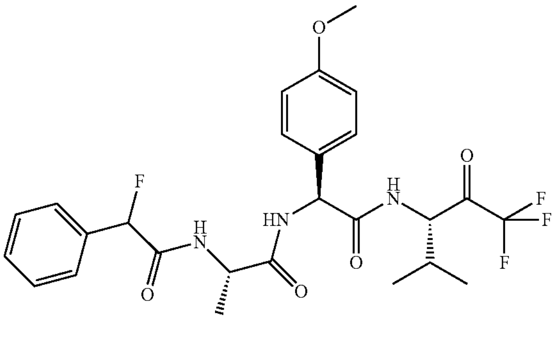<br>Colorless solid | | |
| 32 | 5-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide | Intermediate A-8 and 5-chlorothiophene-2-carboxylic acid | 566.2 |
| | 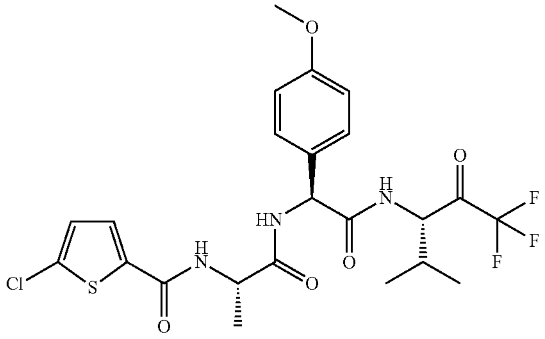<br>Colorless solid | | |
| 33 | 5-bromo-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide | Intermediate A-8 and 5-bromothiophene-2-carboxylic acid | 594.1 |
| | 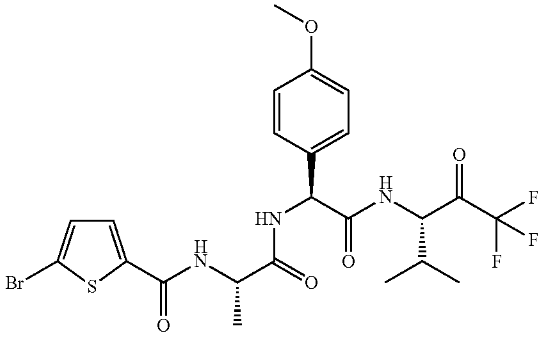<br>Colorless solid | | |
| 34 | (2S)-2-[[2-(4-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-8 and 2-(4-chlorophenyl)-2,2-difluoro-acetic acid | 610.2 |

TABLE 1-continued

| Ex | Name<br>Structure<br>Aspect | Reactant to be used in step [A] | MS (M + H+) |
|---|---|---|---|
| | 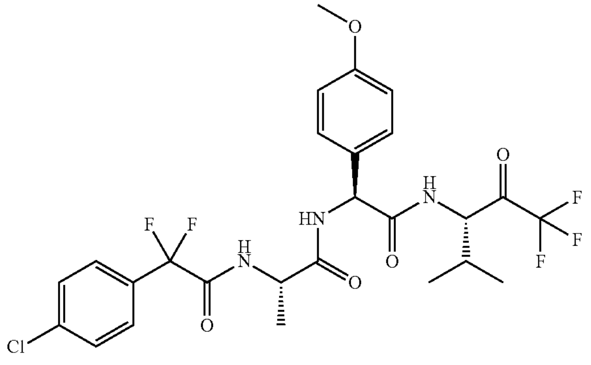<br>Colorless solid | | |
| 35 | (2S)-2-[[2-(3,4-dichlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-8 and 2-(3,4-chlorophenyl)-2,2-difluoro-acetic acid | 626.3 |
| | 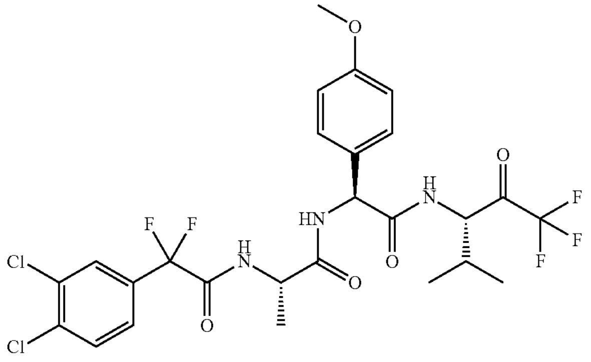<br>Colorless waxy solid | | |
| 36 | 2-(3-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-methylpropanamide | Intermediate A-8 and 2-(3-chlorophenyl)-2-methyl-propanoic acid | 584.3 |
| | 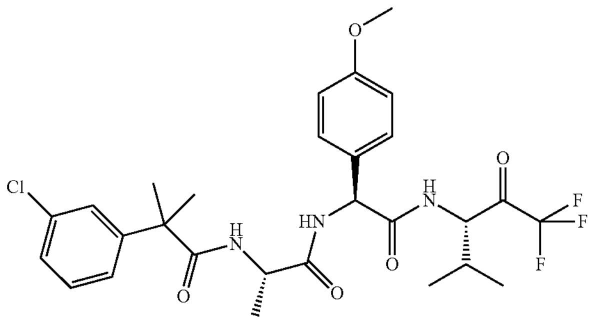<br>Colorless solid | | |
| 37 | (2S)-2-[[2-(3-chlorophenyl)-2,2-difluoroacetyl]amino]-3-methoxy-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-9 and 2-(3-chlorophenyl)-2,2-difluoro-acetic acid | 622.2 |

TABLE 1-continued

| Ex | Name<br>Structure<br>Aspect | Reactant to be used in step [A] | MS (M + H$^+$) |
|---|---|---|---|
| | 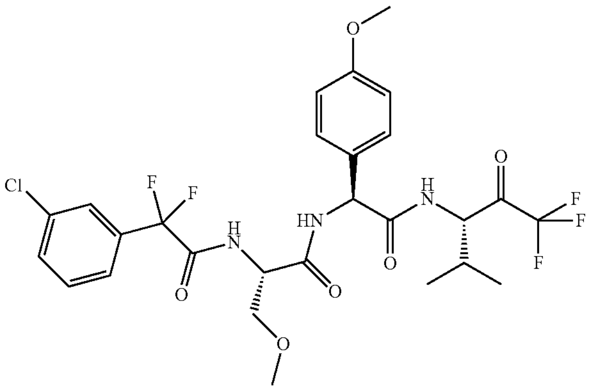<br>Colorless solid | | |
| 38 | 3-chloro-N-[2S)-3-methoxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide | Intermediate A-9<br>and<br>3-chlorobenzoic acid | 572.2 |
| | 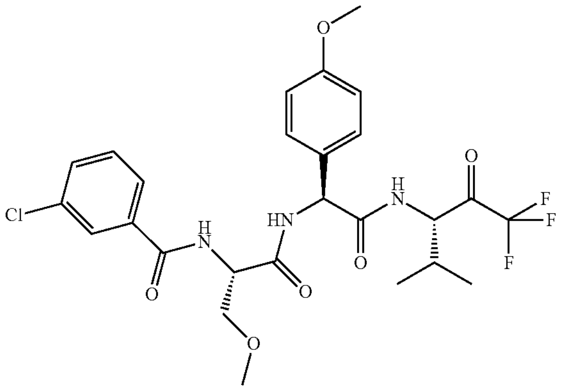<br>Colorless solid | | |
| 39 | (2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-[(2-methylpropan-2-yl)oxy]propanamide | Intermediate A-10<br>and<br>2-(3-chlorophenyl)-2,2-difluoro-acetic acid | 664.5 |

TABLE 1-continued

| Ex | Name<br>Structure<br>Aspect | Reactant to be used in step [A] | MS (M + H+) |
|---|---|---|---|
| | 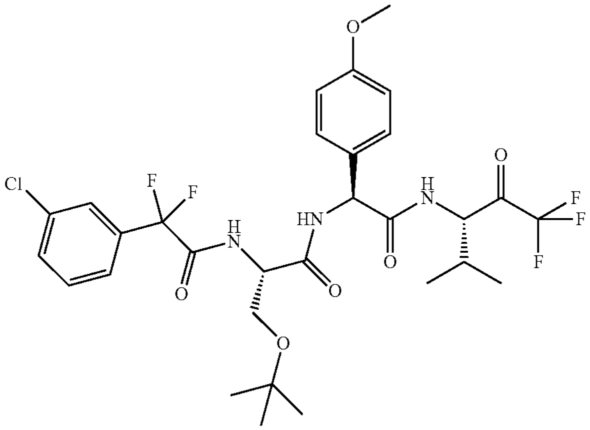 [SMILES: COC[C@H](NC(=O)C(F)(F)c1cccc(Cl)c1)C(=O)N[C@H](C(=O)N[C@H](C(=O)C(F)(F)F)C(C)C)c1ccc(OC)cc1]<br>Colorless solid | | |
| 40 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-3-[(2-methylpropan-2-yl)oxy]-1-oxopropan-2-yl]pyridine-2-carboxamide | Intermediate A-10<br>and<br>pyridine-2-carboxylic acid | 581.5 |
| | 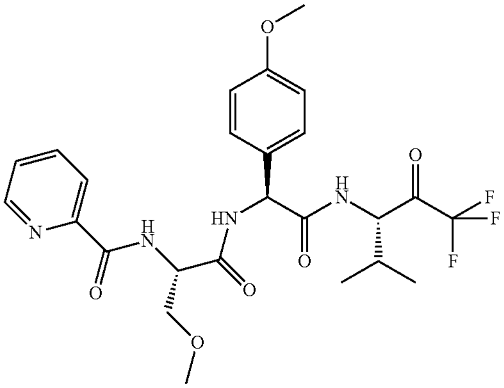<br>Colorless solid | | |
| 41 | 3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-3-[(2-methylpropan-2-yl)oxy]-1-oxopropan-2-yl]benzamide | Intermediate A-10<br>and<br>3-chlorobenzoic acid | 614.5 |

TABLE 1-continued

| Ex | Name<br>Structure<br>Aspect | Reactant to be used in step<br>[A] | MS<br>(M + H$^+$) |
|---|---|---|---|
| | 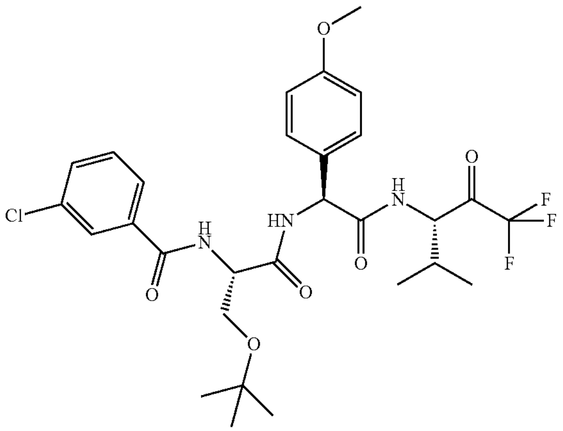 [SMILES: COC[C@H](NC(=O)c1cccc(Cl)c1)C(=O)N[C@H](C(=O)N[C@H](C(=O)C(F)(F)F)C(C)C)c1ccc(OC)cc1]<br>Colorless solid | | |
| 42 | 5-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-3-[(2-methylpropan-2-yl)oxy]-1-oxopropan-2-yl]thiophene-2-carboxamide | Intermediate A-10<br>and<br>5-chlorothiophene-2-carboxylic acid | 620.2 |
| | 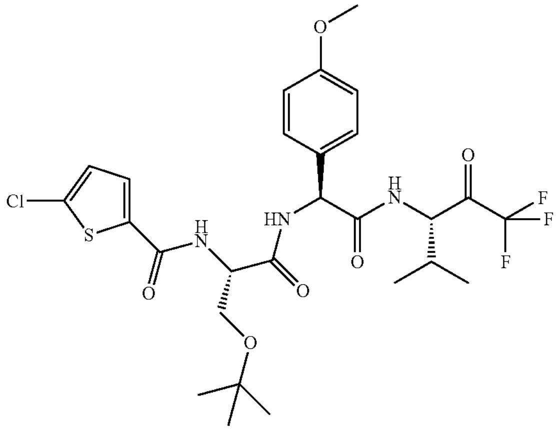<br>Colorless waxy solid | | |
| 43 | (2S)-2-[[2-(2-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-[(2-methylpropan-2-yl)oxy]propanamide | Intermediate A-10<br>and<br>2-(2-chlorophenyl)-2,2-difluoro-acetic acid | 666.3 |

TABLE 1-continued

| Ex | Name<br>Structure<br>Aspect | Reactant to be used in step [A] | MS (M + H$^+$) |
|---|---|---|---|
| | 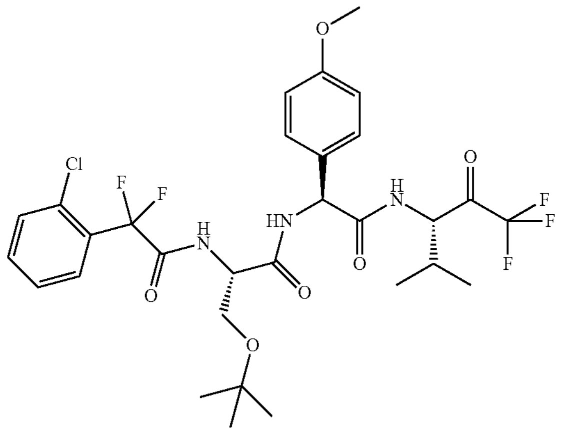<br>Colorless waxy solid | | |
| 44 | 3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-phenylmethoxypropan-2-yl]benzamide<br>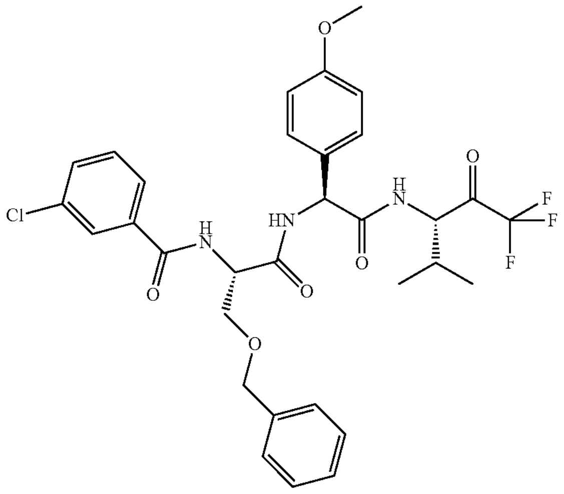<br>Colorless solid | Intermediate A-11 and 3-chlorobenzoic acid | 648.3 |
| 45 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-phenylmethoxypropan-2-yl]pyridine-2-carboxamide | Intermediate A-11 and pyridine-2-carboxylic acid | 615.4 |

TABLE 1-continued

| Ex | Name<br>Structure<br>Aspect | Reactant to be used in step [A] | MS (M + H+) |
|---|---|---|---|
| | 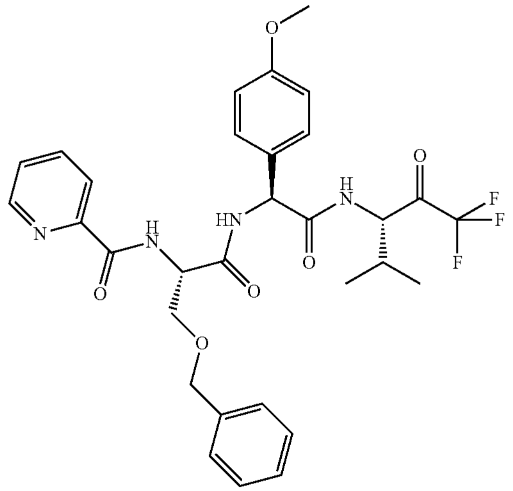<br>Colorless solid | | |
| 46 | tert-butyl (4S)-4-[(3-chlorobenzoyl)amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoate<br>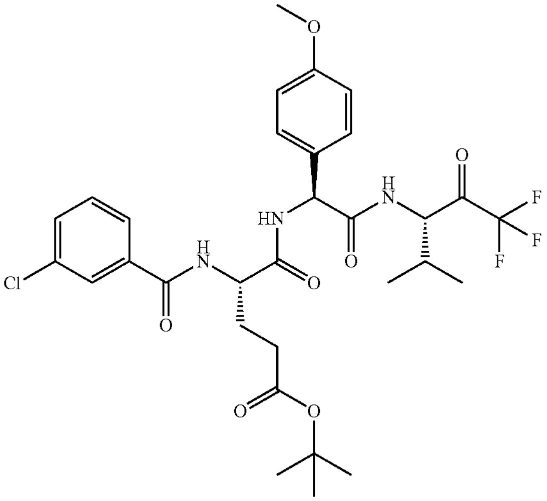<br>Colorless solid | Intermediate A-12 and 3-chlorobenzoic acid | 656.3 |
| 47 | tert-butyl (4S)-4-[[2-(3-chlorophenyl)-2,2-difluoroacetyl]amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoate | Intermediate A-12 and 2-(3-chlorophenyl)-2,2-difluroo-acetic acid | 706.4 |

TABLE 1-continued

| Ex | Name<br>Structure<br>Aspect | Reactant to be used in step<br>[A] | MS<br>(M + H⁺) |
|---|---|---|---|
| | 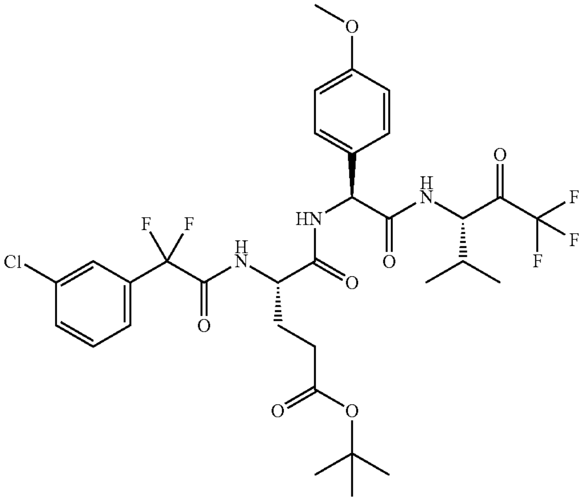<br>Colorless foam | | |
| 48 | N-[(2S)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrazine-2-carboxamide<br>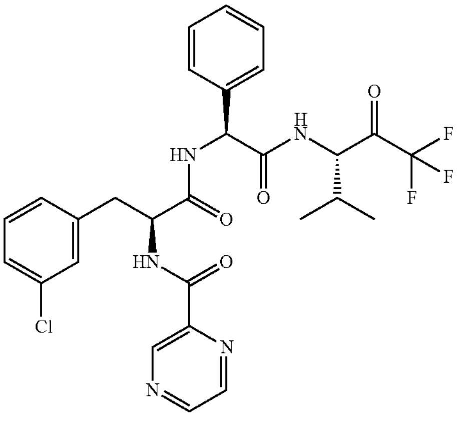<br>Colorless solid | Intermediate B-1 and pyrazine-2-carboxylic acid | 590.2 |
| 49 | N-[(2S)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]-1-methylpyrrolidine-3-carboxamide | Intermediate B-1 and 1-methylpyrroldiine-3-carboxylic acid | $(M + H_2O)^+$ 613.2 |

TABLE 1-continued

| Ex | Name<br>Structure<br>Aspect | Reactant to be used in step [A] | MS (M + $H^+$) |
|---|---|---|---|
| | 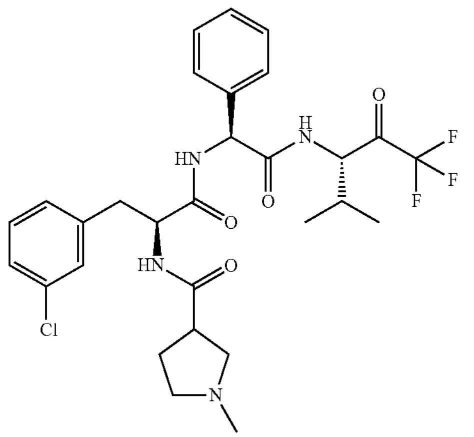<br>Colorless amorphous | | |
| 50 | N-[(2S)-3-(3,4-dichlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrazine-2-carboxamide<br>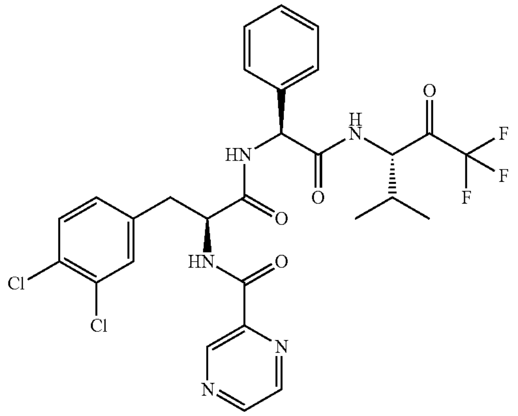<br>Colorless waxy solid | Intermediate B-2 and pyrazine-2-carboxylic acid | 624.2 |
| 51 | N-[(2S)-3-(3,4-dichlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyridine-2-carboxamide | Intermediate B-2 and pyridine-2-carboxylic acid | 623.2 |

TABLE 1-continued

| Ex | Name<br>Structure<br>Aspect | Reactant to be used in step [A] | MS (M + H+) |
|---|---|---|---|
| | 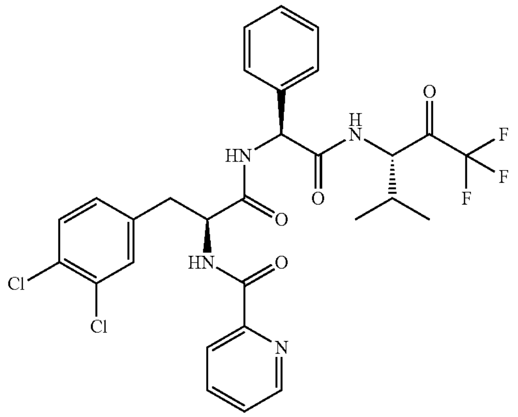<br>Colorless waxy solid | | |
| 52 | N-[(2S)-3-(3,4-dichloropehnyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrimidine-5-carboxamide<br>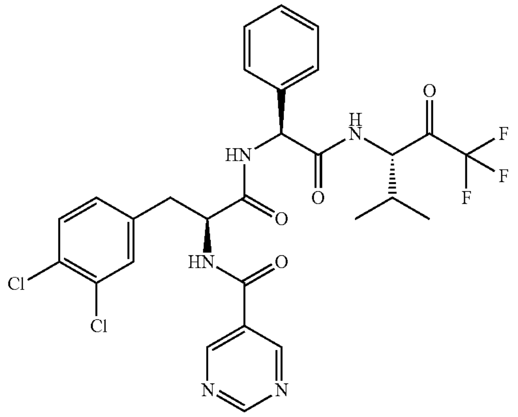<br>Light brown waxy solid | Intermediate B-2<br>and<br>pyrimidine-5-carboxylic acid | 624.1 |
| 53 | N-[(2S)-3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]pyrazine-2-carboxamide | Intermediate C-1<br>and<br>pyrazine-2-carboxylic acid | 620.2 |

TABLE 1-continued

| Ex | Name<br>Structure<br>Aspect | Reactant to be used in step [A] | MS (M + H+) |
|---|---|---|---|
| | 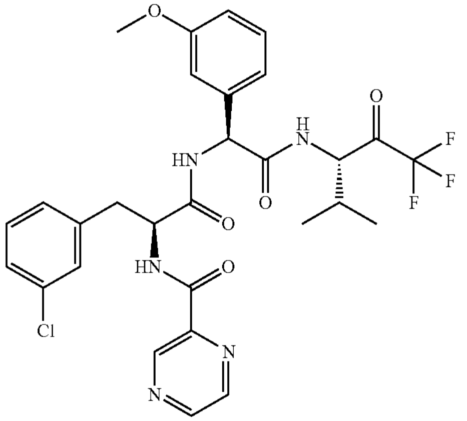<br>Colorless solid | | |
| 54 | N-[(2S)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrazine-2-carboxamide | Intermediate D-1 and pyrazine-2-carboxylic acid | 604.2 |
| | 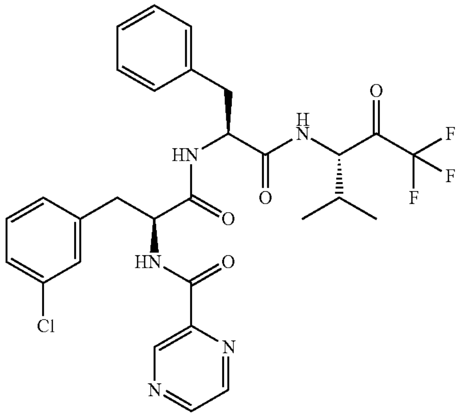<br>Colorless solid | | |
| 55 | N-[(2S)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrimidine-5-carboxamide | Intermediate D-1 and pyrimidine-5-carboxylic acid | 604.2 |

TABLE 1-continued

| Ex | Name<br>Structure<br>Aspect | Reactant to be used in step<br>[A] | MS<br>$(M + H^+)$ |
|---|---|---|---|
| | 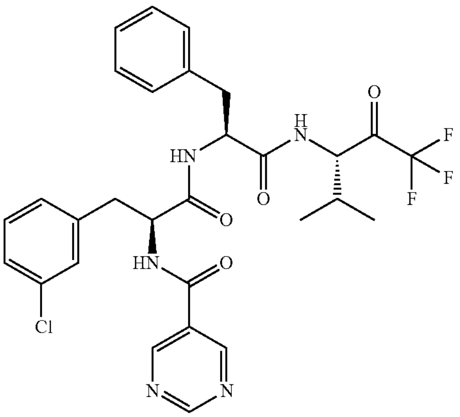<br>Colorless solid | | |
| 56 | N-[(2S)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]-1-methylpiperidine-4-carboxamide<br>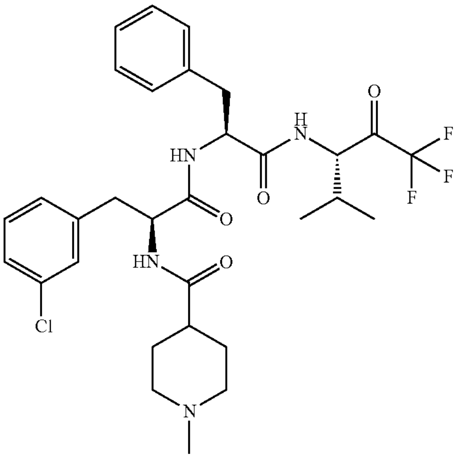<br>Colorless solid | Intermediate D-1<br>and<br>1-methylpiperidine-4- | $(M + H_2O)^+$<br>641.3 |
| 57 | N-[(2R)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrimidine-5-carboxamide | Intermediate D-2<br>and<br>pyrimidine-5-carboxylic acid | 604.2 |

TABLE 1-continued

| Ex | Name<br>Structure<br>Aspect | Reactant to be used in step [A] | MS (M + $H^+$) |
|---|---|---|---|
| | 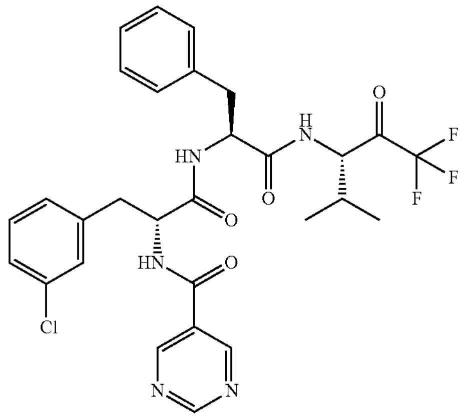<br>Colorless waxy solid | | |
| 58 | N-[(2R)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrazine-2-carboxamide<br>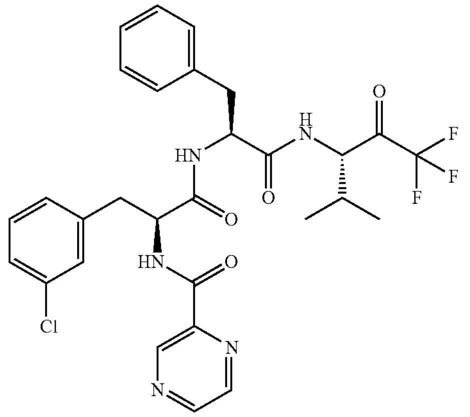<br>Light brown solid | Intermediate D-2 and pyrazine-2-carboxylic acid | 604.2 |
| 59 | N-[(2S)-3-(3,4-dichlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyridine-2-carboxamide | Intermediate D-3 and pyridine-2-carboxylic acid | 637.1 |

TABLE 1-continued

| Ex | Name<br>Structure<br>Aspect | Reactant to be used in step [A] | MS (M + H+) |
|---|---|---|---|
| | 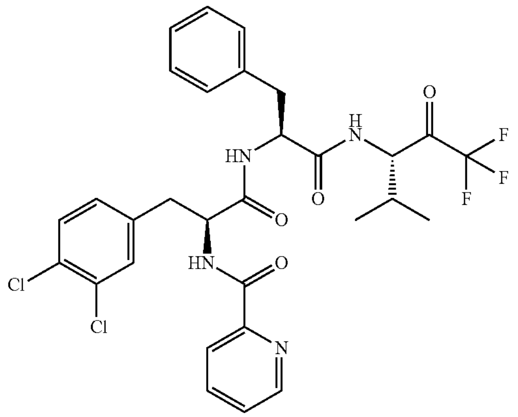<br>Colorless solid | | |
| 60 | N-[(2S)-3-(3,4-dichlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrazine-2-carboxamide<br>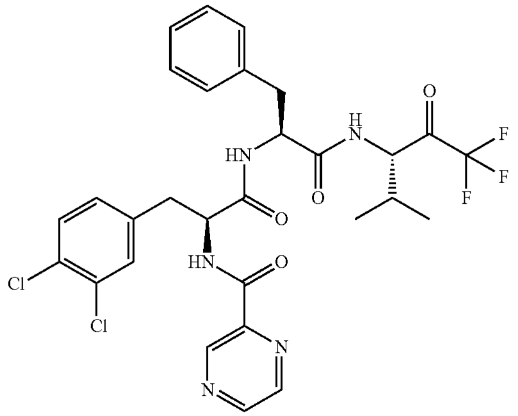<br>Colorless solid | Intermediate D-3 and pyrazine-2-carboxylic acid | 638.2 |
| 61 | N-[(2S)-3-cyclohexyl-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]naphthalene-2-carboxamide | Intermediate D-4 and naphthalene-2-carboxylic acid | 624.3 |

TABLE 1-continued

| Ex | Name<br>Structure<br>Aspect | Reactant to be used in step<br>[A] | MS<br>(M + H⁺) |
|---|---|---|---|
| | 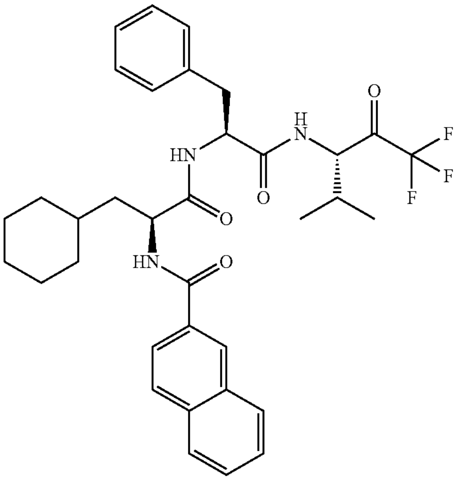<br>Off-white waxy solid | | |
| 62 | tert-butyl N-[2-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]carbamate<br>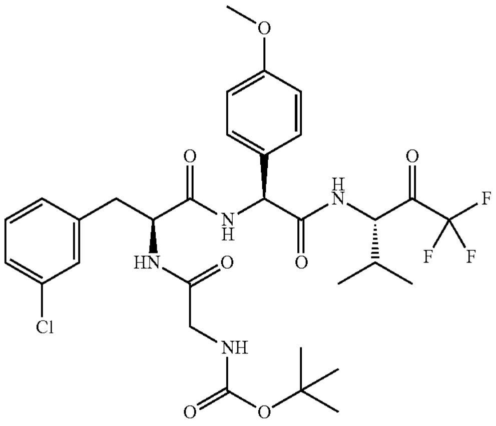<br>Colorless solid | Intermediate A-1 and 2-(tert-butoxycarbonylamino)acetic acid | 671.4 |
| 63 | tert-butyl N-[[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenyl]methyl]carbamate | Intermediate A-1 and 4-[(tert-butoxycarbonylamino)methyl] benzoic acid | 747.7 |

TABLE 1-continued

| Ex | Name<br>Structure<br>Aspect | Reactant to be used in step<br>[A] | MS<br>(M + H⁺) |
|---|---|---|---|
| | 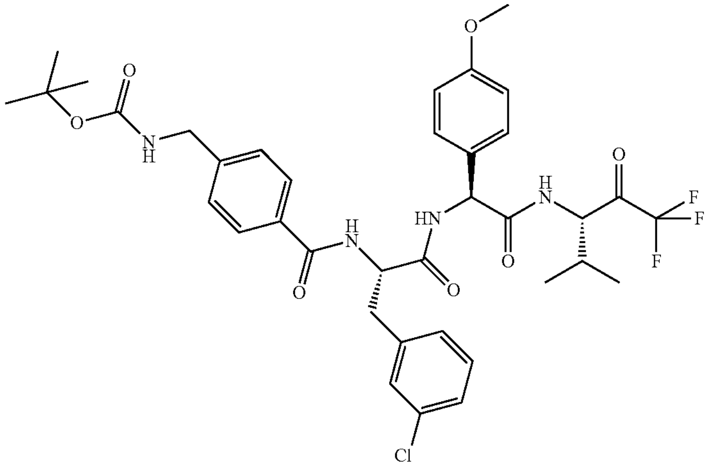<br>Colorless solid | | |
| 64 | tert-butyl N-[[2-chloro-4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenyl]methyl]carbamate | Intermediate A-1<br>and<br>4-[(tert-butoxycarbonylamino)methyl]-3-chloro-benzoic acid | 781.3 |
| | 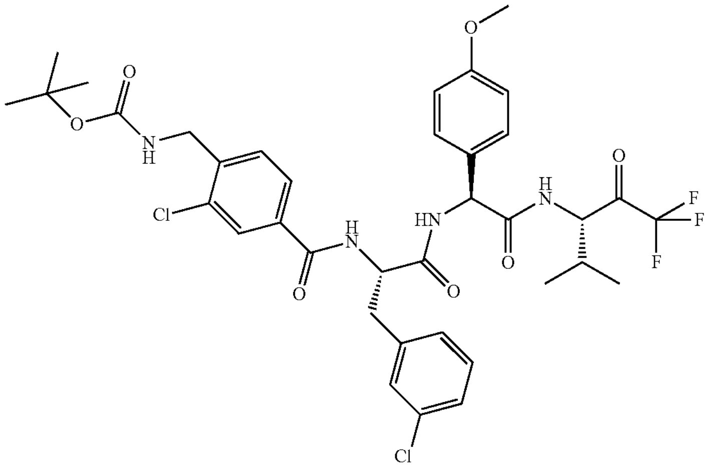<br>Colorless solid | | |
| 65 | tert-butyl N-[[4-[2-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]phenyl]methyl]carbamate | Intermediate A-1<br>and<br>2-[4-[(tert-butoxycarbonylamino)methyl]phenyl]acetic acid | (M − H⁻)<br>759.4 |

TABLE 1-continued

| Ex | Name<br>Structure<br>Aspect | Reactant to be used in step<br>[A] | MS<br>(M + H$^+$) |
|---|---|---|---|
| | 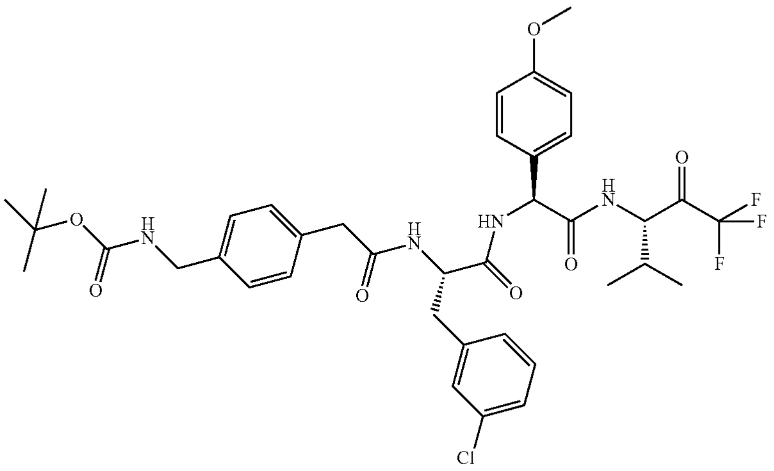<br>Off white solid | | |
| 66 | tert-butyl 2-[6-[[(2S)-3-(3-chlorophenyl)-1-[[(1S)-1-(4-methoxyphenyl)-2-oxo-2-[[(3S)-1,1,1-trifluroo-4-methyl-2-oxopentan-3-yl]amino]ethyl]amino]-1-oxopropan-2-yl]carbamoyl]pyridin-2-yl]oxyacetate | Intermediate A-1<br>and<br>Intermediate L-1 | 749.4 |
| | 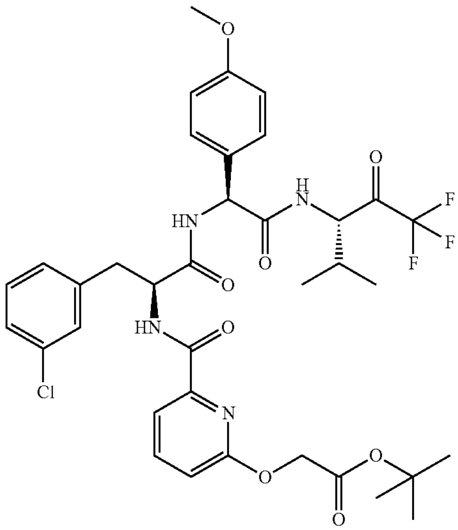<br>Colorless solid | | |
| 67 | tert-butyl 2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetate | Intermediate A-1<br>and<br>4-(2-tert-butoxy-2-oxo-ethoxy)benzoic acid | 748.4 |

TABLE 1-continued

| Ex | Name<br>Structure<br>Aspect | Reactant to be used in step<br>[A] | MS<br>(M + H$^+$) |
|---|---|---|---|
| | 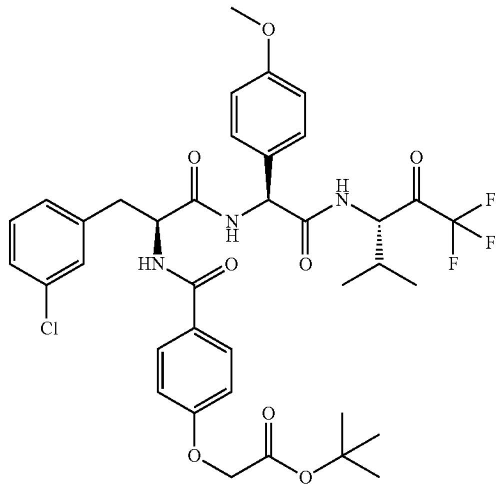<br>Colorless solid | | |
| 68 | tert-butyl 2-[6-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-2-oxopropan-2-yl]carbamoyl]pyridin-3-yl]oxyacetate | Intermediate A-1<br>and<br>Intermediate L-2 | 749.4 |
| | 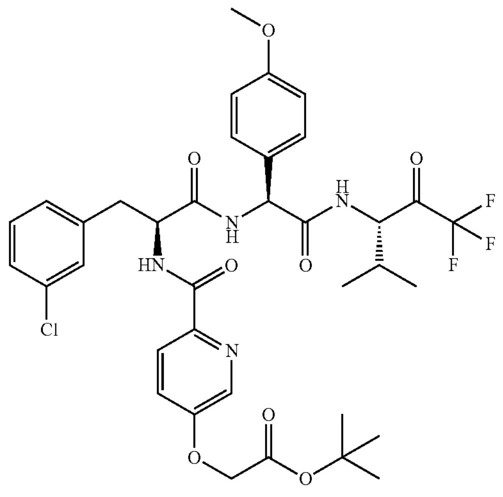<br>Colorless solid | | |
| 69 | tert-butyl 2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-2-oxopropan-2-yl]carbamoyl]-2-oxopyridin-1-yl]acetate | Intermediate A-1<br>and<br>Intermediate L-3 | 749.5 |

TABLE 1-continued

| Ex | Name<br>Structure<br>Aspect | Reactant to be used in step<br>[A] | MS<br>(M + H⁺) |
|---|---|---|---|
| | 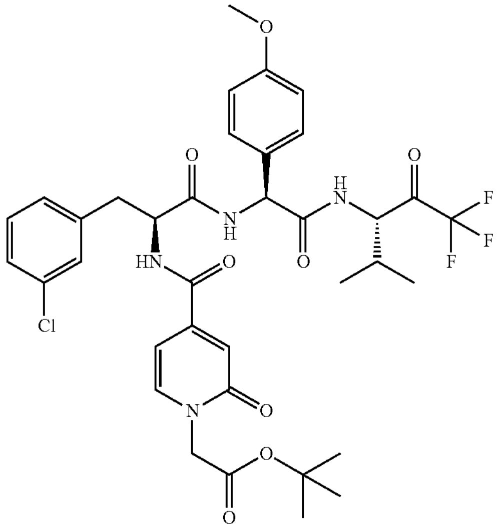<br>Colorless solid | | |
| 70 | tert-butyl 2-[3-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetate | Intermediate A-1<br>and<br>3-(2-tert-butoxy-2-oxo-ethoxy)benzoic acid | 748.5 |
| | 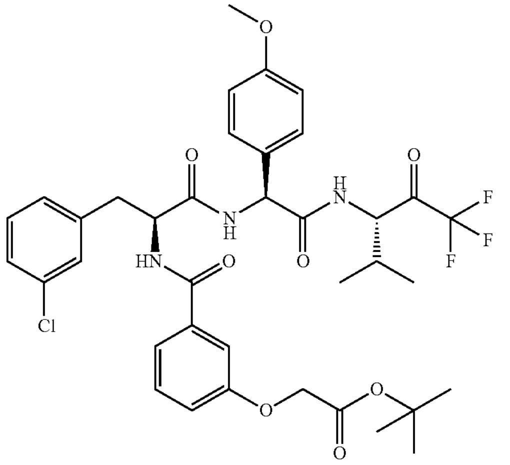<br>Colorless amorphous | | |
| 71 | tert-butyl 2-[5-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]-2-oxopyridin-1-yl]acetate | Intermediate A-1<br>and<br>Intermediate L-4 | 749.4 |

TABLE 1-continued

| Ex | Name<br>Structure<br>Aspect | Reactant to be used in step<br>[A] | MS<br>(M + H⁺) |
|---|---|---|---|
| | 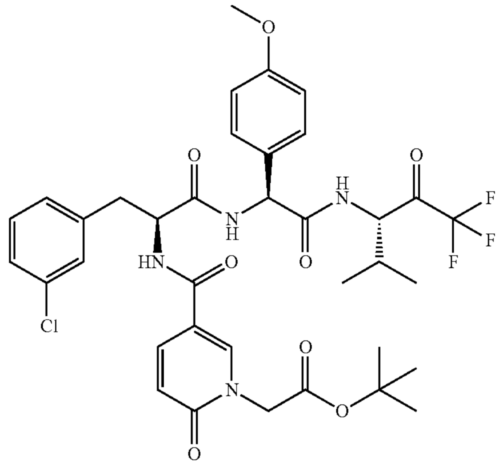<br>Colorless solid | | |
| 72 | tert-butyl 2-[4-[2-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethoxy]phenoxy]acetate<br>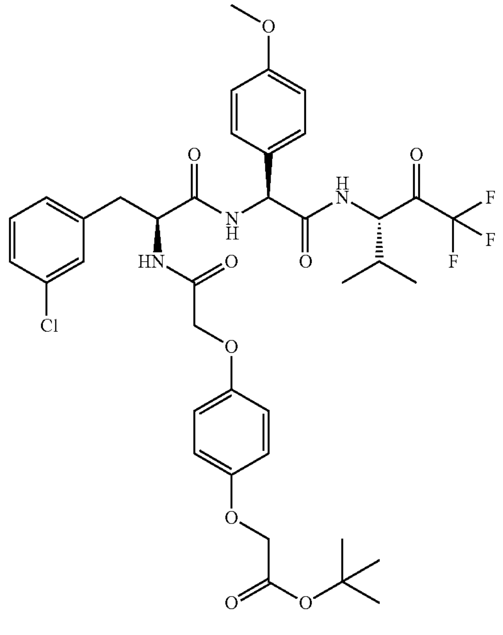<br>Colorless solid | Intermediate A-1<br>and<br>Intermediate K-3 | 778.4 |
| 73 | tert-butyl 2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetate | Intermediate A-3<br>and<br>3-(2-tert-butoxy-2-oxo-ethoxy)benzoic acid | 739.4 |

TABLE 1-continued

| Ex | Name<br>Structure<br>Aspect | Reactant to be used in step [A] | MS (M + H⁺) |
|---|---|---|---|
| | 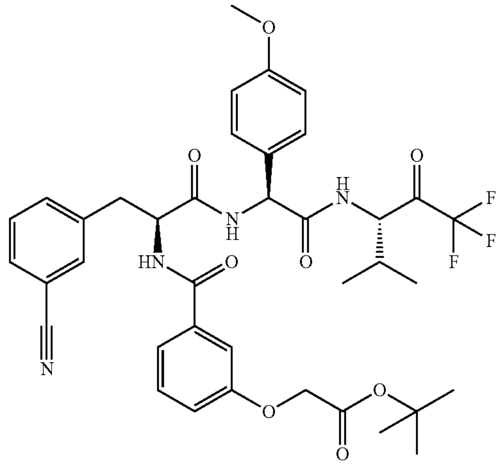<br>Colorless waxy solid | | |
| 74 | tert-butyl 2-[4-[[(2)S-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetate<br>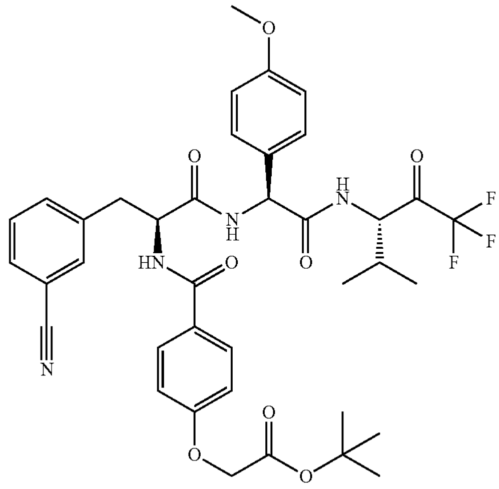<br>Colorless waxy solid | Intermediate A-3 and 4-(2-tert-butoxy-2-oxo-ethoxy)benzoic acid | 739.4 |
| 75 | N-[3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide | Intermediate C-1 and pyridine-2-carboxylic acid | 619.2 |

TABLE 1-continued

| Ex | Name Structure Aspect | Reactant to be used in step [A] | MS (M + H+) |
| --- | --- | --- | --- |
| | 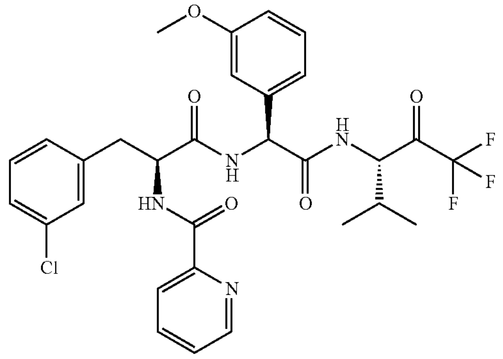 Colorless solid | | |
| 76 | N-[(2S)-3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]-3-methylpyridine-2-carboxamide 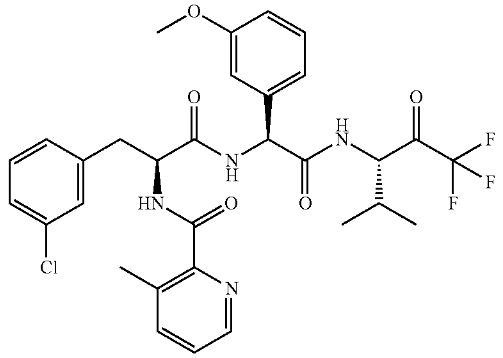 Colorless solid | Intermediate C-1 and 3-methylpyridine-2-carboxylic acid | 633.2 |
| 77 | N-[(2S)-3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]-4-methylpyridine-3-carboxamide 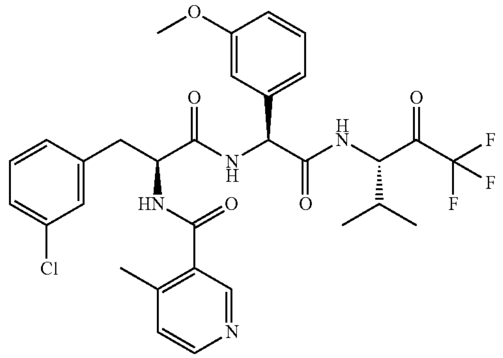 Colorless solid | Intermediate C-1 and 4-methylpyridine-3-carboxylic acid | 633.2 |
| 78 | N-[(2S)-3-(3-cyanophenyl)-1-[[(1S)-1-(4-methoxyphenyl)-2-oxo-2-[[(3S)-1,1,1- | Intermediate A-3 and | 610.3 |

TABLE 1-continued

| Ex | Name<br>Structure<br>Aspect | Reactant to be used in step [A] | MS (M + $H^+$) |
|---|---|---|---|
| | trifluoro-4-methyl-2-oxopentan-3-yl]amino]ethyl]amino]-1-oxopropan-2-yl]pyridine-2-carboxamide<br>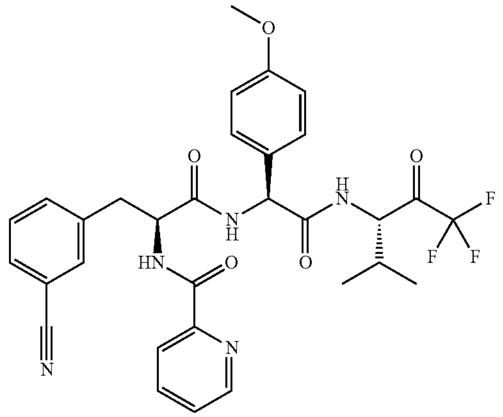<br>Colorless solid | pyridine-2-carboxylic acid | |
| 79 | N-[(2R)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyridine-2-carboxamide<br>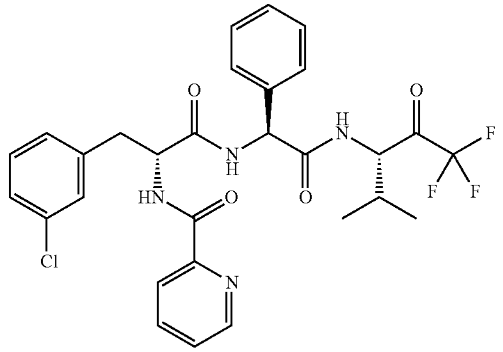<br>Colorless waxy solid | Intermediate B-3<br>and<br>pyridine-2-carboxylic acid | 589.3 |
| 80 | N-[(2R)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrazine-2-carboxamide | Intermediate B-3<br>and<br>pyrazine-2-carboxylic acid | 590.3 |

TABLE 1-continued

| Ex | Name<br>Structure<br>Aspect | Reactant to be used in step [A] | MS (M + H⁺) |
|---|---|---|---|
| | 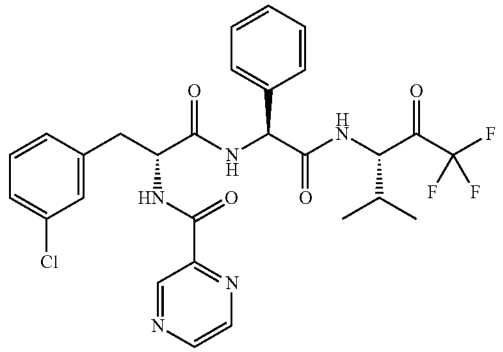<br>Colorless waxy solid | | |
| 81 | N-[(2R)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrimidine-5-carboxamide | Intermediate B-3 and pyrimidine-5-carboxylic acid | 590.2 |
| | 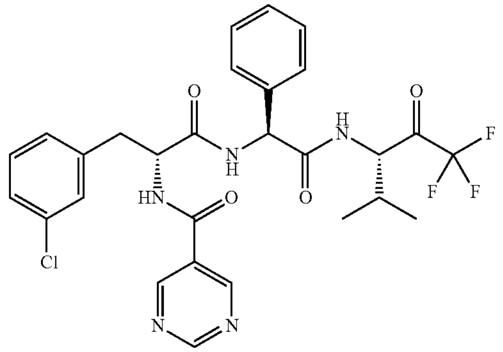<br>Colorless waxy solid | | |
| 82 | tert-butyl N-[[4-[[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenyl]methyl]carbamate | Intermediate A-8 and 4-[(tert-butoxycarbonylamino)methyl] benzoic acid | 637.4 |
| | 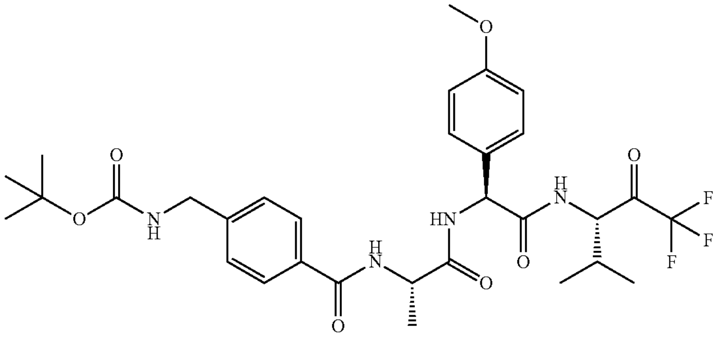<br>Colorless solid | | |

TABLE 1-continued

| Ex | Name<br>Structure<br>Aspect | Reactant to be used in step [A] | MS (M + H⁺) |
|---|---|---|---|
| 83 | tert-butyl N-[[4-[2-[[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]phenyl]methyl]carbamate<br>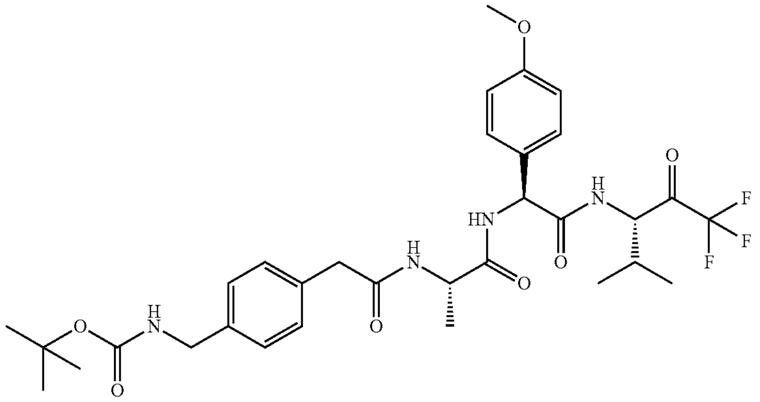<br>Colorless solid | Intermediate A-8<br>and<br>2-[4-[(tert-butoxycarbonylamino)methyl]phenyl]acetic acid | 651.3 |

Example 84 tert-Butyl 2-[[2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetate

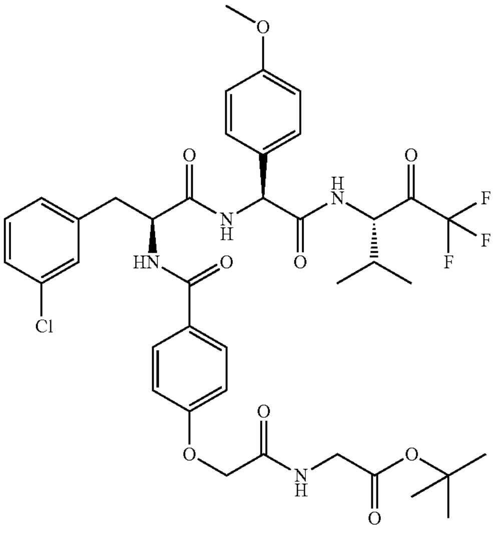 [SMILES: COc1ccc([C@H](NC(=O)[C@H](Cc2cccc(Cl)c2)NC(=O)c2ccc(OCC(=O)NCC(=O)OC(C)(C)C)cc2)C(=O)N[C@H](C(=O)C(F)(F)F)C(C)C)cc1]

[A] tert-Butyl 2-[[2-[4-[[(2S)-3-(3-chlorophenyl)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxopropan-2-yl]carbamoyl]phenoxy]acetyl]amino]acetate

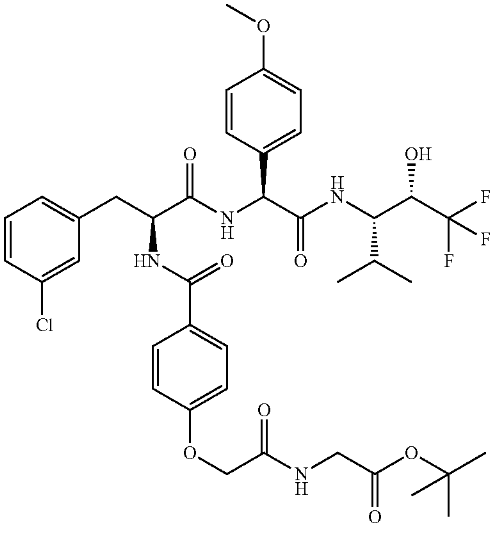 [SMILES: COc1ccc([C@H](NC(=O)[C@H](Cc2cccc(Cl)c2)NC(=O)c2ccc(OCC(=O)NCC(=O)OC(C)(C)C)cc2)C(=O)N[C@@H](C(C)C)[C@H](O)C(F)(F)F)cc1]

In a round-bottomed flask, 2-[4-[[(2S)-3-(3-chlorophenyl)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxopropan-2-yl]carbamoyl]phenoxy]acetic acid (Intermediate A-13, 0.057 g, 0.082 mmol), tert-butyl 2-aminoacetate hydrochloride (0.013 g, 0.098 mmol) and HATU (0.034 g, 0.090 mmol) were dissolved in DMF (1 mL) and the mixture cooled to 0° C. Hunig's base (0.043 mL, 0.246 mmol) was added to the reaction mixture which was stirred at this temperature for 10 min, then allowed to warm up to room temperature and stirring was continued overnight. The mixture was diluted with EtOAc, poured into 1M HCl (5 mL) and the aqueous layer was extracted with EtOAc (2×10 mL). Combined organics were washed with a sat. $NaHCO_3$ solution (5 mL), then brine before being dried over $Na_2SO_4$, filtered and concentrated in vacuo. The residue was purified by silica gel flash chromatography eluting with a 0 to 100% EtOAc-heptane gradient to give the title compound (0.049 g, 67%) as a colorless solid. MS: 807.4 ($M+H^+$).

[B] tert-Butyl 2-[[2-[4-[[(2S)-3-(3-chlorophenyl)-1-[[(1S)-1-(4-methoxyphenyl)-2-oxo-2-[(3S)-1,1,1-trifluoro-4-methyl-2-oxopentan-3-yl]amino]ethyl]amino]-1-oxopropan-2-yl]carbamoyl]phenoxy]acetyl]amino]acetate

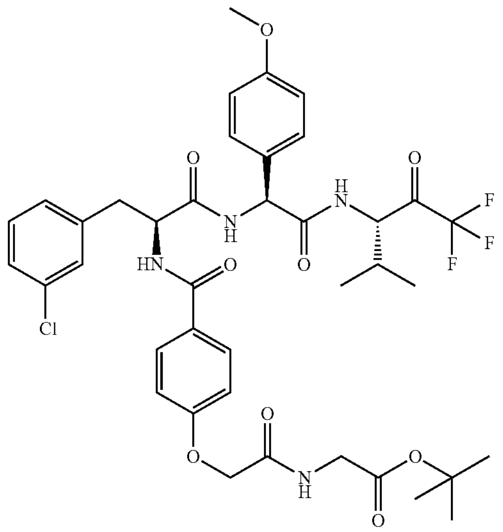 [SMILES: COc1ccc([C@H](NC(=O)[C@H](Cc2cccc(Cl)c2)NC(=O)c2ccc(OCC(=O)NCC(=O)OC(C)(C)C)cc2)C(=O)N[C@H](C(=O)C(F)(F)F)C(C)C)cc1]

was prepared in analogy to example 1[B], but using tert-butyl 2-[[2-[4-[[(2S)-3-(3-chlorophenyl)-1-[[(1S)-1-(4-methoxyphenyl)-2-oxo-2-[[(2S,3S)-1,1,1-trifluoro-2-hydroxy-4-methylpentan-3-yl]amino]ethyl]amino]-1-oxopropan-2-yl]carbamoyl]phenoxy]acetyl]amino]acetate, to give the title compound as colorless solid; MS: 805.5 ($M+H^+$).

The following examples listed in Table 2 were prepared in analogy to the procedures described for the preparation of example 84 by using the indicated intermediate in step [A].

TABLE 2

| Ex | Name<br>Structure<br>Aspect | Reactant to be used in step [A] | MS ($M + H^+$) |
|---|---|---|---|
| 85 | tert-butyl 2-[[2-[3-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetate | Intermediate A-14<br>and<br>tert-butyl 2-aminoacetate HCl | 805.5 |

TABLE 2-continued

| Ex | Name<br>Structure<br>Aspect | Reactant to be used in step<br>[A] | MS<br>(M + H+) |
|---|---|---|---|
| | 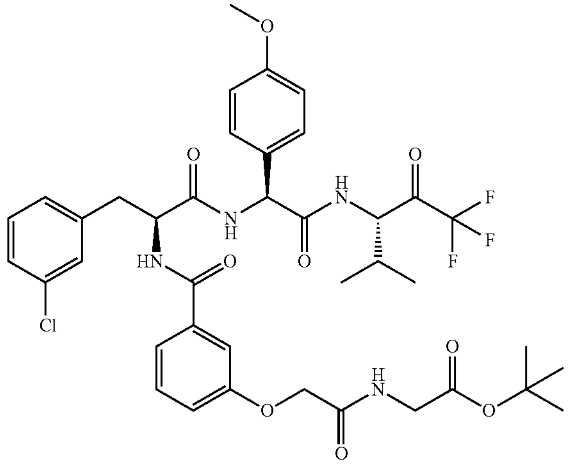<br>Colorless solid | | |
| 86 | tert-butyl 2-[[2-[4-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetate<br>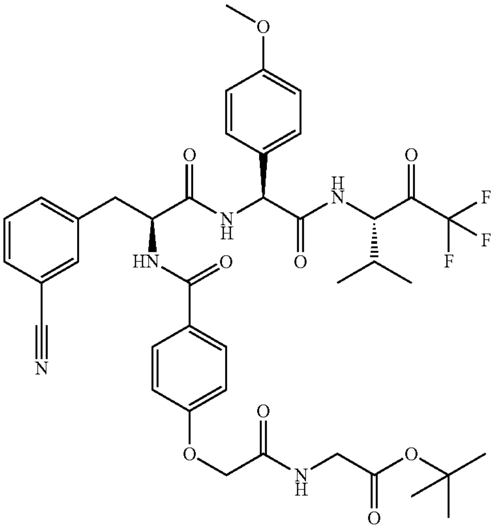<br>Colorless solid | Intermediate A-15<br>and<br>tert-butyl 2-aminoacetate<br>HCl | 796.4 |
| 87 | tert-butyl 2-[[2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetate | Intermediate A-16<br>and<br>tert-butyl 2-aminoacetate<br>HCl | 796.4 |

TABLE 2-continued

| Ex | Name<br>Structure<br>Aspect | Reactant to be used in step [A] | MS (M + H+) |
|---|---|---|---|
| | 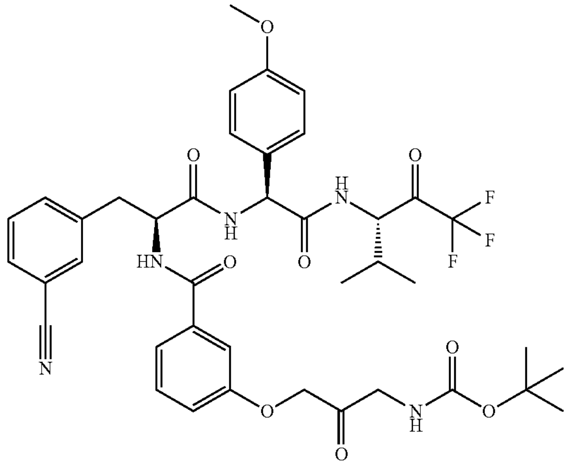<br>Colorless solid | | |

Example 88

2-[4-[(2S)-2-[(3-Chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic Acid

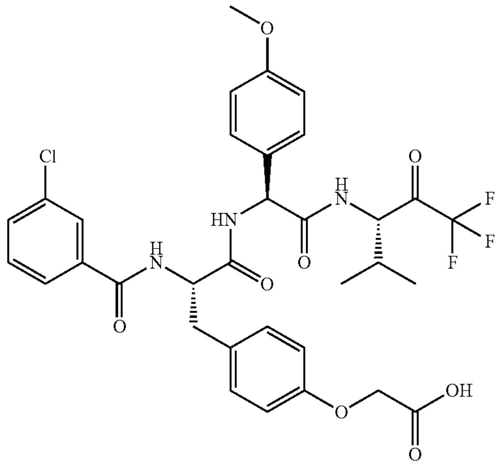 [SMILES: COc1ccc([C@H](NC(=O)[C@H](Cc2ccc(OCC(=O)O)cc2)NC(=O)c2cccc(Cl)c2)C(=O)N[C@H](C(=O)C(F)(F)F)C(C)C)cc1]

To a solution of tert-butyl 2-[4-[(2S)-2-[(3-chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate (Example 15, 0.018 g, 0.024 mmol) in DCM (1 mL) was added TFA (0.092 mL, 1.2 mmol) and the reaction mixture was stirred at room temperature for 4 hours. The mixture was concentrated in vacuo, the residue was triturated in diisopropylether, filtered and further dried under high vacuum. The residue was purified by preparative TLC (silica gel, 7/3 EtOAc/heptane) to give the title compound (0.015 g, 92%) as a colorless solid. MS: 692.6 (M+H$^+$).

The following examples listed in Table 3 were prepared in analogy to the procedure described for the preparation of example 88 by using the indicated starting materials. Carboxylic acids were purified by preparative TLC to remove the traces amounts of remaining tert-butyl intermediate; amine products were triturated in diisopropylether and obtained as TFA salts.

TABLE 3

| Ex | Name<br>Structure<br>Aspect | Reactant: compound obtained in example number indicated | MS (M + H+) |
|---|---|---|---|
| 89 | 2-[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-(pyridine-2-carbonylamino)propyl]phenoxy]acetic acid | Example 16 | 659.3 |

TABLE 3-continued

| Ex | Name<br>Structure<br>Aspect | Reactant: compound obtained in example number indicated | MS (M + H⁺) |
|---|---|---|---|
| | 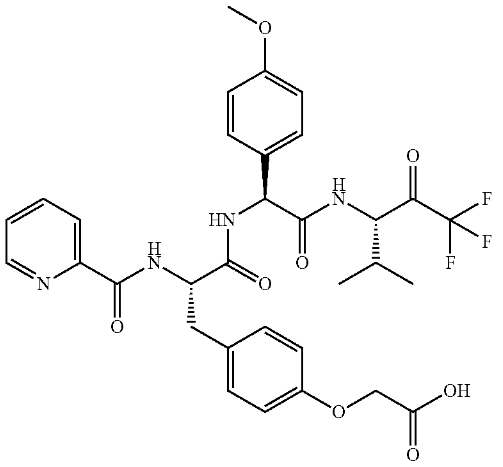<br>Colorless solid | | |
| 90 | 2-[4-[(2S)-2-[[2-(2-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid | Example 17 | 742.3 |
| | 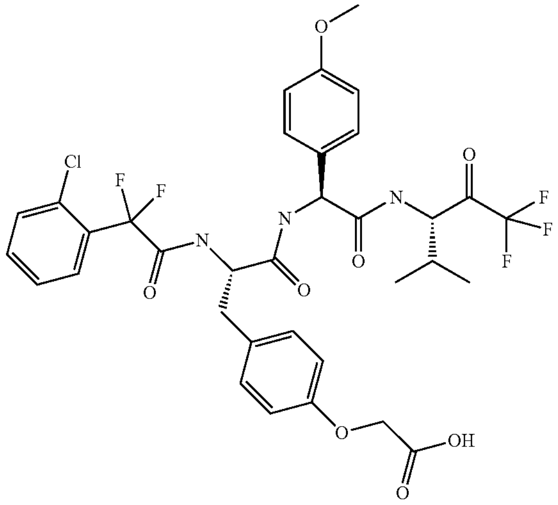<br>Colorless solid | | |
| 91 | 2-[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid | Example 18 | 742.3 |

TABLE 3-continued

| Ex | Name<br>Structure<br>Aspect | Reactant: compound obtained in example number indicated | MS (M + H+) |
|---|---|---|---|
| | 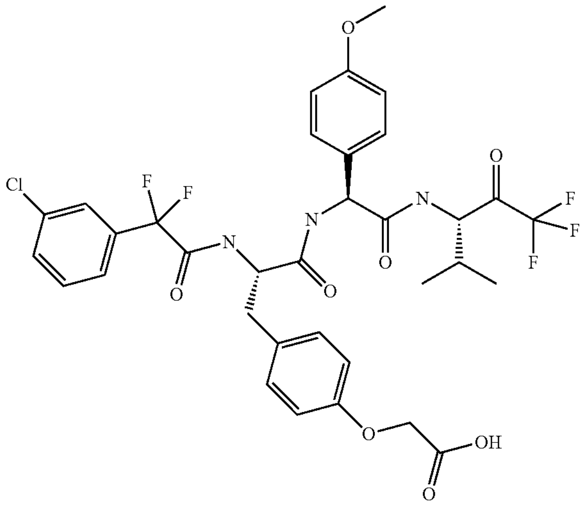<br>Colorless waxy solid | | |
| 92 | 2-[3-[(2S)-2-[(3-chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid<br>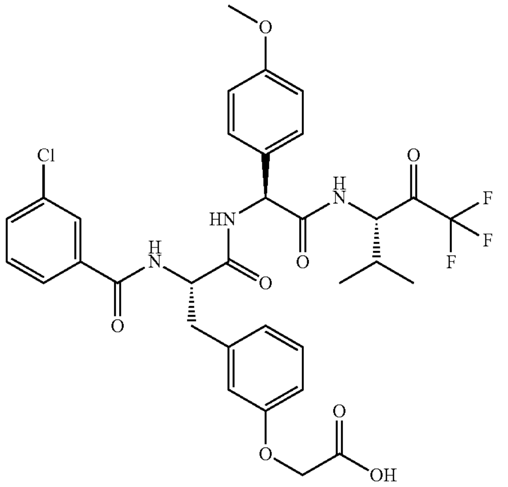<br>Light brown solid | Example 19 | 692.3 |
| 93 | 2-[3-[(2S)-2-[[2-(2-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid | Example 20 | 742.3 |

TABLE 3-continued

| Ex | Name<br>Structure<br>Aspect | Reactant: compound obtained in example number indicated | MS (M + H+) |
|---|---|---|---|
| | 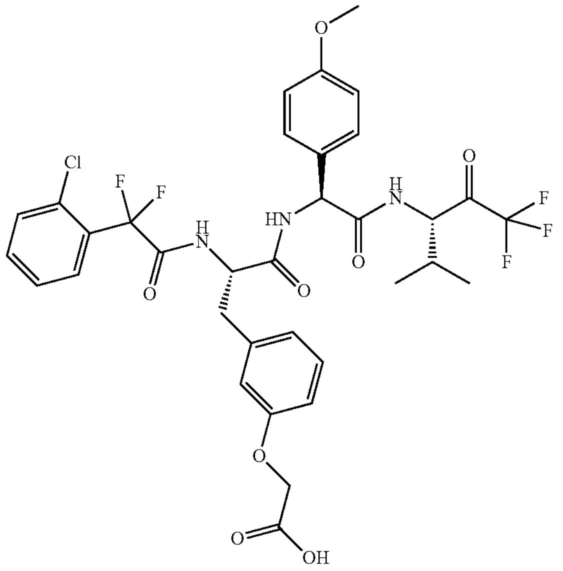<br>Colorless solid | | |
| 94 | (4S)-4-[(3-chlorobenzoyl)amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoic acid<br>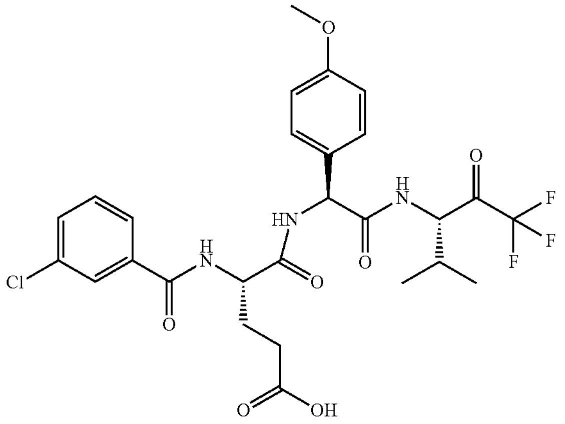<br>Colorless solid | Example 46 | 600.2 |
| 95 | (4S)-4-[[2-(3-chlorophenyl)-2,2-difluoroacetyl]amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoic acid | Example 47 | 650.3 |

TABLE 3-continued

| Ex | Name<br>Structure<br>Aspect | Reactant: compound obtained in example number indicated | MS (M + H$^+$) |
| --- | --- | --- | --- |
| | 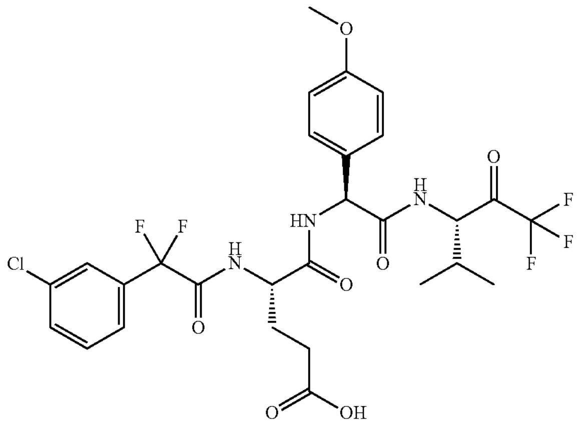<br>Colorless foam | | |
| 96 | (2S)-2-[(2-aminoacetyl)amino]-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]propanamide; TFA salt | Example 62 | 571.3 |
| | 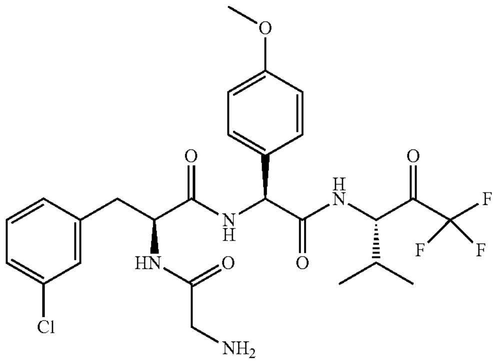<br>Off-white solid | | |
| 97 | 4-(aminomethyl)-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide; TFA salt | Example 63 | 647.5 |

TABLE 3-continued

| Ex | Name<br>Structure<br>Aspect | Reactant: compound obtained in example number indicated | MS<br>(M + H$^+$) |
|---|---|---|---|
| | 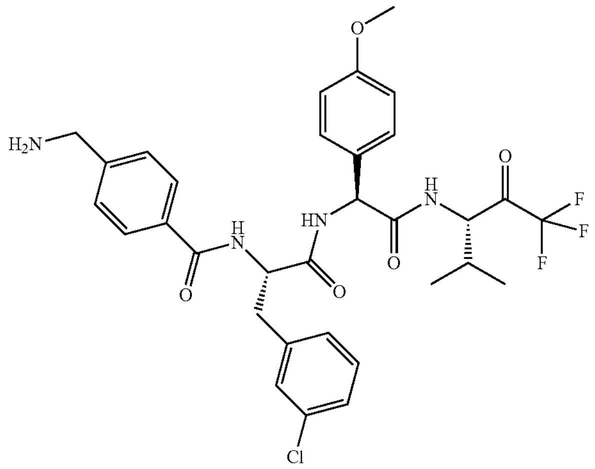<br>Colorless solid | | |
| 98 | 4-(aminomethyl)-3-chloro-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide; TFA salt<br>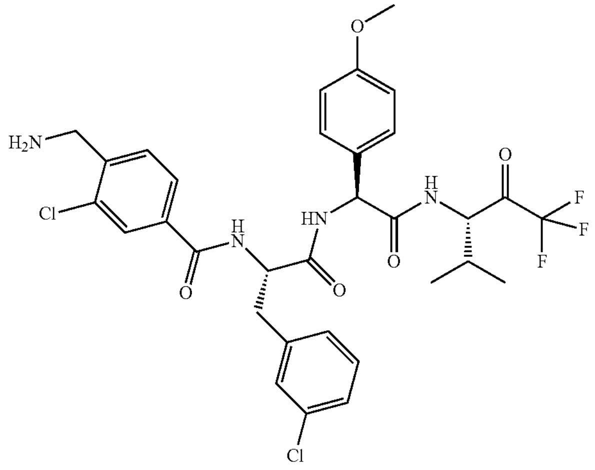<br>Off-white solid | Example 64 | 681.3 |
| 99 | (2S)-2-[[2-[4-(aminomethyl)phenyl]acetyl]amino]-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]propanamide; TFA salt | Example 65 | 661.3 |

TABLE 3-continued

| Ex | Name<br>Structure<br>Aspect | Reactant: compound obtained in example number indicated | MS (M + H⁺) |
|---|---|---|---|
| | 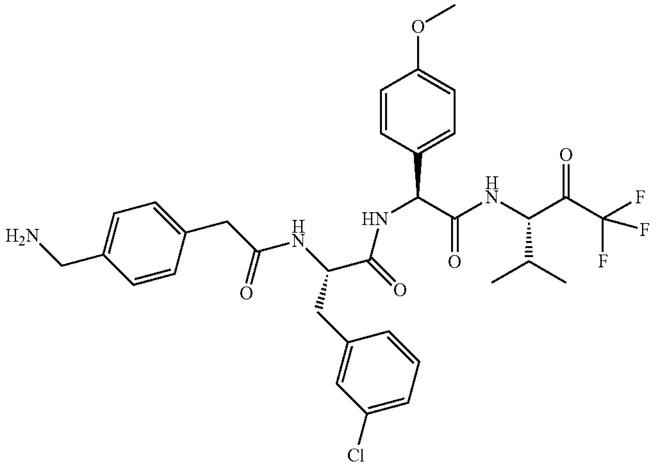<br>Colorless solid | | |
| 100 | 2-[6-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]pyridin-2-yl]oxyacetic acid | Example 66 | 693.3 |
| | 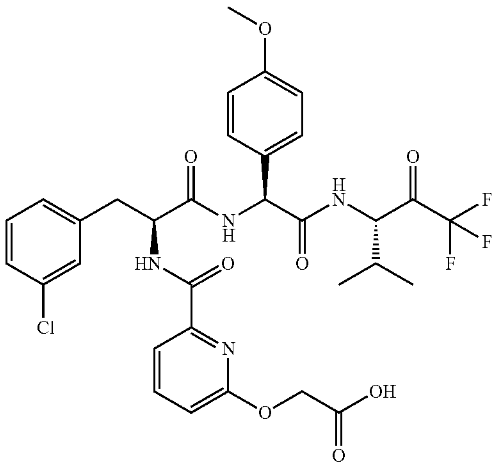<br>Colorless solid | | |
| 101 | 2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid | Example 67 | 692.4 |

TABLE 3-continued

| Ex | Name<br>Structure<br>Aspect | Reactant: compound obtained in example number indicated | MS (M + H+) |
|---|---|---|---|
| | 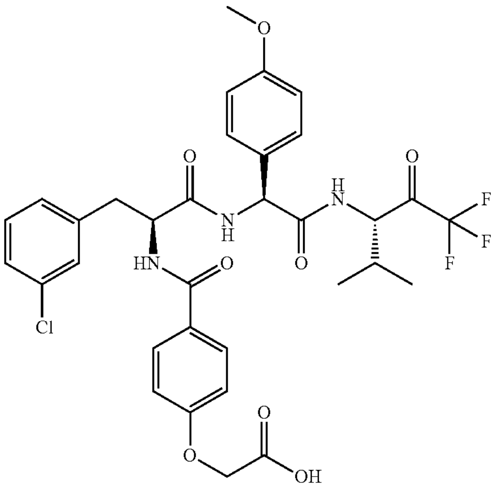<br>Colorless solid | | |
| 102 | 2-[6-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]pyridin-3-yl]oxyacetic acid<br>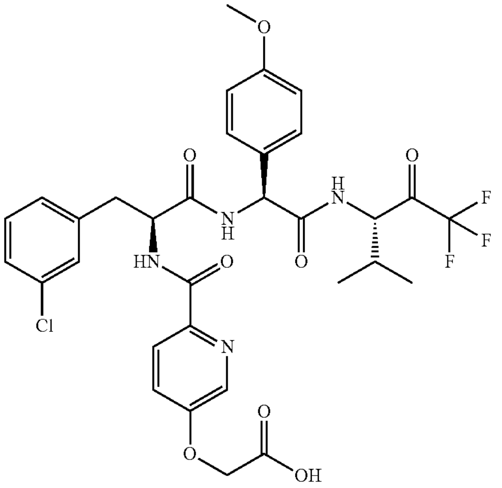<br>Orange solid | Example 68 | 693.3 |
| 103 | 2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]-2-oxopyridin-1-yl]acetic acid | Example 69 | 693.3 |

TABLE 3-continued

| Ex | Name<br>Structure<br>Aspect | Reactant: compound obtained in example number indicated | MS (M + H$^+$) |
|---|---|---|---|
| | 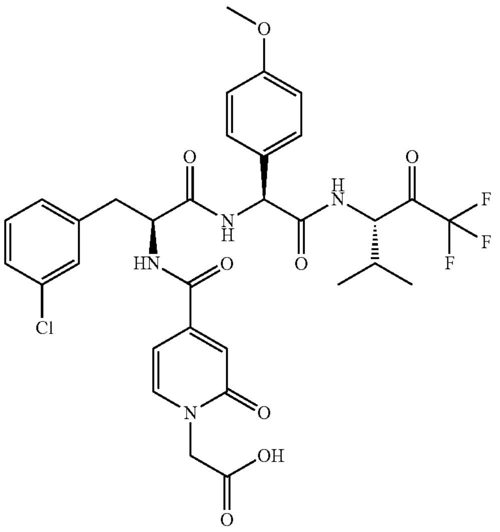<br>Colorless solid | | |
| 104 | 2-[3-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid | Example 70 | 692.4 |
| | 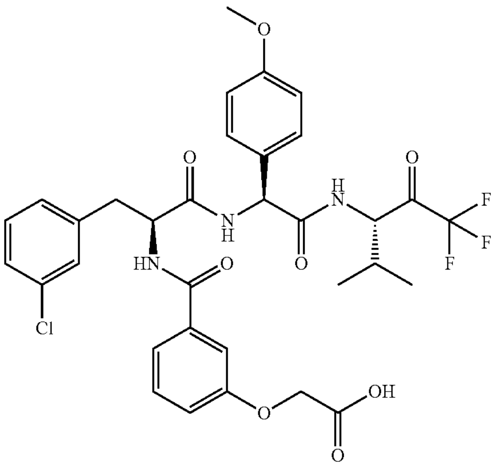<br>Light brown solid | | |
| 105 | 2-[5-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]-2-oxopyridin-1-yl]acetic acid | Example 71 | 693.3 |

TABLE 3-continued

| Ex | Name<br>Structure<br>Aspect | Reactant: compound obtained in example number indicated | MS (M + H$^+$) |
|---|---|---|---|
| | 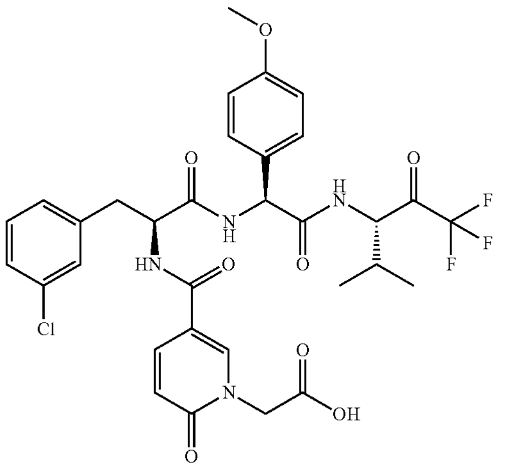<br>Colorless solid | | |
| 106 | 2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid | Example 72 | 722.4 |
| | 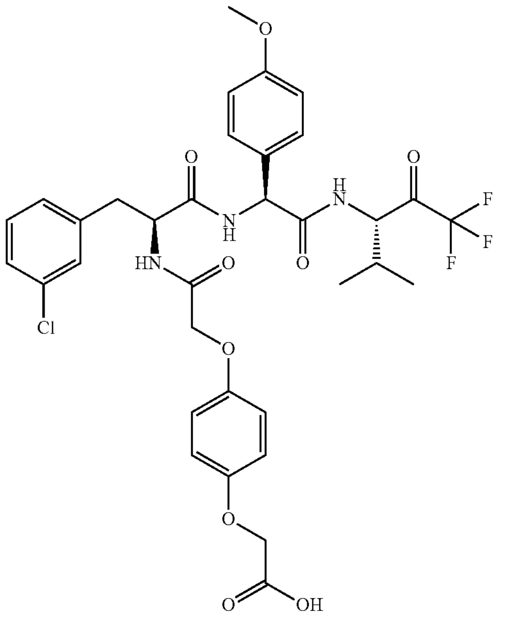<br>Colorless solid | | |
| 107 | 2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid | Example 73 | 683.4 |

TABLE 3-continued

| Ex | Name<br>Structure<br>Aspect | Reactant: compound obtained in example number indicated | MS (M + H+) |
|---|---|---|---|
| | 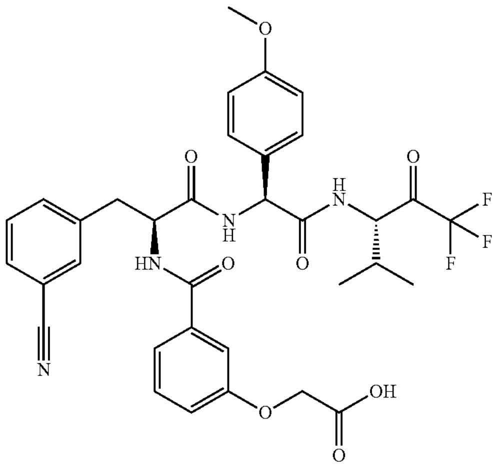<br>Colorless solid | | |
| 108 | 2-[4-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid<br>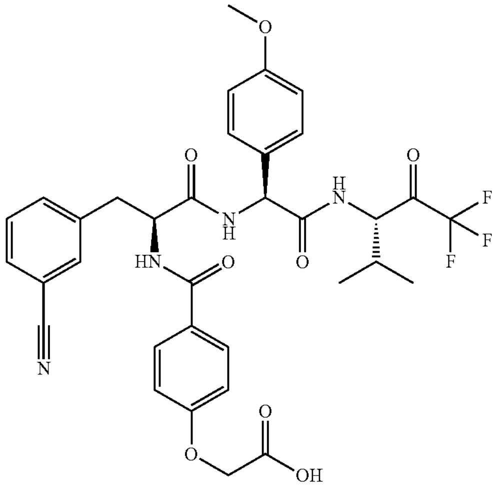<br>Colorless solid | Example 74 | 683.4 |
| 109 | 4-(aminomethyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide; TFA salt | Example 82 | 537.3 |

TABLE 3-continued

| Ex | Name<br>Structure<br>Aspect | Reactant: compound obtained in example number indicated | MS (M + H+) |
|---|---|---|---|
| | 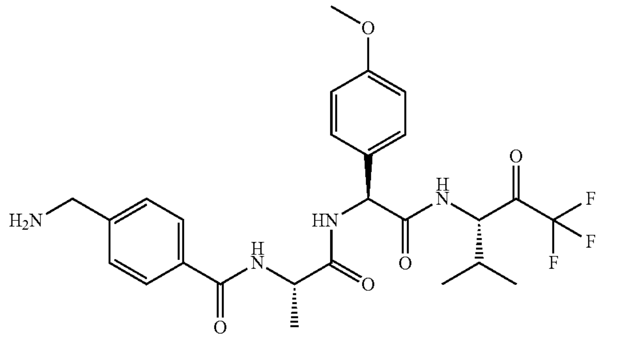<br>Off white solid | | |
| 110 | (2S)-2-[[2-[4-(aminomethyl)phenyl]acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide; TFA salt<br>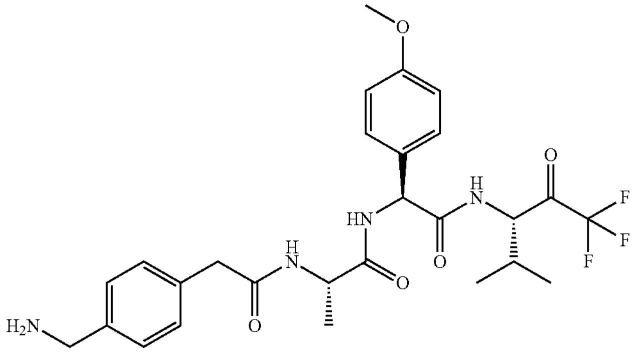<br>Off-white solid | Example 83 | 551.3 |
| 111 | 2-[[2-[4-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid | Example 84 | 749.3 |

TABLE 3-continued

| Ex | Name<br>Structure<br>Aspect | Reactant: compound obtained in example number indicated | MS (M + H+) |
|---|---|---|---|
| | 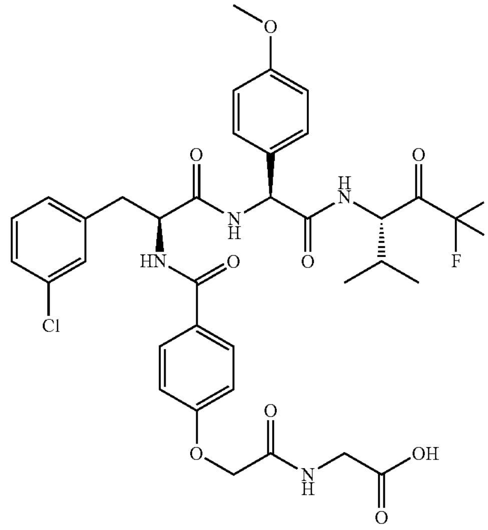<br>Colorless solid | | |
| 112 | 2-[[2-[3-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid | Example 85 | 749.4 |
| | 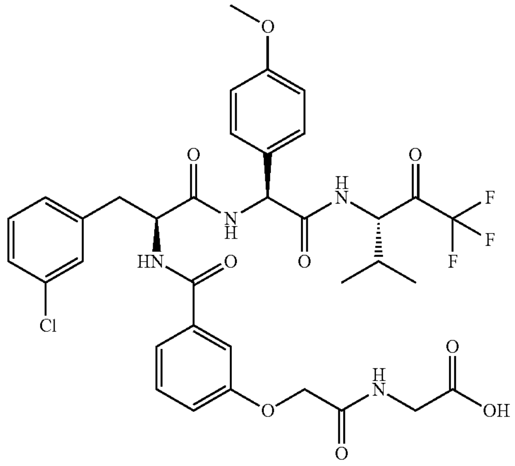<br>Colorless amorphous | | |
| 113 | 2-[[2-[4-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid | Example 86 | 740.4 |

TABLE 3-continued
| Ex | Name<br>Structure<br>Aspect | Reactant: compound obtained in example number indicated | MS (M + H+) |
|---|---|---|---|
| | 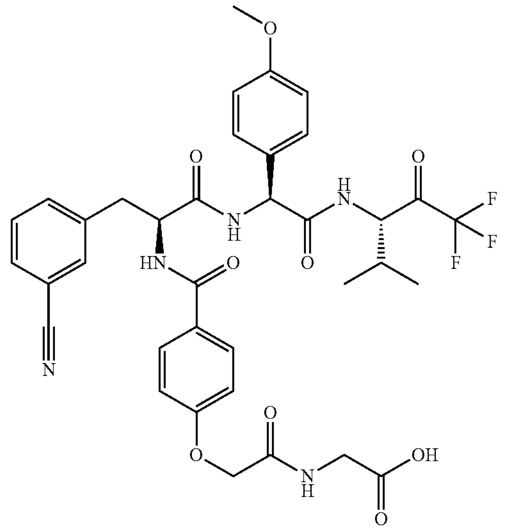<br>Light brown solid | | |
| 114 | 2-[[2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid<br>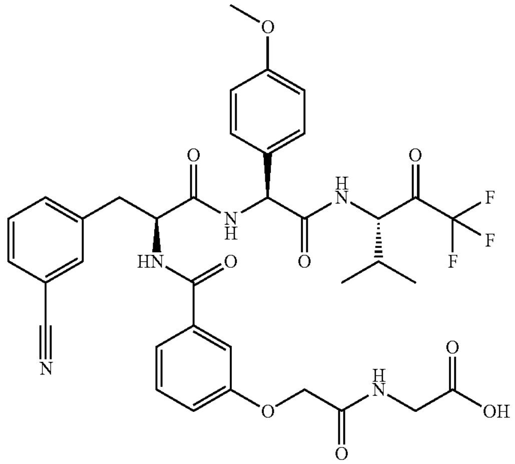<br>Light brown solid | Example 87 | 740.3 |

Example 115

(2S)-2-[[2-(3-Chlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide

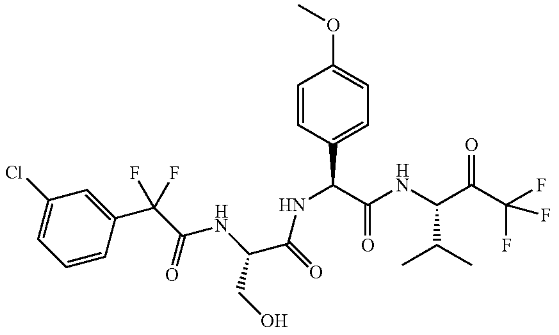 [SMILES: COc1ccc([C@H](NC(=O)[C@H](CO)NC(=O)C(F)(F)c2cccc(Cl)c2)C(=O)N[C@H](C(=O)C(F)(F)F)C(C)C)cc1]

To a solution of (2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-[(2-methylpropan-2-yl)oxy]propanamide (Example 39, 0.044 g, 0.066 mmol) in DCM (1 mL) was added wet TFA (2.5% $H_2O$) (0.355 mL, 4.64 mmol) and the reaction mixture was stirred at room temperature for 4 hours. The mixture was concentrated in vacuo. The residue was purified by silica gel flash chromatography eluting with a 10 to 100% EtOAc-heptane gradient and the resulting material was triturated in diisopropylether, filtered and further dried under high vacuum to give the title compound (0.024 g, 57%) as a colorless solid. MS: 608.2 ($M+H^+$).

The following examples listed in Table 4 were prepared in analogy to the procedure described for the preparation of example 115 by using the indicated starting materials.

TABLE 4

| Ex | Name<br>Structure<br>Aspect | Reactant: compound obtained in example number indicated | MS ($M + H^+$) |
|---|---|---|---|
| 116 | N-[(2S)-3-hydroxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide<br>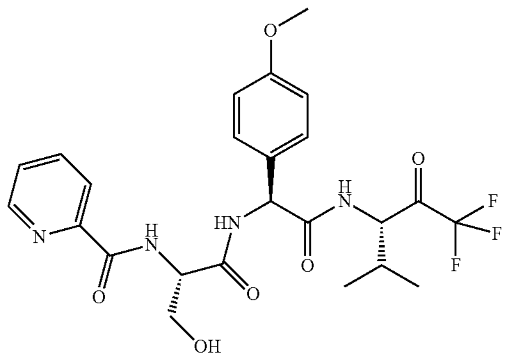<br>Colorless amorphous | Example 40 | 525.4 |
| 117 | 3-chloro-N-[(2S)-3-hydroxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide | Example 41 | 558.4 |

TABLE 4-continued

| Ex | Name<br>Structure<br>Aspect | Reactant: compound obtained in example number indicated | MS (M + H+) |
|---|---|---|---|
| | 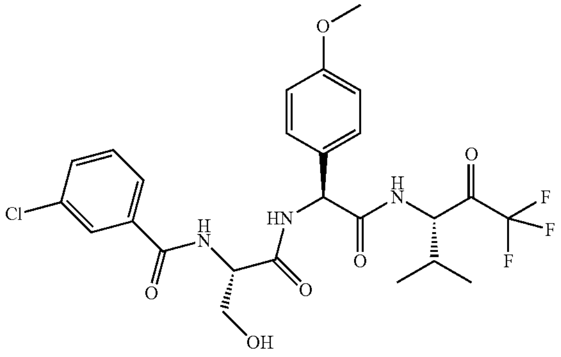<br>Colorless solid | | |
| 118 | 5-chloro-N-[(2S)-3-hydroxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide<br>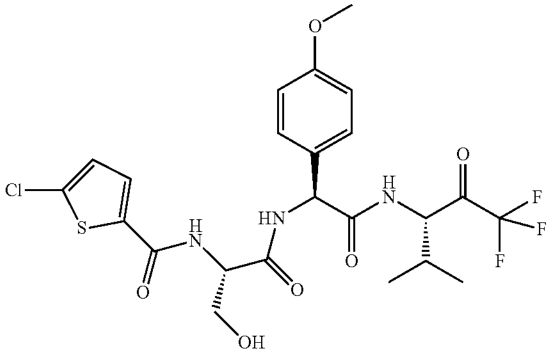<br>Colorless foam | Example 42 | 564.2 |
| 119 | (2S)-2-[[2-(2-chlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide<br>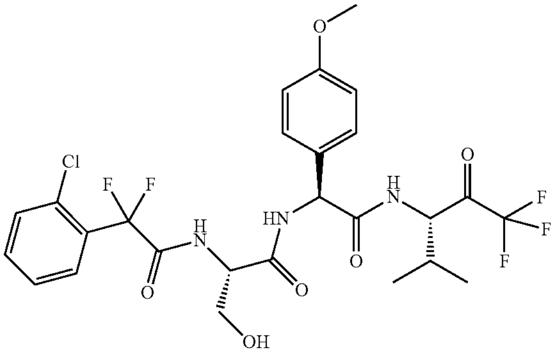<br>Colorless waxy solid | Example 43 | 608.4 |

Example 120

N-[2-[[(2S)-3-(3-Chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]pyridine-2-carboxamide

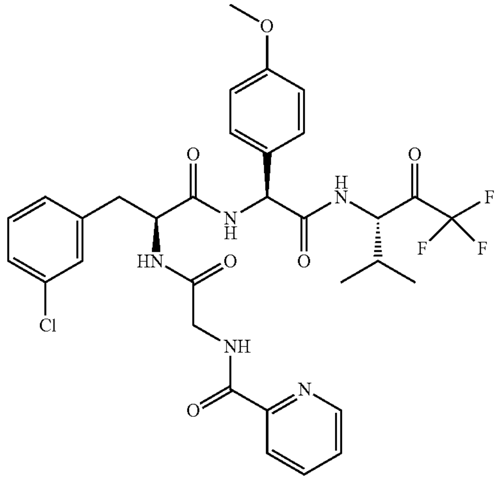 [SMILES: COc1ccc([C@H](NC(=O)[C@H](Cc2cccc(Cl)c2)NC(=O)CNC(=O)c2ccccn2)C(=O)N[C@H](C(=O)C(F)(F)F)C(C)C)cc1]

[A] (2,5-Dioxopyrrolidin-1-yl) pyridine-2-carboxylate

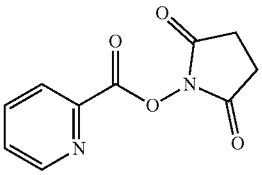 [SMILES: O=C(ON1C(=O)CCC1=O)c1ccccn1]

To a solution of picolinic acid (0.110 g, 0.894 mmol) in DCM (4 mL) were added EDCI (0.206 g, 1.07 mmol) followed by 1-hydroxypyrrolidine-2,5-dione (0.123 mg, 1.07 mmol) and the reaction mixture was stirred at room temperature overnight. The reaction mixture was poured into water (10 mL) and extracted with DCM (2×20 mL). The combined organic layers were washed with brine, dried over $Na_2SO_4$, filtered and concentrated in vacuo to give the title compound (0.180 g, 91%) as off-white solid. The crude material was used in the next step. MS: 221.1 (M+H$^+$).

[B] N-[2-[[(2S)-3-(3-Chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]pyridine-2-carboxamide

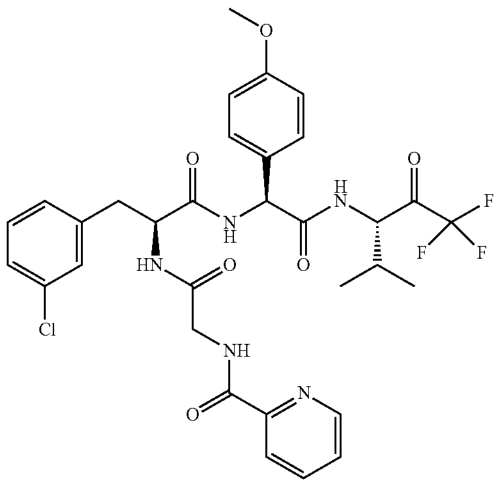 [SMILES: COc1ccc([C@H](NC(=O)[C@H](Cc2cccc(Cl)c2)NC(=O)CNC(=O)c2ccccn2)C(=O)N[C@H](C(=O)C(F)(F)F)C(C)C)cc1]

To a solution of (2S)-2-[(2-aminoacetyl)amino]-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]propanamide; TFA salt (Example 96, 0.020 g, 0.029 mmol) in DCM (1 mL) cooled to −20° C. were added (2,5-dioxopyrrolidin-1-yl) pyridine-2-carboxylate (0.006 g, 0.029 mmol) followed by triethylamine (0.012 mL, 0.088 mmol) and the reaction mixture was stirred at this temperature for 1 hour and then left to stand at 5° C. overnight. The residue was diluted with DCM, poured into water (2 mL) and the aqueous layer was extracted with DCM (2×5 mL). Combined organics were washed with brine, dried over $Na_2SO_4$, filtered and evaporated to dryness. The residue was triturated in diisopropylether, filtered and further dried under high vacuum to give the title compound (0.015 g, 76%) as colorless solid; MS: 676.5 (M+H$^+$).

Example 121

(2S)-3-(3-Chlorophenyl)-2-[[2-(3-chlorophenyl) acetyl]amino]-N-[(1S)-1-(4-methoxyphenyl)-2-oxo-2-[[(3S)-1,1,1-trifluoro-4-methyl-2-oxopentan-3-yl] amino]ethyl]propanamide

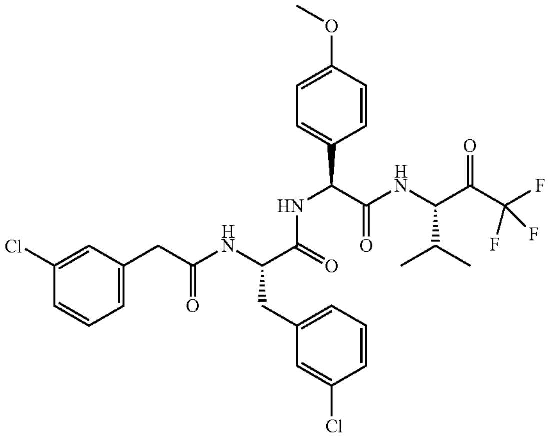 [SMILES: COc1ccc([C@H](NC(=O)[C@H](Cc2cccc(Cl)c2)NC(=O)Cc2cccc(Cl)c2)C(=O)N[C@H](C(=O)C(F)(F)F)C(C)C)cc1]

[A] (2S)-3-(3-Chlorophenyl)-2-[[2-(3-chlorophenyl) acetyl]amino]-N-[(1S)-1-(4-methoxyphenyl)-2-oxo-2-[[(2S,3S)-1,1,1-trifluoro-2-hydroxy-4-methylpentan-3-yl]amino]ethyl]propanamide

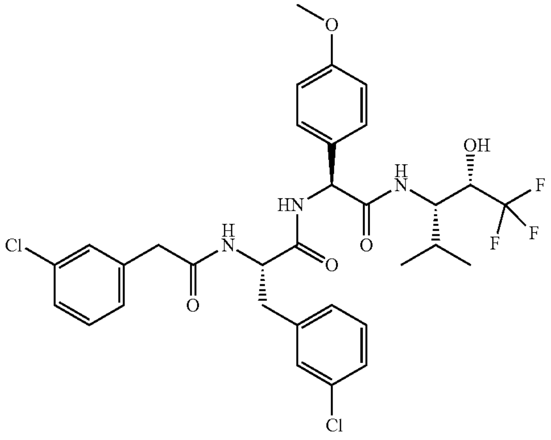 [SMILES: COc1ccc([C@H](NC(=O)[C@H](Cc2cccc(Cl)c2)NC(=O)Cc2cccc(Cl)c2)C(=O)N[C@@H](C(C)C)[C@H](O)C(F)(F)F)cc1]

In a flask, (S)-2-amino-3-(3-chlorophenyl)-N—((S)-1-(4-methoxyphenyl)-2-oxo-2-(((2S,3S)-1,1,1-trifluoro-2-hydroxy-4-methylpentan-3-yl)amino)ethyl)propanamide hydrochloride (Intermediate A-1, 0.033 g, 0.060 mmol), 2-(3-chlorophenyl)acetic acid (0.010 g, 0.060 mmol) and HATU (0.027 g, 0.072 mmol) were dissolved in DMF (1 mL) and the mixture cooled to 0° C. Huenig's base (0.031 mL, 0.179 mmol) was added to the reaction mixture which was stirred at this temperature for 10 min, then allowed to warm up to room temperature and stirring was continued for 2 hours. The mixture was diluted with EtOAc, poured into $H_2O$ (5 mL) and the aqueous layer was extracted with EtOAc (2×10 mL). Combined organics were washed brine, dried over $Na_2SO_4$, filtered and concentrated in vacuo. The residue was purified by silica gel flash chromatography eluting with a 10 to 100% EtOAc-heptane gradient to give the title compound (0.039 g, 96%) as a colorless solid. MS: 668.2 ($M+H^+$).

[B] (2S)-3-(3-Chlorophenyl)-2-[[2-(3-chlorophenyl) acetyl]amino]-N-[1S)-1-(4-methoxyphenyl)-2-oxo-2-[[(3S)-1,1,1-trifluoro-4-methyl-2-oxopenta-3-yl] amino]ethyl]propanamide

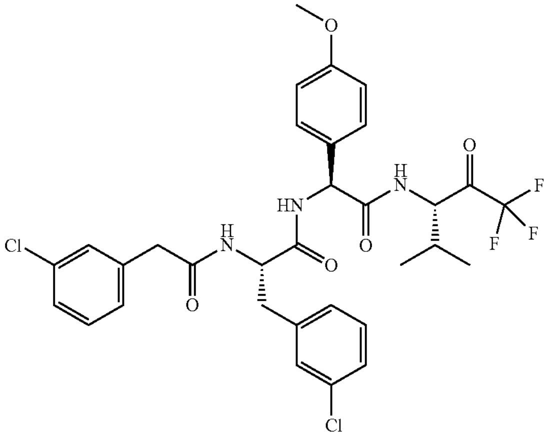 [SMILES: COc1ccc([C@H](NC(=O)[C@H](Cc2cccc(Cl)c2)NC(=O)Cc2cccc(Cl)c2)C(=O)N[C@H](C(=O)C(F)(F)F)C(C)C)cc1]

To a solution of (2S)-3-(3-chlorophenyl)-2-[[2-(3-chlorophenyl)acetyl]amino]-N-[(1S)-1-(4-methoxyphenyl)-2-oxo-2-[[(2S,3S)-1,1,1-trifluoro-2-hydroxy-4-methylpentan-3-yl] amino]ethyl]propanamide (0.039 g, 0.059 mmol) in DCM (1 mL) was added 15% Dess-Martin periodinane in DCM solution (0.369 mL, 0.178 mmol) and the reaction mixture was stirred at room temperature for 2.5 hours. The resulting white suspension was diluted with DCM/water, poured into a sat. $NH_4Cl$ aqueous solution (5 mL) and then extracted with DCM (10 mL). The organic layer was washed with brine, dried over $Na_2SO_4$, filtered and evaporated. The residue was purified by silica gel flash chromatography, eluting with a 10-100% EtOAc-heptane gradient to give the title compound (0.024 g, 58%) as a colorless solid. MS: 666.3 ($M+H^+$).

The following examples listed in Table 5 were prepared in analogy to the procedures described for the preparation of example 121 by using the indicated intermediate and carboxylic acid in step [A]. Alanine synthons (intermediate A-8) can undergo isomerization at variable extent during Dess-Martin oxidation (step [B]), thus the stereochemistry of these final compounds can be described as S and R unless isomerization was not observed to a great extent >5%.

TABLE 5

| Ex | Name<br>Structure<br>Aspect | Reactant to be used in step [A] | MS (M + H⁺) |
|---|---|---|---|
| 122 | 1-(3-chlorophenyl)-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopropane-1-carboxamide<br>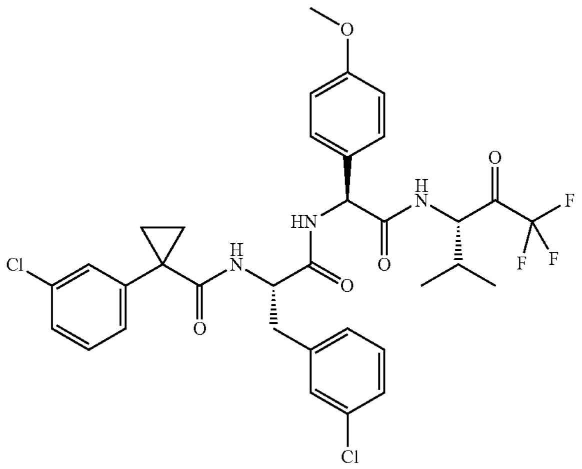<br>Colorless foam | Intermediate A-1 and 1-(3-chlorophenyl)cyclopropane carboxylic acid | 692.3 |
| 123 | 5-bromo-N-[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide<br>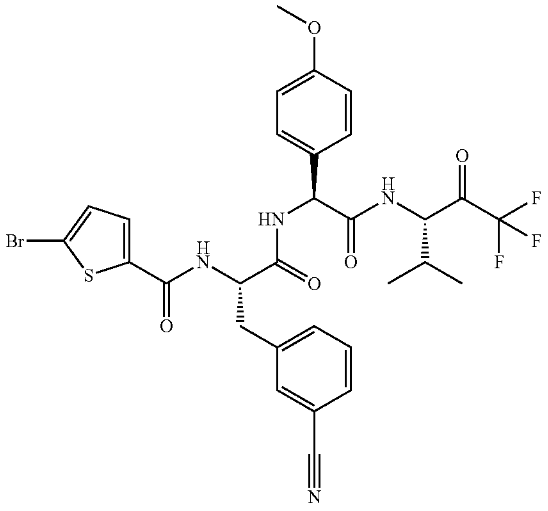<br>Colorless solid | Intermediate A-3 and 5-bromothiophene-2-carboxylic acid | 693.2 |
| 124 | (2S)-2-[[2,2-difluoro-2-(3-fluorophenyl)acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-8 and 2-(3-fluorophenyl)-2,2-difluoro-acetic acid | 575.3 |

TABLE 5-continued

| Ex | Name<br>Structure<br>Aspect | Reactant to be used in step [A] | MS (M + H$^+$) |
|---|---|---|---|
| | 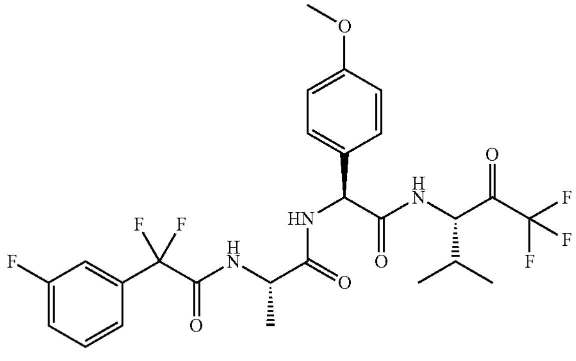<br>Colorless solid | | |
| 125 | 1-(3-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclobutane-1-carboxamide<br>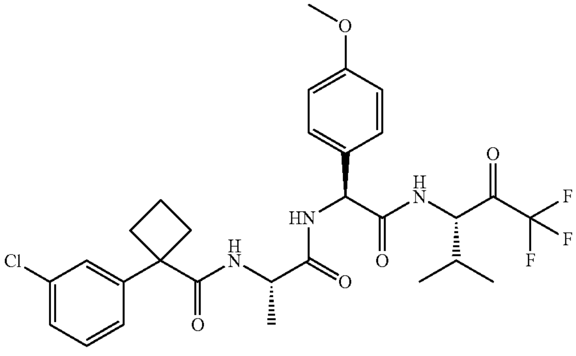<br>Colorless solid | Intermediate A-8 and 1-(3-chlorophenyl)cyclobutane carboxylic acid | 596.2 |
| 126 | (2S)-2-[[2-(2,5-dichlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide<br>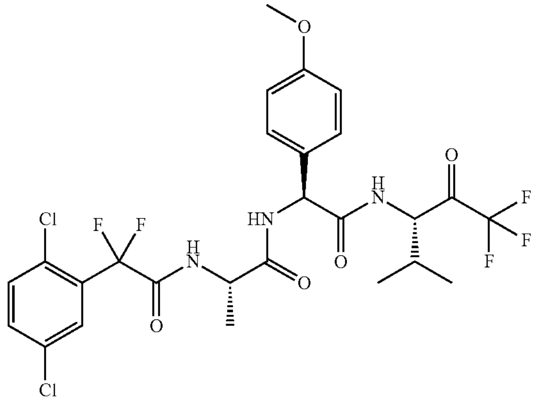<br>Colorless solid | Intermediate A-8 and 2-(2,5-dichlorophenyl)-2,2-difluoroacetic acid | M + $H_2O$ = 644.2 |

TABLE 5-continued

| Ex | Name<br>Structure<br>Aspect | Reactant to be used in step [A] | MS (M + $H^+$) |
|---|---|---|---|
| 127 | (2S)-2-[[2-(2,3-dichlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide<br>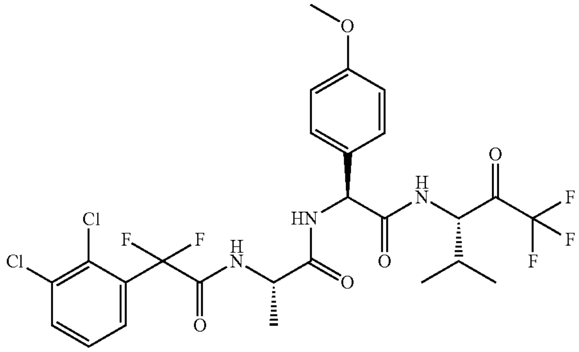<br>Colorless solid | Intermediate A-8 and 2-(2,3-dichlorophenyl)-2,2-difluoroacetic acid | M + $H_2O$ = 644.2 |
| 128 | 2-(3-chlorophenyl)-N-[(2S and 2R)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1,3-dioxolane-2-carboxamide<br>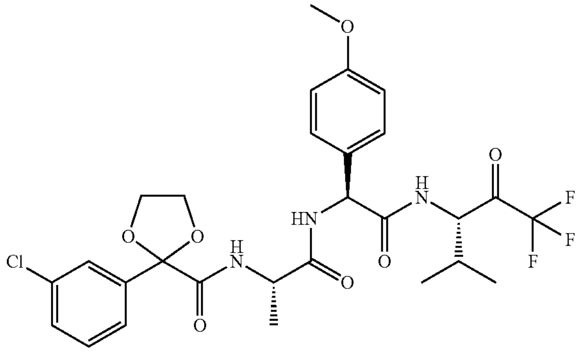<br>Colorless solid | Intermediate A-8 and 2-(3-chlorophenyl)-1,3-dioxolane-2-carboxylic acid (Intermediate J-2) | 614.2 |
| 129 | 1-(4-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopentane-1-carboxamide<br>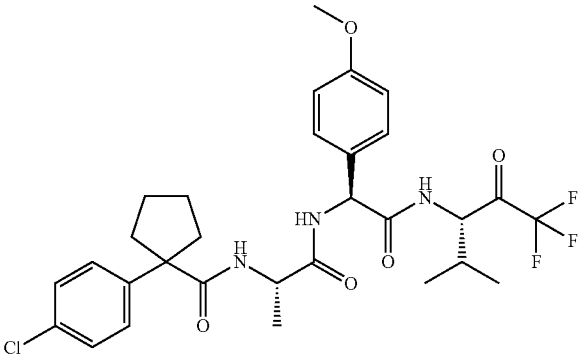<br>Colorless solid | Intermediate A-8 and 1-(4-chlorophenyl)cyclopentane carboxylic acid | 610.2 |

TABLE 5-continued

| Ex | Name<br>Structure<br>Aspect | Reactant to be used in step [A] | MS (M + H+) |
|---|---|---|---|
| 130 | (2S)-2-[[2,2-difluoro-2-[2-(trifluoromethoxy)phenyl]acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide<br>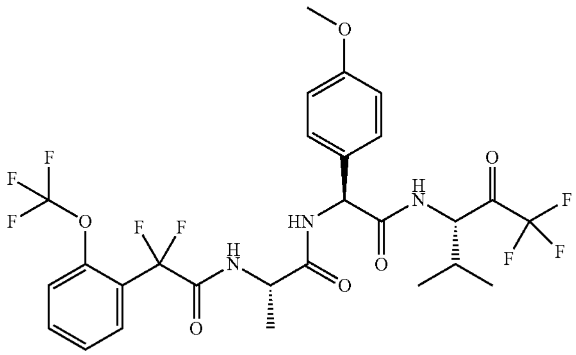<br>Colorless solid | Intermediate A-8 and 2,2-difluoro-2-[2-(trifluoromethoxy)phenyl] acetic acid | 642.2 |
| 131 | (2S)-2-[[2-(2-ethoxyphenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide<br>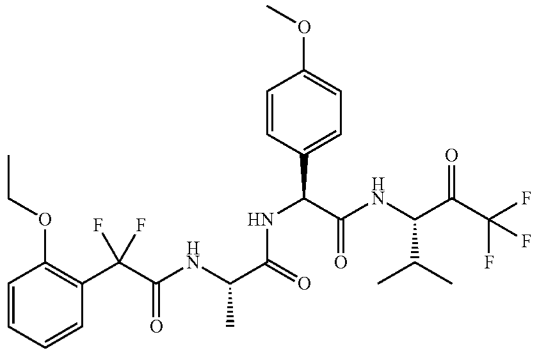<br>Colorless solid | Intermediate A-8 and 2-(2-ethoxyphenyl)-2,2-difluoro-acetic acid | 602.2 |
| 132 | (2S)-2-[[2,2-difluoro-2-[2-(trifluoromethyl)phenyl]acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide<br>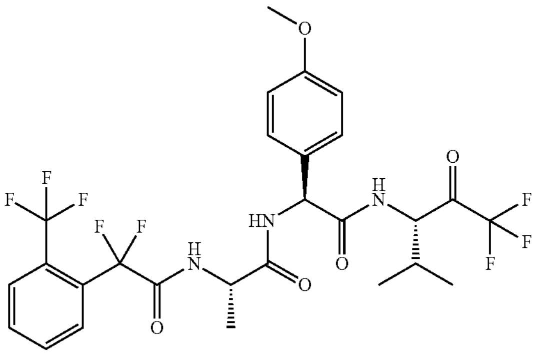<br>Colorless solid | Intermediate A-8 and 2,2-difluoro-2-[2-(trifluoromethyl)phenyl]acetic acid | 626.2 |

TABLE 5-continued

| Ex | Name<br>Structure<br>Aspect | Reactant to be used in step [A] | MS ($M + H^+$) |
|---|---|---|---|
| 133 | 1-(2-chloro-6-fluorophenyl)-N-[(2S and 2R)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopentane-1-carboxamide<br>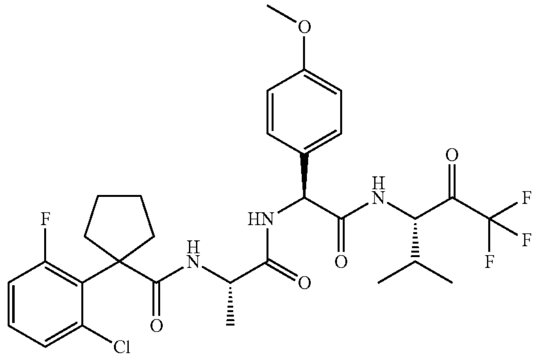<br>Colorless solid | Intermediate A-8 and 1-(2-chloro-6-fluorophenyl)cyclopentane carboxylic acid | 628.2 |
| 134 | 1-(2-fluorophenyl)-N-[(2S and 2R)-1-[[(1S)-1-(4-methoxyphenyl)-2-oxo-2-[(1,1,1-trifluoro-4-methyl-2-oxopentan-3-yl)amino]ethyl]amino]-1-oxopropan-2-yl]cyclopentane-1-carboxamide<br>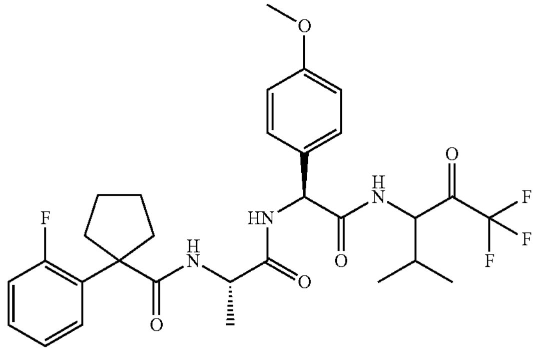<br>Colorless solid | Intermediate A-8 and 1-(2-fluorophenyl)cyclopentane carboxylic acid | 594.2 |
| 135 | 2-(3-chlorophenyl)-3,3,3-trifluoro-2-hydroxy-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]propanamide<br>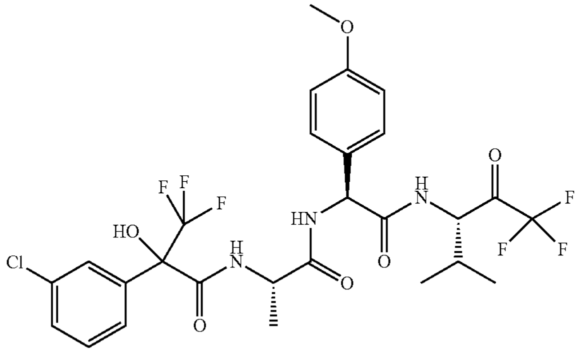<br>Colorless amorphous | Intermediate A-8 and 2-(3-chlorophenyl)-3,3,3-trifluoro-2-hydroxy-propanoic acid | 640.1 |

TABLE 5-continued

| Ex | Name<br>Structure<br>Aspect | Reactant to be used in step<br>[A] | MS<br>(M + H+) |
|---|---|---|---|
| 136 | 3,3,3-trifluoro-2-hydroxy-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-[3-(trifluoromethyl)phenyl]propanamide<br>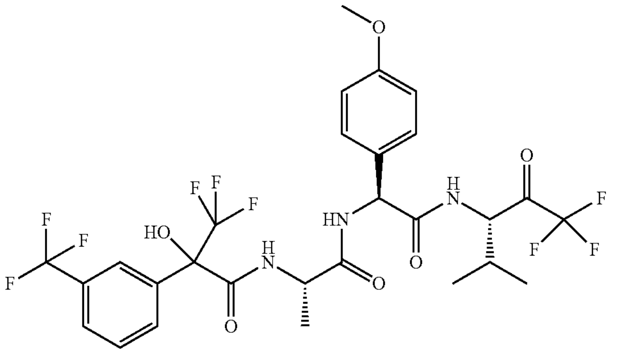<br>Colorless amorphous | Intermediate A-8<br>and<br>3,3,3-trifluoro-2-hydroxy-2-[3-(trifluoromethyl)phenyl]propanoic acid | 674.2 |
| 137 | 2-(3,4-dichlorophenyl)-3,3,3-trifluoro-2-hydroxy-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]propanamide<br>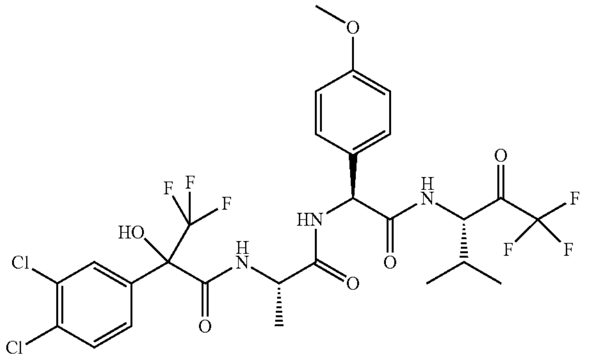<br>Colorless solid | Intermediate A-8<br>and<br>2-(3,4-dichlorophenyl)-3,3,3-trifluoro-2-hydroxy-propanoic acid | 674.1 |
| 138 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-(trifluoromethoxy)benzamide | Intermediate A-8<br>and<br>2-(trifluoromethoxy)benzoic acid | 592.2 |

TABLE 5-continued

| Ex | Name Structure Aspect | Reactant to be used in step [A] | MS (M + H⁺) |
|---|---|---|---|
| | 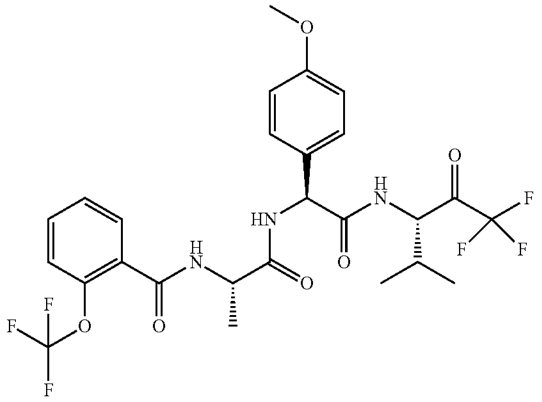 Colorless solid | | |
| 139 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-(trifluoromethyl)benzamide 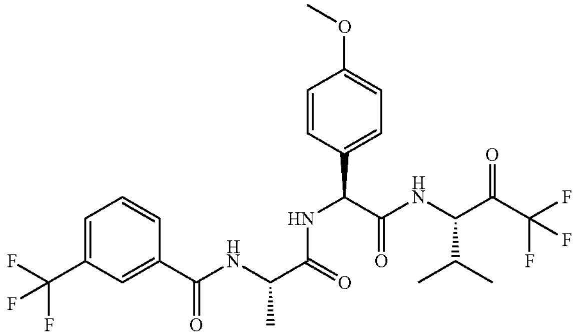 Colorless solid | Intermediate A-8 and 3-(trifluoromethyl)benzoic acid | 576.2 |
| 140 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-(trifluoromethyl)benzamide 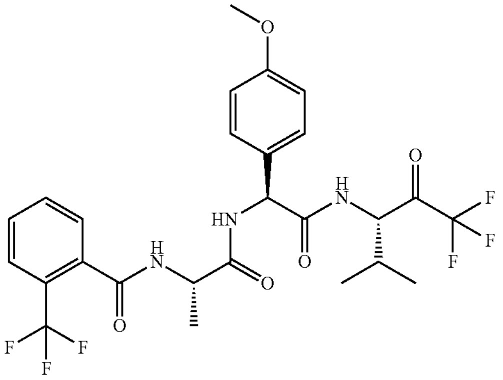 Colorless solid | Intermediate A-8 and 2-(trifluoromethyl)benzoic acid | 576.2 |
| 141 | 2-(4-chlorophenyl)-N-[(2S)-1-[[(1S)-1-(4-methoxyphenyl)-2-oxo-2-[[(3S)-1,1,1-trifluoro-4-methyl-2-oxopentan-3- | Intermediate A-8 and 2-(4-chlorophenyl)-3-methyl- | 598.3 |

TABLE 5-continued

| Ex | Name<br>Structure<br>Aspect | Reactant to be used in step<br>[A] | MS<br>(M + H+) |
|---|---|---|---|
| | yl]amino]ethyl]amino]-1-oxopropan-2-yl]-3-methylbutanamide<br>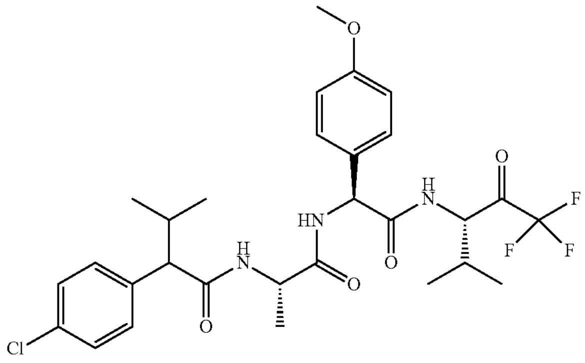<br>Colorless solid | butanoic acid | |
| 142 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-phenylbutanamide<br>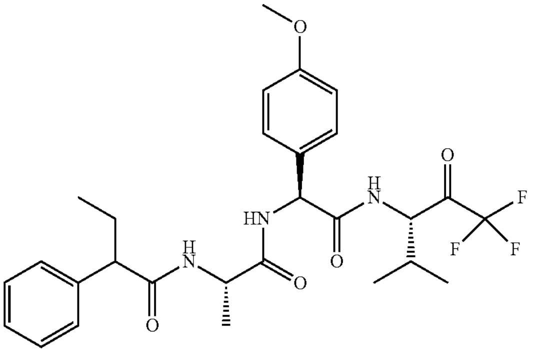<br>Colorless solid | Intermediate A-8<br>and<br>2-phenylbutanoic acid | 550.3 |
| 143 | (2S)-2-[[2-(4-chlorophenyl)-2-cyclopropylacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide<br>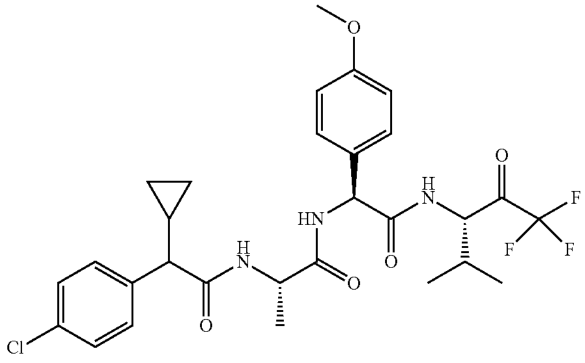<br>Colorless solid | Intermediate A-8<br>and<br>2-(4-chlorophenyl)-2-cyclopropyl-acetic acid | 596.3 |
| 144 | (2S)-2-(4-chlorophenyl)-N-[(2S)-1-[[(1S)-1-(4-methoxyphenyl)-2-oxo-2-[[(3S)-1,1,1-trifluoro-4-methyl-2-oxopentan-3- | Intermediate A-8<br>and<br>(2S)-2-(4-chlorophenyl)-3- | 598.2 |

TABLE 5-continued

| Ex | Name<br>Structure<br>Aspect | Reactant to be used in step<br>[A] | MS<br>(M + H⁺) |
|---|---|---|---|
| | yl]amino]ethyl]amino]-1-oxopropan-2-yl]-3-methylbutanamide<br>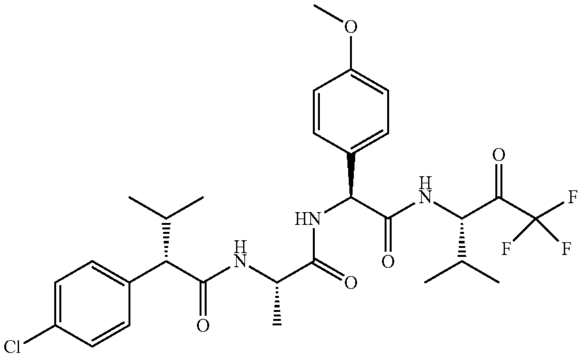<br>Colorless solid | methyl-butanoic acid | |
| 145 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-phenylcyclopentane-1-carboxamide<br>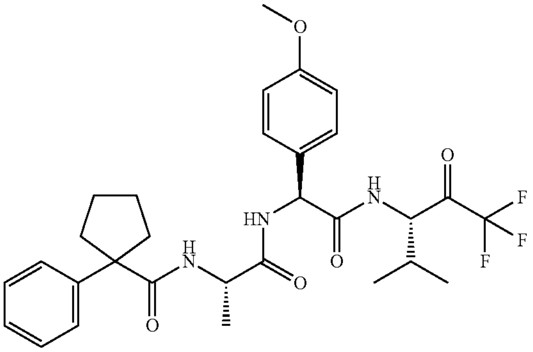<br>Colorless solid | Intermediate A-8<br>and<br>1-phenylcyclopentane carboxylic acid | 576.3 |
| 146 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-methylbenzamide<br>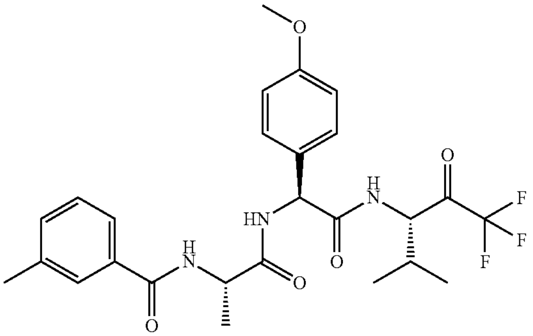<br>Colorless solid | Intermediate A-8<br>and<br>3-methylbenzoic acid | 522.3 |

TABLE 5-continued

| Ex | Name<br>Structure<br>Aspect | Reactant to be used in step<br>[A] | MS<br>(M + H$^+$) |
|---|---|---|---|
| 147 | 3-methoxy-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide<br>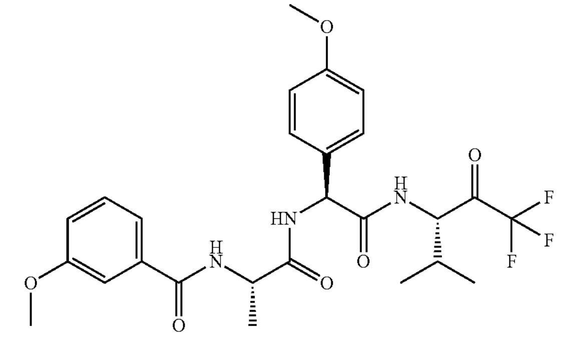<br>Colorless solid | Intermediate A-8<br>and<br>3-methoxybenzoic acid | 538.3 |
| 148 | 3-cyano-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide<br>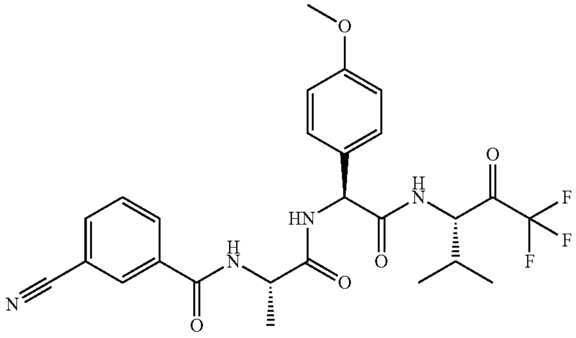<br>Colorless solid | Intermediate A-8<br>and<br>3-cyanobenzoic acid | 533.3 |
| 149 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-(trifluoromethoxy)benzamide<br>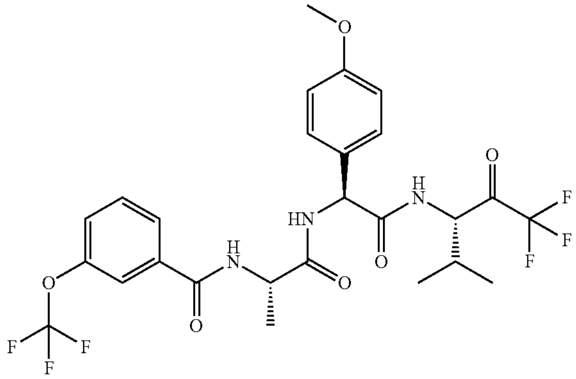<br>Colorless solid | Intermediate A-8<br>and<br>3-(trifluoromethoxy)benzoic acid | 592.3 |

TABLE 5-continued

| Ex | Name<br>Structure<br>Aspect | Reactant to be used in step [A] | MS (M + H⁺) |
|---|---|---|---|
| 150 | 3-ethoxy-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide<br>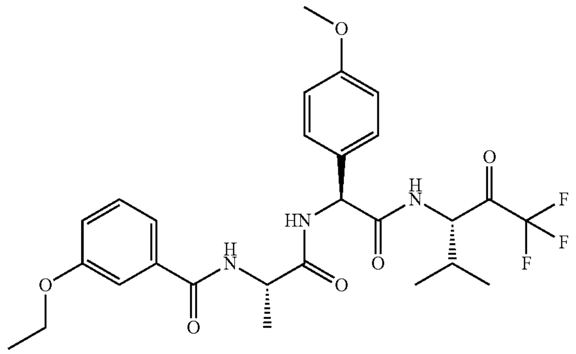<br>Colorless solid | Intermediate A-8<br>and<br>3-ethoxybenzoic acid | 552.3 |
| 151 | (2S)-2-[[2,2-difluoro-2-(2-methoxyphenyl)acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide<br>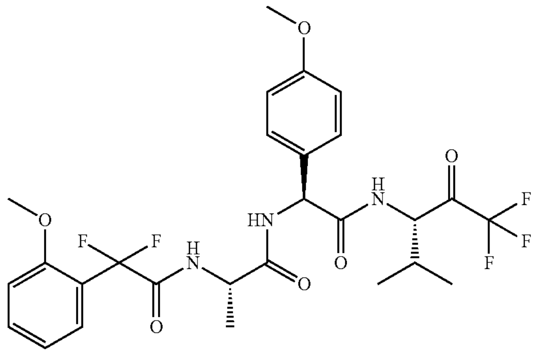<br>Colorless solid | Intermediate A-8<br>and<br>2,2-difluoro-2-(2-methoxyphenyl)acetic acid | 588.3 |
| 152 | 4-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide<br>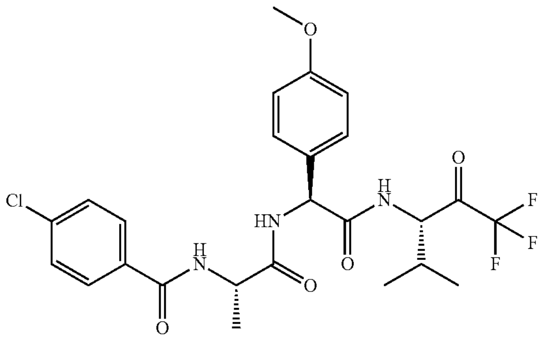<br>Colorless solid | Intermediate A-8<br>and<br>4-chlorobenzoic acid | 542.3 |

TABLE 5-continued

| Ex | Name<br>Structure<br>Aspect | Reactant to be used in step<br>[A] | MS<br>(M + H+) |
| --- | --- | --- | --- |
| 153 | 3,3,3-trifluoro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-[3-(trifluoromethyl)phenyl]propanamide<br>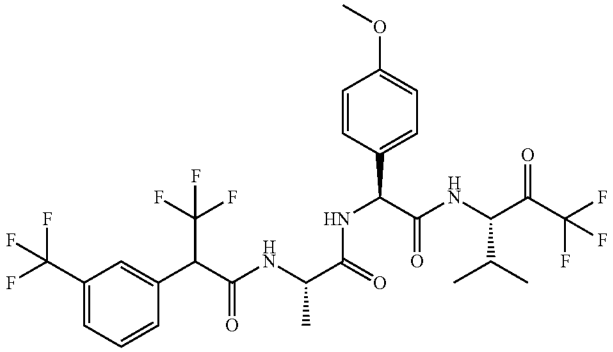<br>Colorless solid | Intermediate A-8<br>and<br>3,3,3-trifluoro-2-[3-(trifluoromethyl)phenyl] propanoic acid<br>(Intermediate J-1) | 676.5 |
| 154 | 2-(difluoromethoxy)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide<br>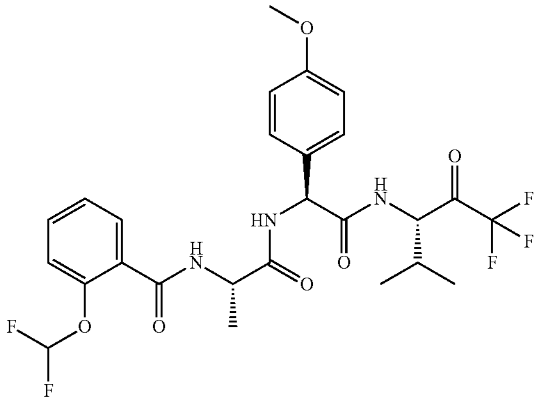<br>Colorless solid | Intermediate A-8<br>and<br>2-(difluoromethoxy)benzoic acid | 574.3 |
| 155 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(trifluoromethyl)cyclobutane-1-carboxamide | Intermediate A-8<br>and<br>1-(trifluoromethyl)cyclobutane carboxylic acid | 554.8 |

TABLE 5-continued

| Ex | Name<br>Structure<br>Aspect | Reactant to be used in step<br>[A] | MS<br>(M + H$^+$) |
|---|---|---|---|
| | 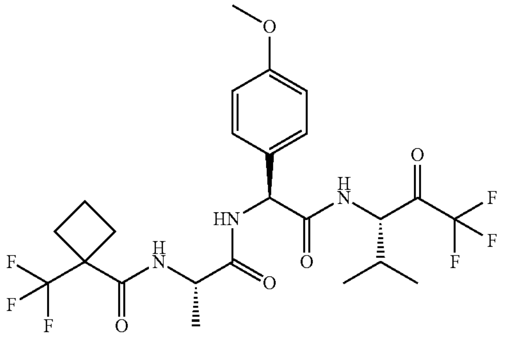<br>Colorless solid | | |
| 156 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(trifluoromethyl)cyclohexane-1-carboxamide | Intermediate A-8<br>and<br>1-(trifluoromethyl)cyclohexane carboxylic acid | 582.8 |
| | 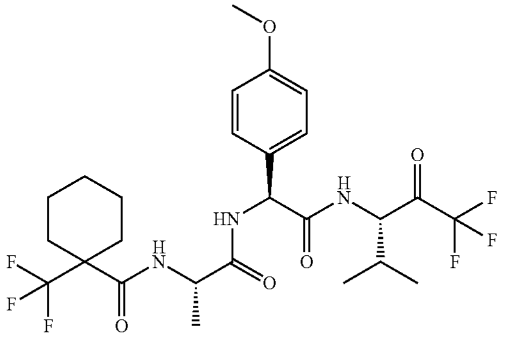<br>Colorless solid | | |
| 157 | N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(trifluoromethyl)cyclopentane-1-carboxamide | Intermediate A-8<br>and<br>1-(trifluoromethyl)cyclopentane carboxylic acid | 568.2 |
| | 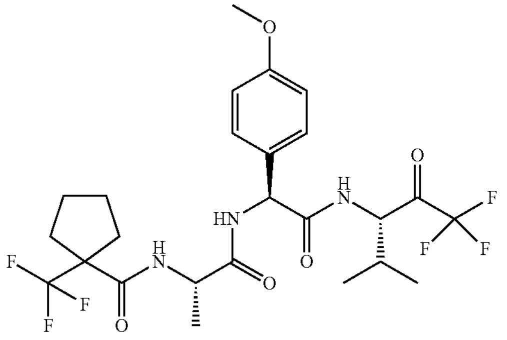<br>Colorless solid | | |
| 158 | (2S)-2-[[(2S)-2-(4-chlorophenyl)-2-cyclobutylacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-8<br>and<br>2-(4-chlorophenyl)-2-cyclobutyl-acetic acid<br>Chiral separation | 610.4 |

TABLE 5-continued

| Ex | Name<br>Structure<br>Aspect | Reactant to be used in step<br>[A] | MS<br>(M + H+) |
|---|---|---|---|
| | 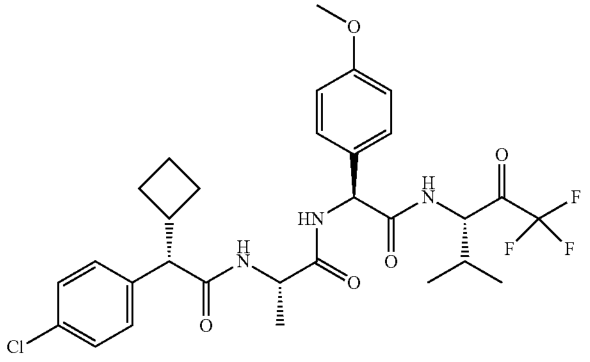<br>Colorless solid | | |
| 159 | (2S)-2-[[(2R)-2-(4-chlorophenyl)-2-cyclobutylacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide | Intermediate A-8<br>and<br>2-(4-chlorophenyl)-2-cyclobutyl-acetic acid<br>Chiral separation | 610.4 |
| | 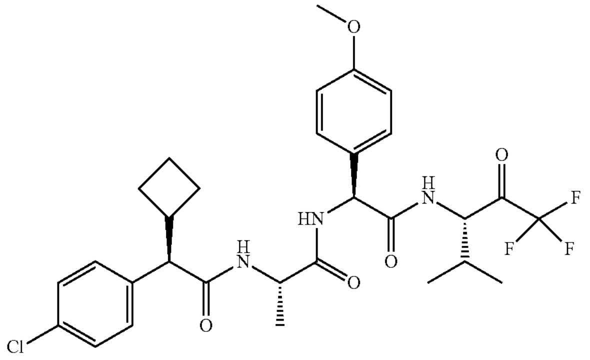<br>Colorless solid | | |
| 160 | N-[(2S)-3-methoxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(trifluoromethyl)cyclopentane-1-carboxamide | Intermediate A-9<br>and<br>1-(trifluoromethyl)cyclopentane carboxylic acid | 598.4 |
| | 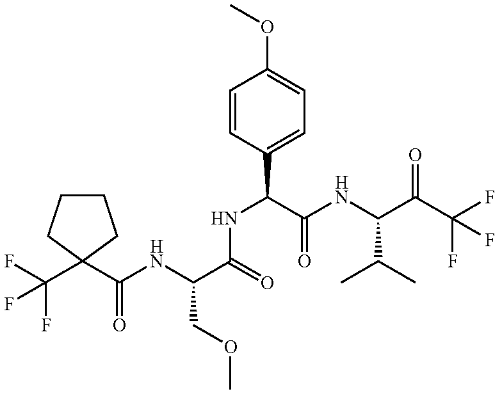<br>Colorless solid | | |
| 161 | 1-fluoro-N-[(2S)-3-methoxy-1-[[(1S)-1-(4-methoxyphenyl)-2-oxo-2-[[(3S)-1,1,1-trifluoro-4-methyl-2-oxopentan-3- | Intermediate A-9<br>and<br>1-fluorocyclopentane | 548.5 |

TABLE 5-continued

| Ex | Name<br>Structure<br>Aspect | Reactant to be used in step [A] | MS (M + H+) |
|---|---|---|---|
| | yl]amino]ethyl]amino]-1-oxopropan-2-yl]cyclopentane-1-carboxamide<br>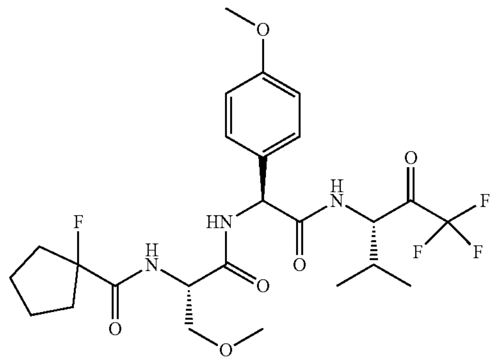<br>Colorless solid | carboxylic acid | |
| 162 | tert-butyl N-[(4S)-4-[(3-chlorobenzoyl)amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentyl]carbamate<br>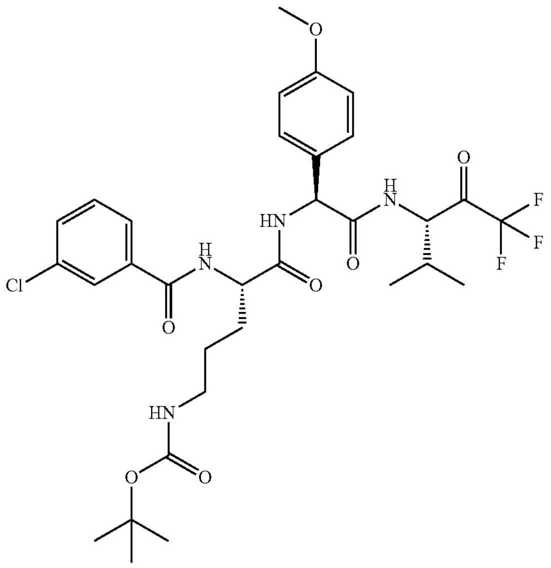<br>Colorless solid | Intermediate A-18<br>and<br>3-chlorobenzoic acid | 685.3 |
| 163 | tert-butyl N-[(5S)-5-[(3-chlorobenzoyl)amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]carbamate | Intermediate A-17<br>and<br>3-chlorobenzoic acid | 699.2 |

TABLE 5-continued

| Ex | Name<br>Structure<br>Aspect | Reactant to be used in step [A] | MS (M + H$^+$) |
|---|---|---|---|
| | 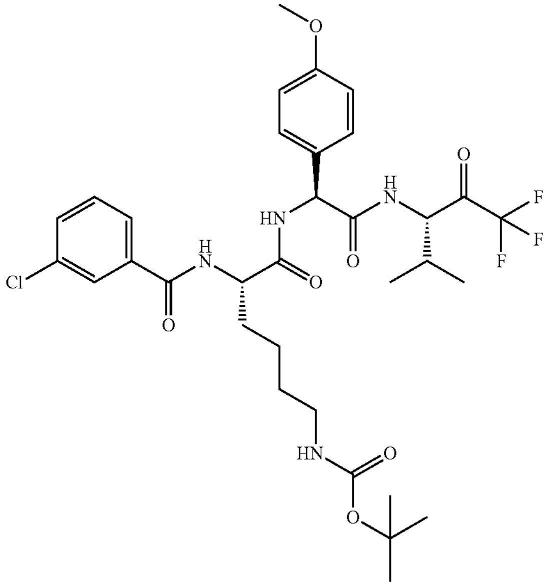<br>Colorless solid | | |
| 164 | tert-butyl N-[(5S)-5-[[2-(3-chlorophenyl)-2,2-difluoroacetyl]amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]carbamate | Intermediate A-17 and 2-(3-chlorophenyl)-2,2-difluoro-acetic acid | 747.4 (M − H$^-$) |
| | 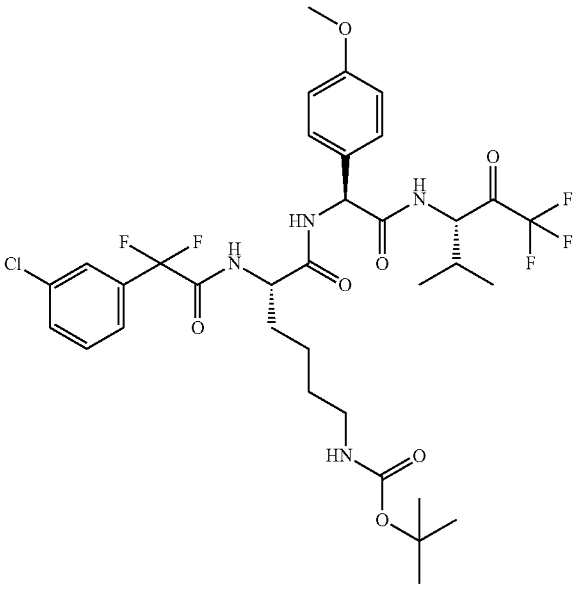<br>Light brown solid | | |
| 165 | tert-butyl N-[[4-[(2S)-2-[(3-chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate | Intermediate A-19 and 3-chlorobenzoic acid | 747.3 |

TABLE 5-continued

| Ex | Name<br>Structure<br>Aspect | Reactant to be used in step<br>[A] | MS<br>(M + H+) |
|---|---|---|---|
| | 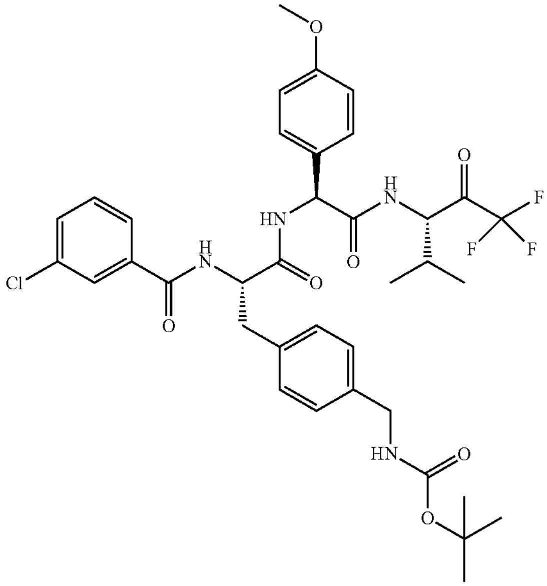<br>Colorless solid | | |
| 166 | tert-butyl N-[[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate | Intermediate A-19<br>and<br>2-(3-chlorophenyl)-2,2-difluoro-acetic acid | 697.3 |
| | 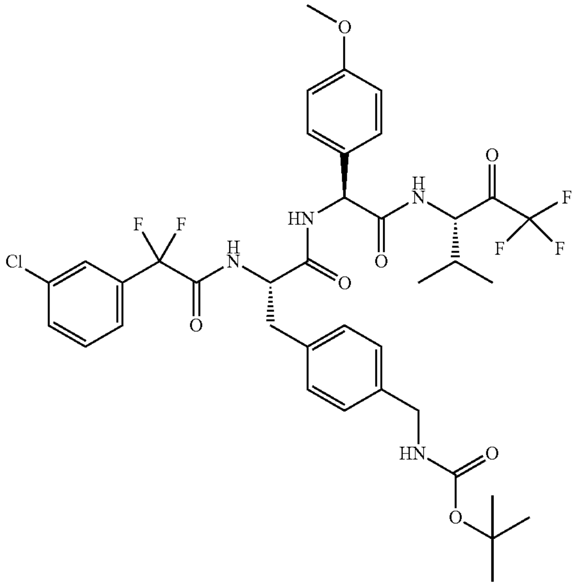<br>Colorless solid | | |
| 167 | tert-butyl N-[[4-[(2S)-2-[[2,2-difluoro-2-[2-(trifluoromethyl)phenyl]acetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate | Intermediate A-19<br>and<br>2,2-difluoro-2-[2-(trifluoromethyl)phenyl]acetic acid | 829.6<br>(M − H−) |

TABLE 5-continued

| Ex | Name<br>Structure<br>Aspect | Reactant to be used in step [A] | MS (M + H+) |
|---|---|---|---|
| | 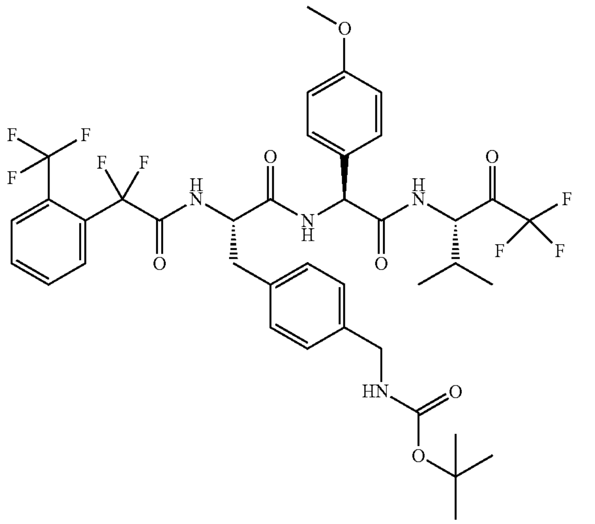<br>Colorless solid | | |
| 168 | tert-butyl N-[[4-[(2S)-2-[[1-(4-chlorophenyl)cyclopentanecarbonyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate | Intermediate A-19 and 1-(4-chlorophenyl)cyclopentane carboxylic acid | 815.5 |
| | 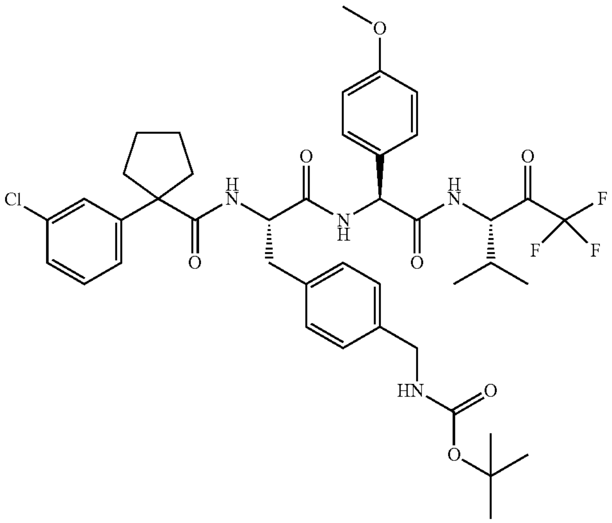<br>Colorless solid | | |
| 169 | tert-butyl N-[[4-[(2S)-2-[(5-chlorothiophene-2-carbonyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate | Intermediate A-19 and 5-chlorothiophene-2-carboxylic acid | 753.3 |

TABLE 5-continued

| Ex | Name<br>Structure<br>Aspect | Reactant to be used in step [A] | MS (M + H⁺) |
|---|---|---|---|
| | 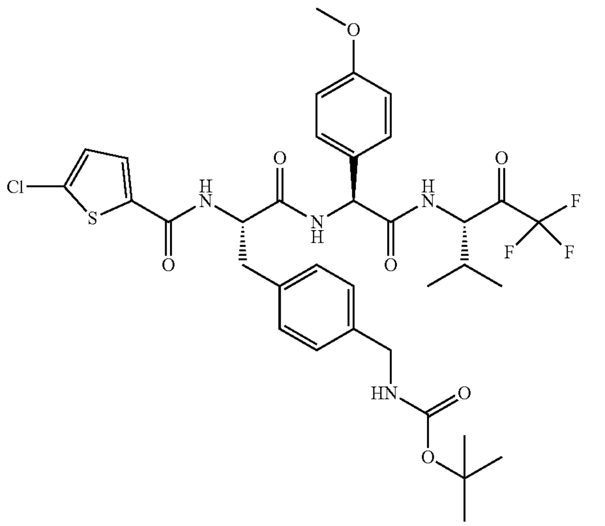<br>Colorless solid | | |
| 170 | tert-butyl N-[[4-[(2S)-2-[[(2S)-2-(4-chlorophenyl)-3-methylbutanoyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate | Intermediate A-19<br>and<br>2-(4-chlorophenyl)-3-methyl-butanoic acid<br>Chiral separation | 803.6 |
| | 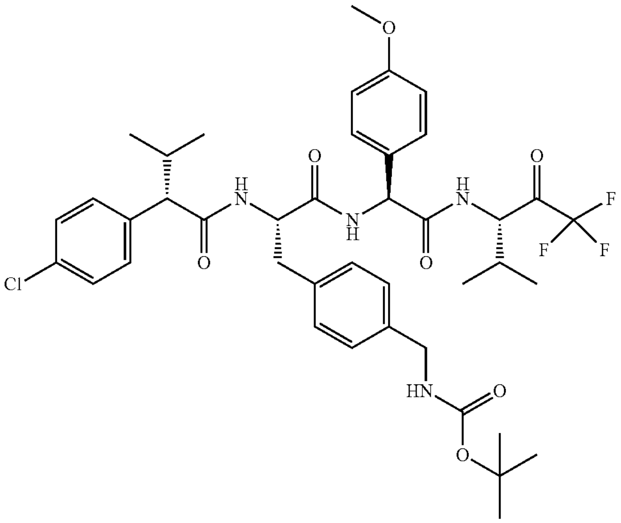<br>Colorless solid | | |
| 171 | tert-butyl N-[[4-[(2S)-2-[[(2R)-2-(4-chlorophenyl)-3-methylbutanoyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate | Intermediate A-19<br>and<br>2-(4-chlorophenyl)-3-methyl-butanoic acid<br>Chiral separation | 803.7 |

TABLE 5-continued

| Ex | Name<br>Structure<br>Aspect | Reactant to be used in step [A] | MS (M + H+) |
|---|---|---|---|
| | 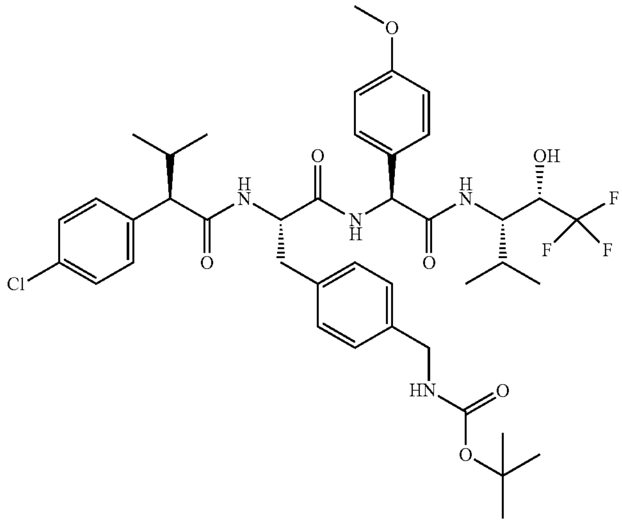<br>Colorless solid | | |
| 172 | tert-butyl N-[[4-[(2S)-2-[[2-(4-chlorophenyl)-2-cyclobutylacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate<br>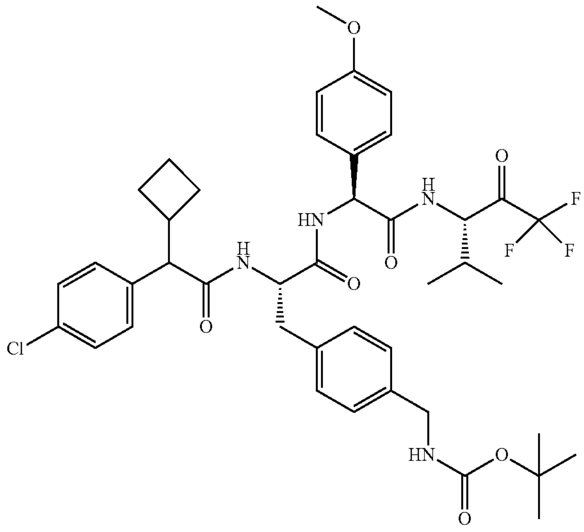<br>Colorless solid | Intermediate A-19 and 2-(4-chlorophenyl)-2-cyclobutyl-acetic acid | 815.8 |
| 173 | tert-butyl N-[[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-[[3-(trifluoromethyl)benzoyl]amino]propyl]phenyl]methyl]carbamate | Intermediate A-19 and 3-(trifluoromethyl)benzoic acid | 825.8 (M − $H^-$) |

TABLE 5-continued

| Ex | Name<br>Structure<br>Aspect | Reactant to be used in step<br>[A] | MS<br>(M + H⁺) |
|---|---|---|---|
| | 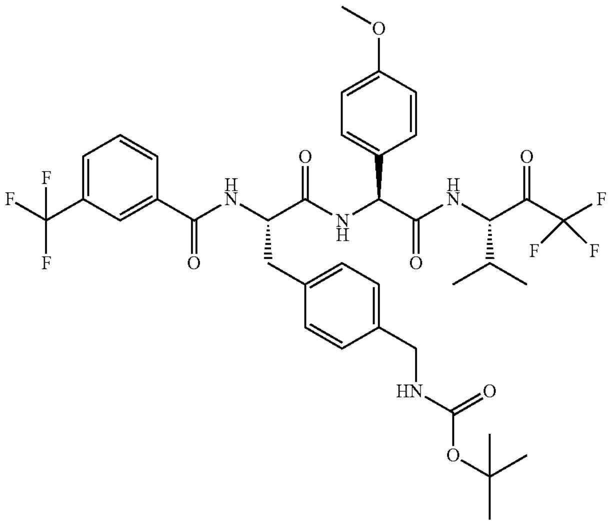<br>Colorless solid | | |
| 174 | tert-butyl N-[[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-[[1-(trifluoromethyl)cyclopentanecarbonyl]amino]propyl]phenyl]methyl]carbamate | Intermediate A-19<br>and<br>1-(trifluoromethyl)cyclopentane carboxylic acid | 773.7 |
| | 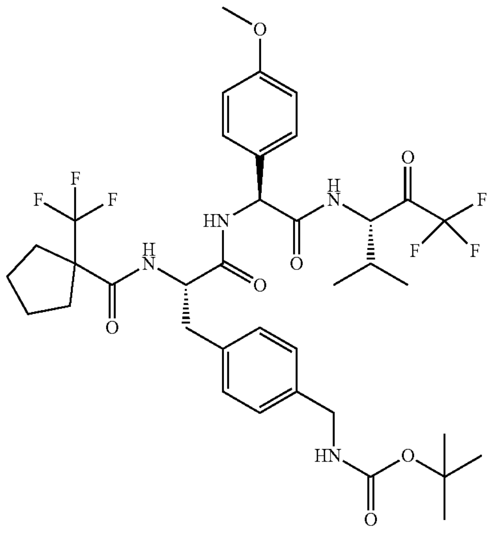<br>Colorless solid | | |
| 175 | tert-butyl N-[[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-[[3,3,3-trifluoro-2-[3-(trifluoromethyl)phenyl]propanoyl]amino]propyl]phenyl]methyl]carbamate | Intermediate A-19<br>and<br>3,3,3-trifluoro-2-[3-(trifluoromethyl)phenyl] propanoic acid<br>(Intermediate J-1) | 861.7<br>(M − H⁻) |

TABLE 5-continued

| Ex | Name<br>Structure<br>Aspect | Reactant to be used in step [A] | MS (M + H⁺) |
|---|---|---|---|
| | 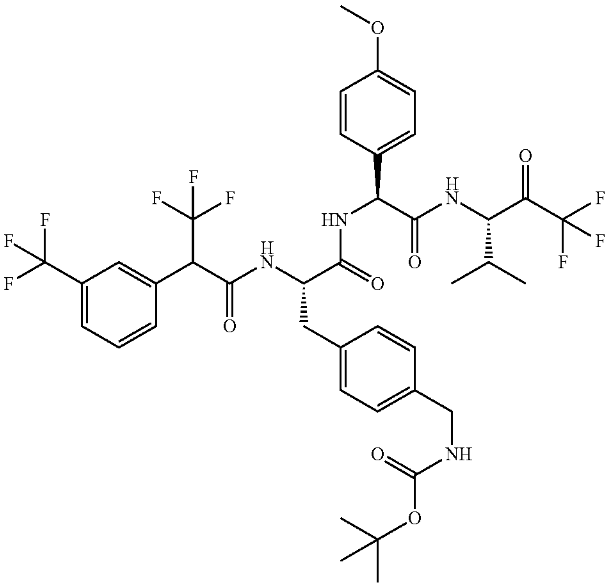<br>Yellow solid | | |
| 176 | 3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-(trifluoromethoxy)propan-2-yl]benzamide | Intermediate A-21 and 3-chlorobenzoic acid | 624.3 (M − H⁻) |
| | 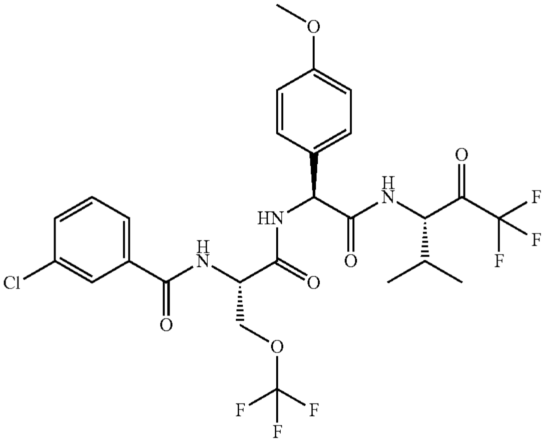<br>Colorless solid | | |
| 177 | (2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-(trifluoromethoxy)propanamide | Intermediate A-21 and 2-(3-chlorophenyl)-2,2-difluoro-acetic acid | 674.3 (M − H⁻) |

TABLE 5-continued

| Ex | Name<br>Structure<br>Aspect | Reactant to be used in step [A] | MS (M + H⁺) |
|---|---|---|---|
| | 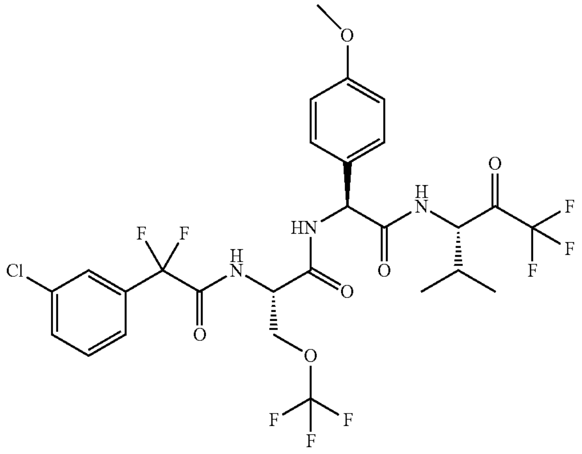<br>Colorless solid | | |
| 178 | (2S)-2-[[2-(3-chlorophenyl)-2,2-difluoroacetyl]amino]-3-cyano-N-[(1S)-1-(4-methoxyphenyl)-2-oxo-2-[[(3S)-1,1,1-trifluoro-4-methyl-2-oxopentan-3-yl]amino]ethyl]propanamide<br>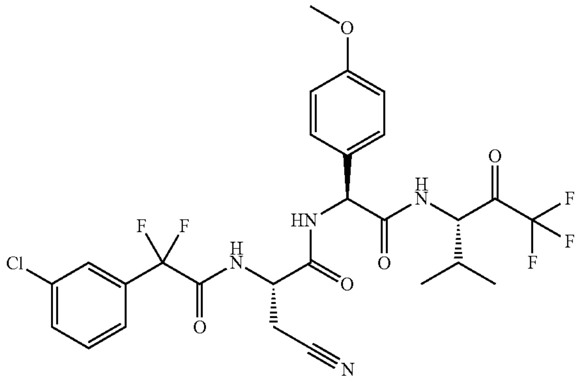<br>Colorless solid | Intermediate A-24 and 2-(3-chlorophenyl)-2,2-difluoro-acetic acid | 617.1 |
| 179 | 3-chloro-N-[(2S)-3-cyano-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide<br>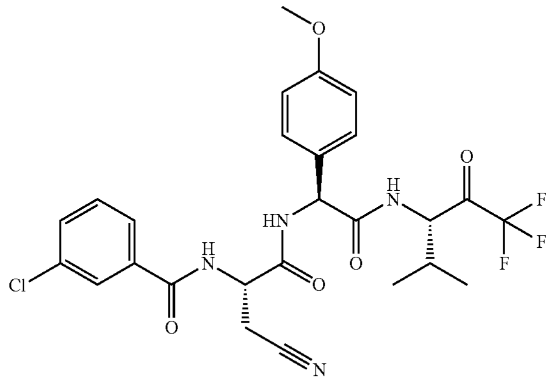<br>Colorless solid | Intermediate A-24 and 3-chlorobenzoic acid | 567.2 |

TABLE 5-continued

| Ex | Name<br>Structure<br>Aspect | Reactant to be used in step [A] | MS (M + H⁺) |
|---|---|---|---|
| 180 | tert-butyl 2-[4-[(1S)-1-[[(2S)-2-[(5-chlorothiophene-2-carbonyl)amino]-3-(3-fluorophenyl)propanoyl]amino]-2-oxo-2-[[(3S)-1,1,1-trifluoro-4-methyl-2-oxopentan-3-yl]amino]ethyl]phenoxy]acetate<br>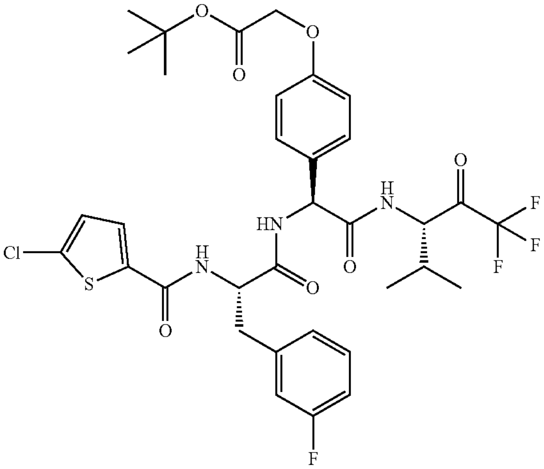<br>Colorless solid | Intermediate E-1<br>and<br>5-chlorothiophene-2-carboxylic acid | 743.4 |
| 181 | tert-butyl 2-[4-[(1S)-1-[[(2S)-2-[[2-(3-chlorophenyl)-2,2-difluoroacetyl]amino]-3-(3-fluorophenyl)propanoyl]amino]-2-oxo-2-[[(3S)-1,1,1-trifluoro-4-methyl-2-oxopentan-3-yl]amino]ethyl]phenoxy]acetate<br>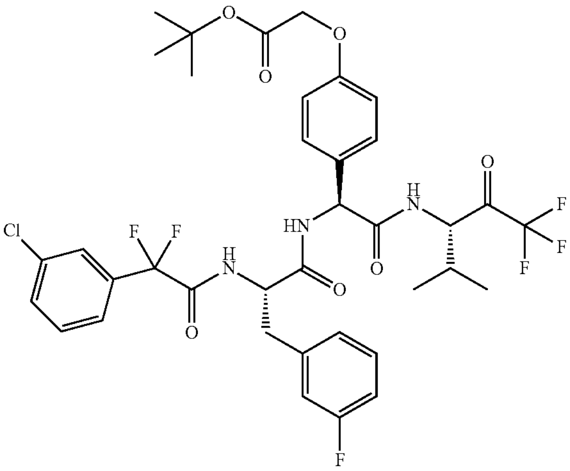<br>Colorless solid | Intermediate E-1<br>and<br>2-(3-chlorophenyl)-2,2-difluoro-acetic acid | 786.5 |

Example 182

N-[(2S)-5-Amino-1-[[(1S)-1-(4-methoxyphenyl)-2-oxo-2-[[(3S)-1,1,1-trifluoro-4-methyl-2-oxopentan-3-yl]amino]ethyl]amino]-1-oxopentan-2-yl]-3-chlorobenzamide

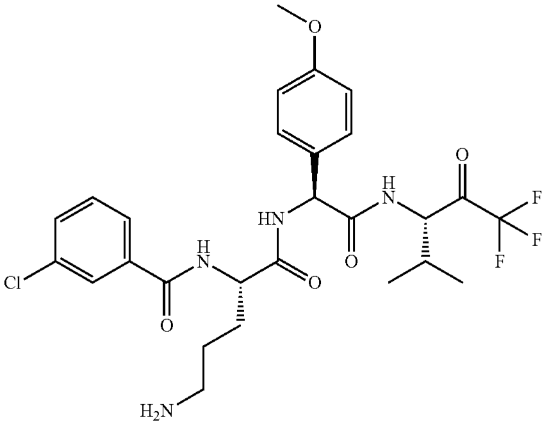 [SMILES: COc1ccc([C@H](NC(=O)[C@H](CCCN)NC(=O)c2cccc(Cl)c2)C(=O)N[C@H](C(=O)C(F)(F)F)C(C)C)cc1]

To a solution of tert-butyl N-[(4S)-4-[(3-chlorobenzoyl)amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentyl]carbamate (Example 162, 0.025 g, 0.036 mmol) in DCM (0.5 mL) was added TFA (0.056 mL, 0.727 mmol) and the reaction mixture was stirred at room temperature for 2 hours. The mixture was concentrated in vacuo, the residue was triturated in diisopropylether, filtered and further dried under high vacuum to give the title compound (0.018 g, 67%, TFA salt) as a colorless solid. MS: 585.2 ($M+H^+$).

The following examples listed in Table 6 were prepared in analogy to the procedures described for the preparation of example 182 by using the indicated starting materials.

Amine products were triturated in diisopropylether and obtained as TFA salts.

TABLE 6

| Ex | Name<br>Structure<br>Aspect | Reactant: compound obtained in example number indicated | MS<br>($M + H^+$) |
|---|---|---|---|
| 183 | N-[(2S)-6-amino-1-[[(1S)-1-(4-methoxyphenyl)-2-oxo-2-[[(3S)-1,1,1-trifluoro-4-methyl-2-oxopentan-3-yl]amino]ethyl]amino]-1-oxohexan-2-yl]-3-chlorobenzamide; TFA salt<br>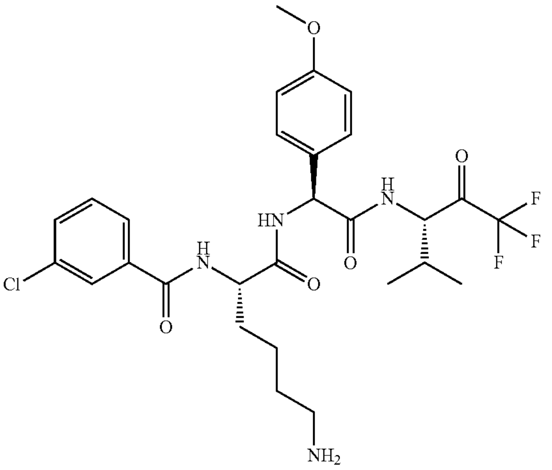<br>Colorless solid | Example 163 | |

TABLE 6-continued

| Ex | Name<br>Structure<br>Aspect | Reactant: compound obtained in example number indicated | MS (M + H+) |
|---|---|---|---|
| 184 | (2S)-6-amino-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]hexanamide; TFA salt<br>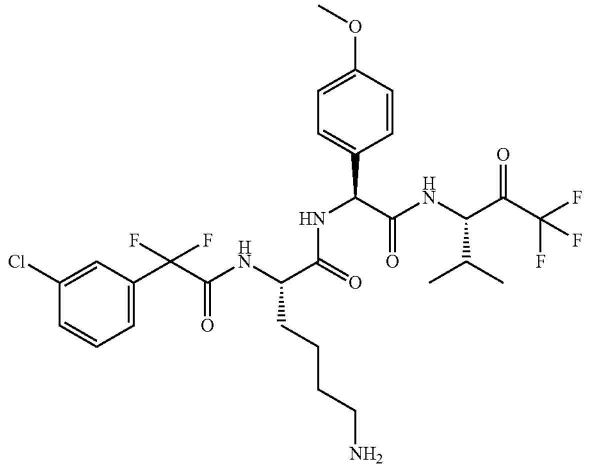<br>Colorless solid | Example 164 | 763.3 |
| 185 | N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-chlorobenzamide; TFA salt<br>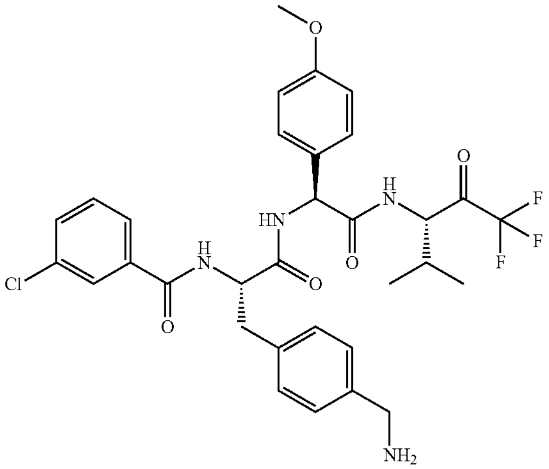<br>Colorless solid | Example 165 | 647.3 |

TABLE 6-continued

| Ex | Name<br>Structure<br>Aspect | Reactant: compound obtained in example number indicated | MS (M + H+) |
| --- | --- | --- | --- |
| 186 | (2S)-3-[4-(aminomethyl)phenyl]-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide; TFA salt<br>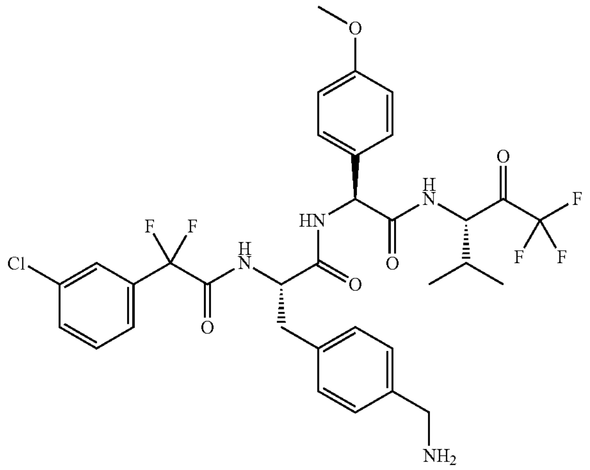<br>Colorless solid | Example 166 | 697.3 |
| 187 | (2S)-3-[4-(aminomethyl)phenyl]-2-[[2,2-difluoro-2-[2-(trifluoromethyl)phenyl]acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide; TFA salt<br>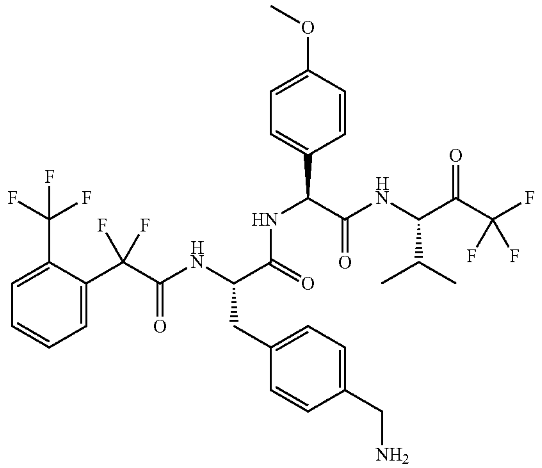<br>Colorless solid | Example 167 | 731.4 |

TABLE 6-continued

| Ex | Name<br>Structure<br>Aspect | Reactant: compound obtained in example number indicated | MS<br>(M + H+) |
|---|---|---|---|
| 188 | N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(4-chlorophenyl)cyclopentane-1-carboxamide; TFA salt<br>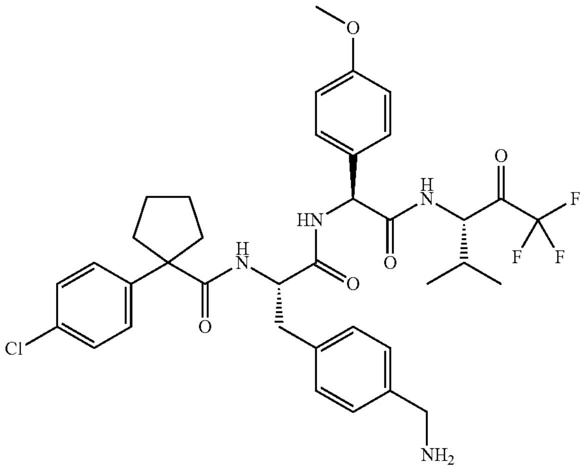<br>Colorless solid | Example 168 | 715.4 |
| 189 | N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-5-chlorothiophene-2-carboxamide; TFA salt<br>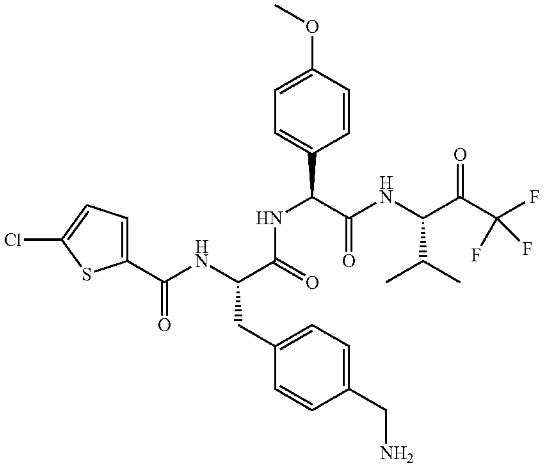<br>Colorless solid | Example 169 | 653.3 |

TABLE 6-continued

| Ex | Name<br>Structure<br>Aspect | Reactant: compound obtained in example number indicated | MS (M + H+) |
|---|---|---|---|
| 190 | (2S)-N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-(4-chlorophenyl)-3-methylbutanamide; TFA salt<br>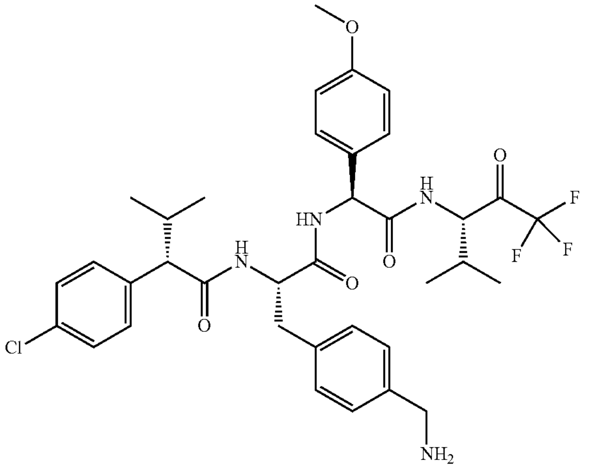<br>Colorless solid | Example 170 | 703.6 |
| 191 | (2R)-N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-(4-chlorophenyl)-3-methylbutanamide; TFA salt<br>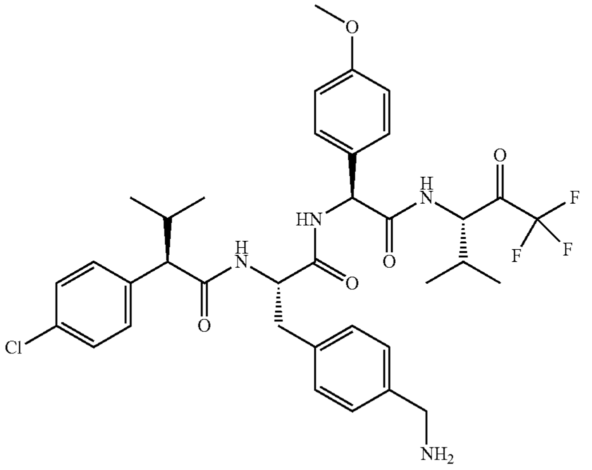<br>Colorless solid | Example 171 | 703.6 |

TABLE 6-continued

| Ex | Name<br>Structure<br>Aspect | Reactant: compound obtained in example number indicated | MS (M + H$^+$) |
|---|---|---|---|
| 192 | (2S)-3-[4-(aminomethyl)phenyl]-2-[[2-(4-chlorophenyl)-2-cyclobutylacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide; TFA salt<br>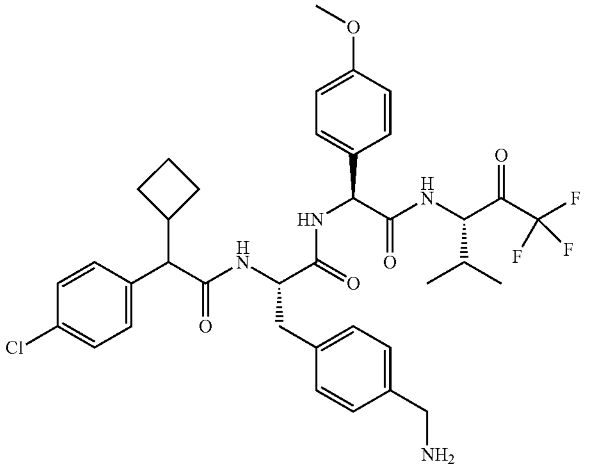<br>Light brown solid | Example 172 | 715.6 |
| 193 | N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-(trifluoromethyl)benzamide; TFA salt<br>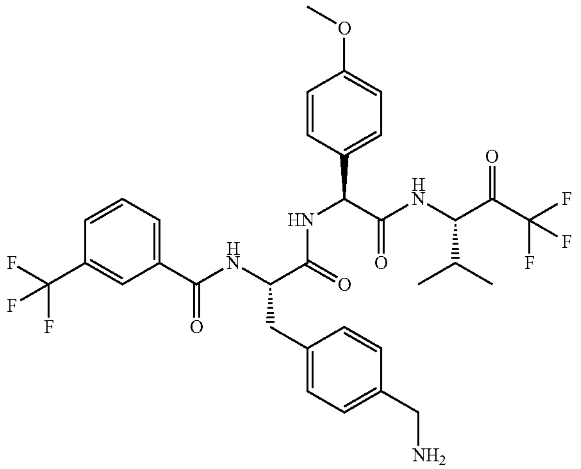<br>Off-white solid | Example 173 | 681.6 |

TABLE 6-continued

| Ex | Name<br>Structure<br>Aspect | Reactant: compound obtained in example number indicated | MS (M + H⁺) |
|---|---|---|---|
| 194 | N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(trifluoromethyl)cyclopentane-1-carboxamide; TFA salt<br>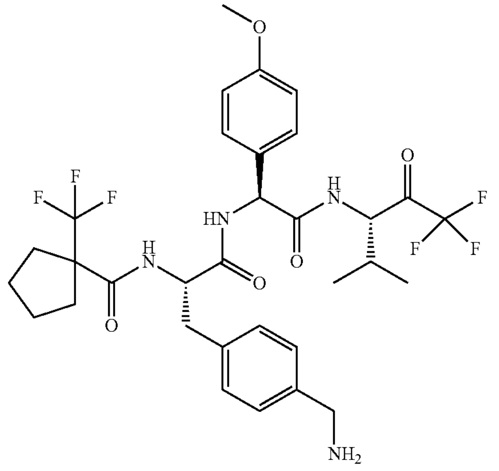<br>Colorless solid | Example 174 | 673.6 |
| 195 | N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3,3,3-trifluoro-2-[3-(trifluoromethyl)phenyl]propanamide; TFA salt<br>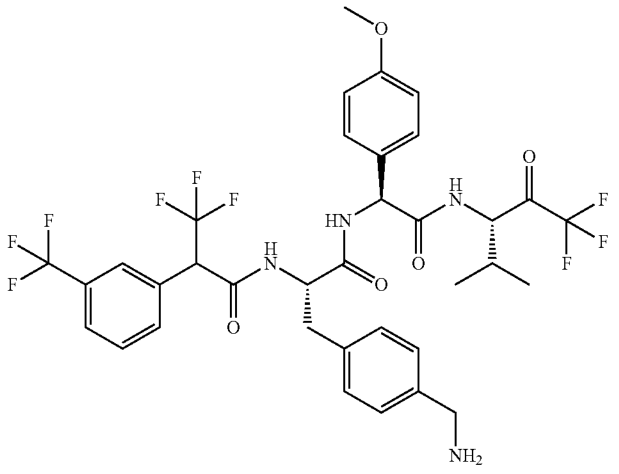<br>Yellow solid | Example 175 | 763.6 |

Example 196

(2S)-2-[[2-(2,5-Dichlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide

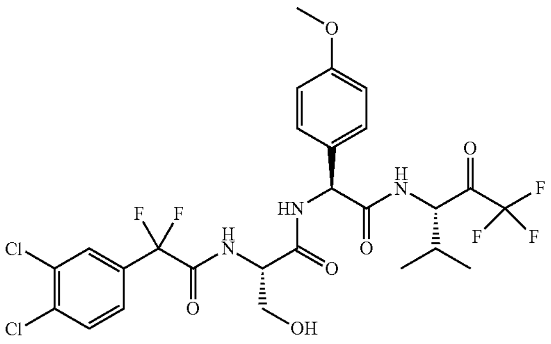 [SMILES: COc1ccc([C@H](NC(=O)[C@H](CO)NC(=O)C(F)(F)c2ccc(Cl)c(Cl)c2)C(=O)N[C@H](C(=O)C(F)(F)F)C(C)C)cc1]

[A] (2S)-3-[tert-Butyl(dimethyl)silyl]oxy-2-[[2-(3,4-dichlorophenyl)-2,2-difluoroacetyl]amino]-N-[(1S)-1-(4-methoxyphenyl)-2-oxo-2-[[(2S,3S)-1,1,1-trifluoro-2-hydroxy-4-methylpentan-3-yl]amino]ethyl]propanamide

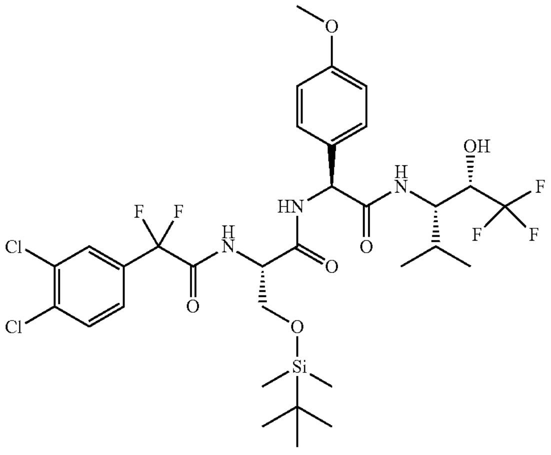 [SMILES: COc1ccc([C@H](NC(=O)[C@H](CO[Si](C)(C)C(C)(C)C)NC(=O)C(F)(F)c2ccc(Cl)c(Cl)c2)C(=O)N[C@@H](C(C)C)[C@H](O)C(F)(F)F)cc1]

In a flask, 2-(3,4-dichlorophenyl)-2,2-difluoroacetic acid (0.020 g, 0.084 mmol) and HATU (0.032 g, 0.084 mmol) were mixed in DMF (2 mL) at 0° C., Huenig's base (0.044 μL, 0.252 mmol) was added and the reaction mixture was stirred at this temperature for 10 min. Then, (2S)-2-amino-3-[tert-butyl(dimethyl)silyl]oxy-N-[(1S)-1-(4-methoxyphenyl)-2-oxo-2-[[(2S,3S)-1,1,1-trifluoro-2-hydroxy-4-methylpentan-3-yl]amino]ethyl]propanamide (Intermediate A-20, 0.045 g, 0.252 mmol) was added and the reaction mixture was stirred at room temperature for 2 hours. After this time, 2-(3,4-dichlorophenyl)-2,2-difluoroacetic acid (0.020 g, 0.084 mmol) and HATU (0.032 g, 0.084 mmol) were added again to the mixture which was stirred at room temperature for a further 2 hours. The mixture was diluted with EtOAc, poured into water (10 mL) and the aqueous layer was extracted with EtOAc (2×20 mL). Combined organics were washed with brine, dried over $Na_2SO_4$, filtered and evaporated. The residue was purified by silica gel flash chromatography, eluting with a 0 to 50% EtOAc/heptane gradient to give the title compound (0.030 g, 47%) as a white solid. MS: 758.3 ($M+H^+$).

[B] (2S)-3-[tert-Butyl(dimethyl)silyl]oxy-2-[[2-(3,4-dichlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide

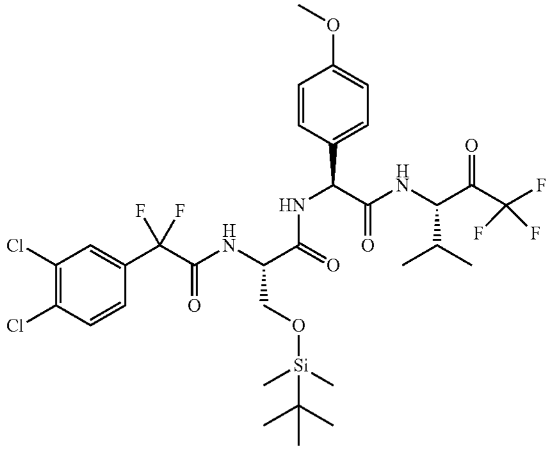 [SMILES: COc1ccc([C@H](NC(=O)[C@H](CO[Si](C)(C)C(C)(C)C)NC(=O)C(F)(F)c2ccc(Cl)c(Cl)c2)C(=O)N[C@H](C(=O)C(F)(F)F)C(C)C)cc1]

To a solution of (2S)-3-[tert-butyl(dimethyl)silyl]oxy-2-[[2-(3,4-dichlorophenyl)-2,2-difluoroacetyl]amino]-N-[(1S)-1-(4-methoxyphenyl)-2-oxo-2-[[(2S,3S)-1,1,1-trifluoro-2-hydroxy-4-methylpentan-3-yl]amino]ethyl]propanamide (0.028 g, 0.037 mmol) in DCM (1.5 mL) was added 15% Dess-Martin periodinane in DCM solution (0.192 mL, 0.092 mmol) and the reaction mixture was stirred at room temperature for 2 hours. The mixture was diluted with DCM/water, poured into a sat. $NH_4Cl$ aqueous solution (5 mL) and extracted with DCM (10 mL). The organic layer was washed with brine, dried over $Na_2SO_4$, filtered and evaporated. The residue was purified by silica gel flash chromatography, eluting with a 0 to 70% EtOAc/heptane gradient to give the title compound (0.020 g, 72%) as a white solid. MS: 756.3 ($M+H^+$).

[C] (2S)-2-[[2-(3,4-Dichlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide

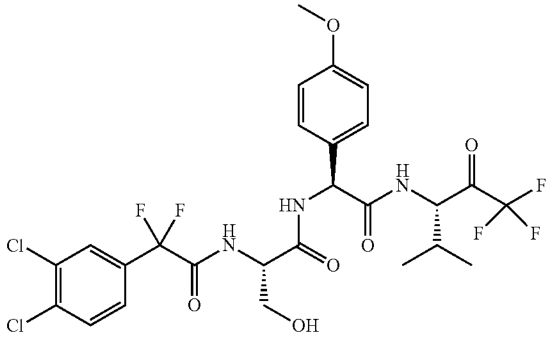 [SMILES: COc1ccc([C@H](NC(=O)[C@H](CO)NC(=O)C(F)(F)c2ccc(Cl)c(Cl)c2)C(=O)N[C@H](C(=O)C(F)(F)F)C(C)C)cc1]

To a solution of (2S)-3-[tert-butyl(dimethyl)silyl]oxy-2-[[2-(3,4-dichlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide (0.020 g, 26.4 mmol) in THF (0.5 mL) and water (0.05 mL) cooled to 0° C. with an ice bath was added 4M HCl (0.099 mL, 0.396 mmol) in dioxane and the reaction mixture was stirred at this temperature for 3 hours. The mixture was poured into water (5 mL) and extracted with EtOAc (10 mL). The organic layer was washed with brine, dried over $Na_2SO_4$ and concentrated in vacuo. The residue was triturated in diisopropylether, the solvent was decanted and the solid precipitate was further dried on the high vacuum to give the title compound (0.012 g, 71%) as a white solid. MS: 642.1 (M+H$^+$).

The following examples listed in Table 7 were prepared in analogy to the procedures described for the preparation of example 196 by using the indicated carboxylic acid in step [A].

TABLE 7

| Ex | Name Structure Aspect | Reactant to be used in step [A] | MS (M + H$^+$) |
|---|---|---|---|
| 197 | (2S)-2-[[2-(2,5-dichlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide 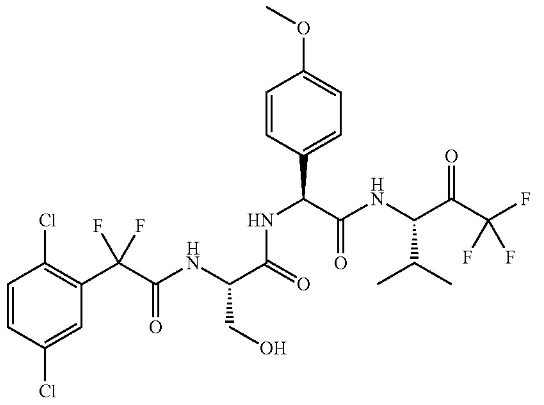 Colorless solid | 2-(2,5-dichlorophenyl)-2,2-difluoroacetic acid | 642.1 |
| 198 | (2S)-2-[[2,2-difluoro-2-(3-fluorophenyl)acetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide 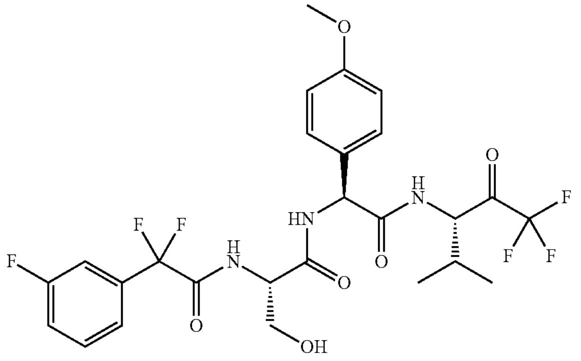 Colorless solid | 2,2-difluoro-2-(3-fluorophenyl)acetic acid | 592.2 |

TABLE 7-continued

| Ex | Name Structure Aspect | Reactant to be used in step [A] | MS (M + H$^{+}$) |
|---|---|---|---|
| 199 | (2S)-2-[[2,2-difluoro-2-[2-(trifluoromethoxy)phenyl]acetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide 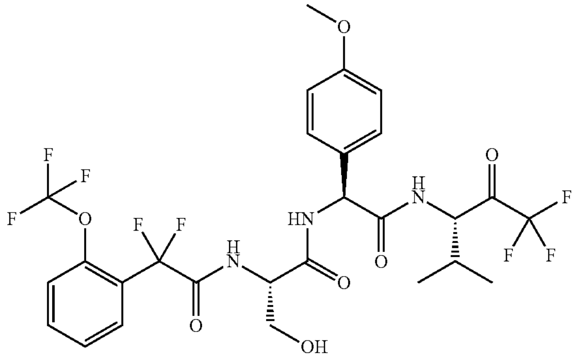 Colorless solid | 2,2-difluoro-2-[2-(trifluoromethoxy)phenyl]acetic acid | 658.2 |
| 200 | (2S)-2-[[2-(2-ethoxyphenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide 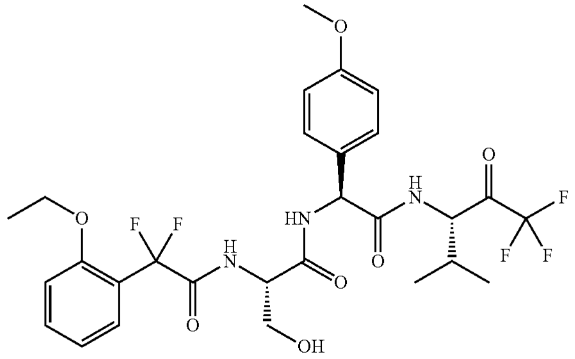 Colorless solid | 2-(2-ethoxyphenyl)-2,2-difluoro-acetic acid | 618.2 |
| 201 | (2S)-2-[[2-(2-ethylphenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide 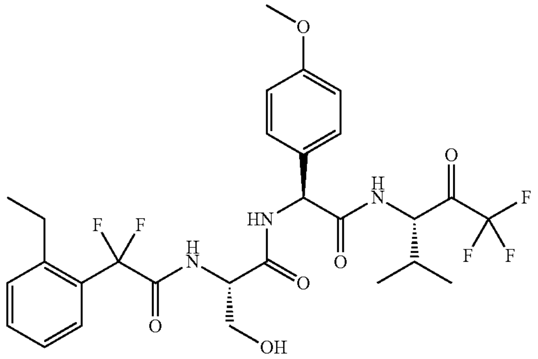 Colorless solid | 2-(2-ethylphenyl)-2,2-difluoro-acetic acid | 602.2 |

TABLE 7-continued

| Ex | Name Structure Aspect | Reactant to be used in step [A] | MS (M + H$^+$) |
|---|---|---|---|
| 202 | 1-(4-chlorophenyl)-N-[(2S)-3-hydroxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopentane-1-carboxamide 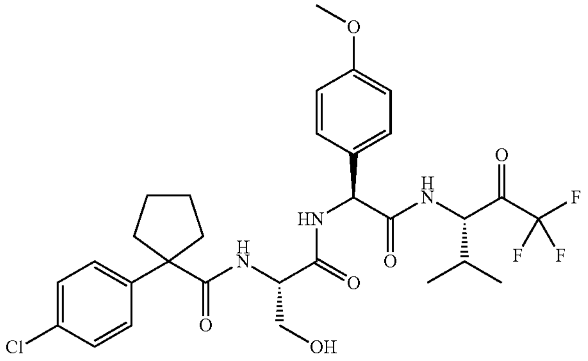 Colorless solid | 1-(4-chlorophenyl)cyclopentane carboxylic acid | 626.2 |
| 203 | (2S)-2-[[2,2-difluoro-2-(2-methoxyphenyl)acetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide 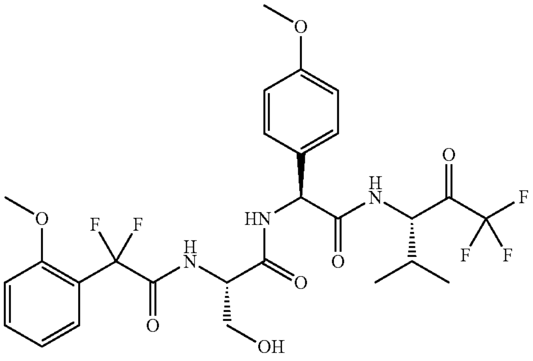 Colorless solid | 2,2-difluoro-2-(2-methoxyphenyl)acetic acid | 604.2 |
| 204 | (2S)-2-[[2-(2-cyanophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide 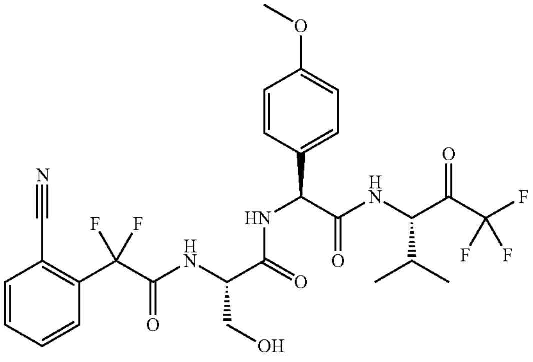 Colorless solid | 2-(2-cyanophenyl)-2,2-difluoro-acetic acid | 599.2 |

Example 205

(2S)-2-[(3-Chlorobenzoyl)amino]-N—[(S)-1-(4-methoxyphenyl)-2-oxo-2-[[(3S)-1,1,1-trifluoro-4-methyl-2-oxopentan-3-yl]amino]ethyl]butanediamide

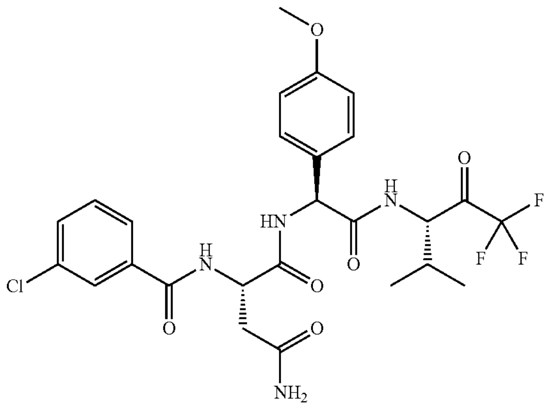 [SMILES: COc1ccc([C@H](NC(=O)[C@H](CC(N)=O)NC(=O)c2cccc(Cl)c2)C(=O)N[C@H](C(=O)C(F)(F)F)C(C)C)cc1]

[A] (2S)-2-[(3-Chlorobenzoyl)amino]-N-[(1S)-1-(4-methoxyphenyl)-2-oxo-2-[[(2S,3S)-1,1,1-trifluoro-2-hydroxy-4-methylpentan-3-yl]amino]ethyl]-N'-[(4-methylphenyl)-diphenylmethyl]butanediamide

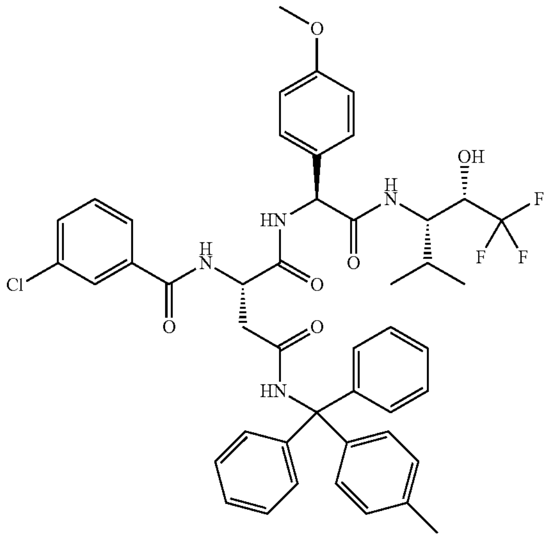 [SMILES: COc1ccc([C@H](NC(=O)[C@H](CC(=O)NC(c2ccccc2)(c2ccccc2)c2ccc(C)cc2)NC(=O)c2cccc(Cl)c2)C(=O)N[C@@H](C(C)C)[C@H](O)C(F)(F)F)cc1]

In a flask, (2S)-2-amino-N-[(1S)-1-(4-methoxyphenyl)-2-oxo-2-[[(2S,3S)-1,1,1-trifluoro-2-hydroxy-4-methylpentan-3-yl]amino]ethyl]-N'-[(4-methylphenyl)-diphenylmethyl] butanediamide (Intermediate A-22, 0.080 g, 0.114 mmol), 3-chlorobenzoic acid (0.018 g, 0.114 mmol) and HATU (0.047 g, 0.125 mmol) were dissolved in DMF (1 mL) and the mixture cooled to 0° C. Huenig's base (0.060 ml, 0.341 mmol) was added to the reaction mixture which was stirred at this temperature for 15 min, then allowed to warm up to room temperature and stirring was continued for 5 hours. The mixture was diluted with EtOAc, poured into water (5 mL) and the aqueous layer was extracted with EtOAc (2×10 mL). Combined organics were washed with brine, dried over $Na_2SO_4$, filtered and evaporated. The residue was purified by silica gel flash chromatography eluting with a 10 to 80% EtOAc-heptane gradient to give the title compound (0.072 g, 71%) as a light brown waxy solid. MS: 841.4 (M–H$^-$).

[B] (2S)-2-[(3-Chlorobenzoyl)amino]-N-[(1S)-1-(4-methoxyphenyl)-2-oxo-2-[[(3S)-1,1,1-trifluoro-4-methyl-2-oxopentan-3-yl]amino]ethyl]-N'-[(4-methylphenyl)-diphenylmethyl]butanediamide

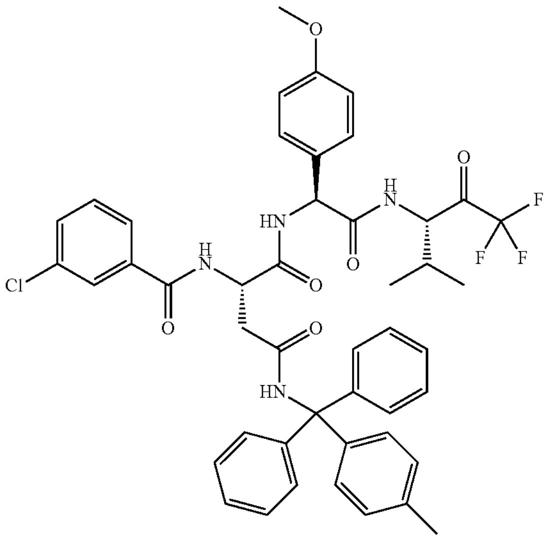 [SMILES: COc1ccc([C@H](NC(=O)[C@H](CC(=O)NC(c2ccccc2)(c2ccccc2)c2ccc(C)cc2)NC(=O)c2cccc(Cl)c2)C(=O)N[C@H](C(=O)C(F)(F)F)C(C)C)cc1]

To a solution of (2S)-2-[(3-chlorobenzoyl)amino]-N-[(1S)-1-(4-methoxyphenyl)-2-oxo-2-[[(2S,3S)-1,1,1-trifluoro-2-hydroxy-4-methylpentan-3-yl]amino]ethyl]-N'-[(4-methylphenyl)-diphenylmethyl]butanediamide (0.072 g, 0.085 mmol) in DCM (1 mL) was added 15% Dess-Martin periodinane in DCM solution (0.532 mL, 0.256 mmol) and the reaction mixture was stirred at room temperature for 4 hours. The mixture was diluted with DCM/water, poured into a sat. $NH_4Cl$ aqueous solution (10 mL) and extracted with DCM (20 mL). The organic layer was washed with brine, dried over $Na_2SO_4$, filtered and evaporated. The residue was purified by silica gel flash chromatography, eluting with a 10 to 100% EtOAc/heptane gradient to give the title compound (0.050 g, 68%) as a colourless waxy solid. MS: 839.4 (M–H$^-$).

[C] (2S)-2-[(3-Chlorobenzoyl)amino]-N-[(1S)-1-(4-methoxyphenyl)-2-oxo-2-[[(3S)-1,1,1-trifluoro-4-methyl-2-oxopentan-3-yl]amino]ethyl]butanediamide

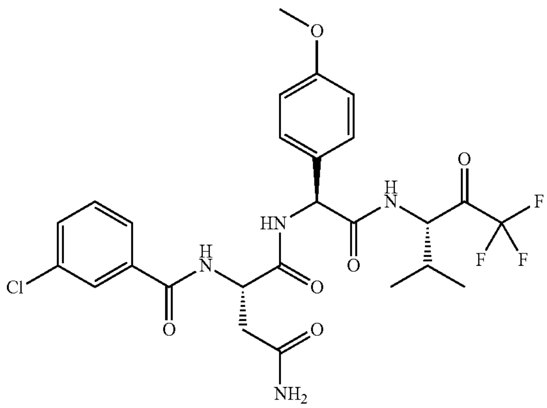 [SMILES: COc1ccc([C@H](NC(=O)[C@H](CC(N)=O)NC(=O)c2cccc(Cl)c2)C(=O)N[C@H](C(=O)C(F)(F)F)C(C)C)cc1]

To a solution of (2S)-2-[(3-chlorobenzoyl)amino]-N-[(1S)-1-(4-methoxyphenyl)-2-oxo-2-[[(3S)-1,1,1-trifluoro-4-methyl-2-oxopentan-3-yl]amino]ethyl]-N'-[(4-methylphenyl)-diphenylmethyl]butanediamide (0.050 g, 0.059 mmol) in DCM (1 mL) cooled to 0° C. was added wet TFA (2.5% water, 0.227 mL, 2.97 mmol) and the reaction mixture was stirred at room temperature for 6 hours. The mixture was concentrated in vacuo and the residue was purified by silica gel flash chromatography, eluting with a 10 to 100% EtOAc/heptane gradient to give the title compound (0.027 g, 73%) as an off-white solid. MS: 585.2 (M−H$^-$).

The following examples listed in Table 8 were prepared in analogy to the procedures described for the preparation of example 205 by using the indicated intermediate and carboxylic acid in step [A]. Except for examples 206, 208 and 210 which were prepared in analogy to the procedure described for the preparation of example 196 by using the indicated intermediate and 2-(3-chlorophenyl)-2,2-difluoro-acetic acid in step [A] then following the procedures described for the preparation of example 205 in step [B] and [C].

Amide products were purified by silica gel flash chromatography; carboxylic acid products were triturated in diisopropylether.

TABLE 8

| Ex | Name Structure Aspect | Reactant to be used in step [A] | MS (M + H$^+$) |
|---|---|---|---|
| 206 | ((2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]butanediamide 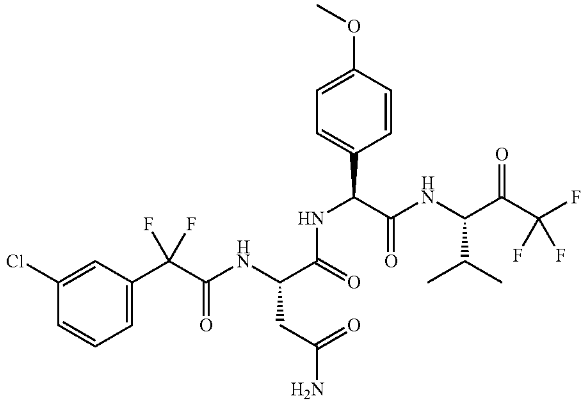 Off-white solid | Intermediate A-22 and 2-(3-chlorophenyl)-2,2-difluoro-acetic acid | 635.2 |

TABLE 8-continued

| Ex | Name Structure Aspect | Reactant to be used in step [A] | MS (M + H+) |
|---|---|---|---|
| 207 | (2S)-2-[(3-chlorobenzoyl)amino]-N-[(1S)-1-(4-methoxyphenyl)-2-oxo-2-[[(3S)-1,1,1-trifluoro-4-methyl-2-oxopentan-3-yl]amino]ethyl]pentanediamide 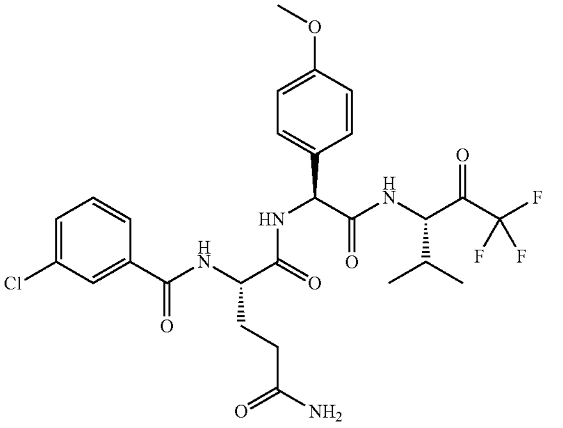 Colorless solid | Intermediate A-23 And 3-chlorobenzoic acid | 599.2 |
| 208 | (2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]pentanediamide 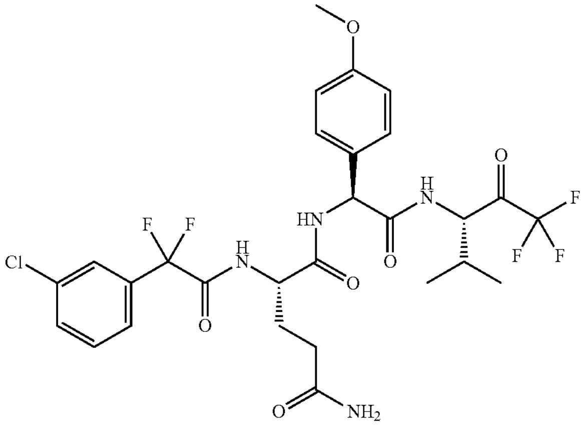 Colorless solid | Intermediate A-23 and 2-(3-chlorophenyl)-2,2-difluoro-acetic acid | 649.2 |

TABLE 8-continued

| Ex | Name Structure Aspect | Reactant to be used in step [A] | MS (M + H+) |
|---|---|---|---|
| 209 | 2-[4-[(1S)-1-[[(2S)-2-[(5-chlorothiophene-2-carbonyl)amino]-3-(3-fluorophenyl)propanoyl]amino]-2-oxo-2-[[(3S)-1,1,1-trifluoro-4-methyl-2-oxopentan-3-yl]amino]ethyl]phenoxy]acetic acid 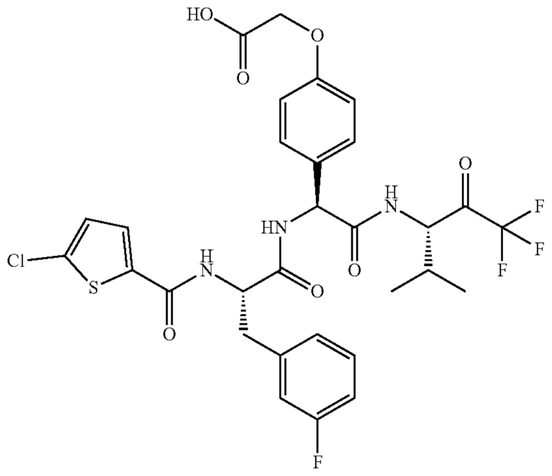 Pink solid | Intermediate A-25 and 5-chlorothiophene-2-carboxylic acid | 686.4 |
| 210 | 2-[4-[(1S)-1-[[(2S)-2-[[2-(3-chlorophenyl)-2,2-difluoroacetyl]amino]-3-(3-fluorophenyl)propanoyl]amino]-2-oxo-2-[[(3S)-1,1,1-trifluoro-4-methyl-2-oxopentan-3-yl]amino]ethyl]phenoxy]acetic acid 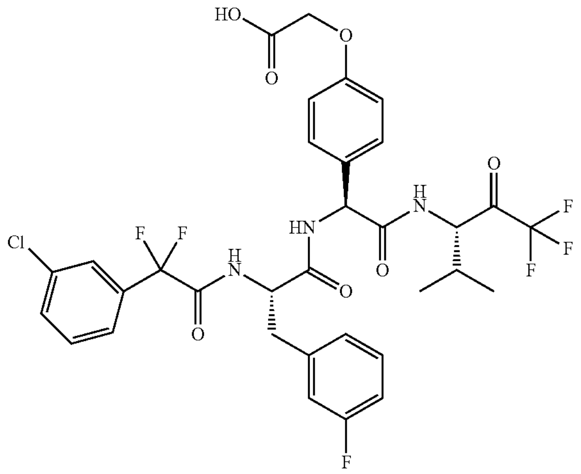 Pink solid | Intermediate A-25 and 2-(3-chlorophenyl)-2,2-difluoro-acetic acid | 730.4 |

Example 211

N-[(5S)-5-[[2-(3,4-Dichlorophenyl)-2,2-difluoro-acetyl]amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]pyridine-2-carboxamide

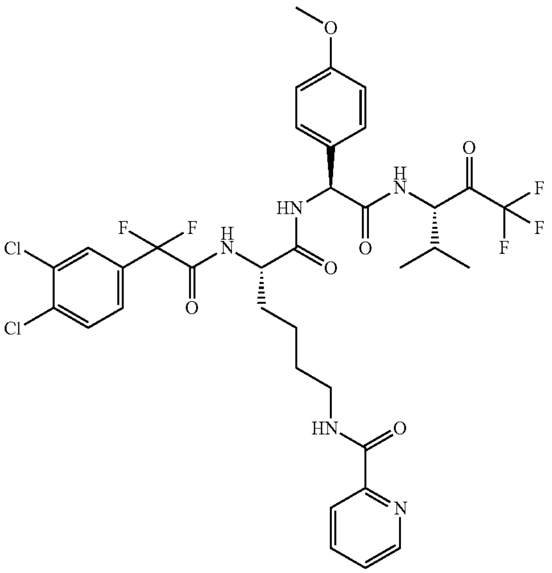 [SMILES: COc1ccc([C@H](NC(=O)[C@H](CCCCNC(=O)c2ccccn2)NC(=O)C(F)(F)c2ccc(Cl)c(Cl)c2)C(=O)N[C@H](C(=O)C(F)(F)F)C(C)C)cc1]

[A] tert-Butyl N-[(5S)-5-[[2-(3,4-dichlorophenyl)-2,2-difluoroacetyl]amino]-6-[[(1S)-1-(4-methoxyphenyl)-2-oxo-2-[[(2S,3S)-1,1,1-trifluoro-2-hydroxy-4-methylpentan-3-yl]amino]ethyl]amino]-6-oxohexyl]carbamate

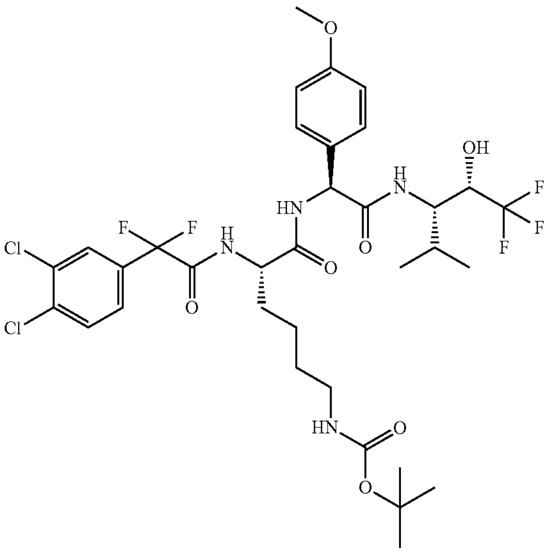 [SMILES: COc1ccc([C@H](NC(=O)[C@H](CCCCNC(=O)OC(C)(C)C)NC(=O)C(F)(F)c2ccc(Cl)c(Cl)c2)C(=O)N[C@@H](C(C)C)[C@H](O)C(F)(F)F)cc1]

In a flask, 2-(3,4-dichlorophenyl)-2,2-difluoroacetic acid (0.045 g, 0.187 mmol) and HATU (0.078 g, 0.205 mmol) were mixed in DMF (1 mL) at 0° C., Huenig's base (0.098 µL, 0.560 mmol) was added and the reaction mixture was stirred at this temperature for 10 min. Then, tert-butyl N-[(5S)-5-amino-6-[[(1S)-1-(4-methoxyphenyl)-2-oxo-2-[[(2S,3S)-1,1,1-trifluoro-2-hydroxy-4-methylpentan-3-yl]amino]ethyl]amino]-6-oxohexyl]carbamate (Intermediate A-17, 0.105 g, 0.187 mmol) was added and the reaction mixture was stirred at room temperature for 4 hours. After this time, 2-(3,4-dichlorophenyl)-2,2-difluoroacetic acid (0.045 g, 0.187 mmol) and HATU (0.078 g, 0.205 mmol) were added again to the mixture which was stirred at room temperature for a further 2 hours. The mixture was diluted with EtOAc, poured into water (10 mL) and the aqueous layer was extracted with EtOAc (2×20 mL). Combined organics were washed with brine, dried over Na2SO4, filtered and evaporated. The residue was purified by silica gel flash chromatography, eluting with a 0 to 100% EtOAc/heptane gradient to give the title compound (0.030 g, 20%) as a light brown solid. MS: 783.4 (M+H$^+$).

[B] (2S)-6-Amino-2-[[2-(3,4-dichlorophenyl)-2,2-difluoroacetyl]amino]-N-[(1S)-1-(4-methoxyphenyl)-2-oxo-2-[[(2S,3S)-1,1,1-trifluoro-2-hydroxy-4-methylpentan-3-yl]amino]ethyl]hexanamide

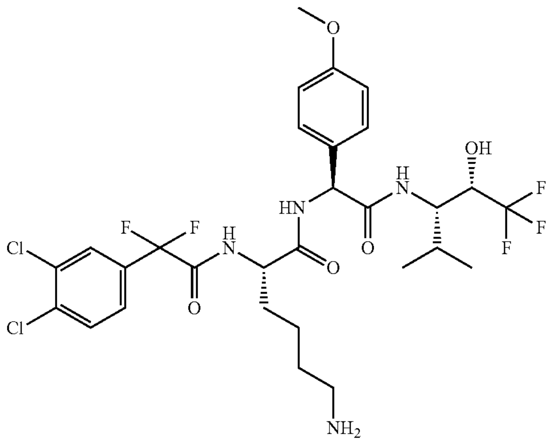 [SMILES: COc1ccc([C@H](NC(=O)[C@H](CCCCN)NC(=O)C(F)(F)c2ccc(Cl)c(Cl)c2)C(=O)N[C@@H](C(C)C)[C@H](O)C(F)(F)F)cc1]

4M HCl in dioxane (0.096 mL, 388 mmol) was added at 0° C. to a solution of tert-butyl N-[(5S)-5-[[2-(3,4-dichlorophenyl)-2,2-difluoroacetyl]amino]-6-[[(1S)-1-(4-methoxyphenyl)-2-oxo-2-[[(2S,3S)-1,1,1-trifluoro-2-hydroxy-4-methylpentan-3-yl]amino]ethyl]amino]-6-oxohexyl]carbamate (0.030 g, 39 mmol) in MeOH (1 mL). The reaction mixture was stirred at this temperature for 10 min and then allowed to warm to room temperature and stirring was continued overnight. The mixture was evaporated to dryness and the residue was triturated with diisopropylether. The solid precipitate was filtered off and further dried under the high vacuum to give the title compound (0.027 g, 93%, HCl salt) as light yellow solid. MS: 683.3 (M+H$^+$).

[C] N-[(5S)-5-[[2-(3,4-Dichlorophenyl)-2,2-difluoroacetyl]amino]-6-[[(1S)-1-(4-methoxyphenyl)-2-oxo-2-[[(2S,3S)-1,1,1-trifluoro-2-hydroxy-4-methylpentan-3-yl]amino]ethyl]amino]-6-oxohexyl]pyridine-2-carboxamide

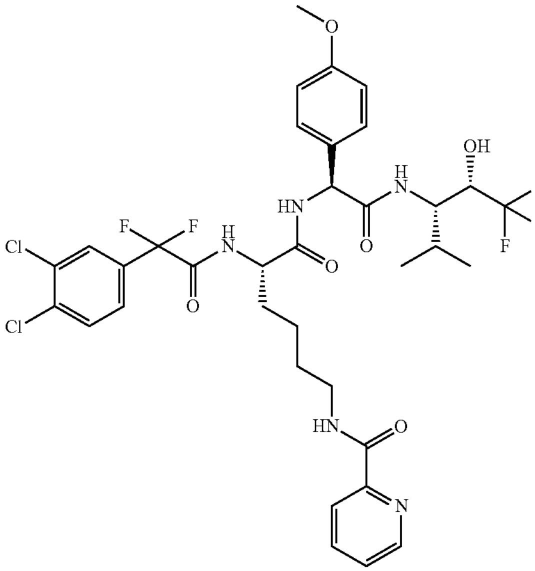

In a flask, (2S)-6-amino-2-[[2-(3,4-dichlorophenyl)-2,2-difluoroacetyl]amino]-N-[(1S)-1-(4-methoxyphenyl)-2-oxo-2-[[(2S,3S)-1,1,1-trifluoro-2-hydroxy-4-methylpentan-3-yl]amino]ethyl]hexanamide hydrochloride (0.027 g, 0.038 mmol), pyridine-2-carboxylic acid (0.005 g, 0.038 mmol) and HATU (0.016 g, 0.042 mmol) were mixed in DMF (1 mL) and the mixture cooled to 0° C. Huenig's base (0.020 mL, 0.114 mmol) was added to the reaction mixture which was stirred at this temperature for 10 min, then allowed to warm up to room temperature and stirring was continued for 4 hours. The mixture was diluted with EtOAc, poured into H2O (5 mL) and the aqueous layer was extracted with EtOAc (2×10 mL). Combined organics were washed brine, dried over $Na_2SO_4$, filtered and concentrated in vacuo. The residue was purified by silica gel flash chromatography eluting with a 0 to 100% EtOAc/heptane gradient to give the title compound (0.021 g, 70%) as a colorless solid. MS: 790.3 (M+H$^+$).

[D] N-[(5S)-5-[[2-(3,4-Dichlorophenyl)-22-difluoroacetyl]amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]pyridine-2-carboxamide

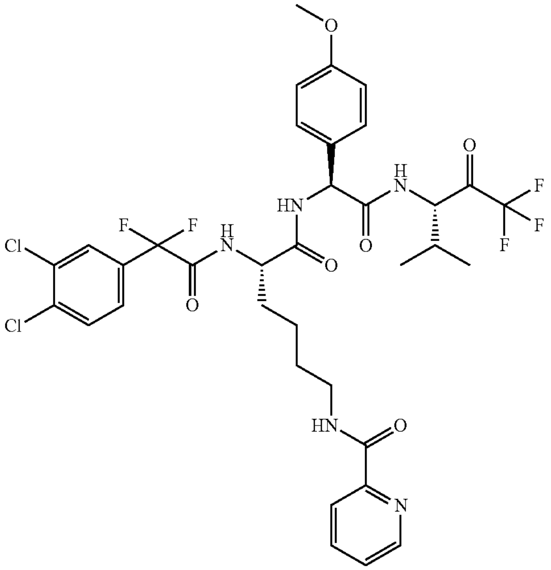 [SMILES: COc1ccc([C@H](NC(=O)[C@H](CCCCNC(=O)c2ccccn2)NC(=O)C(F)(F)c2ccc(Cl)c(Cl)c2)C(=O)N[C@H](C(=O)C(F)(F)F)C(C)C)cc1]

To a solution of N-[(5S)-5-[[2-(3,4-dichlorophenyl)-2,2-difluoroacetyl]amino]-6-[[(1S)-1-(4-methoxyphenyl)-2-oxo-2-[[(2S,3S)-1,1,1-trifluoro-2-hydroxy-4-methylpentan-3-yl]amino]ethyl]amino]-6-oxohexyl]pyridine-2-carboxamide (0.021 g, 0.027 mmol) in DCM (0.5 mL) was added 15% Dess-Martin periodinane in DCM solution (0.168 mL, 0.081 mmol) and the reaction mixture was stirred at room temperature for 3 hours. The resulting white suspension was diluted with DCM/water, poured into a sat. $NH_4Cl$ aqueous solution (5 mL) and then extracted with DCM (10 mL). The organic layer was washed with brine, dried over $Na_2SO_4$, filtered and evaporated. The residue was purified by silica gel flash chromatography, eluting with a 10-100% EtOAc-heptane gradient to give the title compound (0.016 g, 71%) as a colorless solid. MS: 788.2 (M+H$^+$).

The following examples listed in Table 9 were prepared in analogy to the procedures described for the preparation of example 211 by using the indicated intermediate and carboxylic acids in step [A] and [C] respectively.

TABLE 9

| Ex | Name Structure Aspect | Reactant to be used in step [A] and [C] | MS (M + H$^+$) |
|---|---|---|---|
| 212 | N-[(5S)-5-[[2-(3-chlorophenyl)-2,2-difluoroacetyl]amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]pyrazine-2-carboxamide 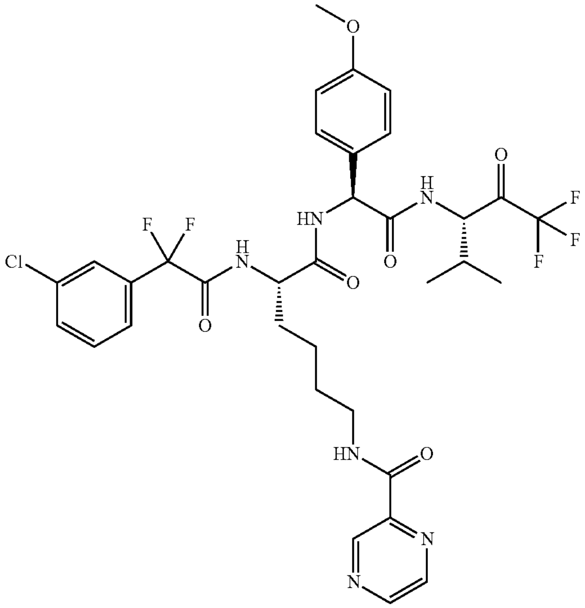 Colorless solid | Intermediate A-17; 2-(3-chlorophenyl)-2,2-difluoro-acetic acid and pyrazine-2-carboxylic acid | 755.2 |
| 213 | N-[(5S)-5-[[2-(3-chlorophenyl)-2,2-difluoroacetyl]amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]pyrimidine-5-carboxamide 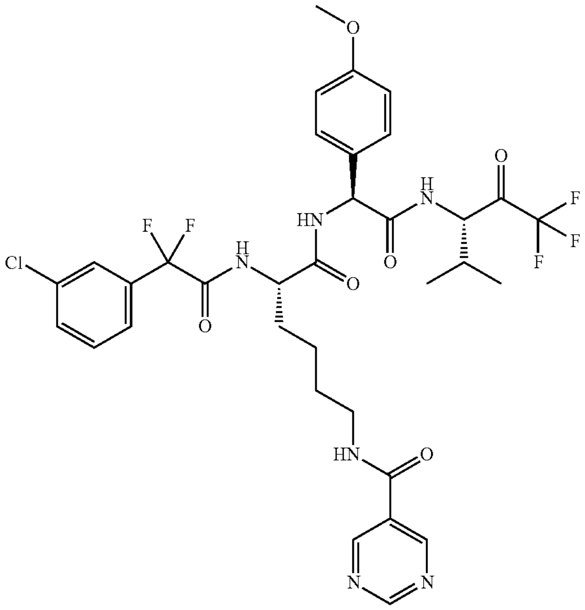 Colorless solid | Intermediate A-17 2-(3-chlorophenyl)-2,2-difluoro-acetic acid and pyrimidine-5-carboxylic acid | 755.4 |

TABLE 9-continued

| Ex | Name Structure Aspect | Reactant to be used in step [A] and [C] | MS (M + H$^+$) |
| --- | --- | --- | --- |
| 214 | N-[(5S)-5-[(3-chlorobenzoyl)amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]pyridine-2-carboxamide 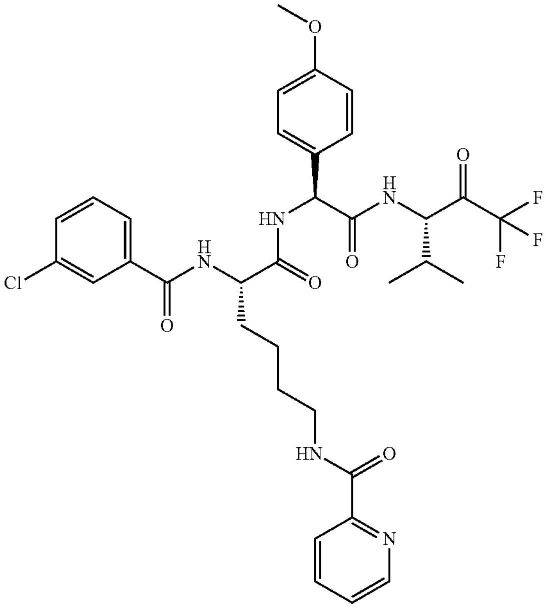 Colorless solid | Intermediate A-17; 3-chlorobenzoic acid and pyridine-2-carboxylic acid | 704.3 |
| 215 | N-[(4S)-4-[(3-chlorobenzoyl)amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentyl]pyridine-2-carboxamide 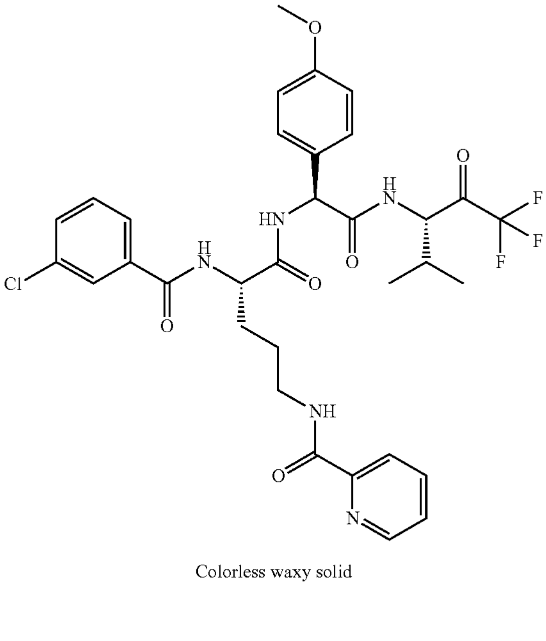 Colorless waxy solid | Intermediate A-18; 3-chlorobenzoic acid and pyridine-2-carboxylic acid | 690.3 |

TABLE 9-continued

| Ex | Name Structure Aspect | Reactant to be used in step [A] and [C] | MS (M + H⁺) |
|---|---|---|---|
| 216 | N-[[4-[(2S)-2-[[2-(3-chlorophenyl)-2,2-difluoroacetyl]amino]-3[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]pyridine-2-carboxamide 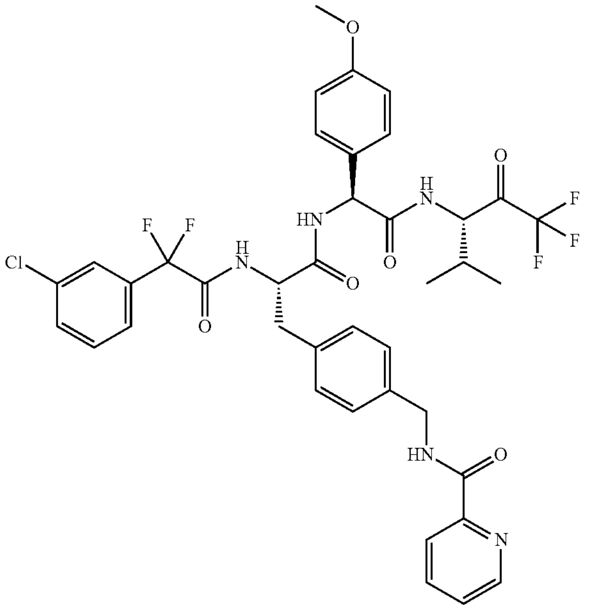 Colorless solid | Intermediate A-19; 2-(3-chlorophenyl)-2,2-difluoro-acetic acid and pyridine-2-carboxylic acid | 802.4 |

Example A

A compound of formula (I) can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| Total amount | 425 mg |

Example B

A compound of formula (I) can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| Total amount | 220.0 mg |

The invention claimed is:

1. A compound of formula (I)

(I)

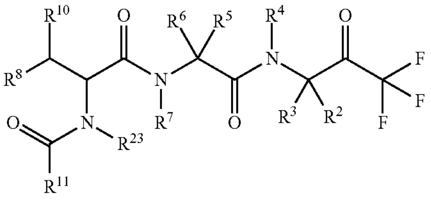

or a pharmaceutically acceptable salt thereof, wherein $R^2$, $R^3$, $R^4$, $R^6$, $R^7$, $R^{10}$ and $R^{23}$ are each independently selected from the group consisting of
(i) H,
(ii) $C_{1-6}$-alkyl, and
(iii) $C_{3-8}$-cycloalkyl;

$R^5$ is selected from the group consisting of
(i) aryl optionally substituted with one or more substituents selected from the group consisting of $R^{12}$, $R^{13}$ and $R^{14}$, ii) aryl-$C_{1-6}$-alkyl optionally substituted with one or more substituents selected from the group consisting of $R^{12}$, $R^{13}$ and $R^{14}$, iii) heteroaryl optionally substituted with one or more substituents selected from the group consisting of $R^{12}$, $R^{13}$ and $R^{14}$, and iv) heteroaryl-$C_{1-6}$-alkyl optionally substituted with one or more substituents selected from the group consisting of $R^{12}$, $R^{13}$ and $R^{14}$;

$R^8$ is selected from the group consisting of i) H, ii) hydroxy, iii) amino-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are optionally substituted with one or more substituents selected from the group consisting of $R^{15}$, $R^{16}$ and $R^{17}$, iv) aminocarbonyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are optionally substituted with one or more substituents selected from the group consisting of $R^{15}$, $R^{16}$ and $R^{17}$, v) aminocarbonyl-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are optionally substituted with one or more substituents selected from the group consisting of $R^{15}$, $R^{16}$ and $R^{17}$, vi) carboxy, vii) carboxy-$C_{1-6}$-alkyl, viii) $C_{1-6}$-alkoxy, ix) $C_{1-6}$-haloalkoxy, x) $C_{1-6}$-alkoxycarbonyl, xi) $C_{1-6}$-alkoxycarbonyl-$C_{1-6}$-alkyl, xii) $C_{3-8}$-cycloalkyl, xiii) aryl optionally substituted with one or more substituents selected from the group consisting of $R^{15}$, $R^{16}$ and $R^{17}$, xiv) aryl-$C_{1-6}$-alkyl optionally substituted with one or more substituents selected from the group consisting of $R^{15}$, $R^{16}$ and $R^{17}$, xv) aryl-$C_{1-6}$-alkoxy optionally substituted with one or more substituents selected from the group consisting of $R^{15}$, $R^{16}$ and $R^{17}$, xvi) heteroaryl optionally substituted with one or more substituents selected from the group consisting of $R^{15}$, $R^{16}$ and $R^{17}$, xvii) heteroaryl-$C_{1-6}$-alkyl optionally substituted with one or more substituents selected from the group consisting of $R^{15}$, $R^{16}$ and $R^{17}$, xviii) heteroaryl-$C_{1-6}$-alkoxy optionally substituted with one or more substituents selected from the group consisting of $R^{15}$, $R^{16}$ and $R^{17}$ xix) heterocycloalkyl optionally substituted with one or more substituents selected from the group consisting of $R^{15}$, $R^{16}$ and $R^{17}$, xx) heterocycloalkyl-$C_{1-6}$-alkyl optionally substituted with one or more substituents selected from the group consisting of $R^{15}$, $R^{16}$ and $R^{17}$, xxi) heterocycloalkyl-$C_{1-6}$-alkoxy optionally substituted with one or more substituents selected from the group consisting of $R^{15}$, $R^{16}$ and $R^{17}$, xxii) cyano-$C_{1-6}$-alkyl, and xxiii) halo-$C_{1-6}$-alkoxy;

$R^{11}$ is selected from the group consisting of i) amino-$C_{1-6}$-alkyl substituted on the nitrogen atom by $R^{21}$ and $R^{22}$, ii) $C_{3-8}$-cycloalkyl optionally substituted with one or more substituents selected from the group consisting of $R^{18}$, $R^{19}$ and $R^{20}$, iii) $C_{3-8}$-cycloalkyl-$C_{1-6}$-alkyl optionally substituted with one or more substituents selected from the group consisting of $R^{18}$, $R^{19}$ and $R^{20}$, iv) $C_{3-8}$-cycloalkyl(halo)-$C_{1-6}$-alkyl optionally substituted with one or more substituents selected from the group consisting of $R^{18}$, $R^{19}$ and $R^{20}$, v) aryl optionally substituted with one or more substituents selected from the group consisting of $R^{18}$, $R^{19}$ and $R^{20}$, vi) aryl-$C_{1-6}$-alkyl optionally substituted with one or more substituents selected from the group consisting of $R^{18}$, $R^{19}$ and $R^{20}$, vii) aryl-$C_{3-8}$-cycloalkyl optionally substituted with one or more substituents selected from the group consisting of $R^{18}$, $R^{19}$ and $R^{20}$, viii) aryl-heterocycloalkyl optionally substituted with one or more substituents selected from the group consisting of $R^{18}$, $R^{19}$ and $R^{20}$ ix) aryl(halo)-$C_{1-6}$-alkyl optionally substituted with one or more substituents selected from the group consisting of $R^{18}$, $R^{19}$ and $R^{20}$, x) aryl(halo)-$C_{3-8}$-cycloalkyl optionally substituted with one or more substituents selected from the group consisting of $R^{18}$, $R^{19}$ and $R^{20}$, xi) aryl(halo)-heterocycloalkyl optionally substituted with one or more substituents selected from the group consisting of $R^{18}$, $R^{19}$ and $R^{20}$, xii) aryloxy-$C_{1-6}$-alkyl optionally substituted with one or more substituents selected from the group consisting of $R^{18}$, $R^{19}$ and $R^{20}$, xiii) aryloxy-$C_{3-8}$-cycloalkyl optionally substituted with one or more substituents selected from the group consisting of $R^{18}$, $R^{19}$ and $R^{20}$, xiv) aryloxy-heterocycloalkyl optionally substituted with one or more substituents selected from the group consisting of $R^{18}$, $R^{19}$ and $R^{20}$, xv) aryloxy(halo)-$C_{3-8}$-cycloalkyl optionally substituted with one or more substituents selected from the group consisting of $R^{18}$, $R^{19}$ and $R^{20}$, xvi) aryloxy(halo)-heterocycloalkyl optionally substituted with one or more substituents selected from the group consisting of $R^{18}$, $R^{19}$ and $R^{20}$, xvii) aryloxy(halo)-$C_{1-6}$-alkyl, xviii) heterocycloalkyl optionally substituted with one or more substituents selected from the group consisting of $R^{18}$, $R^{19}$ and $R^{20}$, xix) heterocycloalkyl-$C_{1-6}$-alkyl optionally substituted with one or more substituents selected from the group consisting of $R^{18}$, $R^{19}$ and $R^{20}$, xx) heterocycloalkyl-$C_{3-8}$-cycloalkyl optionally substituted with one or more substituents selected from the group consisting of $R^{18}$, $R^{19}$ and $R^{20}$, xxi) heterocycloalkyl(halo)-$C_{3-8}$-cycloalkyl optionally substituted with one or more substituents selected from the group consisting of $R^{18}$, $R^{19}$ and $R^{20}$, xxii) heterocycloalkyl(halo)-$C_{1-6}$-alkyl optionally substituted with one or more substituents selected from the group consisting of $R^{18}$, $R^{19}$ and $R^{20}$, xxiii) heteroaryl optionally substituted with one or more substituents selected from the group consisting of $R^{18}$, $R^{19}$ and $R^{20}$, xxiv) heteroaryl-$C_{1-6}$-alkyl optionally substituted with one or more substituents selected from the group consisting of $R^{18}$, $R^{19}$ and $R^{20}$, xxv) heteroaryl-$C_{3-8}$-cycloalkyl optionally substituted with one or more substituents selected from the group consisting of $R^{18}$, $R^{19}$ and $R^{20}$, xxvi) heteroaryl(halo)-$C_{3-8}$-cycloalkyl optionally substituted with one or more substituents selected from the group consisting of $R^{18}$, $R^{19}$ and $R^{20}$, xxvii) heteroaryl(halo)-$C_{1-6}$-alkyl optionally substituted with one or more substituents selected from the group consisting of $R^{18}$, $R^{19}$ and $R^{20}$, xxviii) heteroaryloxy-$C_{1-6}$-alkyl optionally substituted with one or more substituents selected from the group consisting of $R^{18}$, $R^{19}$ and $R^{20}$, xxix) heteroaryloxy-$C_{3-8}$-cycloalkyl optionally substituted with one or more substituents selected from the group consisting of $R^{18}$, $R^{19}$ and $R^{20}$, xxx) heteroaryloxy(halo)-$C_{3-8}$-cycloalkyl optionally substituted with one or more substituents selected from the group consisting of $R^{18}$, $R^{19}$ and $R^{20}$, xxxi) heteroaryloxy(halo)-$C_{1-6}$-alkyl optionally substituted with one or more substituents selected from the group consisting of $R^{18}$, $R^{19}$ and $R^{20}$, xxxii) aryl(cycloalkyl)-$C_{1-6}$-alkyl optionally substituted with one or more substituents selected from the group consisting of $R^{18}$, $R^{19}$ and $R^{20}$, xxxiii) aryl(heterocycloalkyl)-$C_{1-6}$-alkyl optionally substituted with one or more substituents selected from the group consisting of $R^{18}$, $R^{19}$ and $R^{20}$, and xxxiv) aryl(hydroxy, halo)-$C_{1-6}$-alkyl optionally substituted with one or more substituents selected from the group consisting of $R^{18}$, $R^{19}$ and $R^{20}$;

$R^{12}$, $R^{13}$, $R^{14}$, $R^{15}$, $R^{16}$, $R^{17}$, $R^{18}$, $R^{19}$ and $R^{20}$ are each independently selected from the group consisting of i) H, ii) cyano, iii) halogen, iv) oxo, v) $C_{1-6}$-alkyl, vi) amino substituted on the nitrogen atom by two substituents independently selected from H, $C_{1-6}$-alkyl, $C_{1-6}$-alkoxycarbonyl, arylcarbonyl and heteroarylcarbonyl, vii) amino-$C_{1-6}$-alkyl substituted on the nitrogen atom by two substituents independently selected from H, $C_{1-6}$-alkyl, $C_{1-6}$-alkoxycarbonyl, arylcarbonyl and heteroarylcarbonyl, viii) halo-$C_{1-6}$-alkyl, ix) $C_{3-8}$-cycloalkyl, x) $C_{1-6}$-alkoxycarbonyl-$C_{1-6}$-alkyl, xi) carboxy-$C_{1-6}$-alkyl, xii) $C_{1-6}$-alkoxycarbonyl-$C_{1-6}$alkylaminocarbonyl-$C_{1-6}$alkyl, xiii) carboxy-$C_{1-6}$-alkylaminocarbonyl-$C_{1-6}$alkyl, xiv) $C_{1-6}$-alkoxy, xv) halo-$C_{1-6}$-alkoxy, xvi) $C_{1-6}$-alkoxycarbonyl-$C_{1-6}$-alkoxy, xvii) hydroxycarbonyl-$C_{1-6}$-alkoxy, xviii) carboxy-$C_{1-6}$-alkoxy, xix) $C_{1-6}$-alkoxycarbonyl-$C_{1-6}$-alkylaminocarbonyl-$C_{1-6}$-alkoxy, xx) carboxy-$C_{1-6}$-alkylaminocarbonyl-$C_{1-6}$-alkoxy, heterocycloalkyl, and xxi) cyano; and $R^{21}$ and $R^{22}$ are each independently selected from the group consisting of i) H, ii) $C_{1-6}$-alkoxycarbonyl, iii) carboxy-$C_{1-6}$-alkyl, iv) arylcarbonyl, and v) heteroarylcarbonyl.

2. A compound according to claim 1, or a pharmaceutically acceptable salt thereof, wherein $R^2$, $R^3$, $R^4$, $R^6$, $R^7$, $R^{10}$ and $R^{23}$ are each independently selected from the group consisting of i) H, ii) $C_{1-6}$-alkyl, and iii) $C_{3-8}$-cycloalkyl;

$R^5$ is selected from the group consisting of i) aryl optionally substituted with one or more substituents selected from the group consisting of $R^{12}$, $R^{13}$ and $R^{14}$, ii) aryl-$C_{1-6}$-alkyl optionally substituted with one or more substituents selected from the group consisting of $R^{12}$, $R^{13}$ and $R^{14}$, iii) heteroaryl optionally substituted with one or more substituents selected from the group consisting of $R^{12}$, $R^{13}$ and $R^{14}$, and iv) heteroaryl-$C_{1-6}$-alkyl optionally substituted with one or more substituents selected from the group consisting of $R^{12}$, $R^{13}$ and $R^{14}$;

$R^8$ is selected from the group consisting of i) H, ii) hydroxy, iii) amino-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are optionally substituted with one or more substituents selected from the group consisting of $R^{15}$, $R^{16}$ and $R^{17}$, iv) aminocarbonyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are optionally substituted with one or more substituents selected from the group consisting of $R^{15}$, $R^{16}$ and $R^{17}$, v) aminocarbonyl-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are optionally substituted with one or more substituents selected from the group consisting of $R^{15}$, $R^{16}$ and $R^{17}$, vi) carboxy, vii) carboxy-$C_{1-6}$-alkyl, viii) $C_{1-6}$-alkoxy, ix) $C_{1-8}$-haloalkoxy, x) $C_{1-6}$-alkoxycarbonyl, xi) $C_{1-6}$-alkoxycarbonyl-$C_{1-6}$-alkyl, xii) $C_{3-8}$-cycloalkyl, xiii) aryl optionally substituted with one or more substituents selected from the group consisting of $R^{15}$, $R^{16}$ and $R^{17}$, xiv) aryl-$C_{1-6}$-alkyl optionally substituted with one or more substituents selected from the group consisting of $R^{15}$, $R^{16}$ and $R^{17}$, xv) aryl-$C_{1-6}$-alkoxy optionally substituted with one or more substituents selected from the group consisting of $R^{15}$, $R^{16}$ and $R^{17}$, xvi) heteroaryl optionally substituted with one or more substituents selected from the group consisting of $R^{15}$, $R^{16}$ and $R^{17}$, xvii) heteroaryl-$C_{1-6}$-alkyl optionally substituted with one or more substituents selected from the group consisting of $R^{15}$, $R^{16}$ and $R^{17}$, and xviii) heteroaryl-$C_{1-6}$-alkoxy optionally substituted with one or more substituents selected from the group consisting of $R^{15}$, $R^{16}$ and $R^{17}$ xix) heterocycloalkyl optionally substituted with one or more substituents selected from the group consisting of $R^{15}$, $R^{16}$ and $R^{17}$, xx) heterocycloalkyl-$C_{1-6}$-alkyl optionally substituted with one or more substituents selected from the group consisting of $R^{15}$, $R^{16}$ and $R^{17}$, and xxi) heterocycloalkyl-$C_{1-6}$-alkoxy optionally substituted with one or more substituents selected from the group consisting of $R^{15}$, $R^{16}$ and $R^{17}$;

$R^{11}$ is selected from the group consisting of i) amino-$C_{1-6}$-alkyl substituted on the nitrogen atom by $R^{21}$ and $R^{22}$, ii) $C_{3-8}$-cycloalkyl optionally substituted with one or more substituents selected from the group consisting of $R^{18}$, $R^{19}$ and $R^{20}$, iii) $C_{3-8}$-cycloalkyl-$C_{1-6}$-alkyl optionally substituted with one or more substituents selected from the group consisting of $R^{18}$, $R^{19}$ and $R^{20}$, iv) $C_{3-8}$-cycloalkyl(halo)-$C_{1-6}$-alkyl optionally substituted with one or more substituents selected from the group consisting of $R^{18}$, $R^{19}$ and $R^{20}$, v) aryl optionally substituted with one or more substituents selected from the group consisting of $R^{18}$, $R^{19}$ and $R^{20}$, vi) aryl-$C_{1-6}$-alkyl optionally substituted with one or more substituents selected from the group consisting of $R^{18}$, $R^{19}$ and $R^{20}$, vii) aryl-$C_{3-8}$-cycloalkyl optionally substituted with one or more substituents selected from the group consisting of $R^{18}$, $R^{19}$ and $R^{20}$, viii) aryl-heterocycloalkyl optionally substituted with one or more substituents selected from the group consisting of $R^{18}$, $R^{19}$ and $R^{20}$, ix) aryl(halo)-$C_{1-6}$-alkyl optionally substituted with one or more substituents selected from the group consisting of $R^{18}$, $R^{19}$ and $R^{20}$, x) aryl(halo)-$C_{3-8}$-cycloalkyl optionally substituted with one or more substituents selected from the group consisting of $R^{18}$, $R^{19}$ and $R^{20}$, xi) aryl(halo)-heterocycloalkyl optionally substituted with one or more substituents selected from the group consisting of $R^{18}$, $R^{19}$ and $R^{20}$, xii) aryloxy-$C_{1-6}$-alkyl optionally substituted with one or more substituents selected from the group consisting of $R^{18}$, $R^{19}$ and $R^{20}$, xiii) aryloxy-$C_{3-8}$-cycloalkyl optionally substituted with one or more substituents selected from the group consisting of $R^{18}$, $R^{19}$ and $R^{20}$, xiv) aryloxy-heterocycloalkyl optionally substituted with one or more substituents selected from the group consisting of $R^{18}$, $R^{19}$ and $R^{20}$, xv) aryloxy(halo)-$C_{3-8}$-cycloalkyl optionally substituted with one or more substituents selected from the group consisting of $R^{18}$, $R^{19}$ and $R^{20}$, xvi) aryloxy(halo)-heterocycloalkyl optionally substituted with one or more substituents selected from the group consisting of $R^{18}$, $R^{19}$ and $R^{20}$, xvii) aryloxy(halo)-$C_{1-6}$-alkyl, xviii) heterocycloalkyl optionally substituted with one or more substituents selected from the group consisting of $R^{18}$, $R^{19}$ and $R^{20}$, xix) heterocycloalkyl-$C_{1-6}$-alkyl optionally substituted with one or more substituents selected from the group consisting of $R^{18}$, $R^{19}$ and $R^{20}$, xx) heterocycloalkyl-$C_{3-8}$-cycloalkyl optionally substituted with one or more substituents selected from the group consisting of $R^{18}$, $R^{19}$ and $R^{20}$, xxi) heterocycloalkyl(halo)-$C_{3-8}$-cycloalkyl optionally substituted with one or more substituents selected from the group consisting of $R^{18}$, $R^{19}$ and $R^{20}$, xxii) heterocycloalkyl(halo)-$C_{1-6}$-alkyl optionally substituted with one or more substituents selected from the group consisting of $R^{18}$, $R^{19}$ and $R^{20}$, xxiii) heteroaryl optionally substituted with one or more substituents selected from the group consisting of $R^{18}$, $R^{19}$ and $R^{20}$, xxiv) heteroaryl-$C_{1-6}$-alkyl optionally substituted with one or more substituents selected from the group consisting of $R^{18}$, $R^{19}$ and $R^{20}$, xxv) heteroaryl-$C_{3-8}$-cycloalkyl optionally substituted with one or more substituents selected from the group consisting of $R^{18}$, $R^{19}$ and $R^{20}$, xxvi) heteroaryl(halo)-$C_{3-8}$-cycloalkyl optionally substituted with one or more substituents selected from the group consisting of $R^{18}$, $R^{19}$ and $R^{20}$, xxvii) heteroaryl(halo)-$C_{1-6}$-alkyl optionally substituted with one or more substituents selected from the group consisting of $R^{18}$, $R^{19}$ and $R^{20}$, xxviii) heteroaryloxy-$C_{1-6}$-alkyl optionally substituted with one or more substituents selected from the group consisting of $R^{18}$, $R^{19}$ and $R^{20}$, xxix) heteroaryloxy-$C_{3-8}$-cycloalkyl optionally substituted with one or more substituents selected from the group consisting of $R^{18}$, $R^{19}$ and $R^{20}$, xxx) heteroaryloxy(halo)-$C_{3-8}$-cycloalkyl optionally substituted with one or more substituents selected from the group consisting of $R^{18}$, $R^{19}$ and $R^{20}$, and xxxi) heteroaryloxy(halo)-$C_{1-6}$-alkyl optionally substituted with one or more substituents selected from the group consisting of $R^{18}$, $R^{19}$ and $R^{20}$;

$R^{12}$, $R^{13}$, $R^{14}$, $R^{15}$, $R^{16}$, $R^{17}$, $R^{18}$, $R^{19}$ and $R^{20}$ are each independently selected from the group consisting of i) H, ii) cyano, iii) halogen, iv) oxo, v) $C_{1-6}$-alkyl, vi) amino substituted on the nitrogen atom by two substituents independently selected from H, $C_{1-6}$-alkyl, $C_{1-6}$-alkoxycarbonyl, arylcarbonyl and heteroarylcarbonyl, vii) amino-$C_{1-6}$-alkyl substituted on the nitrogen atom by two substituents independently selected from H, $C_{1-6}$-alkyl, $C_{1-6}$-alkoxycarbonyl, arylcarbonyl and heteroarylcarbonyl, viii) $C_{1-6}$-alkyl, ix) halo-$C_{1-6}$-alkyl, x) $C_{3-8}$-cycloalkyl, xi) $C_{1-6}$-alkoxycarbonyl-$C_{1-6}$-alkyl, xii) carboxy-$C_{1-6}$-alkyl, xiii) $C_{1-6}$-alkoxycarbonyl-$C_{1-6}$alkylaminocarbonyl-$C_{1-6}$alkyl, xiv) carboxy-$C_{1-6}$-alkylaminocarbonyl-$C_{1-6}$alkyl, xv) $C_{1-6}$-alkoxy, xvi) halo-$C_{1-6}$-alkoxy, xvii) $C_{1-6}$-alkoxycarbonyl-$C_{1-6}$-alkoxy, xviii) carboxy-$C_{1-6}$-alkoxy, xix) $C_{1-6}$-alkoxycarbonyl-$C_{1-6}$-alkylaminocarbonyl-$C_{1-6}$-alkoxy, xx) carboxy-$C_{1-6}$-alkylaminocarbonyl-$C_{1-6}$-alkoxy, and xxi) heterocycloalkyl;

$R^{21}$ and $R^{22}$ are independently selected from the group consisting of i) H, ii) $C_{1-6}$-alkoxycarbonyl, iii) carboxy-$C_{1-6}$-alkyl, iv) arylcarbonyl, and v) heteroarylcarbonyl.

3. A compound according to claim 1, or a pharmaceutically acceptable salt thereof, wherein $R^2$ is $C_{1-6}$-alkyl;

$R^3$, $R^4$, $R^6$, $R^7$, $R^{10}$ and $R^{23}$ are H;

$R^5$ is selected from i) phenyl optionally substituted with one or more substituents selected from the group consisting of $R^{12}$, $R^{13}$ and $R^{14}$, and ii) phenyl-$C_{1-6}$-alkyl optionally substituted with one or more substituents selected from the group consisting of $R^{12}$, $R^{13}$ and $R^{14}$;

$R^8$ is selected from i) H, ii) hydroxy, iii) carboxy-$C_{1-6}$-alkyl, iv) $C_{1-6}$-alkoxy, v) $C_{1-6}$-alkoxycarbonyl-$C_{1-6}$-alkyl, vi) $C_{3-8}$-cycloalkyl, vii) phenyl optionally substituted with one or more substituents selected from the group consisting of $R^{15}$, $R^{16}$ and $R^{17}$, viii) phenyl-$C_{1-6}$-alkoxy optionally substituted with one or more substituents selected from the group consisting of $R^{15}$, $R^{16}$ and $R^{17}$, ix) pyridinyl optionally substituted with one or more substituents selected from the group consisting of $R^{15}$, $R^{16}$ and $R^{17}$, x) amino-$C_{1-6}$-alkyl substituted on the nitrogen atom by one or two substituents selected from H, $C_{1-6}$-alkoxycarbonyl, pyridinylcarbonyl, pyridazinylcarbonyl and pyrazinylcarbonyl, wherein pyridinylcarbonyl, pyridazinylcarbonyl and pyrazinylcarbonyl are optionally substituted with one or more substituents selected from the group consisting of $R^{15}$, $R^{16}$ and $R^{17}$, xi) aminocarbonyl substituted on the nitrogen atom by H, xii) cyano-$C_{1-6}$-alkyl, and xiii) halo-$C_{1-6}$-alkoxy;

$R^{11}$ is selected from i) amino-$C_{1-6}$-alkyl substituted on the nitrogen atom by $R^{21}$ and $R^{22}$, ii) phenyl optionally substituted with one or more substituents selected from the group consisting of $R^{18}$, $R^{19}$ and $R^{20}$, iii) naphthyl optionally substituted with one or more substituents selected from the group consisting of $R^{18}$, $R^{19}$ and $R^{20}$, iv) phenyl-$C_{1-6}$-alkyl optionally substituted with one or more substituents selected from the group consisting of $R^{18}$, $R^{19}$ and $R^{20}$, v) phenyl-$C_{3-8}$-cycloalkyl optionally substituted with one or more substituents selected from the group consisting of $R^{18}$, $R^{19}$ and $R^{20}$, vi) phenyl(halo)-$C_{1-6}$-alkyl optionally substituted with one or more substituents selected from the group consisting of $R^{18}$, $R^{19}$ and $R^{20}$, vii) phenoxy-$C_{1-6}$-alkyl optionally substituted with one or more substituents selected from the group consisting of $R^{18}$, $R^{19}$ and $R^{20}$, viii) heteroaryl optionally substituted with one or more substituents selected from the group consisting of $R^{18}$, $R^{19}$ and $R^{20}$, wherein heteroaryl is selected from pyrazinyl, pyridinyl, pyrimidinyl and thiophenyl, ix) pyridinyl-$C_{1-6}$-alkyl optionally substituted with one or more substituents selected from the group consisting of $R^{15}$, $R^{16}$ and $R^{17}$, x) heterocycloalkyl optionally substituted with one or more substituents selected from the group consisting of $R^{15}$, $R^{16}$ and $R^{17}$, wherein heterocycloalkyl is selected from pyrrolidinyl and piperidinyl, xi) $C_{3-8}$-cycloalkyl optionally substituted with one or more substituents selected from the group consisting of $R^{18}$, $R^{19}$ and $R^{20}$, xii) phenyl(cycloalkyl)-$C_{1-6}$-alkyl optionally substituted with one or more substituents selected from the group consisting of $R^{18}$, $R^{19}$ and $R^{20}$, xiii) phenyl(heterocycloalkyl)-$C_{1-6}$-alkyl optionally substituted with one or more substituents selected from the group consisting of $R^{18}$, $R^{19}$ and $R^{20}$, and xiv) phenyl(hydroxy, halo)-$C_{1-6}$-alkyl optionally substituted with one or more substituents selected from the group consisting of $R^{18}$, $R^{19}$ and $R^{20}$;

$R^{12}$ is selected from i) H, ii) $C_{1-6}$-alkoxy, iii) $C_{1-6}$-alkoxycarbonyl-$C_{1-6}$-alkoxy, and iv) hydroxycarbonyl-$C_{1-6}$-alkoxy;

$R^{13}$, $R^{14}$, $R^{17}$ and $R^{20}$ are H;

$R^{15}$ is selected from i) H, ii) cyano, iii) halogen, iv) $C_{1-6}$-alkoxycarbonyl-$C_{1-6}$-alkoxy, v) carboxy-$C_{1-6}$-alkoxy, and vi) amino substituted on the nitrogen atom by one H and one substituent selected from H, $C_{1-6}$-alkoxycarbonyl and pyridinylcarbonyl;

$R^{16}$ is selected from i) H, and ii) halogen;

$R^{18}$ is selected from i) H, ii) halogen, iii) oxo, iv) $C_{1-6}$-alkyl, v) amino-$C_{1-6}$-alkyl substituted on the nitrogen atom by one H and one substituents selected from H and $C_{1-6}$-alkoxycarbonyl, vi) $C_{1-6}$-alkoxycarbonyl-$C_{1-6}$-alkoxy, vii) carboxy-$C_{1-6}$-alkoxy, viii) $C_{1-6}$alkoxycarbonyl-$C_{1-6}$alkylaminocarbonyl-$C_{1-6}$alkoxy, ix) carboxy-$C_{1-6}$alkylaminocarbonyl-$C_{1-6}$alkoxy, x) halo-$C_{1-6}$-alkyl, xi) halo-$C_{1-6}$-alkoxy,
xii) $C_{1-6}$-alkoxy, and
xiii) cyano;
$R^{19}$ is selected from
i) H,
ii) halogen,
iii) $C_{1-6}$-alkoxycarbonyl-$C_{1-6}$-alkyl, and
iv) carboxy-$C_{1-6}$-alkoxy;
$R^{21}$ is selected from
i) H,
ii) $C_{1-6}$-alkoxycarbonyl, and
iii) pyridinylcarbonyl; and
$R^{22}$ is H.

4. A compound according to claim 1, or a pharmaceutically acceptable salt thereof, wherein
$R^2$ is $C_{1-6}$-alkyl;
$R^3$, $R^4$, $R^6$, $R^7$, $R^{10}$ and $R^{23}$ are H;
$R^5$ is selected from
i) phenyl optionally substituted with one or more substituents selected from the group consisting of $R^{12}$, $R^{13}$ and $R^{14}$, and
ii) phenyl-$C_{1-6}$-alkyl optionally substituted with one or more substituents selected from the group consisting of $R^{12}$, $R^{13}$ and $R^{14}$;
$R^8$ is selected from
i) H,
ii) hydroxy,
iii) carboxy-$C_{1-6}$-alkyl,
iv) $C_{1-6}$-alkoxy,
v) $C_{1-6}$-alkoxycarbonyl-$C_{1-6}$-alkyl,
vi) $C_{3-8}$-cycloalkyl,
vii) phenyl optionally substituted with one or more substituents selected from the group consisting of $R^{15}$, $R^{16}$ and $R^{17}$,
viii) phenyl-$C_{1-6}$-alkoxy optionally substituted with one or more substituents selected from the group consisting of $R^{15}$, $R^{16}$ and $R^{17}$, and
ix) pyridinyl optionally substituted with one or more substituents selected from the group consisting of $R^{15}$, $R^{16}$ and $R^{17}$;
$R^{11}$ is selected from
i) amino-$C_{1-6}$-alkyl substituted on the nitrogen atom by $R^{21}$ and $R^{22}$,
ii) phenyl optionally substituted with one or more substituents selected from the group consisting of $R^{18}$, $R^{19}$ and $R^{20}$,
iii) naphthyl optionally substituted with one or more substituents selected from the group consisting of $R^{18}$, $R^{19}$ and $R^{20}$,
iv) phenyl-$C_{1-6}$-alkyl optionally substituted with one or more substituents selected from the group consisting of $R^{18}$, $R^{19}$ and $R^{20}$,
v) phenyl-$C_{3-8}$-cycloalkyl optionally substituted with one or more substituents selected from the group consisting of $R^{18}$, $R^{19}$ and $R^{20}$,
vi) phenyl(halo)-$C_{1-6}$-alkyl optionally substituted with one or more substituents selected from the group consisting of $R^{18}$, $R^{19}$ and $R^{20}$,
vii) phenoxy-$C_{1-6}$-alkyl optionally substituted with one or more substituents selected from the group consisting of $R^{18}$, $R^{19}$ and $R^{20}$,
viii) heteroaryl optionally substituted with one or more substituents selected from the group consisting of $R^{18}$, $R^{19}$ and $R^{20}$, wherein heteroaryl is selected from pyrazinyl, pyridinyl, pyrimidinyl and thiophenyl,
ix) pyridinyl-$C_{1-6}$-alkyl optionally substituted with one or more substituents selected from the group consisting of $R^{15}$, $R^{16}$ and $R^{17}$, and
x) heterocycloalkyl optionally substituted with one or more substituents selected from the group consisting of $R^{15}$, $R^{16}$ and $R^{17}$, wherein heterocycloalkyl is selected from pyrrolidinyl and piperidinyl;
$R^{12}$ is selected from
i) H, and
ii) $C_{1-6}$-alkoxy;
$R^{13}$, $R^{14}$, $R^{17}$ and $R^{20}$ are H;
$R^{15}$ is selected from
i) H,
ii) cyano,
iii) halogen,
iv) $C_{1-6}$-alkoxycarbonyl-$C_{1-6}$-alkoxy, and
v) carboxy-$C_{1-6}$-alkoxy;
$R^{16}$ is selected from
i) H, and
ii) halogen;
$R^{18}$ is selected from
i) H,
ii) halogen,
iii) oxo,
iv) $C_{1-6}$-alkyl,
v) amino-$C_{1-6}$-alkyl substituted on the nitrogen atom by one H and one substituent selected from H and $C_{1-6}$-alkoxycarbonyl,
vi) $C_{1-6}$-alkoxycarbonyl-$C_{1-6}$-alkoxy,
vii) carboxy-$C_{1-6}$-alkoxy,
viii) $C_{1-6}$alkoxycarbonyl-$C_{1-6}$alkylaminocarbonyl-$C_{1-6}$alkoxy, and
ix) carboxy-$C_{1-6}$alkylaminocarbonyl-$C_{1-6}$alkoxy;
$R^{19}$ is selected from
i) H,
ii) halogen,
iii) $C_{1-6}$-alkoxycarbonyl-$C_{1-6}$-alkyl, and
iv) carboxy-$C_{1-6}$-alkoxy;
$R^{21}$ is selected from
i) H,
ii) $C_{1-6}$-alkoxycarbonyl, and
iii) pyridinylcarbonyl; and
$R^{22}$ is H.

5. A compound according to claim 1, or a pharmaceutically acceptable salt thereof, wherein $R^2$ is $C_{1-6}$-alkyl.

6. A compound according to claim 1, or a pharmaceutically acceptable salt thereof, wherein $R^2$ is isopropyl.

7. A compound according to claim 1, or a pharmaceutically acceptable salt thereof, wherein $R^3$, $R^4$, $R^6$, $R^7$, $R^{10}$ and $R^{23}$ are H.

8. A compound according to claim 1, or a pharmaceutically acceptable salt thereof, wherein $R^5$ is selected from
i) phenyl optionally substituted with one or more substituents selected from the group consisting of $R^{12}$, $R^{13}$ and $R^{14}$, and
ii) phenyl-$C_{1-6}$-alkyl optionally substituted with one or more substituents selected from the group consisting of $R^{12}$, $R^{13}$ and $R^{14}$.

9. A compound according to claim 1, or a pharmaceutically acceptable salt thereof, wherein $R^5$ is phenyl optionally substituted with one or more substituents selected from the group consisting of one $C_{1-6}$-alkoxy.

10. A compound according to claim 1, or a pharmaceutically acceptable salt thereof, wherein $R^8$ is selected from
i) H,
ii) hydroxy,
iii) carboxy-$C_{1-6}$-alkyl, iv) $C_{1-6}$-alkoxy,
v) $C_{1-6}$-alkoxycarbonyl-$C_{1-6}$-alkyl,
vi) $C_{3-8}$-cycloalkyl,
vii) phenyl optionally substituted with one or more substituents selected from the group consisting of $R^{15}$, $R^{16}$ and $R^{17}$,
viii) phenyl-$C_{1-6}$-alkoxy optionally substituted with one or more substituents selected from the group consisting of $R^{15}$, $R^{16}$ and $R^{17}$,
ix) pyridinyl optionally substituted with one or more substituents selected from the group consisting of $R^{15}$, $R^{16}$ and $R^{17}$,
x) amino-$C_{1-6}$-alkyl substituted on the nitrogen atom by one or two substituents selected from H, $C_{1-6}$-alkoxycarbonyl, pyridinylcarbonyl, pyridazinylcarbonyl and pyrazinylcarbonyl, wherein pyridinylcarbonyl, pyridazinylcarbonyl and pyrazinylcarbonyl are optionally substituted with one or more substituents selected from the group consisting of $R^{15}$, $R^{16}$ and $R^{17}$,
xi) aminocarbonyl substituted on the nitrogen atom by H,
xii) cyano-$C_{1-6}$-alkyl, and
xiii) halo-$C_{1-6}$-alkoxy.

11. A compound according to claim 1, or a pharmaceutically acceptable salt thereof, wherein $R^8$ is selected from
i) H,
ii) hydroxy,
iii) carboxy-$C_{1-6}$-alkyl,
iv) $C_{1-6}$-alkoxy,
v) $C_{1-6}$-alkoxycarbonyl-$C_{1-6}$-alkyl,
vi) $C_{3-8}$-cycloalkyl,
vii) phenyl optionally substituted with one or more substituents selected from the group consisting of $R^{15}$, $R^{16}$ and $R^{17}$,
viii) phenyl-$C_{1-6}$-alkoxy optionally substituted with one or more substituents selected from the group consisting of $R^{15}$, $R^{16}$ and $R^{17}$, and
ix) pyridinyl optionally substituted with one or more substituents selected from the group consisting of $R^{15}$, $R^{16}$ and $R^{17}$.

12. A compound according to claim 1, or a pharmaceutically acceptable salt thereof, wherein $R^8$ is selected from
i) H,
ii) hydroxy,
iii) phenyl optionally substituted with one or more substituents selected from the group consisting of $R^{15}$, $R^{16}$ and $R^{17}$,
iv) phenyl-$C_{1-6}$-alkoxy optionally substituted with one or more substituents selected from the group consisting of $R^{15}$, $R^{16}$ and $R^{17}$, and
v) $C_{1-6}$-alkoxy.

13. A compound according to claim 1, or a pharmaceutically acceptable salt thereof, wherein $R^8$ is selected from
i) H,
ii) hydroxy,
iii) phenyl optionally substituted with one or more substituents selected from the group consisting of $R^{15}$, $R^{16}$ and $R^{17}$, and
iv) phenyl-$C_{1-6}$-alkoxy optionally substituted with one or more substituents selected from the group consisting of $R^{15}$, $R^{16}$ and $R^{17}$.

14. A compound according to claim 1, or a pharmaceutically acceptable salt thereof, wherein $R^8$ is phenyl optionally substituted with one or more substituents selected from the group consisting of $R^{15}$, $R^{16}$ and $R^{17}$.

15. A compound according to claim 1, or a pharmaceutically acceptable salt thereof, wherein $R^{11}$ is selected from
i) amino-$C_{1-6}$-alkyl substituted on the nitrogen atom by $R^{21}$ and $R^{22}$,
ii) phenyl optionally substituted with one or more substituents selected from the group consisting of $R^{18}$, $R^{19}$ and $R^{20}$,
iii) naphthyl optionally substituted with one or more substituents selected from the group consisting of $R^{18}$, $R^{19}$ and $R^{20}$,
iv) phenyl-$C_{1-6}$-alkyl optionally substituted with one or more substituents selected from the group consisting of $R^{18}$, $R^{19}$ and $R^{20}$,
v) phenyl-$C_{3-8}$-cycloalkyl optionally substituted with one or more substituents selected from the group consisting of $R^{18}$, $R^{19}$ and $R^{20}$,
vi) phenyl(halo)-$C_{1-6}$-alkyl optionally substituted with one or more substituents selected from the group consisting of $R^{18}$, $R^{19}$ and $R^{20}$,
vii) phenoxy-$C_{1-6}$-alkyl optionally substituted with one or more substituents selected from the group consisting of $R^{18}$, $R^{19}$ and $R^{20}$,
viii) heteroaryl optionally substituted with one or more substituents selected from the group consisting of $R^{18}$, $R^{19}$ and $R^{20}$, wherein heteroaryl is selected from pyrazinyl, pyridinyl, pyrimidinyl, pyrrolidinyl and thiophenyl,
ix) pyridinyl-$C_{1-6}$-alkyl optionally substituted with one or more substituents selected from the group consisting of $R^{15}$, $R^{16}$ and $R^{17}$, and
x) piperazinyl optionally substituted with one or more substituents selected from the group consisting of $R^{15}$, $R^{16}$ and $R^{17}$,
xi) $C_{3-8}$-cycloalkyl optionally substituted with one or more substituents selected from the group consisting of $R^{18}$, $R^{19}$ and $R^{20}$,
xii) phenyl(cycloalkyl)-$C_{1-6}$-alkyl optionally substituted with one or more substituents selected from the group consisting of $R^{18}$, $R^{19}$ and $R^{20}$,
xiii) phenyl(haloalkyl)-$C_{1-6}$-alkyl optionally substituted with one or more substituents selected from the group consisting of $R^{18}$, $R^{19}$ and $R^{20}$,
xiv) phenyl(heterocycloalkyl)-$C_{1-6}$-alkyl optionally substituted with one or more substituents selected from the group consisting of $R^{18}$, $R^{19}$ and $R^{20}$, and
xv) phenyl(hydroxy,haloalkyl)-$C_{1-6}$-alkyl optionally substituted with one or more substituents selected from the group consisting of $R^{18}$, $R^{19}$ and $R^{20}$.

16. A compound according to claim 1, or a pharmaceutically acceptable salt thereof, wherein $R^{11}$ is selected from
i) amino-$C_{1-6}$-alkyl substituted on the nitrogen atom by $R^{21}$ and $R^{22}$,
ii) phenyl optionally substituted with one or more substituents selected from the group consisting of $R^{18}$, $R^{19}$ and $R^{20}$,
iii) naphtyl optionally substituted with one or more substituents selected from the group consisting of $R^{18}$, $R^{19}$ and $R^{20}$,
iv) phenyl-$C_{1-6}$-alkyl optionally substituted with one or more substituents selected from the group consisting of $R^{18}$, $R^{19}$ and $R^{20}$,
v) phenyl-$C_{3-8}$-cycloalkyl optionally substituted with one or more substituents selected from the group consisting of $R^{18}$, $R^{19}$ and $R^{20}$,
vi) phenyl(halo)-$C_{1-6}$-alkyl optionally substituted with one or more substituents selected from the group consisting of $R^{18}$, $R^{19}$ and $R^{20}$, vii) phenoxy-$C_{1-6}$-alkyl optionally substituted with one or more substituents selected from the group consisting of $R^{18}$, $R^{19}$ and $R^{20}$, viii) heteroaryl optionally substituted with one or more substituents selected from the group consisting of $R^{18}$, $R^{19}$ and $R^{20}$, wherein heteroaryl is selected from pyrazinyl, pyridinyl, pyrimidinyl, pyrrolidinyl and thiophenyl, ix) pyridinyl-$C_{1-6}$-alkyl optionally substituted with one or more substituents selected from the group consisting of $R^{15}$, $R^{16}$ and $R^{17}$, and x) piperazinyl optionally substituted with one or more substituents selected from the group consisting of $R^{15}$, $R^{16}$ and $R^{17}$.

17. A compound according to claim 1, or a pharmaceutically acceptable salt thereof, wherein $R^{11}$ is selected from i) $C_{3-8}$-alkyl optionally substituted with one or more substituents selected from the group consisting of $R^{18}$, $R^{19}$ and $R^{20}$, ii) phenyl optionally substituted with one or more substituents selected from the group consisting of $R^{18}$, $R^{19}$ and $R^{20}$, iii) phenyl-$C_{1-6}$-alkyl optionally substituted with one or more substituents selected from the group consisting of $R^{18}$, $R^{19}$ and $R^{20}$, iv) phenyl(halo)-$C_{1-6}$-alkyl optionally substituted with one or more substituents selected from the group consisting of $R^{18}$, $R^{19}$ and $R^{20}$, and v) thiophenyl optionally substituted with one or more substituents selected from the group consisting of $R^{18}$, $R^{19}$ and $R^{20}$.

18. A compound according to claim 1, or a pharmaceutically acceptable salt thereof, wherein $R^{11}$ is selected from i) phenyl optionally substituted with one or more substituents selected from the group consisting of $R^{18}$, $R^{19}$ and $R^{20}$, ii) phenyl-$C_{1-6}$-alkyl optionally substituted with one or more substituents selected from the group consisting of $R^{18}$, $R^{19}$ and $R^{20}$, iii) phenyl(halo)-$C_{1-6}$-alkyl optionally substituted with one or more substituents selected from the group consisting of $R^{18}$, $R^{19}$ and $R^{20}$, and iv) thiophenyl optionally substituted with one or more substituents selected from the group consisting of $R^{18}$, $R^{19}$ and $R^{20}$.

19. A compound according to claim 1, or a pharmaceutically acceptable salt thereof, wherein $R^{11}$ is selected from i) phenyl optionally substituted with one or more substituents selected from the group consisting of $R^{18}$, $R^{19}$ and $R^{20}$, and ii) phenyl(halo)-$C_{1-6}$-alkyl optionally substituted with one or more substituents selected from the group consisting of $R^{18}$, $R^{19}$ and $R^{20}$.

20. A compound according to claim 1, or a pharmaceutically acceptable salt thereof, wherein $R^{12}$ is selected from i) H, ii) $C_{1-6}$-alkoxy, iii) $C_{1-6}$-alkoxycarbonyl-$C_{1-6}$-alkoxy, and iv) hydroxycarbonyl-$C_{1-6}$-alkoxy.

21. A compound according to claim 1, or a pharmaceutically acceptable salt thereof, wherein $R^{12}$ is selected from i) hydroxycarbonyl-$C_{1-6}$-alkoxy, and ii) $C_{1-6}$-alkoxy.

22. A compound according to claim 1, or a pharmaceutically acceptable salt thereof, wherein $R^{12}$ is selected from i) H, and ii) $C_{1-6}$-alkoxy.

23. A compound according to claim 1, or a pharmaceutically acceptable salt thereof, wherein $R^{12}$ is $C_{1-6}$-alkoxy.

24. A compound according to claim 1, or a pharmaceutically acceptable salt thereof, wherein $R^{13}$, $R^{14}$, $R^{17}$ and $R^{20}$ are H.

25. A compound according to claim 1, or a pharmaceutically acceptable salt thereof, wherein $R^{15}$ is selected from i) H, ii) cyano, iii) halogen, iv) $C_{1-6}$-alkoxycarbonyl-$C_{1-6}$-alkoxy, and v) carboxy-$C_{1-6}$-alkoxy, vi) amino substituted on the nitrogen atom by one H and one substituent selected from H, $C_{1-6}$-alkoxycarbonyl and pyridinylcarbonyl.

26. A compound according to claim 1, or a pharmaceutically acceptable salt thereof, wherein $R^{15}$ is selected from i) H, ii) cyano, iii) halogen, iv) $C_{1-6}$-alkoxycarbonyl-$C_{1-6}$-alkoxy, and v) carboxy-$C_{1-6}$-alkoxy.

27. A compound according to claim 1, or a pharmaceutically acceptable salt thereof, wherein $R^{15}$ is selected from i) H, ii) cyano, iii) halogen, and iv) carboxy-$C_{1-6}$-alkoxy, and v) amino substituted on the nitrogen atom by one H and one substituent selected from H, $C_{1-6}$-alkoxycarbonyl and pyridinylcarbonyl.

28. A compound according to claim 1, or a pharmaceutically acceptable salt thereof, wherein $R^{15}$ is selected from i) H, ii) cyano, iii) halogen, and iv) carboxy-$C_{1-6}$-alkoxy.

29. A compound according to claim 1, or a pharmaceutically acceptable salt thereof, wherein $R^{16}$ is H.

30. A compound according to claim 1, or a pharmaceutically acceptable salt thereof, wherein $R^{18}$ is selected from i) H, ii) halogen, iii) oxo, iv) $C_{1-6}$-alkyl, v) amino-$C_{1-6}$-alkyl substituted on the nitrogen atom by one H and one substituent selected from H and $C_{1-6}$-alkoxycarbonyl, vi) $C_{1-6}$-alkoxycarbonyl-$C_{1-6}$-alkoxy, vii) carboxy-$C_{1-6}$-alkoxy, viii) $C_{1-6}$alkoxycarbonyl-$C_{1-6}$alkylaminocarbonyl-$C_{1-6}$-alkoxy, and ix) carboxy-$C_{1-6}$alkylaminocarbonyl-$C_{1-6}$-alkoxy x) halo-$C_{1-6}$-alkyl, xi) halo-$C_{1-6}$-alkoxy, xii) $C_{1-6}$-alkoxy, and xiii) cyano.

31. A compound according to claim 1, or a pharmaceutically acceptable salt thereof, wherein $R^{18}$ is selected from i) H, ii) halogen, iii) oxo, iv) $C_{1-6}$-alkyl, v) amino-$C_{1-6}$-alkyl substituted on the nitrogen atom by one H and one substituent selected from H and $C_{1-6}$-alkoxycarbonyl, vi) $C_{1-6}$-alkoxycarbonyl-$C_{1-6}$-alkoxy, vii) carboxy-$C_{1-6}$-alkoxy, viii) $C_{1-6}$alkoxycarbonyl-$C_{1-6}$alkylaminocarbonyl-$C_{1-6}$-alkoxy, and ix) carboxy-$C_{1-6}$alkylaminocarbonyl-$C_{1-6}$-alkoxy.

32. A compound according to claim 1, or a pharmaceutically acceptable salt thereof, wherein $R^{18}$ is selected from i) H, ii) halogen, iii) amino-$C_{1-6}$-alkyl substituted on the nitrogen atom by two H, iv) carboxy-$C_{1-6}$-alkoxy, v) $C_{1-6}$-alkyl, and vi) halo-$C_{1-6}$-alkyl.

33. A compound according to claim 1, or a pharmaceutically acceptable salt thereof, wherein $R^{18}$ is selected from i) H, ii) halogen, iii) amino-$C_{1-6}$-alkyl substituted on the nitrogen atom by two H, and iv) carboxy-$C_{1-6}$-alkoxy.

34. A compound according to claim 1, or a pharmaceutically acceptable salt thereof, wherein $R^{18}$ is halogen.

35. A compound according to claim 1, or a pharmaceutically acceptable salt thereof, wherein $R^{19}$ is selected from i) H, ii) halogen, iii) $C_{1-6}$-alkoxycarbonyl-$C_{1-6}$-alkyl, and iv) carboxy-$C_{1-6}$-alkoxy.

36. A compound according to claim 1, or a pharmaceutically acceptable salt thereof, wherein $R^{19}$ is selected from i) H, and ii) halogen.

37. A compound according to claim 1, or a pharmaceutically acceptable salt thereof, wherein $R^{19}$ is halogen.

38. A compound according to claim 1, or a pharmaceutically acceptable salt thereof, wherein $R^{21}$ is selected from i) H, ii) $C_{1-6}$-alkoxycarbonyl, and iii) pyridinylcarbonyl.

39. A compound according to claim 1, or a pharmaceutically acceptable salt thereof, wherein $R^{22}$ is H.

40. A compound according to claim 1, or a pharmaceutically acceptable salt thereof, wherein $R^2$ is $C_{1-6}$-alkyl;

$R^3$, $R^4$, $R^6$, $R^7$, $R^{10}$ and $R^{23}$ are H;

$R^5$ is phenyl optionally substituted with one or more substituents selected from the group consisting of one $C_{1-6}$-alkoxy;

$R^8$ is phenyl optionally substituted with one or more substituents selected from the group consisting of $R^{15}$, $R^{16}$ and $R^{17}$;

$R^{11}$ is selected from i) phenyl optionally substituted with one or more substituents selected from the group consisting of $R^{18}$, $R^{19}$ and $R^{20}$, ii) phenyl(halo)-$C_{1-6}$-alkyl optionally substituted with one or more substituents selected from the group consisting of $R^{18}$, $R^{19}$ and $R^{20}$;

$R^{15}$ is selected from i) H, ii) cyano, iii) halogen, and iv) carboxy-$C_{1-6}$-alkoxy;

$R^{16}$ is H;

$R^{17}$ and $R^{20}$ are H;

$R^{18}$ and $R^{19}$ are is halogen.

41. A compound according to claim 1, selected from

N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

(2S)-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]-2-(3-pyridin-3-ylpropanoylamino)propanamide;

N-[(2S)-3-(3-fluorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

3-chloro-N-[(2S)-3-(3-fluorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

5-chloro-N-[(2S)-3-(3-fluorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

(2S)-2-[[2-(3-chlorophenyl)-2,2-difluoroacetyl]amino]-3-(3-fluorophenyl)-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-chlorophenyl)-2,2-difluoroacetyl]amino]-3-(3-fluorophenyl)-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3-chlorophenyl)-2,2-difluoroacetyl]amino]-3-(3-cyanophenyl)-N-[(1S)-1-(4-methoxyphenyl)-2-oxo-2-[[(3S)-1,1,1-trifluoro-4-methyl-2-oxopentan-3-yl]amino]ethyl]propanamide;

5-chloro-N-[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-pyridin-3-ylpropan-2-yl]benzamide;

3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-pyridin-3-ylpropan-2-yl]benzamide;

(2S)-2-[[2-(2-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-pyridin-3-ylpropanamide;

N-[(2S)-3-(2-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

(2S)-2-[[2-(3-chlorophenyl)-2,2-difluoroacetyl]amino]-3-(2-cyanophenyl)-N-[(1S)-1-(4-methoxyphenyl)-2-oxo-2-[[(3S)-1,1,1-trifluoro-4-methyl-2-oxopentan-3-yl]amino]ethyl]propanamide;

tert-butyl 2-[4-[(2S)-2-[(3-chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate;

tert-butyl 2-[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-(pyridine-2-carbonylamino)propyl]phenoxy]acetate;

tert-butyl 2-[4-[(2S)-2-[[2-(2-chlorophenyl)-2,2-difluoroacetyl]amino]-3-[[(1S)-1-(4-methoxyphenyl)-2-oxo-2-

[[(3S)-1,1,1-trifluoro-4-methyl-2-oxopentan-3-yl]amino]ethyl]amino]-3-oxopropyl]phenoxy]acetate;

tert-butyl 2-[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate;

tert-butyl 2-[3-[(2S)-2-[(3-chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate;

tert-butyl 2-[3-[(2S)-2-[[2-(2-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetate;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

(2S)-2-[(2,2-difluoro-2-phenylacetyl)amino]-N-[(1S)-1-(4-methoxyphenyl)-2-oxo-2-[[(3S)-1,1,1-trifluoro-4-methyl-2-oxopentan-3-yl]amino]ethyl]propanamide;

2,5-dichloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

1-(3-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopropane-1-carboxamide;

(2S)-2-[[2-(2-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3-chlorophenyl)acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

2-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

(2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-chlorophenyl)acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[(2-fluoro-2-phenylacetyl)amino]-N-[(1S)-1-(4-methoxyphenyl)-2-oxo-2-[[(3S)-1,1,1-trifluoro-4-methyl-2-oxopentan-3-yl]amino]ethyl]propanamide;

5-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

5-bromo-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

(2S)-2-[[2-(4-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3,4-dichlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

2-(3-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-methylpropanamide;

(2S)-2-[[2-(3-chlorophenyl)-2,2-difluoroacetyl]amino]-3-methoxy-N-[(1S)-1-(4-methoxyphenyl)-2-oxo-2-[[(3S)-1,1,1-trifluoro-4-methyl-2-oxopentan-3-yl]amino]ethyl]propanamide;

3-chloro-N-[(2S)-3-methoxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

(2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-[(2-methylpropan-2-yl)oxy]propanamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-3-[(2-methylpropan-2-yl)oxy]-1-oxopropan-2-yl]pyridine-2-carboxamide;

3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-3-[(2-methylpropan-2-yl)oxy]-1-oxopropan-2-yl]benzamide;

5-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-3-[(2-methylpropan-2-yl)oxy]-1-oxopropan-2-yl]thiophene-2-carboxamide;

(2S)-2-[[2-(2-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-[(2-methylpropan-2-yl)oxy]propanamide;

3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-phenylmethoxypropan-2-yl]benzamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-phenylmethoxypropan-2-yl]pyridine-2-carboxamide;

tert-butyl (4S)-4-[(3-chlorobenzoyl)amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoate;

tert-butyl (4S)-4-[[2-(3-chlorophenyl)-2,2-difluoroacetyl]amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoate;

N-[(2S)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrazine-2-carboxamide;

N-[(2S)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]-1-methylpyrrolidine-3-carboxamide;

N-[(2S)-3-(3,4-dichlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrazine-2-carboxamide;

N-[(2S)-3-(3,4-dichlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyridine-2-carboxamide;

N-[(2S)-3-(3,4-dichlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrimidine-5-carboxamide;

N-[(2S)-3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]pyrazine-2-carboxamide;

N-[(2S)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrazine-2-carboxamide;

N-[(2S)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrimidine-5-carboxamide;

N-[(2S)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]-1-methylpiperidine-4-carboxamide;

N-[(2R)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrimidine-5-carboxamide;

N-[(2R)-3-(3-chlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrazine-2-carboxamide;

N-[(2S)-3-(3,4-dichlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyridine-2-carboxamide;

N-[(2S)-3-(3,4-dichlorophenyl)-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]pyrazine-2-carboxamide;

N-[(2S)-3-cyclohexyl-1-oxo-1-[[(2S)-1-oxo-3-phenyl-1-[[(3S)-1,1,1-trifluoro-4-methyl-2-oxopentan-3-yl]amino]propan-2-yl]amino]propan-2-yl]naphthalene-2-carboxamide;

tert-butyl N-[2-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]carbamate;

tert-butyl N-[[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenyl]methyl]carbamate;

tert-butyl N-[[2-chloro-4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenyl]methyl]carbamate;

tert-butyl N-[[4-[2-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]phenyl]methyl]carbamate;

tert-butyl 2-[6-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]pyridin-2-yl]oxyacetate;

tert-butyl 2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetate;

tert-butyl 2-[6-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]pyridin-3-yl]oxyacetate;

tert-butyl 2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]-2-oxopyridin-1-yl]acetate;

tert-butyl 2-[3-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetate;

tert-butyl 2-[5-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]-2-oxopyridin-1-yl]acetate;

tert-butyl 2-[4-[2-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethoxy]phenoxy]acetate;

tert-butyl 2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetate;

tert-butyl 2-[4-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetate;

N-[3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

N-[(2S)-3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]-3-methylpyridine-2-carboxamide;

N-[(2S)-3-(3-chlorophenyl)-1-[[(1S and 1R)-1-(3-methoxyphenyl)-2-oxo-2-[[(3S)-1,1,1-trifluoro-4-methyl-2-oxopentan-3-yl]amino]ethyl]amino]-1-oxopropan-2-yl]-4-methylpyridine-3-carboxamide;

N-[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

N-[(2R)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyridine-2-carboxamide;

N-[(2R)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrazine-2-carboxamide;

N-[(2R)-3-(3-chlorophenyl)-1-oxo-1-[[(1S and 1R)-2-oxo-1-phenyl-2-[[(3S)-1,1,1-trifluoro-4-methyl-2-oxopentan-3-yl]amino]ethyl]amino]propan-2-yl]pyrimidine-5-carboxamide;

tert-butyl N-[[4-[[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenyl]methyl]carbamate;

tert-butyl N-[[4-[2-[[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]phenyl]methyl]carbamate;

tert-butyl 2-[[2-[4-[[(2S)-3-(3-chlorophenyl)-1-[[(1S)-1-(4-methoxyphenyl)-2-oxo-2-[[(3S)-1,1,1-trifluoro-4- methyl-2-oxopentan-3-yl]amino]ethyl]amino]-1-oxopropan-2-yl]carbamoyl]phenoxy]acetyl]amino]acetate;

tert-butyl 2-[[2-[3-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetate;

tert-butyl 2-[[2-[4-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetate;

tert-butyl 2-[[2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetate;

2-[4-[(2S)-2-[(3-chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid;

2-[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-(pyridine-2-carbonylamino)propyl]phenoxy]acetic acid;

2-[4-[(2S)-2-[[2-(2-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid;

2-[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid;

2-[3-[(2S)-2-[(3-chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid;

2-[3-[(2S)-2-[[2-(2-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid;

(4S)-4-[(3-chlorobenzoyl)amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoic acid;

(4S)-4-[[2-(3-chlorophenyl)-2,2-difluoroacetyl]amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentanoic acid;

(2S)-2-[(2-aminoacetyl)amino]-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]propanamide, trifluoroacetic acid salt;

4-(aminomethyl)-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide, trifluoroacetic acid salt;

4-(aminomethyl)-3-chloro-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide, trifluoroacetic acid salt;

(2S)-2-[[2-[4-(aminomethyl)phenyl]acetyl]amino]-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]propanamide, trifluoroacetic acid salt;

2-[6-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]pyridin-2-yl]oxyacetic acid;

2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

2-[6-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]pyridin-3-yl]oxyacetic acid;

2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]-2-oxopyridin-1-yl]acetic acid;

2-[3-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

2-[5-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]-2-oxopyridin-1-yl]acetic acid;

2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

2-[4-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

4-(aminomethyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide, trifluoroacetic acid salt;

(2S)-2-[[2-[4-(aminomethyl)phenyl]acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide, trifluoroacetic acid salt;

2-[[2-[4-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid;

2-[[2-[3-[[3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid;

2-[[2-[4-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid;

2-[[2-[3-[[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetyl]amino]acetic acid;

(2S)-2-[[2-(3-chlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

N-[(2S)-3-hydroxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]pyridine-2-carboxamide;

3-chloro-N-[(2S)-3-hydroxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

5-chloro-N-[(2S)-3-hydroxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

(2S)-2-[[2-(2-chlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide; and N-[2-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]amino]-2-oxoethyl]pyridine-2-carboxamide;

or a pharmaceutically acceptable salt thereof.

42. A compound according to claim 1, selected from (2S)-3-(3-Chlorophenyl)-2-[[2-(3-chlorophenyl)acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

1-(3-chlorophenyl)-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopropane-1-carboxamide;

5-bromo-N-[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

(2S)-2-[[2,2-difluoro-2-(3-fluorophenyl)acetyl]amino]-N-[(1S)-1-(4-methoxyphenyl)-2-oxo2-[[(3S)-1,1,1-trifluoro-4-methyl-2-oxopentan-3-yl]amino]ethyl]propanamide;

1-(3-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclobutane-1-carboxamide;

(2S)-2-[[2-(2,5-dichlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2,3-dichlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

2-(3-chlorophenyl)-N-[(2S)-1-[[(1S)-1-(4-methoxyphenyl)-2-oxo-2-[(1,1,1-trifluoro-4-methyl-2-oxopentan-3-yl)amino]ethyl]amino]-1-oxopropan-2-yl]-1,3-dioxolane-2-carboxamide;

1-(4-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopentane-1-carboxamide;

(2S)-2-[[2,2-difluoro-2-[2-(trifluoromethoxy)phenyl]acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-ethoxyphenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2,2-difluoro-2-[2-(trifluoromethyl)phenyl]acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

1-(2-chloro-6-fluorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopentane-1-carboxamide;

1-(2-fluorophenyl)-N-[(2S)-1-[[(1S)-1-(4-methoxyphenyl)-2-oxo-2-[(1,1,1-trifluoro-4-methyl-2-oxopentan-3-yl)amino]ethyl]amino]-1-oxopropan-2-yl]cyclopentane-1-carboxamide;

2-(3-chlorophenyl)-3,3,3-trifluoro-2-hydroxy-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]propanamide;

3,3,3-trifluoro-2-hydroxy-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-[3-(trifluoromethyl)phenyl]propanamide;

2-(3,4-dichlorophenyl)-3,3,3-trifluoro-2-hydroxy-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]propanamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-(trifluoromethoxy)benzamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-(trifluoromethyl)benzamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-(trifluoromethyl)benzamide;

2-(4-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-methylbutanamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-phenylbutanamide;

(2S)-2-[[2-(4-chlorophenyl)-2-cyclopropylacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-(4-chlorophenyl)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-methylbutanamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-phenylcyclopentane-1-carboxamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-methylbenzamide;

3-methoxy-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

3-cyano-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-(trifluoromethoxy)benzamide;

3-ethoxy-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

(2S)-2-[[2,2-difluoro-2-(2-methoxyphenyl)acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

4-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

3,3,3-trifluoro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-[3-(trifluoromethyl)phenyl]propanamide;

2-(difluoromethoxy)-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(trifluoromethyl)cyclobutane-1-carboxamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(trifluoromethyl)cyclohexane-1-carboxamide;

N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(trifluoromethyl)cyclopentane-1-carboxamide;

(2S)-2-[[(2S)-2-(4-chlorophenyl)-2-cyclobutylacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[(2R)-2-(4-chlorophenyl)-2-cyclobutylacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

N-[(2S)-3-methoxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(trifluoromethyl)cyclopentane-1-carboxamide;

1-fluoro-N-[(2S)-3-methoxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopentane-1-carboxamide;

tert-butyl N-[(4S)-4-[(3-chlorobenzoyl)amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentyl]carbamate;

tert-butyl N-[(5S)-5-[(3-chlorobenzoyl)amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]carbamate;

tert-butyl N-[(5S)-5-[[2-(3-chlorophenyl)-2,2-difluoroacetyl]amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]carbamate;

tert-butyl N-[[4-[(2S)-2-[(3-chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate;

tert-butyl N-[[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate;

tert-butyl N-[[4-[(2S)-2-[[2,2-difluoro-2-[2-(trifluoromethyl)phenyl]acetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate;

tert-butyl N-[[4-[(2S)-2-[[1-(4-chlorophenyl)cyclopentanecarbonyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate;

tert-butyl N-[[4-[(2S)-2-[(5-chlorothiophene-2-carbonyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate;

tert-butyl N-[[4-[(2S)-2-[[(2S)-2-(4-chlorophenyl)-3-methylbutanoyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate;

tert-butyl N-[[4-[(2S)-2-[[(2R)-2-(4-chlorophenyl)-3-methylbutanoyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate;

tert-butyl N-[[4-[(2S)-2-[[2-(4-chlorophenyl)-2-cyclobutylacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]carbamate;

tert-butyl N-[[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-[[3-(trifluoromethyl)benzoyl]amino]propyl]phenyl]methyl]carbamate;

tert-butyl N-[[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-[[1-(trifluoromethyl)cyclopentanecarbonyl]amino]propyl]phenyl]methyl]carbamate;

tert-butyl N-[[4-[(2S)-3-[[(1S)-1-(4-methoxyphenyl)-2-oxo-2-[[(3S)-1,1,1-trifluoro-4-methyl-2-oxopentan-3-yl]amino]ethyl]amino]-3-oxo-2-[[3,3,3-trifluoro-2-[3-(trifluoromethyl)phenyl]propanoyl]amino]propyl]phenyl]methyl]carbamate;

3-chloro-N-[(2S)-1-[[(1S)-1-(4-methoxyphenyl)-2-oxo-2-[[(3S)-1,1,1-trifluoro-4-methyl-2-oxopentan-3-yl]amino]ethyl]amino]-1-oxo-3-(trifluoromethoxy)propan-2-yl]benzamide;

(2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-(trifluoromethoxy)propanamide;

(2S)-2-[[2-(3-chlorophenyl)-2,2-difluoroacetyl]amino]-3-cyano-N-[(1S)-1-(4-methoxyphenyl)-2-oxo-2-[[(3S)-1,1,1-trifluoro-4-methyl-2-oxopentan-3-yl]amino]ethyl]propanamide;

3-chloro-N-[(2S)-3-cyano-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

tert-butyl 2-[4-[(1S)-1-[[(2S)-2-[(5-chlorothiophene-2-carbonyl)amino]-3-(3-fluorophenyl)propanoyl]amino]-2-oxo-2-[[(3S)-1,1,1-trifluoro-4-methyl-2-oxopentan-3-yl]amino]ethyl]phenoxy]acetate;

tert-butyl 2-[4-[(1S)-1-[[(2S)-2-[[2-(3-chlorophenyl)-2,2-difluoroacetyl]amino]-3-(3-fluorophenyl)propanoyl]amino]-2-oxo-2-[[(3S)-1,1,1-trifluoro-4-methyl-2-oxopentan-3-yl]amino]ethyl]phenoxy]acetate;

N-[(2S)-5-Amino-1-[[(1S)-1-(4-methoxyphenyl)-2-oxo-2-[[(3S)-1,1,1-trifluoro-4-methyl-2-oxopentan-3-yl]amino]ethyl]amino]-1-oxopentan-2-yl]-3-chlorobenzamide;

N-[(2S)-6-amino-1-[[(1S)-1-(4-methoxyphenyl)-2-oxo-2-[[(3S)-1,1,1-trifluoro-4-methyl-2-oxopentan-3-yl]amino]ethyl]amino]-1-oxohexan-2-yl]-3-chlorobenzamide;2,2,2-trifluoroacetic acid;

(2S)-6-amino-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]hexanamide;2,2,2-trifluoroacetic acid;

N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-chlorobenzamide;2,2,2-trifluoroacetic acid;

(2S)-3-[4-(aminomethyl)phenyl]-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;2,2,2-trifluoroacetic acid;

(2S)-3-[4-(aminomethyl)phenyl]-2-[[2,2-difluoro-2-[2-(trifluoromethyl)phenyl]acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;2,2,2-trifluoroacetic acid;

N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(4-chlorophenyl)cyclopentane-1-carboxamide;2,2,2-trifluoroacetic acid;

N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-5-chlorothiophene-2-carboxamide;2,2,2-trifluoroacetic acid;

(2S)—N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-(4-chlorophenyl)-3-methylbutanamide;2,2,2-trifluoroacetic acid;

(2R)—N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-(4-chlorophenyl)-3-methylbutanamide;2,2,2-trifluoroacetic acid;

(2S)-3-[4-(aminomethyl)phenyl]-2-[[2-(4-chlorophenyl)-2-cyclobutylacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;2,2,2-trifluoroacetic acid;

N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-(trifluoromethyl)benzamide;2,2,2-trifluoroacetic acid;

N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(trifluoromethyl)cyclopentane-1-carboxamide;2,2,2-trifluoroacetic acid;

N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3,3,3-trifluoro-2-[3-(trifluoromethyl)phenyl]propanamide;2,2,2-trifluoroacetic acid;

(2S)-2-[[2-(3,4-dichlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2,5-dichlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2,2-difluoro-2-(3-fluorophenyl)acetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2,2-difluoro-2-[2-(trifluoromethoxy)phenyl]acetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-ethoxyphenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-ethylphenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

1-(4-chlorophenyl)-N-[(2S)-3-hydroxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]cyclopentane-1-carboxamide;

(2S)-2-[[2,2-difluoro-2-(2-methoxyphenyl)acetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-cyanophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[(3-chlorobenzoyl)amino]-N-[(1S)-1-(4-methoxyphenyl)-2-oxo-2-[[(3S)-1,1,1-trifluoro-4-methyl-2-oxopentan-3-yl]amino]ethyl]butanediamide;

(2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]butanediamide;

(2S)-2-[(3-chlorobenzoyl)amino]-N-[(1S)-1-(4-methoxyphenyl)-2-oxo-2-[[(3S)-1,1,1-trifluoro-4-methyl-2-oxopentan-3-yl]amino]ethyl]pentanediamide;

(2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]pentanediamide;

2-[4-[(1S)-1-[[(2S)-2-[(5-chlorothiophene-2-carbonyl)amino]-3-(3-fluorophenyl)propanoyl]amino]-2-oxo-2-[[(3S)-1,1,1-trifluoro-4-methyl-2-oxopentan-3-yl]amino]ethyl]phenoxy]acetic acid;

2-[4-[(1S)-1-[[(2S)-2-[[2-(3-chlorophenyl)-2,2-difluoroacetyl]amino]-3-(3-fluorophenyl)propanoyl]amino]-2-oxo-2-[[(3S)-1,1,1-trifluoro-4-methyl-2-oxopentan-3-yl]amino]ethyl]phenoxy]acetic acid;

N-[(5S)-5-[[2-(3,4-dichlorophenyl)-2,2-difluoroacetyl]amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]pyridine-2-carboxamide;

N-[(5S)-5-[[2-(3-chlorophenyl)-2,2-difluoroacetyl]amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]pyrazine-2-carboxamide;

N-[(5S)-5-[[2-(3-chlorophenyl)-2,2-difluoroacetyl]amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]pyrimidine-5-carboxamide;

N-[(5S)-5-[(3-chlorobenzoyl)amino]-6-[[(1S)-1-(4-methoxyphenyl)-2-oxo-2-[[(3S)-1,1,1-trifluoro-4-methyl-2-oxopentan-3-yl]amino]ethyl]amino]-6-oxohexyl]pyridine-2-carboxamide;

N-[(4S)-4-[(3-chlorobenzoyl)amino]-5-[[(1S)-1-(4-methoxyphenyl)-2-oxo-2-[[(3S)-1,1,1-trifluoro-4-methyl-2-oxopentan-3-yl]amino]ethyl]amino]-5-oxopentyl]pyridine-2-carboxamide; and N-[[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]pyridine-2-carboxamide;

or a pharmaceutically acceptable salt thereof.

43. A compound according to claim 1, selected from

N-[(2S)-3-methoxy-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-1-(trifluoromethyl)cyclopentane-1-carboxamide;

N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-chlorobenzamide;2,2,2-trifluoroacetic acid;

(2S)-3-[4-(aminomethyl)phenyl]-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;2,2,2-trifluoroacetic acid;

(2S)-3-[4-(aminomethyl)phenyl]-2-[[2,2-difluoro-2-[2-(trifluoromethyl)phenyl]acetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;2,2,2-trifluoroacetic acid;

(2S)—N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-2-(4-chlorophenyl)-3-methylbutanamide;2,2,2-trifluoroacetic acid;

N-[(2S)-3-[4-(aminomethyl)phenyl]-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]-3-(trifluoromethyl)benzamide;2,2,2-trifluoroacetic acid;

(2S)-2-[[2-(3,4-dichlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2,5-dichlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2,2-difluoro-2-(3-fluorophenyl)acetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-ethylphenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

2-[4-[(1S)-1-[[(2S)-2-[[2-(3-chlorophenyl)-2,2-difluoroacetyl]amino]-3-(3-fluorophenyl)propanoyl]amino]-2-oxo-2-[[(3S)-1,1,1-trifluoro-4-methyl-2-oxopentan-3-yl]amino]ethyl]phenoxy]acetic acid; and N-[[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenyl]methyl]pyridine-2-carboxamide;

or a pharmaceutically acceptable salt thereof.

44. A compound according to claim 1, selected from

N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

3-chloro-N-[(2S)-3-(3-fluorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide;

(2S)-2-[[2-(3-chlorophenyl)-2,2-difluoroacetyl]amino]-3-(3-fluorophenyl)-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(2-chlorophenyl)-2,2-difluoroacetyl]amino]-3-(3-fluorophenyl)-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3-chlorophenyl)-2,2-difluoroacetyl]amino]-3-(3-cyanophenyl)-N-[(1S)-1-(4-methoxyphenyl)-2-oxo-2-[[(3S)-1,1,1-trifluoro-4-methyl-2-oxopentan-3-yl]amino]ethyl]propanamide;

5-chloro-N-[(2S)-3-(3-cyanophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]thiophene-2-carboxamide;

(2S)-2-[[2-(2-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]-3-pyridin-3-ylpropanamide;

(2S)-2-[[2-(3-chlorophenyl)-2,2-difluoroacetyl]amino]-3-(2-cyanophenyl)-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3-chlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

(2S)-2-[[2-(3,4-dichlorophenyl)-2,2-difluoroacetyl]amino]-N-[(1S)-1-(4-methoxyphenyl)-2-oxo-2-[[(3S)-1,1,1-trifluoro-4-methyl-2-oxopentan-3-yl]amino]ethyl]propanamide;

2-[4-[(2S)-2-[[2-(3-chlorophenyl)-2,2-difluoroacetyl]amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid;

2-[3-[(2S)-2-[(3-chlorobenzoyl)amino]-3-[[(1S)-1-(4-methoxyphenyl)-2-oxo-2-[[(3S)-1,1,1-trifluoro-4-methyl-2-oxopentan-3-yl]amino]ethyl]amino]-3-oxopropyl]phenoxy]acetic acid;

4-(aminomethyl)-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide, trifluoroacetic acid salt;

4-(aminomethyl)-3-chloro-N-[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]benzamide, trifluoroacetic acid salt;

(2S)-2-[[2-[4-(aminomethyl)phenyl]acetyl]amino]-3-(3-chlorophenyl)-N-[(1S)-1-(4-methoxyphenyl)-2-oxo-2-[[(3S)-1,1,1-trifluoro-4-methyl-2-oxopentan-3-yl]amino]ethyl]propanamide, trifluoroacetic acid salt;

2-[4-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

2-[3-[[(2S)-3-(3-chlorophenyl)-1-[[(1S)-1-(4-methoxyphenyl)-2-oxo-2-[[(3S)-1,1,1-trifluoro-4-methyl-2-oxopentan-3-yl]amino]ethyl]amino]-1-oxopropan-2-yl]carbamoyl]phenoxy]acetic acid;

(2S)-2-[[2-(3-chlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide; and (2S)-2-[[2-(2-chlorophenyl)-2,2-difluoroacetyl]amino]-3-hydroxy-N-[(1S)-1-(4-methoxyphenyl)-2-oxo-2-[[(3S)-1,1,1-trifluoro-4-methyl-2-oxopentan-3-yl]amino]ethyl]propanamide;

or a pharmaceutically acceptable salt thereof.

45. A process to prepare a compound according to claim 1, or a pharmaceutically acceptable salt thereof, comprising the reaction of a compound of formula (II) in oxidative conditions

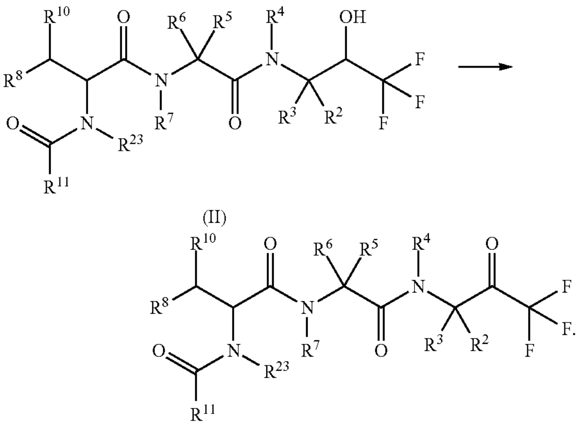

(II) (I)

46. A pharmaceutical composition comprising a compound according to claim 1, or a pharmaceutically acceptable salt thereof, and a therapeutically inert carrier.

47. A method for the treatment of a condition selected from the group consisting of conditions of wet or dry age-related macular degeneration, geographic atrophy, diabetic retinopathy, retinopathy of prematurity and polypoidal choroidal vasculopathy, which method comprises administering an effective amount of a compound according to claim 1, or a pharmaceutically acceptable salt thereof.

48. A compound according to claim 1, or a pharmaceutically acceptable salt thereof, when manufactured according to a process of claim 45.

* * * * *